US00RE46631E

(19) United States
(12) Reissued Patent
Whitehead et al.

(10) Patent Number: US RE46,631 E
(45) Date of Reissued Patent: Dec. 12, 2017

(54) DENGUE TETRAVALENT VACCINE CONTAINING A COMMON 30 NUCLEOTIDE DELETION IN THE 3'-UTR OF DENGUE TYPES 1,2,3, AND 4, OR ANTIGENIC CHIMERIC DENGUE VIRUSES 1,2,3, AND 4

(71) Applicant: The United States of America, as represented by the Secretary, Department of Health & Human Services, Washington, DC (US)

(72) Inventors: Stephen S. Whitehead, Montgomery Village, MD (US); Brian R. Murphy, Bethesda, MD (US); Lewis Markoff, Bethesda, MD (US); Barry Falgout, Rockville, MD (US); Joseph E. Blaney, Gettysburg, PA (US); Kathryn A. Hanley, Las Cruces, NM (US); Ching-Juh Lai, Bethesda, MD (US)

(73) Assignee: The United States of America, as represented by the Secretary, Department of Health and Human Services, Washington, DC (US)

(21) Appl. No.: 13/896,384

(22) Filed: May 17, 2013

Related U.S. Patent Documents

Reissue of:
(64) Patent No.: 7,517,531
Issued: Apr. 14, 2009
Appl. No.: 10/970,640
Filed: Oct. 21, 2004

U.S. Applications:
(63) Continuation of application No. PCT/US03/13279, filed on Apr. 25, 2003.

(60) Provisional application No. 60/377,860, filed on May 3, 2002, provisional application No. 60/436,500, filed on Dec. 23, 2002.

(51) Int. Cl.
*C12N 7/00* (2006.01)
*A61K 39/12* (2006.01)
*A61K 39/00* (2006.01)

(52) U.S. Cl.
CPC ..... *C12N 7/00* (2013.01); *A61K 39/12* (2013.01); *A61K 2039/5254* (2013.01); *A61K 2039/5256* (2013.01); *A61K 2039/70* (2013.01); *C12N 2770/24134* (2013.01); *C12N 2770/24161* (2013.01)

(58) Field of Classification Search
CPC ..... C12N 2770/24134; C12N 2770/24161; C12N 7/00; C12N 2770/24122; C12N 2770/24162; C12N 7/045; A61K 2039/5254; A61K 2039/5256; A61K 39/12; C07K 14/005; C07K 14/1825
USPC ..... 424/202.1, 199.1, 205.1, 218.1; 435/235.1, 236, 320.1
See application file for complete search history.

(56) References Cited

U.S. PATENT DOCUMENTS

| | | | | |
|---|---|---|---|---|
| 7,226,602 | B2 * | 6/2007 | Whitehead et al. | 424/218.1 |
| 7,560,118 | B2 * | 7/2009 | Whitehead et al. | 424/218.1 |
| 8,039,003 | B2 * | 10/2011 | Whitehead et al. | 424/218.1 |
| 8,075,903 | B2 * | 12/2011 | Whitehead et al. | 424/202.1 |

FOREIGN PATENT DOCUMENTS

WO WO 02/095075 11/2002

OTHER PUBLICATIONS

Durbin et al (American Journal of Tropical Medicine and Hygeine 65:405-413, 2001.*
Lai et al (Clinical and Diagnostic Virology 10:173-179, 1998).*
Olsthoorn et al (RNA 7:1370-1377, 2001).*
Blaney et al (Journal of Virology 79:5516-5528, 2005, not prior art).*
Proutski et al (Virus Research 64:107-123, 1999).*
An, J. et al., 1999 "Develpment of a novel mouse model for dengue virus infection." *Virology* 263:70-77.
Barrett, A.D.T. 1997 "Yellow fever vaccines" *Biologicals* 25:17-25.
Blackwell, J.L. et al. 1997 "Translation elongation factor-1 alpha interacts with the 3' stem-loop region of West Nile virus genomic RNA" *J. Virol.* 71:6433-44.
Blaney, J.E. Jr. et al. 2001 "Chemical mutagenesis of dengue virus type 4 yield mutant viruses which are temperature sensitive in vero cells or human liver cells and attenuated in mice" *J. Virol.* 75:9731-40.
Blaney, J.E. Jr. et al. 2002 "Genetic basis of attenuation of dengue virus type 4 small plaque mutants with restricted replication in suckling mice and in SCID mice transplanted with human liver cells." *Virology* 300:125-139.
Blaney, J.E. Jr. et al. 2003 "Mutations which enhance the replication of dengue virus type 4 and antigenic chimeric dengue virus type 2/4 vaccine candidate in Vero cells" *Vaccine* 21:4317-27.
Blaney, J.E. Jr. et al. 2004 "Genetically modified, live attenuated dengue virus type 3 vaccine candidates." *Am. J. Trop. Med. Hyg.* 71:811-821.
Blaney, J.E. Jr. et al. 2004 "Vaccine candidates derived from a novel infectious cDNA clone of an American genotype dengue virus type 2." *BMC Infect. Dis.* 4:39 (10 pages).
Blok, J. et al. 1992 "Comparison of a dengue-2 virus and its candidate vaccine derivative: sequence relationships with the flaviviruses and other viruses" *Virology* 187:573-90.
Bray, M. et al. 1991 "Construction of intertypic chimeric dengue viruses by substitution of structural protein genes" *PNAS USA* 88:10342-6.
Bray, M. et al. 1996 "Monkeys immunized with intertypic chimeric dengue viruses are protected against wild-type virus challenge" *J. Virol.* 70:4162-6.

(Continued)

*Primary Examiner* — Shri Ponnaluri
(74) *Attorney, Agent, or Firm* — Klarquist Sparkman, LLP

(57) ABSTRACT

The invention relates to a dengue virus tetravalent vaccine containing a common 30 nucleotide deletion (Δ30) in the 3'-untranslated region of the genome of dengue virus serotypes 1, 2, 3, and 4, or antigenic chimeric dengue viruses of serotypes 1, 2, 3, and 4.

42 Claims, 15 Drawing Sheets

(56) References Cited

OTHER PUBLICATIONS

Bray, M. et al. 1998 "Genetic determinants responsible for acquisition of dengue type 2 virus mouse nuerovirulence" *J. Virol.* 72:1647-51.
Brinton, M.A. et al. 1986 "The 3'-nucleotides of flavivirus genomic RNA form a conserved secondary structure," *Virology* 153:113-121.
Burke, D.S. et al. 1998 "A prospective study of dengue infections in Bankok" *Am. J. Trop. Med. Hyg.* 38:172-80.
Butrapet, S. et al. 2000 "Attenuation markers of a candidate dengue type 2 vaccine virus, strain 16681 (PDK-53), are define by mutations in the 5' noncoding region and nonstructure proteins 1 and 3." *J. Virol.* 74:3011-3019.
Chambers, T.J. et al. 2003 "Yellow fever virus/dengue-2 virus and yellow fever virus/dengue-4 virus chimeras: biological characterication, immunogenicity, and protection against dengue encephalitis in the mouse model" *J. Virol.* 77:3655-68.
Chen, W. et al. 1995 "Construction of intertypic chimeric dengue viruses exhibition type 3 antigenicity and neurovirulence for mice" *J. Virol.* 69:5186-5190.
Durbin, A.P. et al. 2001 "Attenuation and immunogenicity in humans of a live dengue virus type-4 vaccine candidate with a 30 nucleotide deletion in its 3'-unsaturated region." *Am. J. Trop. Med. Hyg.* 65:405-413.
Gubler, D.J. et al. 1999 "Impact of dengue/dengue hemorrhagic fever on the developing world." *Adv. Virus Res.* 53:35-70.
Guillot, S. et al. 2000 "Natural genetic exchanges between vaccine and wild poliovirus strains in humans." *J. Virol.* 74:8434-8443.
Guirakhoo, F. et al. 2001 "Construction, safety, and immunogenicity in nonhuman primates of a chimeric yellow fever-dengue virus tetravalent vaccine." *J. Virol.* 74:7290-7304.
Guirakhoo, F. et al. 2002 "Viremia and immunogenicity in nonhuman primates of a tetravalent yellow fever-dengue chimeric vaccine: genetic reconstructions, dose adjustment, and antibody responses against wild-type dengue virus isolates" *Virology* 298:146-59.
Hahn, C.S. et al. 1987 "Conserved elements in the 3' untranslated region of flavivirus RNAs and potential cyclization sequences." *J. Mol. Biol.* 198:33-41.
Hanley, K.A. et al. 2004 "Introduction of mutations into the non-structural genes or 3' untranslated region of an attenuated dengue virus type 4 vaccine candidate further decreases replication in rheses monkeys while retaining protective immunity." *Vaccine* 22:3440-3448.
Huang, C.Y.-H. et al. 2000 "Chimeric dengue type 2 (vaccine strain PDK-53)/dengie type 1 virus as a potential candidate dengue type 1 virus vaccine." *J. Virol.* 74:3020-3028.
Kew, O. et al. 2002 "Outbreak of poliomyelitis in Hispaniola associated with circulating type 1 vaccine-derived poliovirus" *Science* 296-356-9.
Khromykh, A.A. et al. 1996 "RNA binding properties of core protein of the flavivirus Kunjin" *Arch. Virol.* 141:685-99.
Lai, C.J. et al. 1991 "Infectious RNA transcribed from stably cloned full-length cDNA of dengue type 4 virus" *PNAS USA* 88:5139-43.
Markoff, L. et al. 1997 "A conserved internal hydrophobic domain mediates the stable membrane integration of the dengue virus capsid protein" *Virology* 233:105-17.
Markoff, L. et al. 2002 "Derivation and characterizarion of a dengue type 1 host range-restricted mutant virus that is attenuated and highly immunogenic in monkeys." *J. Virol.* 76:3318-3328.
Mathew, A. et al. 1998 "Predominance of HLA-restricted cytotoxic T-lymphocyte responses to serotype-cross-reactive epitopes on nonstructural proteins following natural secondary dengue virus infection." *J. Virol.* 72:3999-4004.
Men, R. et al. 1996 "Dengue type 4 virus mutants containing deletions in the 3' noncoding region of the RNA genome: analysis of growth restriction in cell culture and altered viremia pattern and immunogenicity in rhesus monkeys." *J. Virol.* 70:3930-3937.
Pletnev, A.G. et al. 1992 "Construction and characterication of chimeric tick-borne encepalitis/dengue type 4 viruses" *PNAS USA* 89:10532-6.
Pletnev, A.G. et al. 1993 "Chimeric tick-borne encephalitis and dengue type 4 viruses: effects of mutations on neurovirulence in mice" *J. Virol.* 67:4956-63.
Pletnev, A.G. et al. 1998 "Attenuation of the Langat tick-borne flavivirus by chimerization with mosquito-borne flavivirus dengue type 4" *PNAS USA* 95:1746-51.
Pletnev, A.G. et al. 2002 "West Nile virus/dengue type 4 virus chimeras that are reduced in neurovirulence and peripheral virulence without loss of immunogenicity or protective efficacy" *PNAS USA* 99:3036-41.
Polo, S. et al. 1997 "Infectious RNA transcripts from full-length dengue virus type 2cDNA clones made in yeast." *J. Virol.* 71:5366-5374.
Proutski, V. et al. 1997 "Secondary srtucture of the 3' untranslated region of flaviviruses: similarities and differences." *Nucleic Acids Res.* 25:1194-1202.
Puri, B. et al. 1997 "Molecular analysis of dengue virus attenuation after serial passage in primary dog kidney cells." *J. Gen. Virol.* 78:2287-2291.
Puri, B. et al. 2000 "Construction of a full length infectious clone for dengue-1 virus Western Pacific, 74 strain." *Virus Genes* 20:57-63.
Rauscher, S. et al. 1997 "Secondary structure of the 3'-noncoding region of flavivirus genomes: comparative analysis of base pairing probabilities." *RNA* 3:779-791.
Rice, C.M. et al. 1985 "Nucleotide sequence of yellow fever virus: implications for flavivirus gene expression and evolution" *Science* 229:726-33.
Rosen, L. et al. 1985 "Comparative susceptibility of mosquito species and strains to oral and parental infection with dengue and Japanese encephalitis viruses." *Am. J. Trop. Med. Hyg.* 34:603-615.
Rosen, L. et al. 1985 "Comparative susceptibility of five species of *Toxrhynchites* mosquitoes to parential infection with dengue and other flaviviruses." *Am. J. Trop. Med. Hyg.* 34:805-809.
Ta, M. et al. 2000 "Mov34 protein from mouse brain interacts with the 3' noncoding region of Japanese encephalitis virus" *J. Virol.* 74:5108-15.
Thein, S. et al. 1997 "Risk factors in dengue shock syndrome" *Am. J. Trop. Med. Hyg.* 56:566-72.
Troyer, J.M. et al. 2001 "A live attenuated recombinant dengue-4 virus vaccine candidate with restricted capacity for dissemination in mosquitoes and lack of transmission from vaccines to mosquitoes." *Am. J. Trop. Med. Hyg.* 65:414-419.
Whitehead, S.S. et al. 2003 "A live, attenuated dengue virus type 1 vaccine candidate with a 30-nucleotide deletion in the 3' untranslated region is highly attenuated and immunogenic in monkeys" *J. Virol.* 77:1653-1657.
Whitehead, S.S. et al. 2003 "Substitution of the structural genes of dengue virus type 4 with those of type 2 results in chimeric vaccine candidates which are attenuated for mosquitoes, mice, and rhesus monkeys." *Vaccine* 21:4307-4316.
Worobey, M. et al. "Widespread intra-serotype recombinant in natural populations of dengue virus." *PNAS USA* 96:7352-7357.
Zeng, L. et al. 1998 "Identification of specific nucleotide sequence within the conserved 3'-SL in the dengue type 2 virus genome required for replication." *J. Virol.* 72:7510-7522.
Bhamarapravati, N. et al., 2000, "Live attenuated tetravalent dengue vaccine," Vaccine 18: 44-47.
Blaney, Jr. J.E. et al., 2006, "Development of a Live Attenuated Dengue Virus Vaccine Using Reverse Genetics," Viral Immunol. 19: 10-32.
Durbin, A.P. et al. 2003, "The Recombinant Live Attenuated Dengue 4 Candidate Vaccine rDEN4delta30 is Safe, Immunogenic, and Highly Infectious in Healthy Adults," Am. J. Trop. Med. Hyg. p. 361, Abstract 379.
Hanley, K.A. et al., 2002, "Paired Charge-to-Alanine Mutagenesis of Dengue Virus Type 4 NS5 Generated Mutants with Temperature-Sensitive, Host Range, and Mouse Attenuation Phenotypes," J. Virol. 76: 525-531.

(56) References Cited

OTHER PUBLICATIONS

Kanesa-Thasan, N. et al., 2001, "Safety and immunogenicity of attenuated dengue virus vaccines (Aventis Pastuer) in human volunteers," Vaccine 19: 3179-3188.

* cited by examiner 180 172 143 130

NS5 —//— GGCCCGAAGCCAGGAGGAAGCUGUACUCCUGGUGGAAGGACUAGAGGUUAG —//— 3'

Δ30
(172–143)

FIG. 2A

FIG. 2B

```
DEN1        GGGGCCC-AACACCAGGGGAAGCUGUACCCUGGUGGUAAGGACUAGA
DEN1Δ30     GGGGCCC-AA------------------------------GACUAGA
DEN2        GGGGCCC-AAGGUGAGAUGAAGCUGUAGUCUCACUGGAAGGACUAGA
DEN2Δ30     GGGGCCC-AA------------------------------GACUAGA
DEN3        GGGGCCCGAGCUCUGAGGGAAGCUGUACCUCCUUGCAAAGGACUAGA
DEN3Δ30     GGGGCCCAA-------------------------------GACUAGA
DEN4        GGGGCCCGAAGCCAGGAGGAAGCUGUACUCCUGGUGGAAGGACUAGA
DEN4Δ30     GGGGCCC-AA------------------------------GACUAGA

DEN1        GGGGCCC-AacaccagggGAAGCUGUAcccuggugguAAGGACUAGA
DEN2        GGGGCCC-AaggugagauGAAGCUGUAgucucacuggAAGGACUAGA
DEN3        GGGGCCCgAgcucugaggGAAGCUGUAccucccuugcaAAGGACUAGA
DEN4        GGGGCCCgAagccaggagGAAGCUGUAcuccuggugguAAGGACUAGA
```

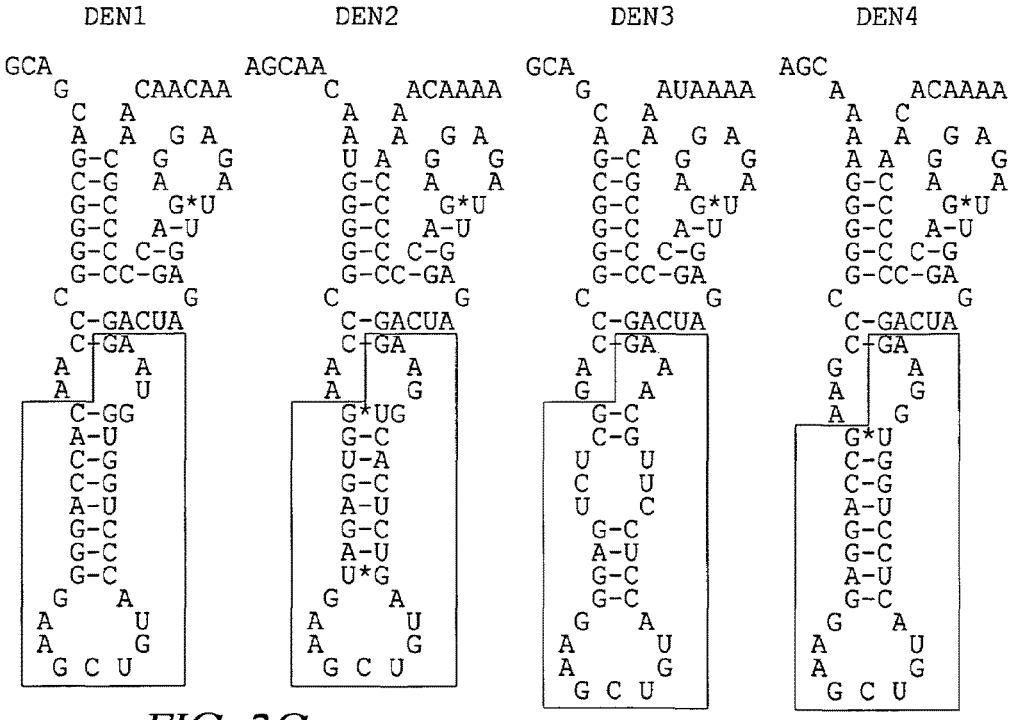

FIG. 2C

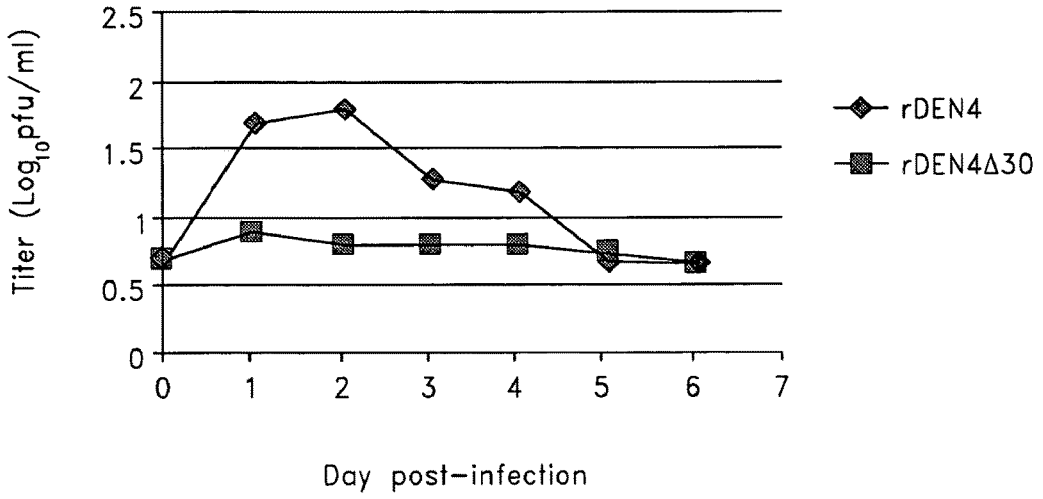
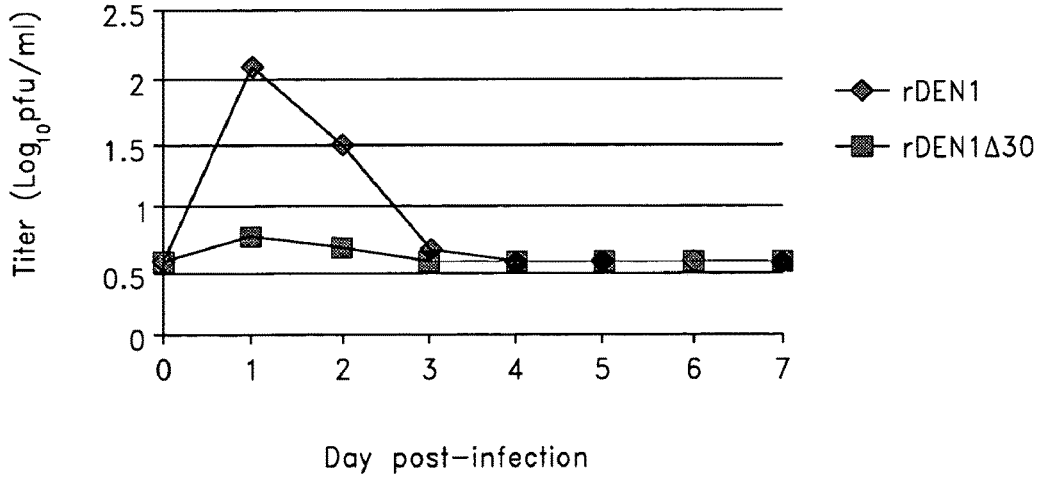
*FIG. 5*

FIG. 9B

```
                 DEN4                  BglII                DEN2
Junction 1:  -CAGTTTGTTTGAATAGAGAGCAGATCTCTGATGAATAACCAACGAAAAAAG-
                                                MetAsnAsnGlnArgLysLys

                 DEN2                  XhoI                 DEN4
Junction 2:  -ATTATCACATGGATAGGAATGAACTCGAGGAACACTTCAATGGCTATGACG-
              IleIleThrTrpIleGlyMetAsnSerArgAsnThrSerMetAlaMetThr

                 DEN4                  PstI                 DEN2
Junction 3:  -ATCTTGAACGGGAGAAAAAGGTCTGCAGGCATGATCATTATGCTGATTCCA-
              IleLeuAsnGlyArgLysArgSerAlaGlyMetIleIleMetLeuIlePro
```

FIG. 11B

Junction 1:

DEN4 | *BglII* | DEN3

-CAGTTTGTTTGAATAGAGAGCAGATCTCTGGAAAAATGAACAACCAACGG-

MetAsnAsnGlnArg

Junction 2:

DEN3 | *XhoI* | DEN4

-CTTTTAACCTGGATAGGGTTGAACTCGAGGAACACTTCAATGGCTATGACG-

LeuLeuThrTrpIleGlyLeuAsnSerArgAsnThrSerMetAlaMetThr

Junction 3:

DEN4 | *PstI* | DEN3

-ATCTTGAACGGGAGAAAAAGGTCTGCAGTCTGTCTCATGATGATGTTACCA-

IleLeuAsnGlyArgLysArgSerAlaValCysLeuMetMetMetLeuPro

FIG. 12B

Junction 1:

DEN4 — *BglII* — DEN1

-CAGTTTGTTTGAATAGAGAGCAGATCTCTGGAAAAATGAACAACCAACGG-

MetAsnAsnGlnArg

Junction 2:

DEN1 — *XhoI* — DEN4

-CTGCTGACATGGCTAGGATTAAACTCGAGGAACACTTCAATGGCTATGACG-

LeuLeuThrTrpLeuGlyLeuAsnSerArgAsnThrSerMetAlaMetThr

Junction 3:

DEN4 — *PstI* — DEN1

-ATCTTGAACGGGAGAAAAAGGTCTGCAGCCATGCTCCTCATGCTGCTGCCC-

IleLeuAsnGlyArgLysArgSerAlaAlaMetLeuLeuMetLeuLeuPro

DENGUE TETRAVALENT VACCINE CONTAINING A COMMON 30 NUCLEOTIDE DELETION IN THE 3'-UTR OF DENGUE TYPES 1,2,3, AND 4, OR ANTIGENIC CHIMERIC DENGUE VIRUSES 1,2,3, AND 4

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

RELATED APPLICATIONS

This application is a continuation and claims the benefit of priority of International Application No. PCT/US03/13279 filed Apr. 25, 2003, designating the United States of America and published in English on Nov. 13, 2003, as WO 03/092592, which claims the benefit of priority of U.S. Provisional Application No. 60/377,860 filed May 3, 2002 and U.S. Provisional Application No. 60/436,500 filed Dec. 23, 2002, all of which are hereby expressly incorporated by reference in their entireties.

FIELD OF THE INVENTION

The invention relates to a dengue virus tetravalent vaccine containing a common 30 nucleotide deletion (Δ30) in the 3'-untranslated region of the genome of dengue virus serotypes 1, 2, 3, and 4, or antigenic chimeric dengue viruses of serotypes 1, 2, 3, and 4.

BACKGROUND OF THE INVENTION

Dengue virus is a positive-sense RNA virus belonging to the Flavivirus genus of the family Flaviviridae. Dengue virus is widely distributed throughout the tropical and semi-tropical regions of the world and is transmitted to humans by mosquito vectors. Dengue virus is a leading cause of hospitalization and death in children in at least eight tropical Asian countries (WHO 1997 Dengue Haemorrhagic Fever: Diagnosis, Treatment, Prevention, and Control 2nd Edition, Geneva). There are four serotypes of dengue virus (DEN1, DEN2, DEN3, and DEN4) that annually cause an estimated 50-100 million cases of dengue fever and 500,000 cases of the more severe form of dengue virus infection known as dengue hemorrhagic fever/dengue shock syndrome (DHF/DSS) (Gubler, D. J. and Meltzer, M. 1999 Adv Virus Res 53:35-70). This latter disease is seen predominantly in children and adults experiencing a second dengue virus infection with a serotype different than that of their first dengue virus infection and in primary infection of infants who still have circulating dengue-specific maternal antibody (Burke, D. S. et al. 1988 Am J Trop Med Hyg 38:172-180; Halstead, S. B. et al. 1969 Am J Trop Med Hyg 18:997-1021; Thein, S. et al. 1997 Am J Trop Med Hyg 56:566-575). A dengue vaccine is needed to lessen disease burden caused by dengue virus, but none is licensed. Because of the association of more severe disease with secondary dengue virus infection, a successful vaccine must simultaneously induce immunity to all four serotypes. Immunity is primarily mediated by neutralizing antibody directed against the envelope (E) glycoprotein, a virion structural protein. Infection with one serotype induces long-lived homotypic immunity and a short-lived heterotypic immunity (Sabin, A. 1955 Am J Trop Med Hyg 4:198-207). Therefore, the goal of immunization is to induce a long-lived neutralizing antibody response against DEN1, DEN2, DEN3, and DEN4, which can best be achieved economically using live attenuated virus vaccines. This is a reasonable goal since a live attenuated vaccine has already been developed for the related yellow fever virus, another mosquito-borne flavivirus present in tropical and semitropical regions of the world (Monath, T. P. and Heinz, F. X. 1996 in: Fields Virology, Fields, D. M et al. eds. Philadelphia: Lippincott-Raven Publishers, pp. 961-1034).

Several live attenuated dengue vaccine candidates have been developed and evaluated in humans and non-human primates. The first live attenuated dengue vaccine candidates were host range mutants developed by serial passage of wild-type dengue viruses in the brains of mice and selection of mutants attenuated for humans (Kimura, R. and Hotta, S. 1944 Jpn J Bacteriol 1:96-99; Sabin, A. B. and Schlesinger, R. W. 1945 Science 101:640; Wisserman, C. L. et al. 1963 Am J Trop Med Hyg 12:620-623). Although these candidate vaccine viruses were immunogenic in humans, their poor growth in cell culture discouraged further development. Additional live attenuated DEN1, DEN2, DEN3, and DEN4 vaccine candidates have been developed by serial passage in non-human tissue culture (Angsubhakorn, S. et al. 1994 Southeast Asian J Trop Med Public Health 25:554-559; Bancroft, W. H. et al. 1981 Infect Immun 31:698-703; Bhamarapravati, N. et al. 1987 Bull World Health Organ 65:189-195; Eckels, K. H. et al. 1984 Am J Trop Med Hyg 33:684-698; Hoke, C. H. Jr. et al. 1990 Am J Trop Med Hyg 43:219-226; Kanesa-Thasan, N. et al. 2001 Vaccine 19:3179-3188) or by chemical mutagenesis (McKee, K. T. et al. 1987 Am J Trop Med Hyg 36:435-442). It has proven very difficult to achieve a satisfactory balance between attenuation and immunogenicity for each of the four serotypes of dengue virus using these approaches and to formulate a tetravalent vaccine that is safe and satisfactorily immunogenic against each of the four dengue viruses (Kanesa-Thasan, N. et al. 2001 Vaccine 19:3179-3188; Bhamarapravati, N. and Sutee, Y. 2000 Vaccine 18:44-47).

Two major advances using recombinant DNA technology have recently made it possible to develop additional promising live attenuated dengue virus vaccine candidates. First, methods have been developed to recover infectious dengue virus from cells transfected with RNA transcripts derived from a full-length cDNA clone of the dengue virus genome, thus making it possible to derive infectious viruses bearing attenuating mutations that have been introduced into the cDNA clone by site-directed mutagenesis (Lai, C. J. et al. 1991 PNAS USA 88:5139-5143). Second, it is possible to produce antigenic chimeric viruses in which the structural protein coding region of the full-length cDNA clone of dengue virus is replaced by that of a different dengue virus serotype or from a more divergent flavivirus (Bray, M. and Lai, C. J. 1991 PNAS USA 88:10342-10346; Chen, W. et al. 1995 J Virol 69:5186-5190; Huang, C. Y. et al. 2000 J Virol 74:3020-3028; Pletnev, A. G. and Men, R. 1998 PNAS USA 95:1746-1751). These techniques have been used to construct intertypic chimeric dengue viruses that have been shown to be effective in protecting monkeys against homologous dengue virus challenge (Bray, M. et al. 1996 J Virol 70:4162-4166). A similar strategy is also being used to develop attenuated antigenic chimeric dengue virus vaccines based on the attenuation of the yellow fever vaccine virus or the attenuation of the cell-culture passaged dengue viruses (Monath, T. P. et al. 1999 Vaccine 17:1869-1882; Huang, C. Y. et al. 2000 J Virol 74:3020-3028).

Another study examined the level of attenuation for humans of a DEN4 mutant bearing a 30-nucleotide deletion (Δ30) introduced into its 3'-untranslated region by site-directed mutagenesis and that was found previously to be attenuated for rhesus monkeys (Men, R. et al. 1996 J Virol 70:3930-3937). Additional studies were carried out to examine whether this Δ30 mutation present in the DEN4 vaccine candidate was the major determinant of its attenuation for monkeys. It was found that the Δ30 mutation was indeed the major determinant of attenuation for monkeys, and that it specified a satisfactory balance between attenuation and immunogenicity for humans (Durbin, A. P. et al. 2001 Am J Trop Med Hyg 65:405-13).

SUMMARY OF THE INVENTION

The previously identified Δ30 attenuating mutation, created in dengue virus type 4 (DEN4) by the removal of 30 nucleotides from the 3'-UTR, is also capable of attenuating a wild-type strain of dengue virus type 1 (DEN1). Removal of 30 nucleotides from the DEN1 3'-UTR in a highly conserved region homologous to the DEN4 region encompassing the Δ30 mutation yielded a recombinant virus attenuated in rhesus monkeys to a level similar to recombinant virus DEN4Δ30. This establishes the transportability of the Δ30 mutation and its attenuation phenotype to a dengue virus type other than DEN4. The effective transferability of the Δ30 mutation, described by this work, establishes the usefulness of the Δ30 mutation to attenuate and improve the safety of commercializable dengue virus vaccines of any serotype. We envision a tetravalent dengue virus vaccine containing dengue virus types 1, 2, 3, and 4 each attenuated by the Δ30 mutation. We also envision a tetravalent dengue virus vaccine containing recombinant antigenic chimeric viruses in which the structural genes of dengue virus types 1, 2, and 3 replace those of DEN4Δ30; 1, 2, and 4 replace those of DEN3Δ30; 1, 3, and 4 replace those of DEN2Δ30; and 2, 3, and 4 replace those of DEN1Δ30. In some instances, such chimeric dengue viruses are attenuated not only by the Δ30 mutation, but also by their chimeric nature. The presence of the Δ30 attenuating mutation in each virus component precludes the reversion to a wild-type virus by intertypic recombination. In addition, because of the inherent genetic stability of deletion mutations, the Δ30 mutation represents an excellent alternative for use as a common mutation shared among each component of a tetravalent vaccine.

BRIEF DESCRIPTION OF THE DRAWINGS

FIG. 2. A. The Δ30 mutation removes 30 contiguous nucleotides (shaded) from the 3' UTR of DEN4. Nucleotides are numbered from the 3' terminus. B. Nucleotide sequence alignment of the TL2 region of DEN1, DEN2, DEN3, and DEN4 and their Δ30 derivatives. Also shown is the corresponding region for each of the four DEN serotypes. Upper case letters indicate sequence homology among all 4 serotypes, underlining indicates nucleotide pairing to form the stem structure. C. Predicted secondary structure of the TL2 region of each DEN serotype. Nucleotides that are removed by the Δ30 mutation are boxed (DEN1—between nts 10562-10591, DEN2 Tonga/74—between nts 10541-10570, DEN3 Sleman/78—between nts 10535-10565, and DEN4—between nts 10478-10507).

FIG. 5. The Δ30 mutation attenuates both DEN1 and DEN4 for rhesus monkeys. Groups of 4 monkeys were immunized subcutaneously with 5.0 $\log_{10}$PFU of the indicated virus. Serum was collected each day following immunization and virus titers were determined and are shown as mean $\log_{10}$PFU/ml.

Brief Description of the Sequences

| Serotype | GenBank Accession No. or description |
|---|---|
| DEN1 | U88535 |
| DEN2 | Tonga/74 |
| DEN3 | Sleman/78 |
| DEN4 | AF326825 |

Brief Description of the SEQ ID NOs

Figure 6A:
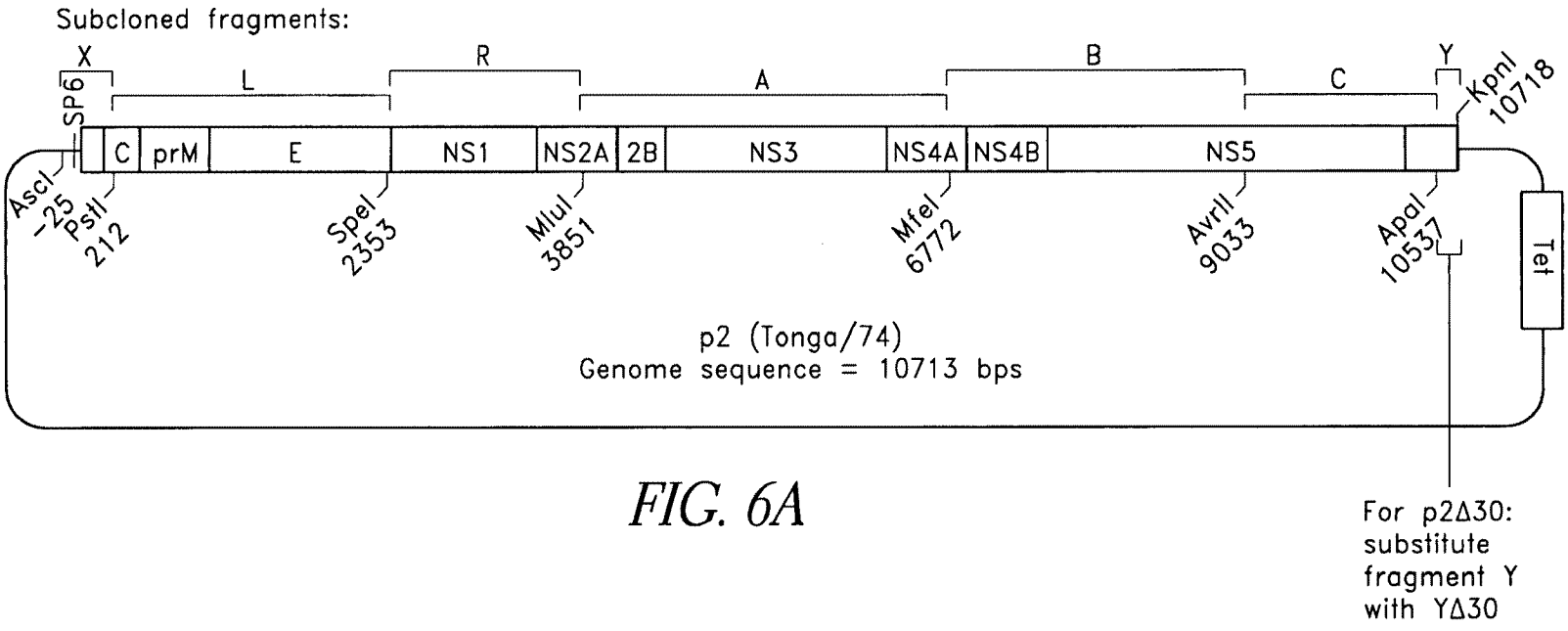
FIG. 6. A. Diagram of the p2 (Tonga/74) full-length cDNA plasmid. Regions subcloned are indicated above the plasmid. Numbering begins at the 5' end of the viral sequence. B. The Δ30 mutation removes the indicated 30 nucleotides from the 3' UTR sequence to create p2Δ30.
Figure 6B:
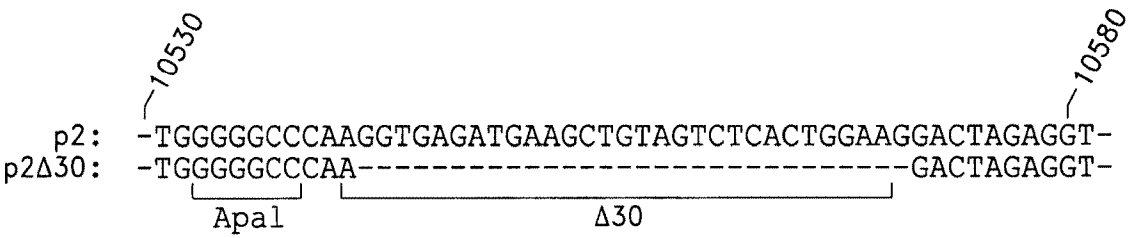
Figure 8A:
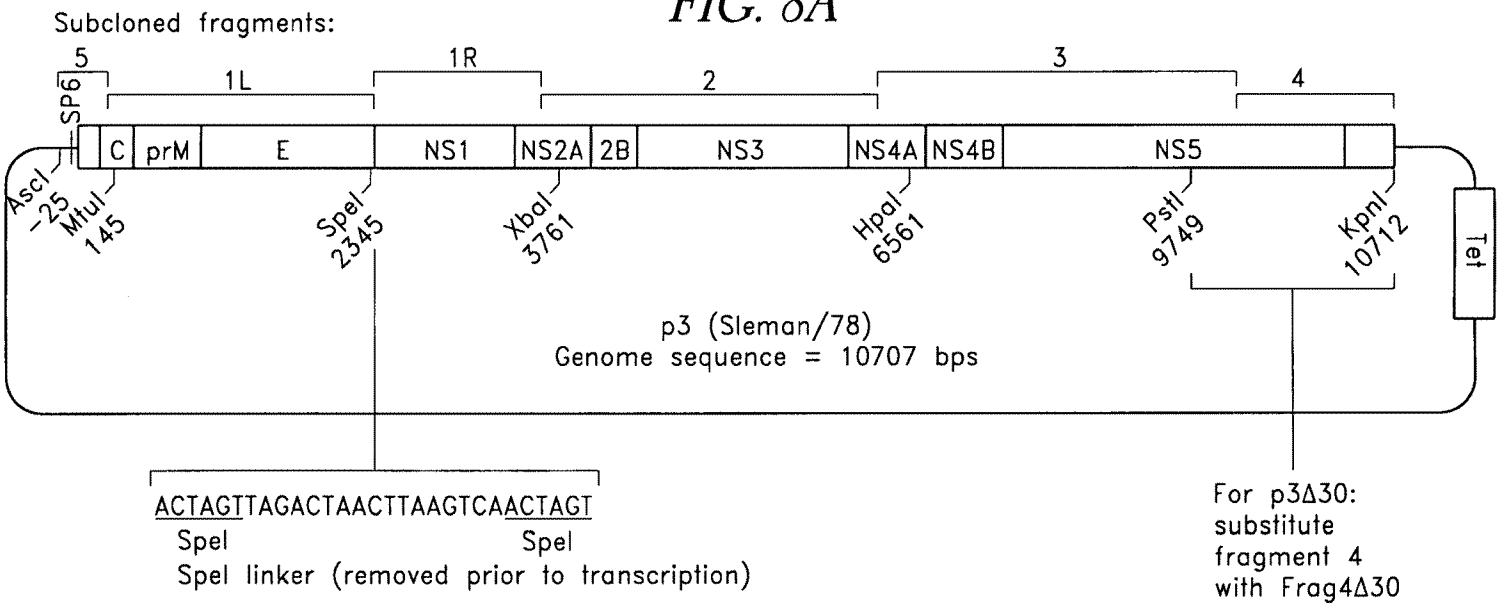
FIG. 8. A. Diagram of the p3 (Sleman/78) full-length cDNA plasmid. Regions subcloned are indicated above the plasmid. Numbering begins at the 5' end of the viral sequence. The sequence and insertion location of the SpeI linker is shown. B. The Δ30 mutation removes the indicated 31 nucleotides from the 3' UTR sequence to create p3Δ30.
Figure 8B:
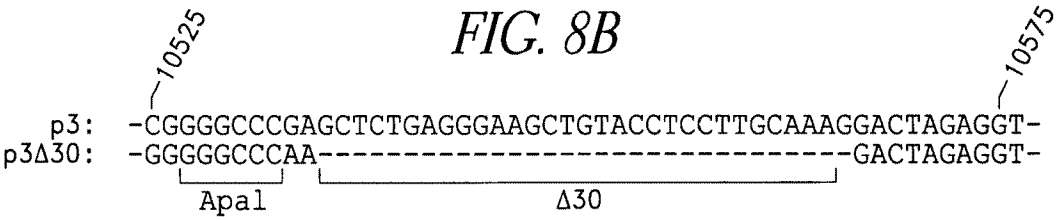

| Identification | Figure, Table, or Appendix | SEQ ID NO. |
|---|---|---|
| TL2 region of DEN1 | FIG. 2C | 1 |
| TL2 region of DEN2 | FIG. 2C | 2 |
| TL2 region of DEN3 | FIG. 2C | 3 |
| TL2 region of DEN4 | FIG. 2C | 4 |
| TL2 region of DEN1Δ30 | FIG. 2B | 5 |
| TL2 region of DEN2Δ30 | FIG. 2B | 6 |
| TL2 region of DEN3Δ30 | FIG. 2B | 7 |
| TL2 region of DEN4Δ30 | FIG. 2B | 8 |
| TL2 region of p2 | FIG. 6B | 9 |
| TL2 region of p2Δ30 | FIG. 6B | 10 |
| TL2 region of p3 | FIG. 8B | 11 |
| TL2 region of p3Δ30 | FIG. 8B | 12 |
| SpeI linker in p3 | FIG. 8A | 13 |
| rDEN2/4 junction 1 | FIG. 9B | 14-nt, 15-aa |
| rDEN2/4 junction 2 | FIG. 9B | 16-nt, 17-aa |
| rDEN2/4 junction 3 | FIG. 9B | 18-nt, 19-aa |
| rDEN3/4 junction 1 | FIG. 11B | 20-nt, 21-aa |
| rDEN3/4 junction 2 | FIG. 11B | 22-nt, 23-aa |
| rDEN3/4 junction 3 | FIG. 11B | 24-nt, 25-aa |
| rDEN1/4 junction 1 | FIG. 12B | 26-nt, 27-aa |
| rDEN1/4 junction 2 | FIG. 12B | 28-nt, 29-aa |
| rDEN1/4 junction 3 | FIG. 12B | 30-nt, 31-aa |
| D4 selected NS4B region | Table 15 | 32-nt, 33-aa |
| D1 selected NS4B region | Table 15 | 34-nt, 35-aa |
| D2 selected NS4B region | Table 15 | 36-nt, 37-aa |
| D3 selected NS4B region | Table 15 | 38-nt, 39-aa |
| CCACGGGCGCCGT | Table 26 | 40 |
| AAGGCCTGGA | Table 26 | 41 |
| TATCCCCGGGAC | Table 26 | 42 |
| AGAGCTCTCTC | Table 26 | 43 |
| GAATCTCCACCCGGA | Table 26 | 44 |

-continued

Brief Description of the SEQ ID NOs

| Identification | Figure, Table, or Appendix | SEQ ID NO. |
|---|---|---|
| CTGTCGAATC | Table 26 | 45 |
| DEN2 (Tonga/74) cDNA plasmid p2 | Appendix 1 | 46-nt, 47-aa |
| DEN3 (Sleman/78) cDNA plasmid p3 | Appendix 2 | 48-nt, 49-aa |
| DEN1 (Puerto Rico/94) CME chimeric region | Appendix 3 | 50-nt, 51-aa |
| DEN1 (Puerto Rico/94) ME chimeric region | Appendix 4 | 52-nt, 53-aa |

DETAILED DESCRIPTION OF THE PREFERRED EMBODIMENT

Introduction

A molecular approach is herewith used to develop a genetically stable live attenuated tetravalent dengue virus vaccine. Each component of the tetravalent vaccine, namely, DEN1, DEN2, DEN3, and DEN4, must be attenuated, genetically stable, and immunogenic. A tetravalent vaccine is needed to ensure simultaneous protection against each of the four dengue viruses, thereby precluding the possibility of developing the more serious illnesses dengue hemorrhagic fever/dengue shock syndrome (DHF/DSS), which occur in humans during secondary infection with a heterotypic wild-type dengue virus. Since dengue viruses can undergo genetic recombination in nature (Worobey, M. et al. 1999 PNAS USA 96:7352-7), the tetravalent vaccine should be genetically incapable of undergoing a recombination event between its four virus components that could lead to the generation of viruses lacking attenuating mutations. Previous approaches to develop a tetravalent dengue virus vaccine have been based on independently deriving each of the four virus components through separate mutagenic procedures, such as passage in tissue culture cells derived from a heterologous host. This strategy has yielded attenuated vaccine candidates (Bhamarapravati, N. and Sutee, Y. 2000 Vaccine 18:44-7). However, it is possible that gene exchanges among the four components of these independently derived tetravalent vaccines could occur in vaccinees, possibly creating a virulent recombinant virus. Virulent polioviruses derived from recombination have been generated in vaccinees following administration of a trivalent poliovirus vaccine (Guillot, S. et al. 2000 J Virol 74:8434-43).

The present invention describes: (1) improvements to the previously described rDEN4Δ30 vaccine candidate, 2) attenuated rDEN1Δ30, rDEN2Δ30, and rDEN3Δ30 recombinant viruses containing a 30 nucleotide deletion (Δ30) in a section of the 3' untranslated region (UTR) that is homologous to that in the rDEN4Δ30 recombinant virus, (3) a method to generate a tetravalent dengue virus vaccine composed of rDEN1Δ30, rDEN2Δ30, rDEN3Δ30, and rDEN4Δ30, 4) attenuated antigenic chimeric viruses, rDEN1/4Δ30, rDEN2/4Δ30, and rDEN3/4Δ30, for which the CME, ME, or E gene regions of rDEN4Δ30 have been replaced with those derived from DEN1, DEN2, or DEN3; alternatively rDEN1/3Δ30, rDEN2/3Δ30, and rDEN4/3Δ30 for which CME, ME, or E gene regions of rDEN3Δ30 have been replaced with those derived from DEN1, 2, or 4; alternatively rDEN1/2Δ30, rDEN3/2Δ30, and rDEN4/2Δ30 for which CME, ME, or E gene regions of rDEN2Δ30 have been replaced with those derived from DEN1, 3, or, 4; and alternatively rDEN2/1Δ30, rDEN3/1Δ30, and rDEN4/1Δ30 for which CME, ME, or E gene regions of rDEN1Δ30 have been replaced with those derived from DEN2, 3, or 4, and 5) a method to generate a tetravalent dengue virus vaccine composed of rDEN1/4Δ30, rDEN2/4Δ30, rDEN3/4Δ30, and rDEN4Δ30, alternatively rDEN1/3Δ30, rDEN2/3Δ30, rDEN4/3Δ30, and rDEN3Δ30, alternatively rDEN1/2Δ30, rDEN3/2Δ30, rDEN4/2Δ30, and rDEN2Δ30, and alternatively rDEN2/1Δ30, rDEN3/1Δ30, rDEN4/1Δ30, and rDEN1Δ30. These tetravalent vaccines are unique since they contain a common shared attenuating mutation which eliminates the possibility of generating a virulent wild-type virus in a vaccinee since each component of the vaccine possesses the same Δ30 attenuating deletion mutation. In addition, the rDEN1Δ30, rDEN2Δ30, rDEN3Δ30, rDEN4Δ30 tetravalent vaccine is the first to combine the stability of the Δ30 mutation with broad antigenicity. Since the Δ30 deletion mutation is in the 3' UTR of each virus, all of the proteins of the four component viruses are available to induce a protective immune response. Thus, the method provides a mechanism of attenuation that maintains each of the proteins of DEN1, DEN2, DEN3, and DEN4 viruses in a state that preserves the full capability of each of the proteins of the four viruses to induce humoral and cellular immune responses against all of the structural and non-structural proteins present in each dengue virus serotype.

Figure 1:
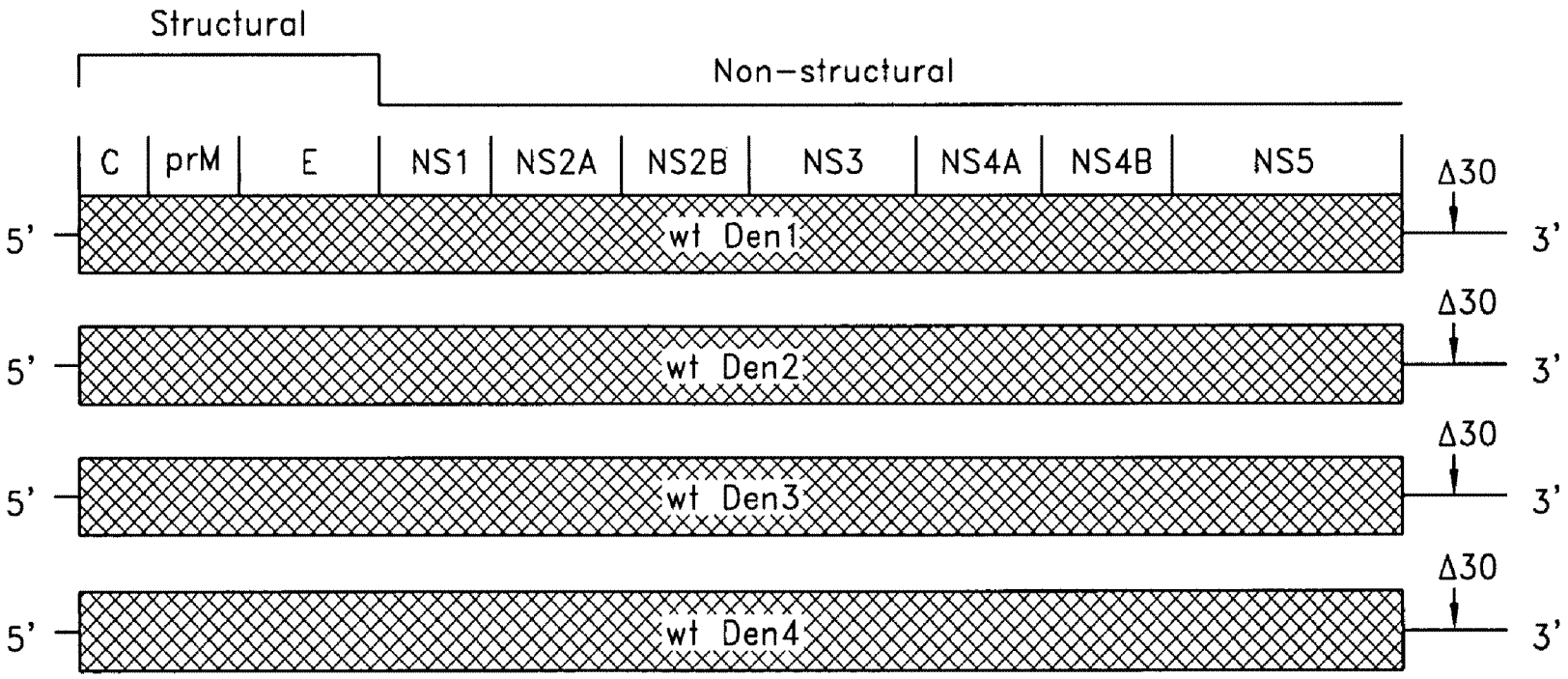
FIG. 1. The live attenuated tetravalent dengue virus vaccine contains dengue viruses representing each of the 4 serotypes, with each serotype containing its full set of unaltered wild-type structural and non-structural proteins and a shared Δ30 attenuating mutation. The relative location of the Δ30 mutation in the 3' untranslated region (UTR) of each component is indicated by an arrow.

As previously described, the DEN4 recombinant virus, rDEN4Δ30 (previously referred to as 2AΔ30), was engineered to contain a 30 nucleotide deletion in the 3'UTR of the viral genome (Durbin, A. P. et al. 2001 Am J Trop Med Hyg 65:405-13; Men, R. et al. 1996 J Virol 70:3930-7). Evaluation in rhesus monkeys showed the virus to be significantly attenuated relative to wild-type parental virus, yet highly immunogenic and completely protective. Also, a phase I clinical trial with adult human volunteers showed the rDEN4Δ30 recombinant virus to be safe and satisfactorily immunogenic (Durbin, A. P. et al. 2001 Am J Trop Med Hyg 65:405-13). To develop a tetravalent vaccine bearing a shared attenuating mutation in a untranslated region, we selected the Δ30 mutation to attenuate wild-type dengue viruses of serotypes 1, 2, and 3 since it attenuated wild-type DEN4 virus for rhesus monkeys and was safe in humans (FIG. 1).

The Δ30 mutation was first described and characterized in the DEN4 virus (Men, R. et al. 1996 J Virol 70:3930-7). In DEN4, the mutation consists of the removal of 30 contiguous nucleotides comprising nucleotides 10478-10507 of the 3' UTR (FIG. 2A) which form a putative stem-loop structure referred to as TL2 (Proutski, V. et al. 1997 Nucleic Acids Res 25:1194-202). Among the flaviviruses, large portions of the UTR form highly conserved secondary structures (Hahn, C. S. et al. 1987 J Mol Biol 198:33-41; Proutski, V. et al. 1997 Nucleic Acids Res 25:1194-202). Although the individual nucleotides are not necessarily conserved in these regions, appropriate base pairing preserves the stem-loop structure in each serotype, a fact that is not readily apparent when only considering the primary sequence (FIG. 2B, C).

Immunogenic Dengue Chimeras and Methods for their Preparation

Immunogenic dengue chimeras and methods for preparing the dengue chimeras are provided herein. The immunogenic dengue chimeras are useful, alone or in combination, in a pharmaceutically acceptable carrier as immunogenic compositions to minimize, inhibit, or immunize individuals and animals against infection by dengue virus.

Chimeras of the present invention comprise nucleotide sequences encoding the immunogenicity of a dengue virus of one serotype and further nucleotide sequences selected from the backbone of a dengue virus of a different serotype. These chimeras can be used to induce an immunogenic response against dengue virus.

In another embodiment, the preferred chimera is a nucleic acid chimera comprising a first nucleotide sequence encoding at least one structural protein from a dengue virus of a first serotype, and a second nucleotide sequence encoding non-structural proteins from a dengue virus of a second serotype different from the first. In another embodiment the dengue virus of the second serotype is DEN4. In another embodiment, the structural protein can be the C protein of a dengue virus of the first serotype, the prM protein of a dengue virus of the first serotype, the E protein of a dengue virus of the first serotype, or any combination thereof.

The term "residue" is used herein to refer to an amino acid (D or L) or an amino acid mimetic that is incorporated into a peptide by an amide bond. As such, the amino acid may be a naturally occurring amino acid or, unless otherwise limited, may encompass known analogs of natural amino acids that function in a manner similar to the naturally occurring amino acids (i.e., amino acid mimetics). Moreover, an amide bond mimetic includes peptide backbone modifications well known to those skilled in the art.

Furthermore, one of skill in the art will recognize that individual substitutions, deletions or additions in the amino acid sequence, or in the nucleotide sequence encoding for the amino acids, which alter, add or delete a single amino acid or a small percentage of amino acids (typically less than 5%, more typically less than 1%) in an encoded sequence are conservatively modified variations, wherein the alterations result in the substitution of an amino acid with a chemically similar amino acid. Conservative substitution tables providing functionally similar amino acids are well known in the art. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

As used herein, the terms "virus chimera," "chimeric virus," "dengue chimera" and "chimeric dengue virus" means an infectious construct of the invention comprising nucleotide sequences encoding the immunogenicity of a dengue virus of one serotype and further nucleotide sequences derived from the backbone of a dengue virus of a different serotype.

As used herein, "infectious construct" indicates a virus, a viral construct, a viral chimera, a nucleic acid derived from a virus or any portion thereof, which may be used to infect a cell.

As used herein, "nucleic acid chimera" means a construct of the invention comprising nucleic acid comprising nucleotide sequences encoding the immunogenicity of a dengue virus of one serotype and further nucleotide sequences derived from the backbone of a dengue virus of a different serotype. Correspondingly, any chimeric virus or virus chimera of the invention is to be recognized as an example of a nucleic acid chimera.

The structural and nonstructural proteins of the invention are to be understood to include any protein comprising or any gene encoding the sequence of the complete protein, an epitope of the protein, or any fragment comprising, for example, three or more amino acid residues thereof.

Dengue Chimeras

Dengue virus is a mosquito-borne flavivirus pathogen. The dengue virus genome contains a 5' untranslated region (5' UTR), followed by a capsid protein (C) encoding region, followed by a premembrane/membrane protein (prM) encoding region, followed by an envelope protein (E) encoding region, followed by the region encoding the non-structural proteins (NS1-NS2A-NS2B-NS3-NS4A-NS4B-NS5) and finally a 3' untranslated region (3' UTR). The viral structural proteins are C, prM and E, and the nonstructural proteins are NS1-NS5. The structural and nonstructural proteins are translated as a single polyprotein and processed by cellular and viral proteases.

The dengue chimeras of the invention are constructs formed by fusing structural protein genes from a dengue virus of one serotype, e.g. DEN1, DEN2, DEN3, or DEN4, with non-structural protein genes from a dengue virus of a different serotype, e.g., DEN1, DEN2, DEN3, or DEN4.

The attenuated, immunogenic dengue chimeras provided herein contain one or more of the structural protein genes, or antigenic portions thereof, of the dengue virus of one serotype against which immunogenicity is to be conferred, and the nonstructural protein genes of a dengue virus of a different serotype.

The chimera of the invention contains a dengue virus genome of one serotype as the backbone, in which the structural protein gene(s) encoding C, prM, or E protein(s) of the dengue genome, or combinations thereof, are replaced with the corresponding structural protein gene(s) from a dengue virus of a different serotype that is to be protected against. The resulting viral chimera has the properties, by virtue of being chimerized with a dengue virus of another serotype, of attenuation and is therefore reduced in virulence, but expresses antigenic epitopes of the structural gene products and is therefore immunogenic.

The genome of any dengue virus can be used as the backbone in the attenuated chimeras described herein. The backbone can contain mutations that contribute to the attenuation phenotype of the dengue virus or that facilitate replication in the cell substrate used for manufacture, e.g., Vero cells. The mutations can be in the nucleotide sequence encoding non-structural proteins, the 5' untranslated region or the 3' untranslated region. The backbone can also contain further mutations to maintain the stability of the attenuation phenotype and to reduce the possibility that the attenuated virus or chimera might revert back to the virulent wild-type virus. For example, a first mutation in the 3' untranslated region and a second mutation in the 5' untranslated region will provide additional attenuation phenotype stability, if desired. In particular, a mutation that is a deletion of 30 nts from the 3' untranslated region of the DEN4 genome between nts 10478-10507 results in attenuation of the DEN4 virus (Men et al. 1996 J. Virology 70:3930-3933; Durbin et al. 2001 Am J Trop Med 65:405-413, 2001). Therefore, the genome of any dengue type 4 virus containing such a mutation at this locus can be used as the backbone in the attenuated chimeras described herein. Furthermore, other dengue virus genomes containing an analogous deletion mutation in the 3' untranslated region of the genomes of other dengue virus serotypes may also be used as the backbone structure of this invention.

Such mutations may be achieved by site-directed mutagenesis using techniques known to those skilled in the art. It will be understood by those skilled in the art that the virulence screening assays, as described herein and as are well known in the art, can be used to distinguish between virulent and attenuated backbone structures.

Construction of Dengue Chimeras

The dengue virus chimeras described herein can be produced by substituting at least one of the structural protein genes of the dengue virus of one serotype against which immunity is desired into a dengue virus genome backbone of a different serotype, using recombinant engineering techniques well known to those skilled in the art, namely, removing a designated dengue virus gene of one serotype and replacing it with the desired corresponding gene of dengue virus of a different serotype. Alternatively, using the sequences provided in GenBank, the nucleic acid molecules encoding the dengue proteins may be synthesized using known nucleic acid synthesis techniques and inserted into an appropriate vector. Attenuated, immunogenic virus is therefore produced using recombinant engineering techniques known to those skilled in the art.

As mentioned above, the gene to be inserted into the backbone encodes a dengue structural protein of one serotype. Preferably the dengue gene of a different serotype to be inserted is a gene encoding a C protein, a prM protein and/or an E protein. The sequence inserted into the dengue virus backbone can encode both the prM and E structural proteins of the other serotype. The sequence inserted into the dengue virus backbone can encode the C, prM and E structural proteins of the other serotype. The dengue virus backbone is the DEN1, DEN2, DEN3, or DEN4 virus genome, or an attenuated dengue virus genome of any of these serotypes, and includes the substituted gene(s) that encode the C, prM and/or E structural protein(s) of a dengue virus of a different serotype, or the substituted gene(s) that encode the prM and/or E structural protein(s) of a dengue virus of a different serotype.

Suitable chimeric viruses or nucleic acid chimeras containing nucleotide sequences encoding structural proteins of dengue virus of any of the serotypes can be evaluated for usefulness as vaccines by screening them for phenotypic markers of attenuation that indicate reduction in virulence with retention of immunogenicity. Antigenicity and immunogenicity can be evaluated using in vitro or in vivo reactivity with dengue antibodies or immunoreactive serum using routine screening procedures known to those skilled in the art.

Dengue Vaccines

The preferred chimeric viruses and nucleic acid chimeras provide live, attenuated viruses useful as immunogens or vaccines. In a preferred embodiment, the chimeras exhibit high immunogenicity while at the same time not producing dangerous pathogenic or lethal effects.

The chimeric viruses or nucleic acid chimeras of this invention can comprise the structural genes of a dengue virus of one serotype in a wild-type or an attenuated dengue virus backbone of a different serotype. For example, the chimera may express the structural protein genes of a dengue virus of one serotype in either of a dengue virus or an attenuated dengue virus background of a different serotype.

The strategy described herein of using a genetic background that contains nonstructural regions of a dengue virus genome of one serotype, and, by chimerization, the properties of attenuation, to express the structural protein genes of a dengue virus of a different serotype has lead to the development of live, attenuated dengue vaccine candidates that express structural protein genes of desired immunogenicity. Thus, vaccine candidates for control of dengue pathogens can be designed.

Viruses used in the chimeras described herein are typically grown using techniques known in the art. Virus plaque or focus forming unit (FFU) titrations are then performed and plaques or FFU are counted in order to assess the viability, titer and phenotypic characteristics of the virus grown in cell culture. Wild type viruses are mutagenized to derive attenuated candidate starting materials.

Chimeric infectious clones are constructed from various dengue serotypes. The cloning of virus-specific cDNA fragments can also be accomplished, if desired. The cDNA fragments containing the structural protein or nonstructural protein genes are amplified by reverse transcriptase-polymerase chain reaction (RT-PCR) from dengue RNA with various primers. Amplified fragments are cloned into the cleavage sites of other intermediate clones. Intermediate, chimeric dengue clones are then sequenced to verify the sequence of the inserted dengue-specific cDNA.

Full genome-length chimeric plasmids constructed by inserting the structural or nonstructural protein gene region of dengue viruses into vectors are obtainable using recombinant techniques well known to those skilled in the art.

Methods of Administration

The viral chimeras described herein are individually or jointly combined with a pharmaceutically acceptable carrier or vehicle for administration as an immunogen or vaccine to humans or animals. The terms "pharmaceutically acceptable carrier" or "pharmaceutically acceptable vehicle" are used herein to mean any composition or compound including, but not limited to, water or saline, a gel, salve, solvent, diluent, fluid ointment base, liposome, micelle, giant micelle, and the like, which is suitable for use in contact with living animal or human tissue without causing adverse physiological responses, and which does not interact with the other components of the composition in a deleterious manner.

The immunogenic or vaccine formulations may be conveniently presented in viral plaque forming unit (PFU) unit or focus forming unit (FFU) dosage form and prepared by using conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers. Formulations suitable for parenteral administration include aqueous and non-aqueous sterile injection solutions which may contain anti-oxidants, buffers, bacteriostats and solutes which render the formulation isotonic with the blood of the intended recipient, and aqueous and non-aqueous sterile suspensions which may include suspending agents and thickening agents. The formulations may be presented in unit-dose or multi-dose containers, for example, sealed ampoules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets commonly used by one of ordinary skill in the art.

Preferred unit dosage formulations are those containing a dose or unit, or an appropriate fraction thereof, of the administered ingredient. It should be understood that in addition to the ingredients particularly mentioned above, the formulations of the present invention may include other agents commonly used by one of ordinary skill in the art.

The immunogenic or vaccine composition may be administered through different routes, such as oral or parenteral, including, but not limited to, buccal and sublingual, rectal, aerosol, nasal, intramuscular, subcutaneous, intradermal, and topical. The composition may be administered in different forms, including, but not limited to, solutions, emulsions and suspensions, microspheres, particles, microparticles, nano-particles and liposomes. It is expected that from about 1 to about 5 doses may be required per immunization schedule. Initial doses may range from about 100 to about 100,000 PFU or FFU, with a preferred dosage range of about 500 to about 20,000 PFU or FFU, a more preferred dosage range of from about 1000 to about 12,000 PFU or FFU and a most preferred dosage range of about 1000 to about 4000 PFU or FFU. Booster injections may range in dosage from about 100 to about 20,000 PFU or FFU, with a preferred dosage range of about 500 to about 15,000, a more preferred dosage range of about 500 to about 10,000 PFU or FFU, and a most preferred dosage range of about 1000 to about 5000 PFU or FFU. For example, the volume of administration will vary depending on the route of administration. Intramuscular injections may range in volume from about 0.1 ml to 1.0 ml.

The composition may be stored at temperatures of from about −100° C. to about 4° C. The composition may also be stored in a lyophilized state at different temperatures including room temperature. The composition may be sterilized through conventional means known to one of ordinary skill in the art. Such means include, but are not limited to, filtration. The composition may also be combined with bacteriostatic agents to inhibit bacterial growth.

Administration Schedule

The immunogenic or vaccine composition described herein may be administered to humans, especially individuals travelling to regions where dengue virus infection is present, and also to inhabitants of those regions. The optimal time for administration of the composition is about one to three months before the initial exposure to the dengue virus. However, the composition may also be administered after initial infection to ameliorate disease progression, or after initial infection to treat the disease.

Adjuvants

A variety of adjuvants known to one of ordinary skill in the art may be administered in conjunction with the chimeric virus in the immunogen or vaccine composition of this invention. Such adjuvants include, but are not limited to, the following: polymers, co-polymers such as polyoxyethylene-polyoxypropylene copolymers, including block co-polymers, polymer p 1005, Freund's complete adjuvant (for animals), Freund's incomplete adjuvant; sorbitan monooleate, squalene, CRL-8300 adjuvant, alum, QS 21, muramyl dipeptide, CpG oligonucleotide motifs and combinations of CpG oligonucleotide motifs, trehalose, bacterial extracts, including mycobacterial extracts, detoxified endotoxins, membrane lipids, or combinations thereof.

Nucleic Acid Sequences

Nucleic acid sequences of dengue virus of one serotype and dengue virus of a different serotype are useful for designing nucleic acid probes and primers for the detection of dengue virus chimeras in a sample or specimen with high sensitivity and specificity. Probes or primers corresponding to dengue virus can be used to detect the presence of a vaccine virus. The nucleic acid and corresponding amino acid sequences are useful as laboratory tools to study the organisms and diseases and to develop therapies and treatments for the diseases.

Nucleic acid probes and primers selectively hybridize with nucleic acid molecules encoding dengue virus or complementary sequences thereof. By "selective" or "selectively" is meant a sequence which does not hybridize with other nucleic acids to prevent adequate detection of the dengue virus sequence. Therefore, in the design of hybridizing nucleic acids, selectivity will depend upon the other components present in the sample. The hybridizing nucleic acid should have at least 70% complementarity with the segment of the nucleic acid to which it hybridizes. As used herein to describe nucleic acids, the term "selectively hybridizes" excludes the occasional randomly hybridizing nucleic acids, and thus has the same meaning as "specifically hybridizing." The selectively hybridizing nucleic acid probes and primers of this invention can have at least 70%, 80%, 85%, 90%, 95%, 97%, 98% and 99% complementarity with the segment of the sequence to which it hybridizes, preferably 85% or more.

The present invention also contemplates sequences, probes and primers that selectively hybridize to the encoding nucleic acid or the complementary, or opposite, strand of the nucleic acid. Specific hybridization with nucleic acid can occur with minor modifications or substitutions in the nucleic acid, so long as functional species-species hybridization capability is maintained. By "probe" or "primer" is meant nucleic acid sequences that can be used as probes or primers for selective hybridization with complementary nucleic acid sequences for their detection or amplification, which probes or primers can vary in length from about 5 to 100 nucleotides, or preferably from about 10 to 50 nucleotides, or most preferably about 18-24 nucleotides. Isolated nucleic acids are provided herein that selectively hybridize with the species-specific nucleic acids under stringent conditions and should have at least five nucleotides complementary to the sequence of interest as described in Molecular Cloning: A Laboratory Manual, 2nd ed., Sambrook, Fritsch and Maniatis, Cold Spring Harbor Laboratory, Cold Spring Harbor, N.Y., 1989.

If used as primers, the composition preferably includes at least two nucleic acid molecules which hybridize to different regions of the target molecule so as to amplify a desired region. Depending on the length of the probe or primer, the target region can range between 70% complementary bases and full complementarity and still hybridize under stringent conditions. For example, for the purpose of detecting the presence of dengue virus, the degree of complementarity between the hybridizing nucleic acid (probe or primer) and the sequence to which it hybridizes is at least enough to distinguish hybridization with a nucleic acid from other organisms.

The nucleic acid sequences encoding dengue virus can be inserted into a vector, such as a plasmid, and recombinantly expressed in a living organism to produce recombinant dengue virus peptide and/or polypeptides.

The nucleic acid sequences of the invention include a diagnostic probe that serves to report the detection of a cDNA amplicon amplified from the viral genomic RNA template by using a reverse-transcription/polymerase chain reaction (RT/PCR), as well as forward and reverse amplimers that are designed to amplify the cDNA amplicon. In certain instances, one of the amplimers is designed to contain a vaccine virus-specific mutation at the 3'-terminal end of the amplimer, which effectively makes the test even more specific for the vaccine strain because extension of the primer at the target site, and consequently amplification, will occur only if the viral RNA template contains that specific mutation.

Automated PCR-based nucleic acid sequence detection systems have been recently developed. TaqMan assay (Applied Biosystems) is widely used. A more recently developed strategy for diagnostic genetic testing makes use of molecular beacons (Tyagi and Kramer, 1996 Nature Biotechnology 14:303-308). Molecular beacon assays employ quencher and reporter dyes that differ from those used in the TaqMan assay. These and other detection systems may used by one skilled in is the art.

EXAMPLE 1

Improvement of Dengue Virus Vaccine Candidate rDEN4Δ30

The safety of recombinant live-attenuated dengue-4 vaccine candidate rDEN4Δ30 was evaluated in twenty human volunteers who received a dose of 5.0 $\log_{10}$plaque forming units (PFU) (Durbin A. P. et al. 2001 Am J Trop Med Hyg 65:405-413). The vaccine candidate was found to be safe, well-tolerated and immunogenic in all of the vaccinees. However, five of the vaccinees experienced a transient elevation in alanine aminotransferase levels, three experienced neutropenia and ten vaccinees developed an asymptomatic macular rash, suggesting that it may be necessary to further attenuate this vaccine candidate.

Currently, a randomized, double-blind, placebo-controlled, dose de-escalation study is being conducted to determine the human infectious dose 50 ($HID_{50}$) of rDEN4Δ30. Each dose cohort consists of approximately twenty vaccinees and four placebo recipients. To date, complete data for doses of 3.0 $\log_{10}$PFU and 2.0 $\log_{10}$PFU has been collected. rDEN4Δ30 infected 100% of vaccinees when 3.0 $\log_{10}$PFU was administered and 95% of vaccinees when 2.0 $\log_{10}$PFU was administered (Table 1). The vaccine candidate caused no symptomatic illness at either dose (Table 1). One vaccinee who received 3.0 $\log_{10}$PFU experienced a transient elevation in alanine aminotransferase levels and approximately one fourth of the vaccinees experienced neutropenia at both doses (Table 1). Neutropenia was transient and mild. More than half of the vaccinees developed a macular rash at both doses; the occurrence of rash was not correlated with vaccination dose or with viremia (Table 1 and Table 2). Neither peak titer nor onset of viremia differed between the 3.0 $\log_{10}$PFU and 2.0 $\log_{10}$PFU doses, though both measures of viremia were significantly lower for these doses than for a dose of 5.0 $\log_{10}$PFU (Table 3). The vaccine candidate was immunogenic in 95% of vaccinees at both doses and neutralizing antibody did not decline between days 28 and 42 post-vaccination (Table 4). Although the $HID_{50}$ has not been determined yet, it is clearly less than 2.0 $\log_{10}$PFU. Interestingly, decreases in the dose of vaccine have had no consistent effect on immunogenicity, viremia, benign neutropenia or the occurrence of rash. Thus will not necessarily be possible to further attenuate rDEN4Δ30 by decreasing the dose of virus administered, and other approaches must be developed.

TABLE 1 rDEN4Δ30 clinical summary

| No. of subjects | Dose[a] | No. infected | No. with viremia | Mean peak titer[b] | No. volunteers with: Fever | Rash | Neutropenia[c] | ↑ALT |
|---|---|---|---|---|---|---|---|---|
| 20 | 5.0 | 20 | 14 | 1.2 (0.2) | 1[d] | 10 | 3 | 5 |
| 20 | 3.0 | 20 | 7 | 0.4 (0.0) | 0 | 11 | 5 | 1[e] |
| 20 | 2.0 | 19 | 11 | 0.6 (0.1) | 1[d] | 16 | 4 | 0 |
| 8 | 0 | 0 | 0 | 0 | 0 | 0 | 0 | 0 |

[a]$Log_{10}$ pfu
[b]$Log_{10}$ pfu/mL
[c]Neutropenia defined as ANC < 1500/dl
[d]T Max in volunteer = 100.4° F.
[e]ALT day 0 = 78, ALT max = 91 (day 14)

TABLE 2

Pattern of rash in vaccinees

| Dose[a] | No. with viremia | No. with rash | Viremia & rash | Viremia no rash | Mean day of onset ± SD | Mean duration (days ± SD) |
|---|---|---|---|---|---|---|
| 5 | 14/20 | 10/20 | 9/20 | 5/20 | 8.1 ± 1.3 [A][a] | 3.6 ± 2.0 [A] |
| 3 | 7/20 | 11/20 | 6/20 | 1/20 | 12.2 ± 1.4 [B] | 5.0 ± 2.1 [A] |
| 2 | 11/20 | 16/20 | 9/20 | 2/20 | 11.2 ± 1.4 [B] | 6.9 ± 1.7 [B] |

[a]$log_{10}$ pfu
[b]Means in each column with different letters are significantly different (α = 0.05)

TABLE 3 rDEN4Δ30 viremia summary

| Dose[a] | # with viremia | Mean peak titer ($log_{10}$ pfu/mL) | Mean onset of viremia (day ± SD) | Mean duration of viremia (day ± SD) |
|---|---|---|---|---|
| 5 | 14 | 1.2 ± 0.2 [A] | 5.8 ± 2.4 [A][b] | 4.4 ± 2.4 [A] |
| 3 | 7 | 0.4 ± 0.0 [B] | 9.1 ± 2.5 [B] | 1.6 ± 1.0 [B] |
| 2 | 11 | 0.6 ± 0.1 [B] | 8.7 ± 2.4 [B] | 2.6 ± 2.0 [A] |

[a]$log_{10}$ pfu
[b]Means in each column with different letters are significantly different (α = 0.05)

TABLE 4

Immunogenicity of rDEN4Δ30

| No. of subjects | Dose ($log_{10}$) | No. infected | Geometric mean serum neutralizing antibody titer (range) Day 28 | Day 42 | % seroconversion |
|---|---|---|---|---|---|
| 20 | 5.0 | 20 | 567 (72-2455) | 399 (45-1230) | 100 |
| 20 | 3.0 | 20 | 156 (5-2365) | 158 (25-1222) | 95 |
| 20 | 2.0 | 19 | 163 (5-943) | 165 (5-764) | 95 |
| 8 | 0 | 0 | 0 | 0 | 0 |

Two approaches have been taken to further attenuate rDEN4Δ30. This first is the generation and characterization of attenuating point mutations in rDEN4 using 5' fluorouracil mutagenesis (Blaney, J. E. Jr. et al. 2002 Virology 300: 125-139; Blaney, J. E. Jr. et al. 2001 J. Virol. 75: 9731-9740). This approach has identified a panel of point mutations that confer a range of temperature sensitivity (ts) and small plaque (sp) phenotypes in Vero and HuH-7 cells and attenuation (att) phenotypes in suckling mouse brain and SCID mice engrafted with HuH-7 cells (SCID-HuH-7 mice). In this example, a subset of these mutations has been introduced to rDEN4Δ30 and the phenotypes of the resulting viruses evaluated.

A second approach was to create a series of paired charge-to-alanine mutations in contiguous pairs of charged amino acid residues in the rDEN4 NS5 gene. As demonstrated previously, mutation of 32 individual contiguous pairs of charged amino acid residues in rDEN4 NS5 conferred a range of ts phenotypes in Vero and HuH-7 cells and a range of att phenotypes in suckling mouse brain (Hanley, K. H. et al. 2002 J. Virol. 76 525-531). As demonstrated below, these mutations also confer an att phenotype in SCID-HuH-7 mice. These mutations have been introduced, either as single pairs or sets of two pairs, into rDEN4Δ30 to determine whether they are compatible with the Δ30 mutation and whether they enhance the att phenotypes of rDEN4Δ30.

A panel of rDEN4 viruses bearing individual point mutations have been characterized which possess temperature sensitive and/or small plaque phenotypes in tissue culture and varying levels of attenuated replication in suckling mouse brain when compared to wild type rDEN4 virus (Blaney, J. E. et al. 2002 Virology 300:125-139; Blaney, J. E. et al. 2001 J Virol. 75:9731-9740). Three mutations have been selected to combine with the Δ30 deletion mutation to evaluate their ability to further restrict replication of rDEN4Δ30 in rhesus monkeys. First, the missense mutation in NS3 at nucleotide 4995 (Ser>Pro) which confers temperature sensitivity in Vero and HuH-7 cells and restricted replication in suckling mouse brain was previously combined with the Δ30 mutation (Blaney, J. E. et al. 2001 J Virol. 75:9731-9740). The resulting virus, rDEN4Δ30-4995, was found to be more restricted (1,000-fold) in mouse brain replication than rDEN4Δ30 virus (<5-fold) when compared to wild type rDEN4 virus. Second, a missense mutation at nucleotide 8092 (Glu>Gly) which also confers temperature sensitivity in Vero and HuH-7 cells and 10,000-fold restricted replication in suckling mouse brain was combined with the Δ30 mutation here. Third, a substitution in the 3' UTR at nucleotide 10634 which confers temperature sensitivity in Vero and HuH-7 cells, small plaque size in HuH-7 cells, and approximately 1,000-fold restricted replication in suckling mouse brain and SCID mice transplanted with HuH-7 cells was combined with the Δ30 mutation here (Blaney, J. E. et al. 2002 Virology 300:125-139).

For the present investigation, subcloned fragments of p4 (Durbin, A. P. et al. 2001 Am J Trop Med Hyg 65:405-13) containing the above mutations were introduced into the p4Δ30 cDNA clone. For transcription and recovery of virus, cDNA was linearized with Acc65I (isoschizomer of KpnI which cleaves leaving only a single 3' nucleotide) and used as template for transcription by SP6 RNA polymerase as previously described (Blaney, J. E. et al. 2002 Virology 300:125-139). C6/36 mosquito cells were transfected using liposome-mediated transfection and cell culture supernatants were harvested between days five and seven. Recovered virus was terminally diluted twice in Vero cells and passaged two (rDEN4Δ30-4995) or three (rDEN4Δ30-8092 and rDEN4Δ30-10634) times in Vero cells.

The complete genomic sequences of rDEN4Δ30-4995, rDEN4Δ30-8092, and rDEN4Δ30-10634 viruses were determined as previously described (Durbin et al. 2001 Am. J. Trop. Med. Hyg. 65:405-413). As expected, each rDEN4Δ30 virus derivative contained the Δ30 mutation. Unexpectedly, in rDEN4Δ30-4995 virus, the nucleotide changes in the codon containing nucleotide 4995, resulted in a Ser>Leu amino acid change rather than a Ser>Pro change since the p4Δ30-4995 cDNA was designed to introduce the Ser>Pro change (Table 5). The p4Δ30-4995 cDNA clone was indeed found to encode a Ser>Pro change at nucleotide 4995, so it is unclear how the virus population acquired the Ser>Leu mutation. Nevertheless, this virus was evaluated to assess the phenotype specified by this missense mutation. rDEN4Δ30-4995 virus was also found to contain an incidental mutation at nucleotides 4725-6 which resulted in a single amino acid change (Ser>Asp). The rDEN4Δ30-8092 and rDEN4Δ30-10634 viruses contained the appropriate nucleotide substitutions as well as additional incidental mutations in E, NS4B and NS4B, respectively (Table 5).

TABLE 5

Missense and UTR mutations present in rDEN4Δ30 virus derivatives bearing introduced point mutations.

| Virus | Gene | Nucleotide position | Nucleotide substitution | Amino acid position[a] | Amino acid change |
|---|---|---|---|---|---|
| rDEN4Δ30-4995 | NS3 | 4725 | U > G | 1542 | Ser > Asp |
| | NS3 | 4726 | C > A | 1542 | Ser > Asp |
| | NS3 | 4995[b] | U > C | 1632 | Ser > Leu |
| rDEN4Δ30-8092 | E | 1612 | A > C | 504 | Asp > Ala |
| | NS4B | 7131 | A > G | 2344 | Thr > Ala |
| | NS5 | 8092[b] | A > G | 2664 | Glu > Gly |
| rDEN4Δ30-10634 | NS4B | 6969 | A > U | 2290 | Met > Leu |
| | NS4B | 7182 | G > C | 2361 | Gly > Arg |
| | 3' UTR | 10634[b] | U > C | none | none |

[a]Amino acid position in DEN4 polyprotein beginning with the methionine residue of the C protein (nucleotides 102-104) as position 1.
[b]Mutation restricts replication in mouse models of DEN4 infection which were introduced by Kunkel mutagenesis.

Replication of the three modified rDEN4Δ30 viruses were compared to rDEN4Δ30 and wild type rDEN4 virus in the suckling mouse brain model and SCID mice transplanted with HuH-7 cells (SCID-HuH-7 mice). Experiments were conducted as previously described (Blaney, J. E. et al. 2002 Virology 300:125-139; Blaney, J. E. et al. 2001 J Virol. 75:9731-9740). Briefly, for infection of suckling mouse brain, groups of six seven-day-old mice were inoculated intracerebrally with 4.0 $\log_{10}$PFU of virus and the brain of each mouse was removed five days later. Clarified supernatants of 10% brain suspensions were then frozen at −70° C., and the virus titer was determined by plaque assay in Vero cells. For analysis of DEN4 virus replication in SCID-HuH-7 mice, four to six week-old SCID mice were injected intraperitoneally with $10^7$ HuH-7 cells. Five to six weeks after transplantation, mice were infected by direct inoculation into the tumor with 4.0 $\log_{10}$PFU of virus, and serum for virus titration was obtained by tail-nicking on day 7. The virus titer was determined by plaque assay in Vero cells.

Wild type rDEN4 virus replicated to 6.0 $\log_{10}$PFU/g in suckling mouse brain, and rDEN4Δ30 was restricted in replication by 0.7 $\log_{10}$PFU/g, which is similar to previous observations (Table 6) (Blaney, J. E. et al. 2001 J Virol. 75:9731-9740). rDEN4Δ30-4995, rDEN4Δ30-8092, and rDEN4Δ30-10634 viruses were found to have restricted replication in suckling mouse brain when compared to rDEN4 virus of 3.3, 2.8, and 2.4 $\log_{10}$PFU/g, respectively. These results indicate that the additional attenuating mutations serve to further restrict replication of the rDEN4Δ30 virus in mouse brain ranging from 50-fold (rDEN4Δ30-10634) to 400-fold (rDEN4Δ30-4995). In SCID-HuH-7 mice, virus titer of rDEN4Δ30 virus was 0.4 $\log_{10}$PFU/ml lower than rDEN4 virus, which is also similar to previous studies (Blaney, J. E. et al. 2002 Virology 300:125-139). Each modified rDEN4Δ30 virus was found to be further restricted in replication in SCID-HuH-7 mice (Table 6). rDEN4Δ30-4995, rDEN4Δ30-8092, and rDEN4Δ30-10634 viruses had restricted replication in SCID-HuH-7 mice when compared to rDEN4 virus of 2.9, 1.1, and 2.3 $\log_{10}$PFU/g below the level of wild type rDEN4 virus, respectively. Two important observations were made: (1) The 4995, 8092 and 10634 mutations were compatible for viability with the Δ30 mutation, and (2) These three modified rDEN4Δ30 viruses had between a 10 and 1,000-fold reduction in replication in comparison to rDEN4 wild-type virus, which allows viruses with a wide range of attenuation in this model to be further evaluated in monkeys or humans.

TABLE 6

Addition of point mutations in NS3, NS5, or the 3' UTR to rDEN4Δ30 virus further attenuates the virus for suckling mouse brain and SCID-HuH-7 mice.

| | Replication in suckling mouse brain[a] | | | Replication in SCID-HuH-7 mice[c] | | |
|---|---|---|---|---|---|---|
| Virus | No. of mice | Virus titer ± SE $\log_{10}$ PFU/g brain | Mean $\log_{10}$-unit reduction from wt[b] | No. of mice | Virus titer ± SE $\log_{10}$ PFU/ml serum | Mean $\log_{10}$-unit reduction from wt[b] |
| rDEN4 | 12 | 6.0 ± 0.1 | — | 13 | 6.4 ± 0.2 | — |
| rDEN4Δ30 | 12 | 5.3 ± 0.1 | 0.7 | 20 | 6.0 ± 0.2 | 0.4 |
| rDEN4Δ30-4995 | 6 | 2.7 ± 0.4 | 3.3 | 5 | 3.5 ± 0.3 | 2.9 |
| rDEN4Δ30-8092 | 6 | 3.2 ± 0.2 | 2.8 | 7 | 5.0 ± 0.4 | 1.1 |
| rDEN4Δ30-10634 | 12 | 3.6 ± 0.1 | 2.4 | 5 | 4.4 ± 0.3 | 2.3 |

[a]Groups of 6 suckling mice were inoculated i.c. with $10^4$ PFU of virus. Brains were removed 5 days later, homogenized, and titered in Vero cells.
[b]Comparison of mean virus titers of mice inoculated with mutant virus and concurrent rDEN4 wt control.
[c]Groups of HuH-7-SCID mice were inoculated directly into the tumor with $10^4$ PFU virus. Serum was collected on day 6 and 7 and titered in Vero cells.

Based on the findings in the two mouse models of DEN4 virus infection, each of the rDEN4Δ30-4995, rDEN4Δ30-8092, and rDEN4Δ30-10634 viruses was evaluated in the rhesus macaque model of DEN4 infection which has been previously described (Durbin et al. 2001 Am. J. Trop. Med. Hyg. 65:405-413). Briefly, groups of four (rDEN4Δ30-4995, rDEN4Δ30-8092, and rDEN4Δ30-10634) or two (rDEN4, rDEN4Δ30, mock) monkeys were inoculated with 5.0 $\log_{10}$PFU virus subcutaneously. Monkeys were observed daily and serum was collected on days 0 to 6, 8, 10, and 12, and virus titers were determined by plaque assay in Vero cells for measurement of viremia. On day 28, serum was drawn and the level of neutralizing antibodies was tested by plaque reduction assay in Vero cells as previously described (Durbin et al. 2001 Am. J. Trop. Med. Hyg. 65:405-413).

Figure 3:
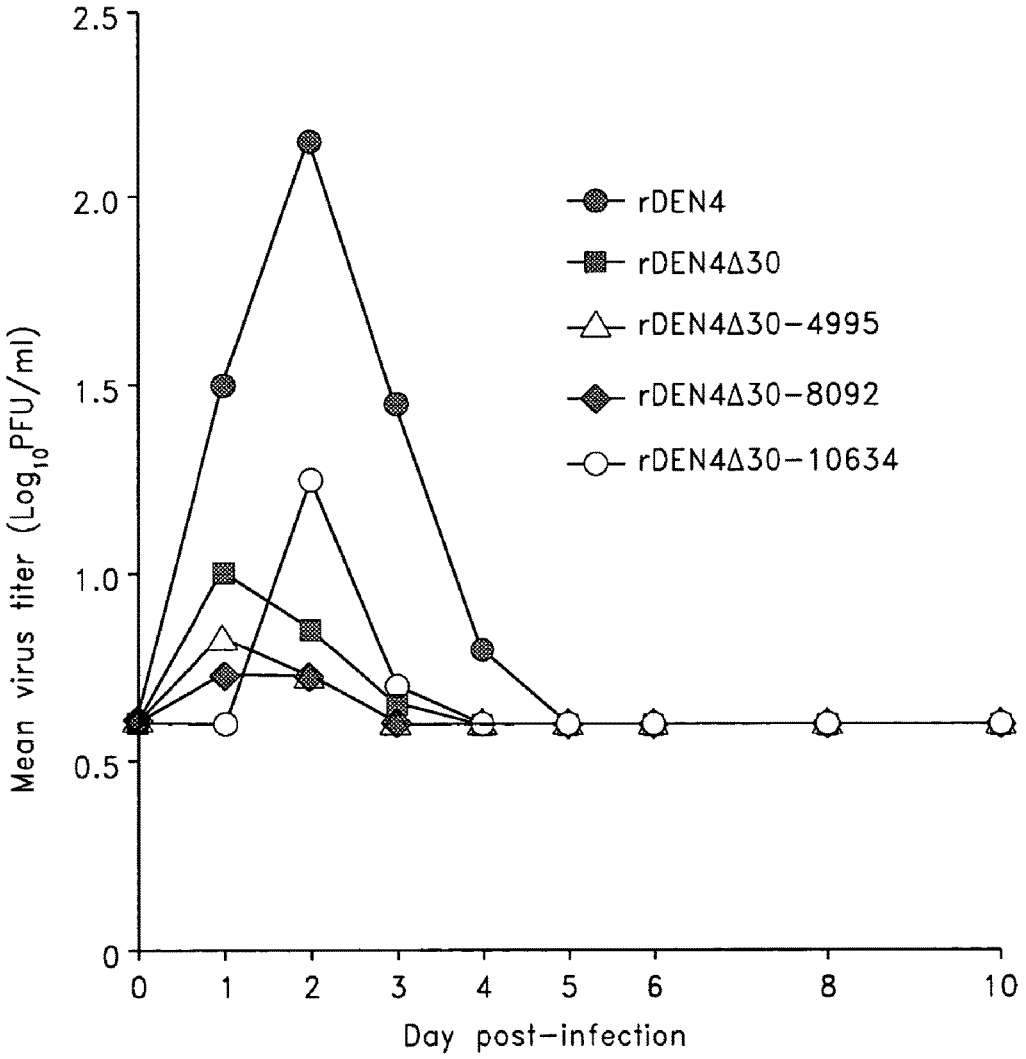
FIG. 3. Viremia levels in rhesus monkeys inoculated with rDEN4 vaccine candidates bearing 5-FU derived mutations. Groups of four or two (rDEN4 and rDEN4Δ30) monkeys were inoculated with 5.0 $\log_{10}$PFU virus subcutaneously. Serum was collected daily and virus titers were determined by plaque assay in Vero cells. The limit of virus detection was 0.7 $\log_{10}$PFU/ml. Mean virus titers are indicated for each group.

Viremia was detected beginning on day 1 post-infection and ended by day 4 in all monkeys (Table 7, FIG. 3). Viremia was present in each monkey infected with rDEN4, rDEN4Δ30, or rDEN4Δ30-10634 virus, but only 2 out of 4 monkeys infected with rDEN4Δ30-4995 or rDEN4Δ30-8092 virus had detectable viremia. As expected, infection with rDEN4 virus resulted in the highest mean number of viremic days per monkey (3.0 days) as well as mean peak virus titer (2.2 $\log_{10}$PFU/ml). Monkeys infected with rDEN4Δ30 virus had both a lower mean number of viremic days per monkey (2.0 days) and mean peak virus titer (1.1 $\log_{10}$PFU/ml) compared to rDEN4 virus. Groups of monkeys infected with each of the modified rDEN4Δ30 viruses had a further restricted mean number of viremic days with those inoculated with rDEN4Δ30-8092 virus having the lowest value, 0.5 days, a 4-fold reduction compared to rDEN4Δ30 virus. The mean peak virus titer of monkeys infected with rDEN4Δ30-4995 (0.9 $\log_{10}$PFU/ml) or rDEN4Δ30-8092 (0.7 $\log_{10}$PFU/ml) was also lower than those infected with rDEN4Δ30 virus. However, the mean peak virus titer of monkeys infected with rDEN4Δ30-10634 (1.3 $\log_{10}$PFU/ml) was slightly higher than those infected with rDEN4Δ30 particularly on day 2 (FIG. 3).

TABLE 7

Addition of point mutations to rDEN4Δ30 further attenuates the virus for rhesus monkeys.

| Virus[a] | No. of monkeys | No. of monkeys with viremia | Mean no. of viremic days per monkey[b] | Mean peak virus titer ($\log_{10}$ PFU/ml ± SE) | Geometric mean serum neutralizing antibody titer (reciprocal dilution) Day 0 | Day 28 |
|---|---|---|---|---|---|---|
| mock | 2 | 0 | 0 | <0.7 | <10 | <10 |
| rDEN4 | 2 | 2 | 3.0 | 2.2 ± 0.6 | <10 | 398 |
| rDEN4Δ30 | 2 | 2 | 2.0 | 1.1 ± 0.4 | <10 | 181 |
| rDEN4Δ30-4995 | 4 | 2 | 0.8 | 0.9 ± 0.2 | <10 | 78 |
| rDEN4Δ30-8092 | 4 | 2 | 0.5 | 0.7 ± 0.1 | <10 | 61 |
| rDEN4Δ30-10634 | 4 | 4 | 1.3 | 1.3 ± 0.2 | <10 | 107 |

[a]Groups of rhesus monkeys were inoculated subcutaneously with $10^5$ PFU of the indicated virus in a 1 ml dose. Serum was collected on days 0 to 6, 8, 10, 12, and 28. Virus titer was determined by plaque assay in Vero cells.
[b]Viremia was not detected in any monkey after day 4.

Serum collected on day 0 and 28 was tested for the level of neutralizing antibodies against rDEN4. No detectable neutralizing antibodies were found against DEN4 on day 0, as expected, since the monkeys were pre-screened to be negative for neutralizing antibodies against flaviviruses (Table 7). On day 28, monkeys infected with rDEN4 had a mean serum neutralizing antibody titer (reciprocal dilution) of 398 which was approximately two-fold higher than monkeys infected with rDEN4Δ30 virus (1:181). This result and the two-fold higher level of viremia in rDEN4 virus-infected monkeys are similar to results obtained previously (Durbin et al. 2001 Am. J. Trop. Med. Hyg. 65:405-413). Monkeys infected with rDEN4Δ30-4995 (1:78), rDEN4Δ30-8092 (1:61), and rDEN4Δ30-10634 (1:107) viruses each had a reduced mean serum neutralizing antibody titer compared to monkeys infected with rDEN4Δ30 virus. The four monkeys which had no detectable viremia did have serum neutralizing antibody titers indicating that they were indeed infected. Despite the slight increase in mean peak virus titer of rDEN4Δ30-10634 virus compared with rDEN4Δ30 virus, rDEN4Δ30-10634 virus had a lower mean serum neutralizing antibody titer compared to monkeys infected with rDEN4Δ30 virus. This and the lower mean number of viremic days per monkey suggests that the 10634 mutation can attenuate the replication of rDEN4Δ30 virus in monkeys.

On day 28 after inoculation, all monkeys were challenged with 5.0 $\log_{10}$PFU wild type rDEN4 virus subcutaneously. Monkeys were observed daily and serum was collected on days 28 to 34, 36, and 38, and virus titers were determined by plaque assay in Vero cells for measurement of viremia after challenge. Twenty eight days after rDEN4 virus challenge, serum was drawn and the level of neutralizing antibodies was tested by plaque reduction assay in Vero cells. Mock-inoculated monkeys had a mean peak virus titer of 2.3 $\log_{10}$PFU/ml after challenge with a mean number of viremic days of 3.5 (Table 8). However, monkeys inoculated with rDEN4, rDEN4Δ30, or each of the modified rDEN4Δ30 viruses had no detectable viremia, indicating that despite the decreased replication and immunogenicity of rDEN4Δ30-4995, rDEN4Δ30-8092, and rDEN4Δ30-10634 viruses, each was sufficiently immunogenic to induce protection against wild type rDEN4. Increases in mean neutralizing antibody titer were minimal (<3-fold) following challenge in all inoculation groups except mock-infected providing further evidence that the monkeys were protected from the challenge.

TABLE 8 rDEN4Δ30 containing additional point mutations protects rhesus monkeys from wt DEN4 virus challenge

| Virus[a] | No. of monkeys | Mean no. of viremic days per monkey after rDEN4 challenge | Mean peak virus titer ($log_{10}$ PFU/ml ± SE) | Geometric mean serum neutralizing antibody titer (reciprocal dilution) Day 28 | Day 56 |
|---|---|---|---|---|---|
| Mock | 2 | 3.5 | 2.3 ± 0.1 | <10 | 358 |
| rDEN4 | 2 | 0.0 | <0.7 | 398 | 753 |
| rDEN4Δ30 | 2 | 0.0 | <0.7 | 181 | 202 |
| rDEN4Δ30-4995 | 4 | 0.0 | <0.7 | 78 | 170 |
| rDEN4Δ30-8092 | 4 | 0.0 | <0.7 | 61 | 131 |
| rDEN4Δ30-10634 | 4 | 0.0 | <0.7 | 107 | 177 |

[a]28 days after primary inoculation with the indicated viruses, rhesus monkeys were challenged subcutaneously with $10^5$ PFU rDEN4 virus in a 1 ml dose. Serum was collected on days 28 to 34, 36, 38, and 56. Virus titer was determined by plaque assay in Vero cells.

Taken together, these results indicate that the three point mutations, 4995, 8092, and 10634) described above do further attenuate the rDEN4Δ30 vaccine candidate in suckling mouse brain, SCID-HuH-7 mice, and rhesus monkeys. Because of additional incidental mutations (Table 4) present in each modified rDEN4Δ30 virus, the phenotypes cannot be directly attributed to the individual 4995, 8092, and 10634 point mutations. However, the presence of similar mouse-attenuation phenotypes in other rDEN4 viruses bearing one of these three mutations supports the contention that the 4995, 8092, and 10634 point mutations are responsible for the att phenotypes of the modified rDEN4Δ30 viruses. Since rDEN4Δ30-4995, rDEN4Δ30-8092, and rDEN4Δ30-10634 virus demonstrated decreased replication in rhesus monkeys while retaining sufficient immunogenicity to confer protective immunity, these viruses are contemplated as dengue vaccines for humans.

DEN4 viruses carrying both Δ30 and charge-to-alanine mutations were next generated. A subset of seven groups of charge-to-alanine mutations described above were identified that conferred between a 10-fold and 1,000-fold decrease in replication in SCID-HuH-7 mice and whose unmutated sequence was well-conserved across the four dengue serotypes. These mutations were introduced as single pairs and as two sets of pairs to rDEN4Δ30 using conventional cloning techniques. Transcription and recovery of virus and terminal dilution of viruses were conducted as described above. Assay of the level of temperature sensitivity of the charge-cluster-to-alanine mutant viruses in Vero and HuH-7 cells, level of replication in the brain of suckling mice and level of replication in SCID-HuH-7 mice was conducted as described above.

Introduction of one pair of charge-to-alanine mutations to rDEN4 produced recoverable virus in all cases (Table 9). Introduction of two pairs of charge-to-alanine mutations produced recoverable virus in two out of three cases (rDEN4Δ30-436-437-808-809 was not recoverable).

rDEN4Δ30 is not ts in Vero or HuH-7 cells. In contrast, seven of the seven sets of charge-to-alanine mutations used in this example conferred a ts phenotype in HuH-7 cells and five also conferred a ts phenotype in Vero cells. All six viruses carrying both Δ30 and charge-to-alanine mutations showed a ts phenotype in both Vero and HuH-7 cells (Table 9). rDEN4Δ30 is not attenuated in suckling mouse brain, whereas five of the seven sets of charge-to-alanine mutations conferred an att phenotype in suckling mouse brain (Table 10). Four of the viruses carrying both Δ30 and charge-to-alanine mutations were attenuated in suckling mouse brain (Table 10). In one case (rDEN4Δ30-23-24-396-397) combination of two mutations that did not attenuate alone resulted in an attenuated virus. Generally, viruses carrying both Δ30 and charge-to-alanine mutations showed levels of replication in the suckling mouse brain more similar to their charge-to-alanine mutant parent virus than to rDEN4Δ30.

rDEN4Δ30 is attenuated in SCID-HuH-7 mice, as are six of the seven charge-to-alanine mutant viruses used in this example. Viruses carrying both Δ30 and charge-to-alanine mutations tended to show similar or slightly lower levels of replication in SCID-HuH-7 mice compared to their charge-to-alanine mutant parent virus (Table 10). In three cases, viruses carrying both Δ30 and charge-to-alanine mutations showed at least a fivefold greater reduction in SCID-HuH-7 mice than rDEN4Δ30.

The complete genomic sequence of five viruses (rDEN4-200-201, rDEN4Δ30-200-201, rDEN4-436-437 [clone 1], rDEN4Δ30-436-437, and rDEN4-23-24-200-201) that replicated to >$10^5$ PFU/ml in Vero cells at 35° C. and that showed a hundredfold or greater reduction in replication in SCID-HuH-7 mice was determined (Table 11). Each of the five contained one or more incidental mutations. In one virus, rDEN4Δ30-436-437, the one additional mutation has been previously associated with Vero cell adaptation (Blaney, J. E. Jr. et al. 2002 Virology 300:125-139). Each of the remaining viruses contained at least one incidental mutation whose phenotypic effect is unknown. Consequently, the phenotypes described cannot be directly attributed to the charge-to-alanine mutations. However, the fact that rDEN4 and rDEN4Δ30 viruses carrying the same charge-to-alanine mutations shared similar phenotypes provides strong support for the ability of charge-to-alanine mutations to enhance the attenuation of rDEN4Δ30. Because rDEN4-436-437 [clone 1] contained 4 incidental mutations, a second clone of this virus was prepared. rDEN4-436-437 [clone2] contained only one incidental mutation (Table 11), and showed the same phenotypes as rDEN4-436-437 in cell culture and SCID-HuH-7 mice. rDEN4-436-437 [clone 2] was used in the rhesus monkey study described below.

TABLE 9

Addition of charge-to-alanine mutations to rDEN4Δ30 confers a ts phenotype in both Vero and HuH-7 cells.

| | | | Mean virus titer ($log_{10}$ PFU/ml) at indicated temperature (° C.)[a] | | | | | | | | | |
|---|---|---|---|---|---|---|---|---|---|---|---|---|
| | AA | No. nt | Vero | | | | | HuH-7 | | | | |
| Virus | changed[b] | changed | 35 | 37 | 38 | 39 | Δ[c] | 35 | 37 | 38 | 39 | Δ |
| rDEN4 | none | 0 | 7.4 | 7.1 | 7.7 | 7.2 | 0.2 | 7.7 | 7.5 | 7.5 | 7.4 | 0.3 |
| rDEN4Δ30 | none | 30 | 6.6 | 6.6 | 6.5 | 6.5 | 0.1 | 7.4 | 6.9 | 7.0 | 6.4 | 1.0 |
| rDEN4-23-24 | KE | 3 | 6.7 | 6.6 | 6.0 | 6.5 | 0.2 | 7.1 | 7.3 | 5.6 | <1.7 | >5.4 |
| rDEN4Δ30-23-24 | | | 6.1 | 5.5 | 4.9 | <1.7 | 4.4 | 6.5 | 5.9 | 4.7 | <1.7 | >4.2 |
| rDEN4-200-201 | KH | 4 | 5.3 | 4.8 | 4.8 | 4.3 | 1.0 | 5.7 | 5.4 | 2.7 | <1.7 | >4.0 |
| rDEN4Δ30-200-201 | | | 6.0 | 5.3 | 5.6 | <1.7 | >4.3 | 5.8 | 5.0 | 5.9 | <1.7 | >4.1 |
| rDEN4-436-437 | DK | 4 | 5.2 | 4.2 | 3.4 | 1.9 | 3.3 | 5.9 | 4.9 | 3.2 | <1.7 | >4.2 |
| rDEN4Δ30-436-437 [clone1] | | | 6.3 | 5.7 | 5.5 | <1.7 | >4.6 | 6.5 | 5.7 | 5.1 | <1.7 | >4.8 |
| rDEN4-808-809 | ED | 3 | 4.6 | 4.1 | <1.7 | <1.7 | >2.9 | 5.2 | <1.7 | <1.7 | <1.7 | >3.5 |
| rDEN4Δ30-808-809 | | | 5.6 | 4.9 | 4.9 | <1.7 | >3.9 | 5.9 | 4.8 | 5.1 | <1.7 | >4.2 |
| rDEN4-23-24-200-201 | KE, KH | 7 | 6.0 | 5.2 | 4.2 | <1.7 | >4.3 | 6.9 | 6.3 | <1.7 | <1.7 | >5.2 |
| rDEN4Δ30-23-24-200-201 | | | 4.5 | 4.2 | 4.8 | <1.7 | >2.8 | 4.9 | 4.5 | 2.9 | <1.7 | >3.2 |
| rDEN4-23-24-396-397 | KE, RE | 7 | 6.5 | 5.8 | 5.5 | <1.7 | >4.8 | 7.1 | 5.9 | 5.4 | <1.7 | >5.4 |
| rDEN4Δ30-23-24-396-397 | | | 6.1 | 5.2 | 4.8 | <1.7 | >4.4 | 6.9 | 5.4 | 4.9 | <1.7 | >5.2 |
| rDEN-436-437-808-809 | DK, ED | 7 | 4.9 | 4.9 | 5.1 | <1.7 | >3.2 | 5.5 | 3.2 | <1.7 | <1.7 | >3.8 |

[a]Underlined values indicate a 2.5 or 3.5 $log_{10}$ PFU/ml reduction in titer in Vero or HuH-7 cells, respectively, at the indicated temperature when compared to the permissive temperature (35° C.).
[b]Amino acid pair(s) changed to pair of Ala residues.
[c]Reduction in titer ($log_{10}$ pfu/ml) compared to the permissive temperature (35° C.).

TABLE 10

Addition of charge-to-alanine mutations attenuates rDEN4Δ30 in suckling mouse brain and enhances attenuation in SCID-HuH-7 mice.

| | Replication in suckling mice[a] | | | Replication in SCID-HuH-7 mice[b] | | |
|---|---|---|---|---|---|---|
| Virus | n | Mean virus titer ± SE ($log_{10}$ PFU/g brain) | Mean log reduction from wt[b] | n | Mean virus titer ± SE ($log_{10}$ PFU/ml serum) | Mean log reduction from wt[d] |
| rDEN4 | 18 | 6.2 ± 0.4 | — | 33 | 5.4 ± 0.3 | — |
| rDEN4Δ30 | 12 | 5.9 ± 0.8 | 0.2 | 8 | 3.4 ± 0.3 | **2.3** |
| rDEN4-23-24 | 18 | 4.7 ± 0.1 | **1.6** | 19 | 4.7 ± 0.5 | 1.3 |
| rDEN4Δ30-23-24 | 6 | 5.6 ± 0.3 | 0.7 | 7 | 4.6 ± 0.4 | **1.5** |
| rDEN4-200-201 | 12 | 5.5 ± 0.5 | 0.6 | 12 | 3.7 ± 0.2 | **2.6** |
| rDEN4Δ30-200-201 | 6 | 5.5 ± 0.6 | 0.1 | 4 | 3.3 ± 0.6 | **1.8** |
| rDEN4-436-437 | 18 | 2.7 ± 0.4 | **3.5** | 10 | 2.9 ± 0.7 | **2.5** |
| rDEN4Δ30-436-437 [clone 1] | 6 | 2.9 ± 0.3 | **3.4** | 4 | 2.3 ± 0.4 | **2.8** |
| rDEN4-808-809 | 6 | 1.8 ± 0.1 | **3.1** | 8 | 3.2 ± 0.4 | **3.0** |
| rDEN4Δ30-808-809 | 12 | 3.9 ± 0.7 | **2.1** | 4 | 3.7 ± 0.6 | **2.4** |
| rDEN4-23-24-200-201 | 12 | 5.3 ± 0.5 | 0.7 | 13 | 3.4 ± 0.1 | **2.9** |
| rDEN4Δ30-23-24-200-201 | 6 | 3.0 ± 0.2 | **2.6** | 5 | 1.8 ± 0.1 | **3.3** |
| rDEN4-23-24-396-397 | 12 | 4.6 ± 0.9 | **1.5** | 8 | 3.6 ± 0.3 | **2.3** |
| rDEN4Δ30-23-24-396-397 | 6 | 3.0 ± 0.2 | **2.6** | 5 | 2.2 ± 0.3 | **2.9** |
| rDEN-436-437-808-809 | 6 | <1.7 ± 0.0 | **3.6** | 8 | 2.1 ± 0.3 | **2.4** |

[a]Groups of six suckling mice were inoculated i.c. with $10^4$ PFU virus in a 30 μl inoculum. The brain was removed 5 days later, homogenized, and virus was quantitated by titration in Vero cells.
[b]Determined by comparing the mean viral titers in mice inoculated with sample virus and concurrent wt controls (n = 6). The attenuation (att) phenotype is defined as a reduction of ≥1.5 $log_{10}$ PFU/g compared to wt virus; reductions of 1.5 are listed in boldface.
[c]Groups of SCID-HuH-7 mice were inoculated directly into the tumor with $10^4$ PFU virus.
[d]Determined by comparing mean viral titers in mice inoculated with sample virus and concurrent wt controls.

The attenuation phenotype is defined as a reduction of ≥1.5 $log_{10}$PFU/g compared to wt virus; reductions of ≥1.5 are listed in boldface.

TABLE 11

Missense and UTR mutations present in rDEN4 virus derivatives bearing charge-to-alanine and the Δ30 mutation.

| Virus | Gene[a,b] | Nucleotide position | Nucleotide substitution | Amino acid position[c] | Amino acid change[b] |
|---|---|---|---|---|---|
| rDEN4-200-201 | prM | 626 | A > T | 61 | Glu > Asp |
| | **NS4A** | 6659 | C > T | 93 | Leu > Phe |
| | NS5 | 8160-8165 | AAACA > GCAGC | 200-201 | LysHis > AlaAla |

TABLE 11-continued

Missense and UTR mutations present in rDEN4 virus derivatives bearing charge-to-alanine and the Δ30 mutation.

| Virus | Gene[a,b] | Nucleotide position | Nucleotide substitution | Amino acid position[c] | Amino acid change[b] |
|---|---|---|---|---|---|
| rDEN4Δ30-200-201 | NS3 | 4830 | G > A | 102 | Gly > Arg |
| | NS5 | 8106 | G > A | 181 | Val > Ile |
| | **NS5** | 8160-8165 | AAACA > GCAGC | 200-201 | LysHis > AlaAla |
| | **3' UTR** | 10478-10507 | Δ30 deletion | None | None |
| rDEN4-436-437 [clone 1] | E | 2331 | T > G | 464 | Trp > Gly |
| | NS1 | 2845 | C > T | 140 | Ser > Phe |
| | NS3* | 4891 | T > C | 122 | Ile > Thr |
| | **NS5** | 8869-8873 | GACAA > GCAGC | 436-437 | AspLys > AlaAla |
| | NS5 | 9659 | A > G | 699 | Lys > Arg |
| rDEN4-436-437 [clone 2] | NS4B | 7153 | T > C | 108 | Val > Ala |
| | NS5 | 8869-8873 | GACAA > GCAGC | 436-437 | AspLys > AlaAla |
| rDEN4Δ30-436-437 | NS4B* | 7163 | A > C | 111 | Leu > Phe |
| | **NS5** | 8869-73 | GACAA > GCAGC | 436-437 | AspLys > AlaAla |
| | **3' UTR** | 10478-10507 | Δ30 deletion | None | None |
| rDEN4-23-24-200-201 | NS3 | 6751 | A > C | 124 | Lys > Thr |
| | **NS5** | 7629-7633 | AAAGA > GCAGC | 23-24 | LysGlu > AlaAla |
| | **NS5** | 8160-8165 | AAACA > GCAGC | 200-201 | LysHis > AlaAla |

[a]Asterisk indicates previously identified Vero cell adaptation mutation.
[b]Bold values indicate mutations designed to occur in the designated virus.
[c]Amino acid position in the protein product of the designated DEN4 gene; numbering starts with the amino terminus of the protein.

Figure 4:
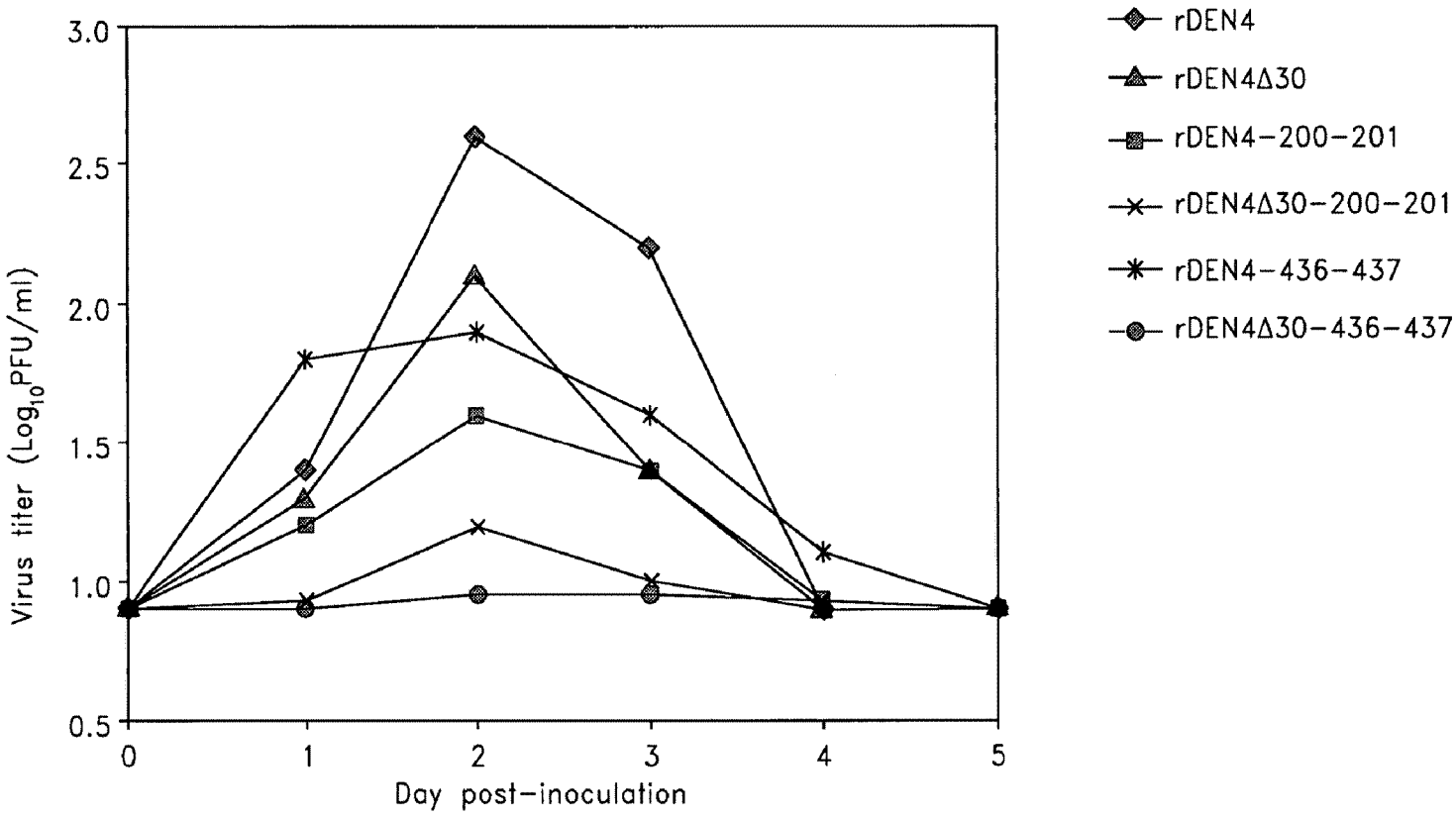
FIG. 4. Viremia levels in rhesus monkeys inoculated with rDEN4 vaccine candidates bearing pairs of charge-to-alanine mutations in NS5. Groups of four or two (rDEN4 and rDEN4Δ30) monkeys were inoculated with 5.0 $\log_{10}$PFU virus subcutaneously. Serum was collected daily and virus titers were determined by plaque assay in Vero cells. The limit of virus detection was 1.0 $\log_{10}$PFU/ml. Mean virus titers are indicated for each group. Viremia was not detected in any monkey after day 4.

Based on the attenuation in the SCID-HuH7 mouse model, four of the charge-to-alanine mutant viruses (rDEN4-200-201, rDEN4Δ30-200-201, rDEN4-436-437 [clone 2], rDEN4Δ30-436-437) were evaluated in rhesus macaques as described above. As with the study of viruses carrying attenuating point mutations, viremia was detected on day 1 post-infection and ended by day 4 in all monkeys (FIG. 4, Table 12). Viremia was detected in most of the monkeys infected; only one of the four monkeys infected with rDEN4Δ30-200-201 and one of the four monkeys infected with rDEN4Δ30-436-437 showed no detectable viremia. Monkeys infected with rDEN4 showed the highest mean peak virus titer; and in each case viruses carrying the Δ30 mutation showed an approximately 0.5 log decrease in mean peak virus titer relative to their parental viruses and a 0.5 to 2 day decrease in mean number of viremic days per monkey. Monkeys infected with viruses carrying both the Δ30 and charge-to-alanine mutations showed a two-fold reduction in mean peak viremia relative to those infected with rDEN4Δ30. This suggests that addition of the charge-to-alanine mutations further attenuates rDEN4Δ30 for rhesus macaques.

As expected, none of the monkeys in this study showed detectable levels of neutralizing antibody on day 0. On day 28, every monkey infected with a virus showed a detectable levels of neutralizing antibody, indicating that all of the monkeys, even those that showed no detectable viremia, had indeed been infected. As in the study of attenuating point mutations, monkeys infected with rDEN4 had a mean serum neutralizing antibody titer (reciprocal dilution) which was approximately twice that of monkeys that had been infected with rDEN4Δ30. Monkeys infected with rDEN4-200-201 and rDEN4-436-437 [clone 2] had similar mean neutralizing antibody titers to rDEN4, and those infected with rDEN4Δ30-200-201 and rDEN4Δ30-436-437 had similar mean neutralizing antibody titers to rDEN4. In each case the addition of the Δ30 mutation to a virus resulted in a two-fold decrease in neutralizing antibody. Thus, although the addition of charge-to-alanine mutations to rDEN4Δ30 decreased mean peak viremia below that of rDEN4Δ30 alone, it did not affect levels of neutralizing antibody.

TABLE 12

Addition of paired charge-to-alanine mutations to rDEN4Δ30 further attenuates the virus for rhesus monkeys.

| Virus[a] | No. of monkeys | No. of monkeys with viremia | Mean no. of viremic days per monkey[b] | Mean peak virus titer ($\log_{10}$ PFU/ml ± SE) | Geometric mean serum neutralizing antibody titer (reciprocal dilution) Day 0 | Day 28 |
|---|---|---|---|---|---|---|
| mock | 2 | 0 | 0 | <0.7 | <5 | <5 |
| rDEN4 | 2 | 2 | 2.5 | 2.6 ± 0.3 | <5 | 276 |
| rDEN4Δ30 | 2 | 2 | 2.0 | 2.1 ± 0.1 | <5 | 131 |
| rDEN4-200, 201 | 4 | 4 | 2.3 | 1.8 ± 0.3 | <5 | 212 |
| rDEN4Δ30-200, 201 | 4 | 3 | 1.5 | 1.3 ± 0.2 | <5 | 139 |

TABLE 12-continued

Addition of paired charge-to-alanine mutations to rDEN4Δ30 further attenuates the virus for rhesus monkeys.

| Virus[a] | No. of monkeys | No. of monkeys with viremia | Mean no. of viremic days per monkey[b] | Mean peak virus titer ($log_{10}$ PFU/ml ± SE) | Geometric mean serum neutralizing antibody titer (reciprocal dilution) Day 0 | Day 28 |
|---|---|---|---|---|---|---|
| rDEN4-436, 437 [cl 2) | 4 | 4 | 3.3 | 1.8 ± 0.2 | <5 | 273 |
| rDEN4Δ30-436, 437 | 4 | 3 | 1.3 | 1.0 ± 0.0 | <5 | 143 |

[a]Groups of rhesus monkeys were inoculated subcutaneously with $10^5$ PFU of the indicated virus in a 1 ml dose. Serum was collected on days 0 to 6, 8, 10 and 28. Virus titer was determined by plaque assay in Vero cells.
[b]Viremia was not detected in any monkey after day 4.

After challenge with rDEN4 on day 28, mock-infected monkeys had a mean peak virus titer of 1.5 $log_{10}$PFU/ml and a mean number of viremic days of 3.0 (Table 13). However, none of the monkeys previously inoculated with rDEN4, rDEN4Δ30 or the charge-to-alanine mutant viruses showed detectable viremia. Additionally, none of the monkeys showed a greater than four-fold increase in serum neutralizing antibody titer. Together these data indicate that infection with any of the viruses, including those carrying both Δ30 and the charge-to-alanine mutations, protected rhesus macaques from challenge with rDEN4.

TABLE 13 rDEN4Δ30 containing charge-to-alanine mutations protects rhesus monkeys from wt DEN4 virus challenge

| Virus[a] | No. of monkeys | Mean no. of viremic days per monkey after rDEN4 challenge | Mean peak virus titer ($log_{10}$ PFU/ml ± SE) | Geometric mean serum neutralizing antibody titer (reciprocal dilution) Day 28 | Day 56 |
|---|---|---|---|---|---|
| mock | 2 | 3.0 | 1.5 ± 0.7 | <5 | 284 |
| rDEN4 | 2 | 0.0 | <0.7 | 276 | 316 |
| rDEN4Δ30 | 2 | 0.0 | <0.7 | 131 | 96 |
| rDEN4-200, 201 | 4 | 0.0 | <0.7 | 212 | 356 |
| rDEN4Δ30-200, 201 | 4 | 0.0 | <0.7 | 139 | 132 |
| rDEN4-436, 437 [cl 2] | 4 | 0.0 | <0.7 | 273 | 401 |
| rDEN4Δ30-436, 437 | 4 | 0.0 | <0.7 | 143 | 182 |

[a]28 days after primary inoculation with the indicated viruses, rhesus monkeys were challenged subcutaneously with $10^5$ PFU rDEN4 virus in a 1 ml dose. Serum was collected on days 28 to 34, 36, 10, and 56. Virus titer was determined by plaque assay in Vero cells.

Addition of charge-to-alanine mutations to rDEN4Δ30 can confer a range of is phenotypes in both Vero and HuH-7 cells and att phenotypes in suckling mouse brain and can either enhance or leave unchanged attenuation in SCID-HuH-7 mice. Most importantly, addition of these mutations can decrease the viremia produced by rDEN4Δ30 in rhesus macaques without decreasing neutralizing antibody titer or protective efficacy. Thus addition of such mutations to rDEN4Δ30 is contemplated as enhancing attenuation in humans. Also, mutations are contemplated as being added that do not change the overall level of attenuation, but stabilize the attenuation phenotype because they themselves are independently attenuating even in the absence of the Δ30 mutation. Charge-to-alanine mutations are particularly useful because they occur outside of the structural gene regions, and so can be used to attenuate structural gene chimeric viruses. Moreover, they involve at least three nucleotide changes, making them unlikely to revert to wild type sequence.

A series of point mutations that enhance the replication of rDEN4 in Vero cells tissue culture have been identified; these are primarily located in the NS4B gene (Blaney, J. E. et. al. 2002 Virology 300:125-139; Blaney, J. E. et al. 2001 J Virol 75:9731-9740). Vero cell adaptation mutations confer two desirable features upon a vaccine candidate. First, they enhance virus yield in Vero cells, the intended substrate for vaccine production, and thus render vaccine production more cost-effective. Second, although each of these Vero adaptation mutations are point mutations, they are likely to be extremely stable during vaccine manufacture, because they give a selective advantage in Vero cells. At least one Vero cell adaptation mutation, at position 7129, was also shown to decrease mosquito infectivity of rDEN4; poor mosquito infectivity is another desirable characteristic of a dengue vaccine candidate. To investigate the generality of this finding, we tested the effect of the remaining Vero cell adaptation mutations on the ability of rDEN4 to infect Aedes aegypti mosquitoes fed on an infectious bloodmeal. Table 14 shows the infectivity of each virus carrying a single Vero cell adaptation mutation at high titer. Of these, only one mutation, at position 7182, was associated with a large decrease in mosquito infectivity. Thus 7182 may be a particularly valuable mutation to include in an rDEN4 vaccine candidate, as it has opposite effects on replication in Vero cells and in mosquitoes.

TABLE 14

Effect of Vero cell adaptation mutations on rDEN4 mosquito infectivity

| | Aedes aegypti (oral infection) | | | |
|---|---|---|---|---|
| | Dose[a] | | % infected[b] | |
| Virus | ($log_{10}$ pfu) | No. tested | Midgut | Head |
| rDEN4 | 4.3 | 27 | 70 | 25 |
| rDEN4-4891 | 4.4 | 23 | 74 | 13 |
| rDEN4-4995 | 4.8 | 20 | 80 | 50 |
| rDEN4-7153 | 4.8 | 20 | 80 | 30 |
| rDEN4-7546 | 4.6 | 20 | 55 | 10 |
| rDEN4-7162 | 5.0 | 20 | 55 | 25 |
| rDEN4-7163 | 4.9 | 15 | 73 | 72 |
| rDEN4-7182 | 5.0 | 20 | 20 | 0 |
| rDEN4-7630 | 4.3 | 10 | 70 | 10 |

[a]Virus titer ingested, assuming a 2 μl bloodmeal.
[b]Percentage of mosquitoes with IFA detectable antigen in midgut or head tissue prepared 21 days after oral infection.

EXAMPLE 2

Generation and Characterization of a Recombinant DEN1 Virus Containing the Δ30 Mutation We first sought to determine if the Δ30 mutation was able to satisfactorily attenuate a wild-type DEN virus other than the DEN4 serotype. To do this, the Δ30 mutation was introduced into the cDNA for DEN1 (Western Pacific). The pRS424DEN1WP cDNA clone (Puri, B. et al. 2000 Virus Genes 20:57-63) was digested with BamHI and used as template in a PCR using Pfu polymerase with forward primer 30 (DEN1 nt 10515-10561 and 10592-10607) and the M13 reverse sequencing primer (101 nt beyond the 3' end of DEN1 genome sequence). The resulting PCR product was 292 bp and contained the Δ30 mutation. The pRS424DEN1WP cDNA was partially digested with Apa I, then digested to completion with Sac II and the vector was gel isolated, mixed with PCR product, and used to transform yeast strain YPH857 to yield growth on plates lacking tryptophan (Polo, S. et al. 1997 J Virol 71:5366-74). Positive yeast colonies were confirmed by PCR and restriction enzyme analysis. DNA isolated from two independent yeast colonies was used to transform E. coli strain STBL2. Plasmid DNA suitable for generating RNA transcripts was prepared and the presence of the Δ30 mutation was verified by sequence analysis.

For transcription and generation of virus, cDNA (designated pRS424DEN1Δ30) that was linearized with Sac II was used as template in a transcription reaction using SP6 RNA polymerase as described (Polo, S. et al. 1997 J Virol 71:5366-74). Transcription reactions were electroporated into LLC-MK2 cells and infection was confirmed by observation of CPE and immunofluorescence and harvested on day 14. Virus stocks were amplified on C6/36 mosquito cells and titered on LLC-MK2 cells. The genome of the resulting virus, rDEN1Δ30, was sequenced to confirm the presence of the Δ30 mutation. The Δ30 mutation removes nucleotides 10562-10591 of DEN1 (FIG. 2B, C), which corresponds to the TL2 of DEN1. The virus replicates efficiently in Vero cell culture to titers of 6.5 $log_{10}$PFU/ml, indicating that the Δ30 mutation is compatible with efficient growth of DEN1 in cell culture, a property essential for manufacture of the vaccine. Using similar techniques, parent virus rDEN1 was generated. Incidental mutations arising from virus passage in tissue culture were identified in both rDEN1 and rDEN1Δ30 using sequence analysis and are listed in Table 15. An additional rDEN1Δ30 virus was derived by transfection and amplification in Vero cells. Although this virus was not evaluated in the studies described below, its sequence analysis is included in Table 15. The properties of rDEN1Δ30 as a vaccine in vivo were next examined.

TABLE 15

Missense mutations present among the recombinant DEN1 viruses and correlation of NS4B region mutations with those found in DEN4

| Virus | Transfection cell type | Gene | Nucleotide position | Nucleotide change | Amino acid position | Amino acid change |
|---|---|---|---|---|---|---|
| wt rDEN1 | LLC-MK2 | prM | 816 | C > U | 241 | Ala > Val |
| | | NS4B | 7165[a] | U > G | 2357 | Phe > Leu |
| | | NS4B | 7173[b] | U > C | 2360 | Val > Ala |
| rDEN1Δ30 | LLC-MK2 | E | 1748 | A > U | 552 | Thr > Ser |
| rDEN1Δ30 | Vero | E | 1545 | A > G | 484 | Lys > Arg |

[a]Same nucleotide as 7154 in rDEN4.
[b]Same nucleotide as 7162 in rDEN4

* Nucleotide and amino acid comparison of selected NS4B region:

```
             7         7         7         7         7         7
DEN4         1         1         1         1         1         1
base         3         4         5         6         7         8
Number:  890123456789012345678901234567890123456789012345678901234
         567
         ++    ++  + +++++ +  +  +  + ++  +   ++++++++ ++ ++ ++ ++

D4 7128- CCAACAACCUUGACAGCAUCCUUAGUCAUGCUUUUAGUCCAUUAUGCAAUAA
         UAGGCCCA
         P  T  T  L  T  A  S  L  V  M  L  L  V  H  T  A  I  I  G  P

D1 7139- CCGCUGACGCUGACAGCGGCGGUAUUUAUGCUAGUGGCUCAUUAUGCCAUA
         AUUGGACCC
         P  L  T  L  T  A  A  V  P  M  L  V  A  H  T  A  I  I  G  P

D2 7135- CCUAUAACCCUCACAGCGGCUCUUCUUUUAUUGGUAGCACAUUAUGCCAUCAUAG
         GACCG
         P  I  T  L  T  A  A  L  L  L  L  V  A  H  T  A  I  I  G  P
```

-continued

```
D3 7130-  CCACUAACUCUCACAGCGGCAGUUCUCCUGCUAGUCACGCAUUAUGCUAU
          UAUAGGUCCA
          P  L  T  L  T  A  A  V  L  L  L  V  T  H  T  A  I  I  G  P
          +     +  +  +  +              +        +  +  +  +  +  +  +
D4 = rDEN4
D1 = rDEN1(WP)
D2 = rDEN2(Tonga/74)
D3 = rDEN3(Sleman/78)
+Homology among all four serotypes
Nucleotides are underlined in even multiples of 10.
```

Evaluation of the replication, immunogenicity, and protective efficacy of rDEN1Δ30 and wild-type parental rDEN1 virus (derived from the pRS424DEN1WP cDNA) in juvenile rhesus monkeys was performed as follows. Dengue virus-seronegative monkeys were injected subcutaneously with 5.0 $\log_{10}$PFU of virus in a 1 ml dose divided between two injections in each side of the upper shoulder area. Monkeys were observed daily and blood was collected on days 0-10 and 28 and serum was stored at −70° C. Titer of virus in serum samples was determined by plaque assay in Vero cells as described previously (Durbin, A. P. et al. 2001 Am J Trop Med Hyg 65:405-13). Plaque reduction neutralization titers were determined for the day 28 serum samples as previously described (Durbin, A. P. et al. 2001 Am J Trop Med Hyg 65:405-13). All monkeys were challenged on day 28 with a single dose of 5.0 $\log_{10}$PFU of wild-type rDEN1 and blood was collected for 10 days. Virus titer in post-challenge sera was determined by plaque assay in Vero cells. Monkeys inoculated with full-length wild-type rDEN1 were viremic for 2-3 days with a mean peak titer of 2.1 $\log_{10}$PFU/ml (Table 16), and monkeys inoculated with rDEN1Δ30 were viremic for less than 1 day with a mean peak titer of 0.8 $\log_{10}$PFU/ml, indicating that the Δ30 mutation is capable of attenuating DEN1. As expected for an attenuated virus, the immune response, as measured by neutralizing antibody titer, was lower following inoculation with rDEN1Δ30 compared to inoculation with wild-type rDEN1 (Table 16), yet sufficiently high to protect the animals against wild-type DEN1 virus challenge. Wild-type rDEN1 virus was not detected in any serum sample collected following virus challenge, indicating that monkeys were completely protected following immunization with either full-length wild-type rDEN1 or recombinant virus rDEN1Δ30. The level of attenuation specified by the Δ30 mutation was comparable in both the DEN1 and DEN4 genetic backgrounds (FIG. 5).

TABLE 16

The Δ30 mutation attenuates rDEN1 for rhesus monkeys

| Virus* | n | Mean no. days with viremia | Mean peak titer ($\log_{10}$ pfu/ml) | Mean neutralization titer | Mean peak titer of challenge virus |
|---|---|---|---|---|---|
| rDEN1 | 4 | 2.8 | 2.1 | 1230 | <0.7 |
| rDEN1Δ30 | 4 | 0.5 | 0.8 | 780 | <0.7 |

*Rhesus monkeys were inoculated subcuateously with 5.0 $\log_{10}$ PFU of virus. Serum samples were collected daily for 10 days. Serum for neutralization assay was collected on day 28. All monkeys were challenged on day 28 with 5.0 $\log_{10}$ PFU of rDEN1.

As previously reported, rDEN4 virus replicated to greater than 6.0 $\log_{10}$PFU/ml serum in SCID-HuH-7 mice, while the replication of rDEN4 virus bearing the Δ30 mutation was reduced by about 10-fold (Blaney, J. E. Jr. et al. 2002 Virology 300:125-139). The replication of rDEN1Δ30 was compared to that of wt rDEN1 in SCID-HuH-7 mice (Table 17). rDEN1Δ30 replicated to a level approximately 100-fold less than its wt rDEN1 parent. This result further validates the use of the SCID-HuH-7 mouse model for the evaluation of attenuated strains of DEN virus, with results correlating closely with those observed in rhesus monkeys.

TABLE 17

The Δ30 mutation attenuates rDEN1 for HuH-7-SCID mice

| Virus | No. of Mice[5] | Mean peak virus titer[6] ($\log_{10}$ pfu/ml ± SE) |
|---|---|---|
| wt rDEN1 | 9 | 7.3 ± 0.2 |
| rDEN1Δ30 | 8 | 5.0 ± 0.3 |

[5]Groups of HuH-7-SCID mice were inoculated directly into the tumor with 4.0 $\log_{10}$ pfu virus. Serum was collected on day 6 and 7, and virus titer was determined by plaque assay in Vero cells.

[6]Significant difference was found between rDEN1 and rDEN1Δ30 viruses, Tukey-Kramer test ($P < 0.005$).

Finally, the infectivity of rDEN1 and rDEN1Δ30 for mosquitoes was assessed, using the methods described in detail in Example 5. Previously, the Δ30 mutation was shown to decrease the ability of rDEN4 to cross the mosquito midgut barrier and establish a salivary gland infection (Troyer, J. M. et al. 2001 Am J Trop Med Hyg 65:414-419). However neither rDEN1 nor rDEN1Δ30 was able to infect the midgut of Aedes aegypti mosquitoes efficiently via an artificial bloodmeal (Table 18), so it was not possible to determine whether Δ30 might further block salivary gland infection. A previous study also showed that the Δ30 had no effect on the infectivity of rDEN4 for Toxorhynchites splendens mosquitoes infected via intrathoracic inoculation (Troyer, J. M. et al. 2001 Am J Trop Med Hyg 65:414-419), and a similar pattern was seen for rDEN1 and rDEN1Δ30 (Table 18). The genetic basis for the inability of rDEN1 to infect the mosquito midgut has not been defined at this time. However, this important property of restricted infectivity for the mosquito midgut is highly desirable in a vaccine candidate since it would serve to greatly restrict transmission of the vaccine virus from a vaccinee to a mosquito vector.

TABLE 18

DEN1 and DEN1Δ30 viruses are both highly infectious for Toxorhynchites splendens, but do not infect Aedes aegypti efficiently.

| | Toxorhynchites splendens (intrathoracic inoculation) | | | Aedes aegypti (oral infection) | | | |
|---|---|---|---|---|---|---|---|
| | Dose[a] | | | Dose[c] | | % infected[d] | |
| Virus | ($log_{10}$ pfu) | No. tested | % infected[b] | ($log_{10}$ pfu) | No. tested | Midgut | Head |
| rDEN1 | 3.5 | 7 | 100 | 4.0 | 26 | 11 | 0 |
| | 2.5 | 8 | 75 | | | | |
| | 1.5 | 7 | 71 | | | | |
| | 0.5 | 5 | 60 | | | | |
| | | | $MID_{50}$ < 0.5 | | | $MID_{50}$ ≥ 4.4 | |
| rDEN1 | 2.7 | 8 | 100 | 3.2 | 20 | 10 | 0 |
| Δ30 | 1.7 | 7 | 100 | | | | |
| | 0.7 | 6 | 83 | | | | |
| | | | $MID_{50}$ < 0.7 | | | $MID_{50}$ ≥ 3.6 | |

[a]Amount of virus present in 0.22 μl inoculum.

[b]Percentage of mosquitoes with IFA detectable antigen in head tissue prepared 14 days after inoculation.

[c]Virus titer ingested, assuming a 2 μl bloodmeal.

[d]Percentage of mosquitoes with IFA detectable antigen in midgut or head tissue prepared 21 days after oral infection. When virus infection was detected, but did not exceed a frequency of 50% at the highest dose of virus ingested, the $MID_{50}$ was estimated by assuming that a 10-fold more concentrated virus dose would infect 100% of the mosquitoes.

Thus, the Δ30 mutation, first described in DEN4, was successfully transferred to rDEN1. The resulting virus, rDEN1Δ30, was shown to be attenuated in monkeys and SCID-HuH-7 mice to levels similar to recombinant virus rDEN4Δ30, thereby establishing the conservation of the attenuation phenotype specified by the Δ30 mutation in a different DEN virus background. Based on the favorable results of rDEN4Δ30 in recent clinical trials (Durbin, A. P. et al. 2001 Am J Trop Med Hyg 65:405-13), it is predicted that rDEN1Δ30 will be suitably attenuated in humans. To complete the tetravalent vaccine, attenuated rDEN2 and rDEN3 recombinant viruses bearing the Δ30 mutation are contemplated as being prepared (See Examples 3 and 4 below). The demonstration that the Δ30 mutation specifies a phenotype that is transportable to another DEN serotype has important implications for development of the tetravalent vaccine. This indicates that the Δ30 mutation is expected to have a corresponding effect on DEN2 and DEN3 wild-type viruses.

EXAMPLE 3

Generation and Characterization of a Recombinant DEN2 Virus Containing the Δ30 Mutation Evaluation of rDEN1Δ30 showed that it was satisfactorily attenuated. Based on this result, we sought to extend our technology to the creation of a DEN2 vaccine candidate. To do this, the Δ30 mutation was introduced into the cDNA of DEN2. A DEN2 virus isolate from a 1974 dengue epidemic in the Kingdom of Tonga (Tonga/74) (Gubler, D. J. et al. 1978 Am J Trop Med Hyg 27:581-589) was chosen to represent wt DEN2. The genome of DEN2 (Tonga/74) was sequenced in its entirety and served as consensus sequence for the construction of a full-length cDNA clone (Appendix 1). cDNA fragments of DEN2 (Tonga/74) were generated by reverse-transcription of the genome as indicated in FIG. 6A. Each fragment was subcloned into a plasmid vector and sequenced to verify that it matched the consensus sequence as determined for the virus. This yielded seven cloned cDNA fragments spanning the genome. Cloned fragments were modified as follows: Fragment X, representing the 5' end of the genome was abutted to the SP6 promoter; Fragment L was modified to contain a translationally-silent SpeI restriction site at genomic nucleotide 2353; Fragment R was modified to contain a translationally-silent SpeI restriction site also at genomic nucleotide 2353, and to stabilize the eventual full-length clone, two additional translationally-silent mutations at nucleotides 2362-2364 and 2397 were created to ensure that translation stop codons were present in all reading frames other than that used to synthesize the virus polyprotein; Fragment A was modified at nucleotide 3582 to ablate a naturally occurring SpeI restriction site and at nucleotide 4497 to ablate a naturally occurring KpnI restriction site; Fragment C was modified at nucleotide 9374 to ablate a naturally occurring KpnI restriction site; and Fragment Y, representing the 3' end of the genome was abutted to a KpnI restriction site. Each fragment was added incrementally between the AscI and KpnI restriction sites of DEN4 cDNA clone p4 (Durbin, A. P. et al. 2001 Am J Trop Med Hyg 65:405-13) to generate a full-length DEN2 cDNA clone (p2) with the same vector background successfully used to generate rDEN4 and rDEN4Δ30. cDNA clone p2 was sequenced to confirm that the virus genome region matched the DEN2 (Tonga/74) consensus sequence, with the exception of the translationally-silent modifications noted above. The Δ30 mutation was introduced into Fragment Y to generate Fragment YΔ30. To create p2Δ30, the Fragment Y region of p2 was replaced with Fragment YΔ30 (FIG. 6A, B).

For transcription and generation of infectious virus, cDNA (p2 and p2Δ30) was linearized with Acc65I (isoschizomer of KpnI which cleaves leaving only a single 3' nucleotide) and used as template in a transcription reaction using SP6 RNA polymerase as previously described (Blaney, J. E. et. al. 2002 Virology 300:125-139). Transcripts were introduced into Vero cells or C6/36 mosquito cells using liposome-mediated transfection and cell culture supernatants were harvested on day 7.

rDEN2 virus was recovered from the p2 cDNA in both Vero and C6/36 cells, while rDEN2Δ30 was recovered from the p2Δ30 cDNA clone in only C6/36 cells (Table 19). The level of infectious virus recovered in C6/36 cells was comparable for the p2 and p2Δ30 cDNA clones when assayed by plaque titration and immunostaining in Vero or C6/36 cells. As previously observed, the efficiency of transfection in C6/36 cells was higher than that in Vero cells. Two rDEN2Δ30 viruses were recovered from independent cDNA clones, #2 and #10.

TABLE 19 rDEN2 virus is recovered in Vero and C6/36 cells, but rDEN2Δ30 virus is recovered only in C6/36 cells.

| Transfection cell type | cDNA construct | Clone | Virus | Virus titer of transfection harvest (day 7) determined in the indicated cell type ($log_{10}$ PFU/ml) Vero cells | C6/36 cells |
|---|---|---|---|---|---|
| Vero cells | p2 | #8A | rDEN2 | 3.1 | 4.3 |
| | p2Δ30 | #2 | rDEN2Δ30 | <0.7 | <0.7 |
| | p2Δ30 | #10 | rDEN2Δ30 | <0.7 | <0.7 |
| C6/36 cells | p2 | #8A | rDEN2 | 5.5 | 7.5 |
| | p2Δ30 | #2 | rDEN2Δ30 | 4.8 | 7.6 |
| | p2Δ30 | #10 | rDEN2Δ30 | 4.6 | 7.5 |

To produce working stocks of rDEN2 and rDEN2Δ30 viruses, transfection harvests were passaged and terminally diluted in Vero cells, and genomic sequences of the viruses were determined. The Vero cell transfection harvest of rDEN2 virus was terminally diluted once in Vero cells, and individual virus clones were passaged once in Vero cells. To assess whether any homologous Vero cell adaptation mutations identified in the rDEN4 NS4B 7100-7200 region were present in these virus clones, seven independent terminally diluted clones were sequenced over this region. Each of the seven rDEN2 viruses contained a single nucleotide substitution in this region at nucleotide 7169 (U>C) resulting in a Val>Ala amino acid change. This nucleotide corresponds to the 7162 mutation identified in rDEN4 (Blaney, J. E. et. al. 2002 Virology 300:125-139), which has a known Vero cell adaptation phenotype suggesting that this mutation may confer a replication enhancement phenotype in rDEN2 virus. One rDEN2 virus clone was completely sequenced and in addition to the 7169 mutation, a missense mutation (Glu>Ala) was found in NS5 at residue 3051 (Table 20).

TABLE 20

Missense mutations which accumulate in rDEN2 and rDEN2Δ30 viruses after transfection or passage in Vero cells.

| Virus | Gene | Nucleotide position | Nucleotide substitution | Amino acid position[a] | Amino acid change |
|---|---|---|---|---|---|
| rDEN2[b] | NS4B | 7169[c] | U > C | 2358 | Val > Ala |
| (Vero) | NS5 | 9248 | A > C | 3051 | Glu > Ala |
| rDEN2Δ30[d] | NS3 | 4946 | A > G | 1617 | Lys > Arg |
| (Vero) | NS4B | 7169[c] | U > C | 2358 | Val > Ala |

[a]Amino acid position in DEN2 polyprotein beginning with the methionine residue of the C protein (nucleotides 97-99) as position 1.
[b]Virus was recovered in Vero cells and terminally-diluted once in Vero cells. Virus stock was prepared in Vero cells.
[c]Same nucleotide position as 7162 in rDEN4.
[d]Virus was recovered in C6/36 cells and passaged three times in Vero cells. Virus was then terminally diluted and a stock was prepared in Vero cells.

Because both rDEN2 and rDEN2Δ30 viruses grown in Vero cells acquired the same mutation at nucleotide 7169, which corresponds to the Vero cell adaptation mutation previously identified in rDEN4 at nucleotide 7162, it was reasoned that this mutation is associated with growth adaptation of rDEN2 and rDEN2Δ30 in Vero cells. In anticipation that the 7169 mutation may allow rDEN2Δ30 to be recovered directly in Vero cells, the mutation was introduced into the rDEN2Δ30 cDNA plasmid to create p2Δ30-7169. Transcripts synthesized from p2Δ30-7169, as well as p2 and p2Δ30 were introduced into Vero cells or C6/36 mosquito cells using liposome-mediated transfection as described above. Virus rDEN2Δ30-7169 was recovered from the p2Δ30-7169 cDNA in both Vero and C6/36 cells, while rDEN2Δ30 was recovered from the p2Δ30 cDNA clone in only C6/36 cells (Table 21). The 7169 mutation is both necessary and sufficient for the recovery of rDEN2Δ30 in Vero cells.

TABLE 21 rDEN2Δ30-7169 virus containing the 7169 Vero cell adaptation mutation is recovered in both Vero and C6/36 cells

| Transfection cell type | cDNA construct | Clone | Virus | Virus titer of transfection harvest (day 14) determined in C6/36 cells ($log_{10}$ PFU/ml) |
|---|---|---|---|---|
| Vero cells | p2 | #8A | rDEN2 | 6.8 |
| | p2Δ30 | #2 | rDEN2Δ30 | <0.7 |
| | p2Δ30-7169[a] | #37 | rDEN2Δ30-7169 | 5.1 |
| C6/36 cells | p2 | #8A | rDEN2 | 6.9 |
| | p2Δ30 | #2 | rDEN2Δ30 | 7.1 |
| | p2Δ30-7169 | #37 | rDEN2Δ30-7169 | 7.2 |

[a]Nucleotide 7169 in rDEN2 corresponds to nucleotide 7162 in rDEN4 which has been shown to be associated with growth adaptation in Vero cells.

To initially assess the ability of the Δ30 mutation to attenuate rDEN2 virus in an animal model, the replication of DEN2 (Tonga/74), rDEN2, and rDEN2Δ30 viruses was evaluated in SCID-HuH-7 mice. Previously, attenuation of vaccine candidates in SCID-HuH-7 mice has been demonstrated to be predictive of attenuation in the rhesus monkey model of infection (Examples 1 and 2). The recombinant viruses tested in this experiment were recovered in C6/36 cells. The DEN2 Tonga/74 virus isolate, rDEN2, and two independent rDEN2Δ30 viruses, (clones 20A and 21A) which were derived from two independent p2Δ30 cDNA clones, were terminally diluted twice in C6/36 cells prior to production of a working stock in C6/36 cells. These viruses should not contain any Vero cell adaptation mutations. DEN2 Tonga/74 virus replicated to a mean virus titer of 6.2 $log_{10}$PFU/ml in the serum of SCID-HuH-7 mice, and rDEN2 virus replicated to a similar level, 5.6 $log_{10}$ PFU/ml (Table 22). Both rDEN2Δ30 viruses were greater than 100-fold restricted in replication compared to rDEN2 virus. These results indicate that the Δ30 mutation has an attenuating effect on replication of rDEN2 virus similar to that observed for rDEN4 and rDEN1 viruses.

TABLE 22

The Δ30 mutation restricts rDEN2 virus replication in SCID-HuH-7 mice.

| Virus | No. of mice | Mean virus titer ± SE ($log_{10}$ PFU/ml serum)[a] | Mean $log_{10}$-unit reduction from value for wt[b] |
|---|---|---|---|
| DEN2 (Tonga/74) | 8 | 6.2 ± 0.3 | — |
| rDEN2 | 9 | 5.6 ± 0.2 | — |
| rDEN2Δ30 (clone 20A) | 9 | 3.1 ± 0.2 | 2.5 |
| rDEN2Δ30 (clone 21A) | 9 | 2.9 ± 0.3 | 2.7 |

[a]Groups of SCID-HuH-7 mice were inoculated directly into the tumor with $10^4$ PFU virus grown in C6/36 cells. Serum was collected on day 7 and titered in C6/36 cells.
[b]Comparison of mean virus titers of mice inoculated with mutant virus and concurrent rDEN2 control.

DEN2 virus replication in SCID-HuH-7 mice was also determined using DEN2 (Tonga/74), rDEN2, and rDEN2Δ30 which were passaged in Vero cells (see Table 20, footnotes b and d). Both rDEN2 and rDEN2Δ30 had acquired a mutation in NS4B, nucleotide 7169, corresponding to the 7162 mutation identified in rDEN4 as Vero cell adaptation mutation. In the presence of the 7169 mutation, the Δ30 mutation reduced replication of rDEN2Δ30 by 1.0 $\log_{10}$PFU/ml (Table 23). Previously, using virus grown in C6/36 cells and lacking the 7169 mutation, the Δ30 mutation reduced replication of rDEN2Δ30 by about 2.5 $\log_{10}$PFU/ml (Table 22). These results indicate that Vero cell growth adaptation in DEN2 may also confer a slight growth advantage in HuH-7 liver cells. Nevertheless, the attenuation conferred by the Δ30 mutation is still discernible in these Vero cell growth adapted viruses.

TABLE 23

The Δ30 mutation restricts Vero cell adapted rDEN2 virus replication in SCID-HuH-7 mice.

| Virus | No. of mice | Mean virus titer ± SE ($\log_{10}$ PFU/ml serum)[a] | Mean $\log_{10}$-unit reduction from value for wt[b] |
|---|---|---|---|
| DEN2 (Tonga/74) | 6 | 5.9 ± 0.3 | — |
| rDEN2 | 7 | 5.9 ± 0.2 | — |
| rDEN2Δ30 | 9 | 4.9 ± 0.3 | 1.0 |

[a]Groups of SCID-HuH-7 mice were inoculated directly into the tumor with $10^4$ PFU virus. Serum was collected on day 7 and titered in C6/36 cells.
[b]Comparison of mean virus titers of mice inoculated with rDEN2Δ30 and rDEN2 control.

Evaluation of the replication, immunogenicity, and protective efficacy of rDEN2Δ30 and wild-type parental rDEN2 virus in juvenile rhesus monkeys was performed as follows. Dengue virus-seronegative monkeys were injected subcutaneously with 5.0 $\log_{10}$PFU of virus in a 1 ml dose divided between two injections in each side of the upper shoulder area. Monkeys were observed daily and blood was collected on days 0-10 and 28 and serum was stored at −70° C. Viruses used in this experiment were passaged in Vero cells, and recombinant viruses contained the mutations shown in Table 20 (See footnotes b and d). Titer of virus in serum samples was determined by plaque assay in Vero cells as described previously (Durbin, A. P. et al. 2001 Am J Trop Med Hyg 65:405-13). Plaque reduction neutralization titers were determined for the day 28 serum samples as previously described (Durbin, A. P. et al. 2001 Am J Trop Med Hyg 65:405-13). All monkeys were challenged on day 28 with a single dose of 5.0 $\log_{10}$PFU of wt DEN2 (Tonga/74) and blood was collected for 10 days. Virus titer in post-challenge sera was determined by plaque assay in Vero cells. Monkeys inoculated with wt DEN2 (Tonga/74) or rDEN2 were viremic for 4-5 days with a mean peak titer of 2.1 or 1.9 $\log_{10}$PFU/ml, respectively.

Figure 7:
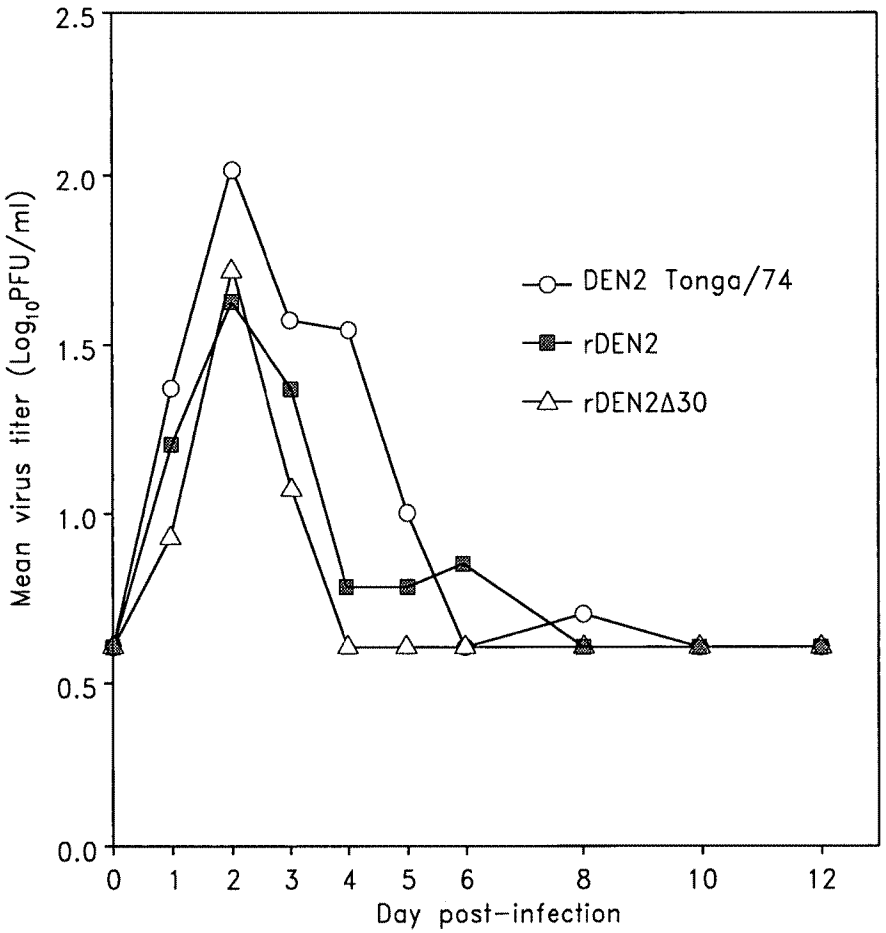
FIG. 7. Viremia levels in rhesus monkeys inoculated with DEN2 (Tonga/74), rDEN2, and rDEN2Δ30 vaccine candidate. Groups of four monkeys were inoculated with 5.0 $\log_{10}$PFU virus subcutaneously. Serum was collected daily and virus titers were determined by plaque assay in Vero cells. The limit of virus detection was 0.7 $\log_{10}$PFU/ml. Mean virus titers are indicated for each group. Viremia was not detected in any monkey after day 8.

Monkeys inoculated with rDEN2Δ30 were viremic for 2-3 days with a mean peak titer of 1.7 $\log_{10}$PFU/ml (Table 24, FIG. 7), indicating that the Δ30 mutation is capable of attenuating DEN2, although not to the same low level observed in rDEN1Δ30 (Table 16). As expected for an attenuated virus, the immune response, as measured by neutralizing antibody titer, was lower following inoculation with rDEN2Δ30 compared to inoculation with wt DEN2 (Tonga/74) or rDEN2 (Table 24), yet sufficiently high to protect the animals against wt DEN2 virus challenge (Table 25). Thus, the decreased number of days of viremia for rDEN2Δ30, the decreased mean peak titer, and the decreased serum antibody response indicate that the Δ30 mutation attenuates rDEN2 for rhesus monkeys.

TABLE 24 rDEN2Δ30 is slightly more attenuated for rhesus monkeys than rDEN2

| Virus[a] | No. of monkeys | No. of monkeys with viremia | Mean no. of viremic days per monkey[b] | Mean peak virus titer ($\log_{10}$ PFU/ml ± SE) | Geometric mean serum neutralizing antibody titer (reciprocal dilution) Day 0 | Day 28 |
|---|---|---|---|---|---|---|
| mock | 2 | 0 | 0 | <0.7 | <10 | <10 |
| DEN2 (Tonga/74) | 4 | 4 | 4.5 | 2.1 ± 0.3 | <10 | 311 |
| rDEN2 (Vero) | 4 | 4 | 4.0 | 1.9 ± 0.1 | <10 | 173 |
| rDEN2Δ30 (Vero) | 4 | 4 | 2.8 | 1.7 ± 0.2 | <10 | 91 |

[a]Groups of rhesus monkeys were inoculated subcutaneously with $10^5$ PFU of the indicated virus in a 1 ml dose. Serum was collected on days 0 to 6, 8, 10, 12, and 28. Virus titer was determined by plaque assay in Vero cells.
[b]Viremia was not detected in any monkey after day 8.

TABLE 25 rDEN2Δ30 protects rhesus monkeys from wt DENT2 virus challenge

| Virus[a] | No. of monkeys | Mean no. of viremic days per monkey after DEN2 challenge | Mean peak virus titer ($\log_{10}$ PFU/ml ± SE) | Geometric mean serum neutralizing antibody titer (reciprocal dilution) Day 28 | Day 56 |
|---|---|---|---|---|---|
| Mock | 2 | 4.0 | 2.1 ± 0.1 | <10 | 338 |
| DEN2 (Tonga/74) | 4 | 0 | <0.7 | 311 | 334 |

TABLE 25-continued rDEN2Δ30 protects rhesus monkeys from wt DENT2 virus challenge

| Virus[a] | No. of monkeys | Mean no. of viremic days per monkey after DEN2 challenge | Mean peak virus titer ($log_{10}$ PFU/ml ± SE) | Geometric mean serum neutralizing antibody titer (reciprocal dilution) Day 28 | Day 56 |
|---|---|---|---|---|---|
| rDEN2 (Vero) | 4 | 0 | <0.7 | 173 | 318 |
| rDEN2Δ30 (Vero) | 4 | 0 | <0.7 | 91 | 267 |

[a]28 days after inoculation with the indicated viruses, monkeys were challenged subcutaneously with $10^5$ PFU DEN2 (Tonga/74) in a 1 ml dose. Serum was collected on days 28 to 34, 36, 38, and 56. Virus titer was determined by plaque assay in Vero cells.

The infectivity of DEN2 (Tonga/74), rDEN2 and rDEN2Δ30 for Aedes aegypti mosquitoes via an artificial bloodmeal was evaluated using the methods described in detail in Example 5. However at doses of 3.3 to 3.5 $log_{10}$pfu ingested, none of these three viruses infected any mosquitoes, indicating that DEN2 (Tonga/74) is poorly infectious for Aedes aegypti. As with rDEN1, the genetic basis for this lack of infectivity remains to be defined. The important property of restricted infectivity for the mosquito midgut is highly desirable in a vaccine candidate because it would serve to greatly restrict transmission of the virus from a vaccinee to a mosquito vector.

Several missense mutation identified in rDEN4 have been demonstrated to confer attenuated replication in suckling mouse brain and/or SCID-HuH-7 mice (Blaney, J. E. et al. 2002 Virology 300:125-139; Blaney, J. E. et al. 2001 J Virol 75:9731-9740). In addition, missense mutations that enhance replication of rDEN4 virus in Vero cells have been characterized. The significant sequence conservation among the DEN virus serotypes provides a strategy by which the mutations identified in rDEN4 viruses are contemplated as being used to confer similar phenotypes upon rDEN2 virus. Six mutations identified in rDEN4 virus that are at a site conserved in rDEN2 virus are being introduced into the p2 and p2Δ30 cDNA clones (Table 26). Specifically, two rDEN4 mutations, NS3 4891 and 4995, which confer Vero cell adaptation phenotypes and decreased replication in mouse brain, one mutation, NS4B 7182, which confers a Vero cell adaptation phenotype, and three mutations, NS1 2650, NS3 5097, and 3' UTR 10634 which confer decreased replication in mouse brain and SCID-HuH-7 mice are being evaluated. These mutations have been introduced into subcloned fragments of the p2 and p2Δ30 cDNA clones, and have been used to generate mutant full-length cDNA clones (Table 26), from which virus has been recovered in C6/36 cells (Table 27). The evaluation of these mutant rDEN2 viruses is contemplated as determining that such point mutations can be transported into a different DEN virus serotype and confer a similar useful phenotype, as has been demonstrated for the Δ30 deletion mutation.

TABLE 26

Introduction of conserved point mutations characterized in rDEN4 viruses into rDEN2 Tonga/74 virus.

| Phenotype in rDEN4 virus | | | Mutation in rDEN4 virus | | | | Mutation introduced into DEN2 virus | | | | |
|---|---|---|---|---|---|---|---|---|---|---|---|
| Vero Adaptation[a] | Mouse brain att[b] | SCID-HuH-7 att[c] | Gene/region | Nucleotide position | Amino acid position[d] | Amino acid change | Nucleotide position | Amino acid position[d] | Amino acid change | RE site/mutagenic region[e] |
| + | + | - | NS3 | 4891 | 1597 | Ile > Thr | 4889 | 1598 | Ile > Thr | Nar I CCAcgGGcGCCGT |
| + | + | - | NS3 | 4995 | 1632 | Ser > Pro | 4993 | 1633 | Ser > Pro | Stu I AAGGccTGGA |
| + | - | - | NS4b | 7182 | 2361 | Gly > Ser | 7189 | 2365 | Gly > Ser | Xma I TAtccCCGGGAC |
| - | + | + | NS1 | 2650 | 850 | Asn > Ser | 2648 | 851 | Asn > Ser | Sac I AGAgcTctcTC |
| - | + | + | NS3 | 5097 | 1666 | Asp > Asn | 5095 | 1667 | Asp > Asn | Xma I GaATCTCCACCCgGA |

TABLE 26-continued

Introduction of conserved point mutations characterized in rDEN4 viruses into rDEN2 Tonga/74 virus.

| Phenotype in rDEN4 virus | | | | Mutation in rDEN4 virus | | | Mutation introduced into DEN2 virus | | | |
|---|---|---|---|---|---|---|---|---|---|---|
| Vero Adaptation[a] | MouseSCID-brainHuH-7 att[b] | att[c] | Gene/region | Nucleotide position | Amino acid position[d] | Amino acid change | Nucleotide position | Amino acid position[d] | Amino acid change | RE site/mutagenic region[e] |
| – | + | + | 3' UTR | 10634 | n/a[f] | n/a | 10698 | n/a | n/a | none CTGTcGAATC |

[a]Presence of the indicated mutation increases plaque size in Vero cells two-fold or greater than rDEN4 virus.
[b]Presence of the indicated mutation restricts replication in 7-day-old mouse brain greater than 100-fold compared to rDEN4 virus.
[c]Presence of the indicated mutation restricts replication in SCID-HuH-7 mice greater than 100-fold compared to rDEN4 virus.
[d]Amino acid position in DEN4 or DEN2 polyprotein beginning with the methionine residue of the C protein (nucleotides 102-104 or 97-99, respectively) as position 1.
[e]Primers were engineered which introduced (underline) translationally-silent restriction enzyme (RE) sites. Lowercase letters indicate nt changes and bold letters indicate the site of the 5-FU mutation, which in some oligonucleotides differs from the original nucleotide substitution change in order to create a unique RE site. The change preserves the codon for the amino acid substitution.
[f]Nucleotide substitution in the 3' UTR is U > C in DEN4 and DEN2 virus.

TABLE 27 rDEN2 viruses containing conserved 5-FU mutations are recovered in C6/36 cells.

| Virus (nucleotide position in rDEN2) | Nucleotide position in rDEN4 | Virus titer of transfection harvest (day 7) determined in C6/36 cells ($log_{10}$ PFU/ml) |
|---|---|---|
| rDEN2-4889 | 4891 | 7.6 |
| rDEN2-4993 | 4995 | 7.2 |
| rDEN2-7189 | 7182 | 3.5 |
| rDEN2-2648 | 2650 | —[a] |
| rDEN2-5095 | 5097 | —[a] |
| rDEN2-10698 | 10634 | 7.7 |

[a]Transfection has not yet been attempted.

EXAMPLE 4

Generation and Characterization of a Recombinant DEN3 Virus Containing the Δ30 Mutation Because rDEN1Δ30 was satisfactorily attenuated, we sought to extend our technology to the creation of a DEN3 vaccine candidate. To do this, the Δ30 mutation was introduced into the cDNA of DEN3, similar to the method used to create rDEN2Δ30. A DEN3 virus isolate from a 1978 dengue epidemic in rural Sleman, Central Indonesia (Sleman/78) (Gubler, D. J. et al. 1981 Am J Trop Med Hyg 30:1094-1099) was chosen to represent wt DEN3. The genome of DEN3 (Sleman/78) was sequenced in its entirety and served as consensus sequence for the construction of a full-length cDNA clone (Appendix 2). cDNA fragments of DEN3 (Sleman/78) were generated by reverse-transcription of the genome as indicated in FIG. 8A. Each fragment was subcloned into a plasmid vector and sequenced to verify that it matched the consensus sequence as determined for the virus. This yielded six cloned cDNA fragments spanning the genome. Cloned fragments were modified as follows: Fragment 5, representing the 5' end of the genome was abutted to the SP6 promoter preceded by an AscI restriction site; Fragment 1L was modified to contain a translationally-silent SpeI restriction site at genomic nucleotide 2345; Fragment 1R was modified to contain a translationally-silent SpeI restriction site also at genomic nucleotide 2345, and to stabilize the eventual full-length clone, three additional translationally-silent mutations at nucleotides 2354-2356, 2360-2362, and 2399 were created to ensure that translation stop codons were present in all reading frames other than that used to synthesize the virus polyprotein; Fragment 3 was modified at nucleotide 9007 to ablate a naturally occurring KpnI restriction site; and Fragment 4, representing the 3' end of the genome was abutted to a KpnI restriction site. Each fragment was added incrementally between the AscI and KpnI restriction sites of DEN4 cDNA clone p4 (Durbin, A. P. et al. 2001 Am J Trop Med Hyg 65:405-13) to generate a full-length DEN3 cDNA clone with the same vector background successfully used to generate rDEN4 and rDEN2. However, a stable, full-length clone could not be recovered in E. coli when fragments 1L and 1R were combined into the same cDNA molecule. To overcome this instability, a synthetic DNA linker (FIG. 8A) containing redundant termination codons in each of the forward and reverse open reading frames was introduced into the SpeI restriction site at the same time that fragment 1L was added to complete the full-length cDNA construct. The resulting p3 clone containing the linker sequence was stable in E. coli, indicating that the linker sequence was sufficient to interrupt whatever deleterious element exists in this region. cDNA clone p3 was sequenced and the virus genome was found to match the DEN3 (Sleman/78) consensus sequence, with the exception of the linker sequence and translationally-silent modifications noted above (Appendix 2—shown with the linker sequence removed). The Δ30 mutation was introduced into Fragment 4 to generate Fragment 4Δ30. To create p3Δ30, the Fragment 4 region of p3 was replaced with Fragment 4Δ30 (FIG. 8A, B).

For transcription and generation of infectious virus, cDNA plasmids p3 and p3Δ30 were digested with SpeI and religated to remove the linker sequence, linearized with Acc65I (isoschizomer of KpnI which cleaves leaving only a single 3' nucleotide), and used as templates in a transcription reaction using SP6 RNA polymerase as previously described (Blaney, J. E. et. al. 2002 Virology 300:125-139). Transcripts were introduced into Vero cells or C6/36 mosquito cells using liposome-mediated transfection and cell culture supernatants were harvested on day 14.

rDEN3 virus was recovered from the p3 cDNA in both Vero and C6/36 cells, while rDEN3Δ30 was recovered from the p3Δ30 cDNA clone in only C6/36 cells (Table 28). The level of infectious virus recovered in C6/36 cells was comparable for the p3 and p3Δ30 cDNA clones when assayed by plaque titration in Vero or C6/36 cells. As previously observed, the efficiency of transfection in C6/36 cells was higher than that in Vero cells. Two rDEN3Δ30 viruses were recovered from independent cDNA clones, #22 and #41.

TABLE 28 rDEN3 virus is recovered in Vero and C6/36 cells, but rDEN3Δ30 virus is recovered only in C6/36 cells.

| Transfection cell type | cDNA construct | Clone | Virus | Virus titer of transfection harvest (day 14) determined in the indicated cell type ($log_{10}$ PFU/ml) Vero cells | C6/36 cells |
|---|---|---|---|---|---|
| Vero cells | p3 | #50 | rDEN3 | 5.2 | 6.3 |
| | p3Δ30 | #22 | rDEN3Δ30 | <0.7 | <0.7 |
| | p3Δ30 | #41 | rDEN3Δ30 | <0.7 | <0.7 |
| C6/36 cells | p3 | #50 | rDEN3 | 5.2 | 6.0 |
| | p3Δ30 | #22 | rDEN3Δ30 | 5.9 | 6.9 |
| | p3Δ30 | #41 | rDEN3Δ30 | 5.1 | 7.2 |

To produce working stocks of viruses, transfection harvests will be passaged and terminally diluted in Vero cells, and genomic sequences of the viruses will be determined. To improve virus yield in Vero cells, the Vero cell adaptation mutation previously identified in rDEN4 at nucleotide 7162 was introduced into the homologous NS4B region of p3 and p3Δ30 to create p3-7164 and p3Δ30-7164. This mutation creates a Val to Ala substitution at amino acid position 2357. As demonstrated for rDEN2Δ30, this mutation allowed for the direct recovery of virus in Vero cells (Table 27) and is anticipated to have the same effect for rDEN3Δ30.

To initially assess the ability of the Δ30 mutation to attenuate rDEN3 virus in an animal model, the replication of DEN3 (Sleman/78), rDEN3, and rDEN3Δ30 viruses will be evaluated in SCID-HuH-7 mice and rhesus monkeys. Previously, attenuation of vaccine candidates in SCID-HuH-7 mice has been demonstrated to be predictive of attenuation in the rhesus monkey model of infection (Examples 1 and 2). The evaluation of these mutant rDEN3 viruses is contemplated as determining that the Δ30 deletion mutations can be transported into the DEN3 virus serotype and confer a similar useful phenotype, as has been demonstrated for DEN1, DEN2, and DEN4.

In summary, the strategy of introducing the Δ30 mutation into wild-type DEN viruses of each serotype to generate a suitably attenuated tetravalent vaccine formulation is a unique and attractive approach for several reasons. First, the mutation responsible for attenuation is a 30-nucleotide deletion in the 3' UTR, thus assuring that all of the structural and non-structural proteins expressed by each of the four components of the tetravalent vaccine are authentic wild-type proteins. Such wild-type proteins should elicit an antibody response that is broad based, rather than based solely on the M and E proteins that are present in chimeric dengue virus vaccine candidates (Guirakhoo, F. et al. 2001 J Virol 75:7290-304; Huang, C. Y. et al. 2000 J Virol 74:3020-8). The uniqueness of this approach derives from the fact that other live attenuated dengue virus vaccines have mutations in their structural or non-structural proteins (Butrapet, S. et al. 2000 J Virol 74:3011-9; Puri, B. et al. 1997 J Gen Virol 78:2287-91), therefore the immune response induced by these viruses will be to a mutant protein, rather than a wild-type protein. Second, deletion mutations are genetically more stable than point mutations, and reversion of the attenuation phenotype is unlikely. In humans, DEN4Δ30 present in serum of vaccinees retained its Δ30 mutation, confirming its genetic stability in vivo (Durbin, A. P. et al. 2001 Am J Trop Med Hyg 65:405-13). The attenuating mutations in other existing dengue live attenuated vaccine candidates are based on less stable point mutations (Butrapet, S. et al. 2000 J Virol 74:3011-9: Puri, B. et al. 1997 J Gen Virol 78:2287-91). Third, since the Δ30 mutation is common to each of the four viruses of the tetravalent vaccine, recombination between any of the four vaccine serotypes would not lead to loss of the attenuating mutation or reversion to a wild-type phenotype. Recombination between components of the trivalent polio vaccine has been observed (Guillot, S. et al. 2000 J Virol 74:8434-43), and naturally occurring recombinant dengue viruses have been described (Worobey, M. et al. 1999 PNAS USA 96:7352-7) indicating the ability of this flavivirus to exchange genetic elements between two different viruses. Clearly, gene exchange is readily achieved between different DEN virus serotypes using recombinant cDNA techniques (Bray, M. and Lai, C. J. 1991 PNAS USA 88:10342-6). Fourth, viruses with wild-type structural proteins appear more infectious than viruses with altered structural proteins (Huang, C. Y. et al. 2000 J Virol 74:3020-80). This permits the use of a low quantity of each of the four virus components in the final vaccine, contributing to the low cost of manufacture. Low-cost manufacture is an essential element in defining the ultimate utility of a dengue virus vaccine.

EXAMPLE 5

Generation and Characterization of Intertypic Chimeric DEN2 Viruses Containing the Δ30 Mutation The four serotypes of dengue virus are defined by antibody responses induced by the structural proteins of the virus, primarily by a neutralizing antibody response to the envelope (E) protein. These structural proteins include the E glycoprotein, a membrane protein (M), and a capsid (C) protein. The mature virus particle consists of a well-organized outer protein shell surrounding a lipid bilayer membrane and a less-well-defined inner nucleocapsid core (Kuhn, R. J. et al. 2002 Cell 108:717-25). The E glycoprotein is the major protective antigen and readily induces virus neutralizing antibodies that confer protection against dengue virus infection. An effective dengue vaccine must therefore minimally contain the E protein of all four serotypes, namely DEN1, DEN2, DEN3, and DEN4, thereby inducing broad immunity and precluding the possibility of developing the more serious illnesses DHF/DSS, which occur in humans during secondary infection with a heterotypic wild-type dengue virus. Based on a previously reported strategy (Bray, M. and Lai, C. J. 1991 PNAS USA 88:10342-6), a recombinant cDNA technology is being used to develop a live attenuated tetravalent dengue virus vaccine composed of a set of intertypic chimeric dengue viruses bearing the structural proteins of each serotype.

Figure 9A:
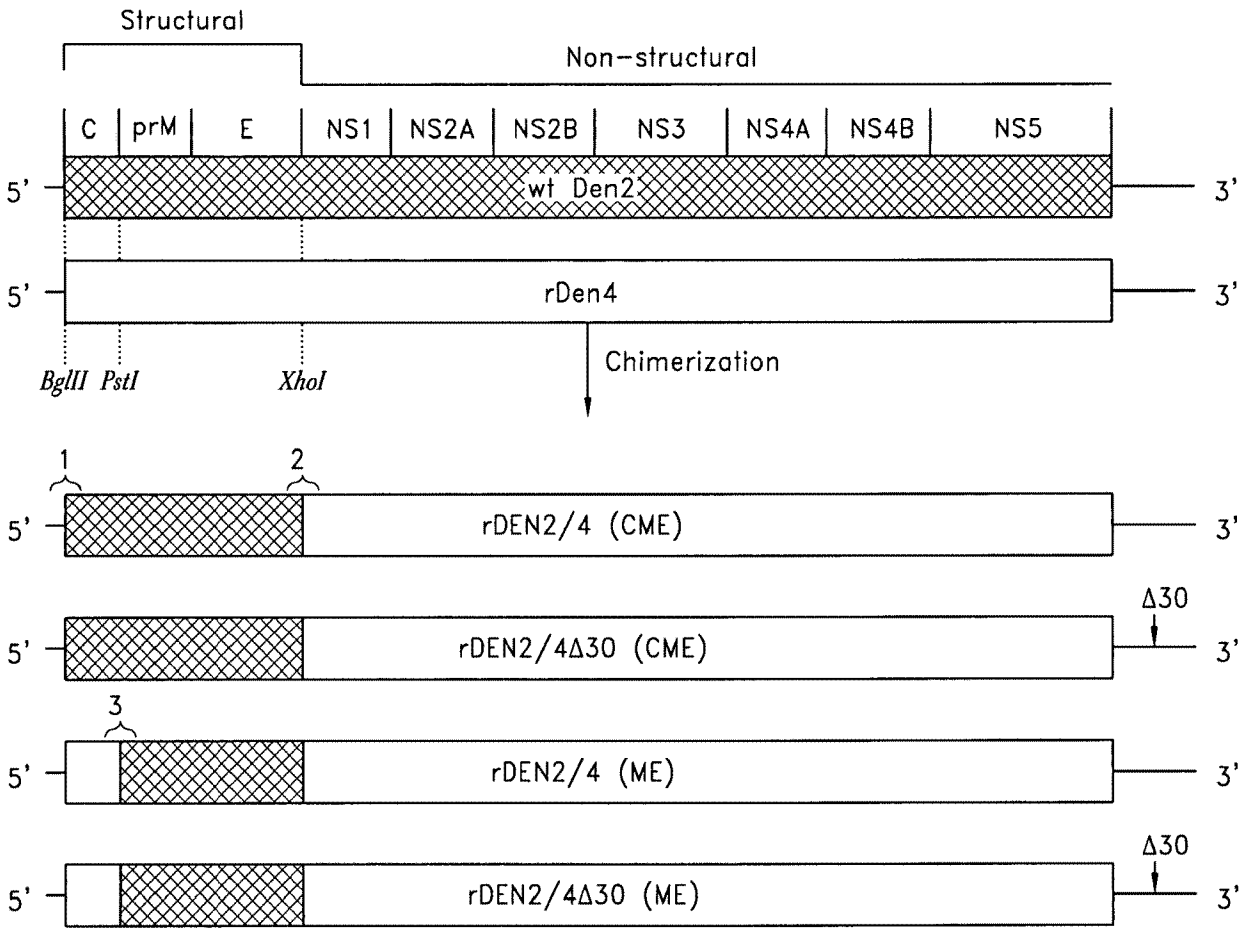
FIG. 9. A. Recombinant chimeric dengue viruses were constructed by introducing either the CME or the ME regions of DEN2 (Tonga/74) into the DEN4 genetic background. The relative location of the Δ30 mutation in the 3' UTR is indicated by an arrow and intertypic junctions 1, 2, and 3 are indicated. B. Nucleotide and amino acid sequence of the intertypic junction regions. Restriction enzyme recognition sites used in assembly of each chimeric cDNA are indicated.

Following the identification of a suitably attenuated and immunogenic DEN4 recombinant virus, namely DEN4Δ30 (Durbin, A. P et al. 2001 Am J Trop Med Hyg 65:405-13), chimeric viruses based on the DEN4 cDNA have been generated in which the C-M-E (CME) or M-E (ME) genes have been replaced with the corresponding genes derived from the prototypic DEN2 New Guinea C (NGC) strain (FIG. 9A). To create the CME chimeric viruses, the BglII/XhoI region of the cDNA for either rDEN4 or rDEN4Δ30 was replaced with a similar region derived from DEN2. Likewise, to create the ME chimeric viruses, the PstI/XhoI region of the cDNA for either rDEN4 or rDEN4Δ30 was replaced with a homologous region derived from DEN2. The nucleotide and amino acid sequences of the resulting junctions are shown in FIG. 9B. The GenBank accession number for the nucleotide sequence of rDEN4Δ30 is AF326837. The GenBank accession number for DEN2 NGC is M29095, which represents the mouse neurovirulent strain of DEN2 NGC and differs from the prototypic strain used here as previously documented (Bray, M. et al. 1998 J Virol 72:1647-51).

For transcription and generation of virus, chimeric cDNA clones were linearized and used as template in a transcription reaction using SP6 RNA polymerase as described (Durbin, A. P et al. 2001 Am J Trop Med Hyg 65:405-13). Transcripts were introduced into Vero cells using liposome-mediated transfection and recombinant dengue virus was harvested on day 7. The genomes of the resulting viruses were confirmed by sequence analysis of viral RNA isolated from recovered virus as previously described (Durbin, A. P et al. 2001 Am J Trop Med Hyg 65:405-13). Incidental mutations arising from virus passage in tissue culture were identified in all viruses and are listed in Table 29. Notably, each virus contained a missense mutation in NS4B corresponding to a previously identified mutation from rDEN4 and associated with adaptation to replication in Vero cells (See Table 30 for correlation of nucleotide positions between rDEN4 and chimeric viruses). All viruses replicated in Vero cells to titers in excess of 6.0 $\log_{10}$PFU/ml, indicating that the chimeric viruses, even those containing the Δ30 mutation, replicate efficiently in cell culture, a property essential for manufacture of the vaccine.

TABLE 29

Missense mutations observed among the Vero cell-grown chimeric DEN2/4 viruses

| Virus | Gene | Nucleotide position | Nucleotide change | Amino acid position | Amino acid change |
|---|---|---|---|---|---|
| rDEN2/4(CME) | NS4B | 7161[a] | A > U | 2355 | Leu > Phe |
| rDEN2/4Δ30(CME) | M | 743 | G > A | 216 | Gly > Glu |
| | E | 1493 | C > U | 466 | Ser > Phe |
| | NS4B | 7544[b] | C > T | 2483 | Ala > Val |
| rDEN2/4(ME) | E | 1065 | U > C | 322 | Phe > Leu |
| | NS4B | 7163[a] | A > U | 2354 | Leu > Phe |
| rDEN2/4Δ30(ME) | NS4B | 7163[a] | A > C | 2354 | Leu > Phe |

[a]Same nucleotide position as 7163 in rDEN4.
[b]Same nucleotide position as 7546 in rDEN4.

TABLE 30

Nucleotide (nt) length differences for DEN chimeric viruses compared to rDEN4.

| rDEN chimeric virus | nt difference from rDEN4 (following CME region) | ORF start (nt position) | Amino acid length C | M | E |
|---|---|---|---|---|---|
| 1/4 ME | 0 | 102 | 113 | 166 | 495 |
| 1/4 CME | +3 | 102 | 114 | 166 | 495 |
| 2/4 ME | 0 | 102 | 113 | 166 | 495 |
| 2/4 CME | −2 | 97 | 114 | 166 | 495 |
| 3/4 ME | −6 | 102 | 113 | 166 | 493 |

TABLE 30-continued

Nucleotide (nt) length differences for DEN chimeric viruses compared to rDEN4.

| rDEN chimeric virus | nt difference from rDEN4 (following CME region) | ORF start (nt position) | Amino acid length C | M | E |
|---|---|---|---|---|---|
| 3/4 CME | −3 | 102 | 114 | 166 | 493 |
| rDEN4 | — | 102 | 113 | 166 | 495 |

Results of a safety, immunogenicity, and efficacy study in monkeys are presented in Table 31. Monkeys inoculated with wild-type DEN2 were viremic for approximately 5 days with a mean peak titer of 2.1 $\log_{10}$PFU/ml, while monkeys inoculated with any of the chimeric DEN2 viruses were viremic for 1.2 days or less and had a mean peak titer of less than 1.0 $\log_{10}$PFU/ml. This reduction in the magnitude and duration of viremia clearly indicates that the chimeric viruses containing either the CME or ME proteins of DEN2 were more attenuated than the parental DEN2 NGC virus. Neither the animals receiving the wild-type DEN2 nor the DEN2/4 chimeric viruses were ill. The decreased replication of the attenuated viruses in monkeys is accompanied by a reduction in the immune response of inoculated monkeys. This is indicated in Table 31 by approximately a 5-fold reduction in the level of neutralizing antibody following inoculation with the chimeric viruses in comparison to titers achieved in animals inoculated with wild-type virus. Addition of the Δ30 mutation to the CME chimeric virus further attenuated the virus, such that rDEN2/4Δ30(CME) did not replicate in monkeys to a detectable level and did not induce a detectable immune response. This virus appeared over-attenuated, and if similar results were seen in humans, this virus would not be suitable for use as a vaccine. However, addition of the Δ30 mutation to the ME chimeric virus did not further attenuate this chimeric virus and the resulting rDEN2/4Δ30(ME) virus appears satisfactorily attenuated and immunogenic for use as a vaccine.

TABLE 31

Chimerization between dengue virus types 2 and 4 results in recombinant viruses which are attenuated for rhesus monkeys.

| Group* | Virus | n | Mean no. days with viremia | Mean peak virus titer ($\log_{10}$ pfu/ml) | Geometric mean neutralizing antibody titer (reciprocal) |
|---|---|---|---|---|---|
| 1 | rDEN2/4 (CME) | 6 | 1.2 | 0.9 | 50 |
| 2 | rDEN2/4Δ30 (CME) | 8 | 0 | <0.7 | <5 |
| 3 | rDEN2/4 (ME) | 4 | 1.0 | 0.8 | 76 |
| 4 | rDEN2/4Δ30 (ME) | 4 | 0.3 | 0.7 | 62 |
| 5 | DEN2 NGC | 6 | 5.5 | 2.1 | 312 |

*Rhesus monkeys were inoculated subcutaneously with 5.0 $\log_{10}$ PFU of virus. Serum samples were collected daily for 10 days. Serum for neutralization assay was collected on day 28. Serum samples obtained before virus inoculation had a neutralizing antibody titer of <5.

As described in the previous examples, SCID mice transplanted with the HuH-7 cells are a sensitive model for the evaluation of dengue virus attenuation. Each chimeric DEN2/4 virus was inoculated into groups of SCID-HuH-7 mice and levels of virus in the serum were determined (Table 32). Chimeric viruses replicated to levels between 20- and 150-fold lower than either of the parental viruses (rDEN4 and DEN2-NGC). CME chimeric viruses were slightly more attenuated than the comparable ME chimeric viruses, with the Δ30 mutation providing a 0.5 $\log_{10}$ reduction in replication. This level of attenuation by the Δ30 mutation was similar to that observed previously for rDEN4Δ30.

TABLE 32

Chimerization between dengue virus types 2 and 4 results in recombinant viruses which are attenuated for HuH-7-SCID mice.

| Virus[a] | No. of mice | Mean peak virus titer ($\log_{10}$ pfu/ml ± SE) | Statistical group[b] |
|---|---|---|---|
| rDEN4 | 32 | 6.3 ± 0.2 | A |
| DEN2-NGC | 9 | 6.1 ± 0.2 | A |
| rDEN2/4 (CME) | 7 | 4.4 ± 0.3 | B |
| rDEN2/4Δ30 (CME) | 7 | 3.9 ± 0.3 | B |
| rDEN2/4 (ME) | 6 | 4.8 ± 0.5 | B |
| rDEN2/4Δ30 (ME) | 9 | 4.3 ± 0.2 | B |

[a]Groups of HuH-7-SCID mice were inoculated into the tumor with 4.0 $\log_{10}$ PFU of the indicated virus. Serum was collected on day 7 and virus titer was determined in Vero cells.
[b]Mean peak titers were assigned to statistical groups using the Tukey post-hoc test ($P < 0.05$). Groups with the same letter designation are not significantly different.

To evaluate the replication levels of each DEN2/4 chimeric virus in mosquitoes, two different genera of mosquitoes were experimentally infected. Aedes aegypti were infected by ingesting a virus-containing blood meal. By evaluating the presence of virus antigen in both the midgut and head tissue, infectivity could be determined for the local tissues (midgut), and the ability of virus to disseminate and replicate in tissues beyond the midgut barrier (head) could also be measured. The presence of virus in the head is limited by the ability of the ingested virus to replicate in the midgut and then disseminate to the salivary glands in the head, as well as the innate ability of the virus to replicate in the salivary glands. Intrathoracic inoculation of virus into Toxorhynchites splendens bypasses the mosquito midgut barrier. Parental viruses rDEN4 and DEN2-NGC readily infect Ae. aegypti and T splendens (Table 33), with DEN2-NGC appearing to be much more infectious in T. splendens. Each of the rDEN2/4 chimeric viruses was also tested in both mosquito types. In many cases it was not possible to inoculate Ae. aegypti with an undiluted virus stock of sufficient titer to achieve a detectable infection due to the very low infectivity of several of the viruses. Nevertheless, it is clear that the rDEN2/4 chimeric viruses are less infectious for the midgut and head. Parental viruses rDEN4 and DEN2-NGC, administered at a maximum dose of approximately 4.0 $\log_{10}$PFU, were detectable in 74% and 94% of midgut preparations, and 32% and 71% of head preparations, respectively. Among the chimeric viruses, the highest level of infectivity, as observed for rDEN2/4Δ30 (CME), resulted in only 26% infected midgut samples and 6% head samples. In the more permissive T. splendens, the rDEN2/4 chimeric viruses were generally less infectious than either parental virus, with CME chimeric viruses being less infectious than ME viruses. It has previously been reported for DEN4 that the Δ30 mutation does not have a discernable effect on virus infectivity in T. splendens similar to that observed here for the rDEN2/4 chimeric viruses (Troyer, J. M. et al. 2001 Am J Trop Med Hyg 65:414-419).

TABLE 33

Dengue 2/4 chimeric viruses are less infectious compared to either parental virus strain in mosquitoes

| | *Toxorhynchites splendens* (intrathoracic inoculation) | | | *Aedes aegypti* (oral infection) | | | |
|---|---|---|---|---|---|---|---|
| | Dose[a] | No. | % | Dose[c] | No. | % infected[d] | |
| Virus | $\log_{10}$ pfu | tested | infected[b] | $\log_{10}$ pfu | tested | Midgut | Head |
| rDEN4 | 3.3 | 6 | 83 | 3.8 | 38 | 74 | 32 |
| | 2.3 | 7 | 57 | 2.8 | 15 | 26 | 6 |
| | 1.3 | 6 | 0 | 1.8 | 20 | 10 | 5 |
| | | | $MID_{50}$ = 2.2 | | | $MID_{50}$ = 3.4 | $MID_{50}$ ≥ 4.1 |
| DEN2-NGC | 2.5 | 5 | 100 | 4.0 | 17 | 94 | 71 |
| | 1.2 | 15 | 93 | 3.0 | 25 | 36 | 16 |
| | 0.2 | 4 | 75 | 2.0 | 30 | 0 | 0 |
| | 0.02 | 8 | 38 | | | $MID_{50}$ = 3.2 | $MID_{50}$ = 3.6 |
| | | | $MID_{50}$ = 0.5 | | | | |
| rDEN2/4 (CME) | 3.9 | 9 | 11 | 4.4 | 11 | 9 | 0 |
| | 2.9 | 5 | 0 | 3.4 | 10 | 0 | 0 |
| | | | $MID_{50}$ ≥ 4.3 | | | $MID_{50}$ ≥ 4.9 | Nc[e] |
| rDEN2/4Δ30 | 3.5 | 6 | 17 | 4.0 | 15 | 26 | 6 |
| (CME) | 2.5 | 6 | 17 | 3.0 | 10 | 0 | 0 |
| | | | $MID_{50}$ ≥ 3.9 | | | $MID_{50}$ ≥ 4.3 | $MID_{50}$ ≥ 4.5 |
| rDEN2/4 (ME) | 3.4 | 6 | 100 | 3.9 | 23 | 4 | 0 |
| | 2.4 | 5 | 20 | | | $MID_{50}$ ≥ 4.4 | Nc |
| | 1.4 | 5 | 0 | | | | |
| | | | $MID_{50}$ = 2.8 | | | | |
| rDEN2/4Δ30 | 2.6 | 11 | 9 | 3.1 | 30 | 0 | 0 |
| (ME) | | | $MID_{50}$ ≥ 3.0 | | | nc | Nc |

[a]Amount of virus present in 0.22 μl inoculum.
[b]Percentage of mosquitoes with IFA detectable antigen in head tissue prepared 14 days after inoculation.
[c]Virus titer ingested, assuming a 2 μl bloodmeal.
[d]Percentage of mosquitoes with IFA detectable antigen in midgut or head tissue prepared 21 days after oral infection. When virus infection was detected, but did not exceed a frequency of 50% at the highest dose of virus ingested, the $MID_{50}$ was estimated by assuming that a 10-fold more concentrated virus dose would infect 100% of the mosquitoes.
[e]nc = not calculated, since virus antigen was not detected.

Chimerization of the DEN2 structural genes with rDEN4Δ30 virus resulted in a virus, rDEN2/4Δ30(CME), that had decreased replication in Vero cells compared to either parent virus. To evaluate Vero cell adaptation mutations (Blaney, J. E. et al. 2002 Virology 300:125-139) as a means of increasing the virus yield of a DEN vaccine candidate in Vero cells, selected mutations were introduced into this chimeric virus. Accordingly, rDEN2/4Δ30(CME) viruses bearing adaptation mutations were recovered, terminally diluted, and propagated in C6/36 cells to determine if the virus yield in Vero cells could be increased.

rDEN2/4Δ30(CME) viruses bearing Vero cell adaptation mutations were generated as follows. DNA fragments were excised from rDEN4 cDNA constructs encompassing single or double DEN4 Vero cell adaptation mutations and introduced into the cDNA clone of rDEN2/4Δ30(CME). The presence of the Vero cell adaptation mutation was confirmed by sequence analysis, and RNA transcripts derived from the mutant cDNA clones were transfected, terminally diluted, and propagated in C6/36 cells.

For evaluation of growth kinetics, Vero cells were infected with the indicated viruses at a multiplicity of infection (MOI) of 0.01. Confluent cell monolayers in duplicate 25-$cm^2$ tissue culture flasks were washed and overlaid with a 1 ml inoculum containing the indicated virus. After a two hour incubation at 37° C., cells were washed three times in MEM and 5 ml of MEM supplemented with 2% FBS was added. A 1 ml aliquot of tissue culture medium was removed, replaced with fresh medium, and designated the day 0 time-point. At the indicated time points post-infection, 1 ml samples of tissue culture medium were removed, clarified by centrifugation, and frozen at −80° C. The level of virus replication was assayed by plaque titration in C6/36 cells and visualized by immunoperoxidase staining. The limit of detection was <0.7 $\log_{10}$PFU/ml.

Figure 10:
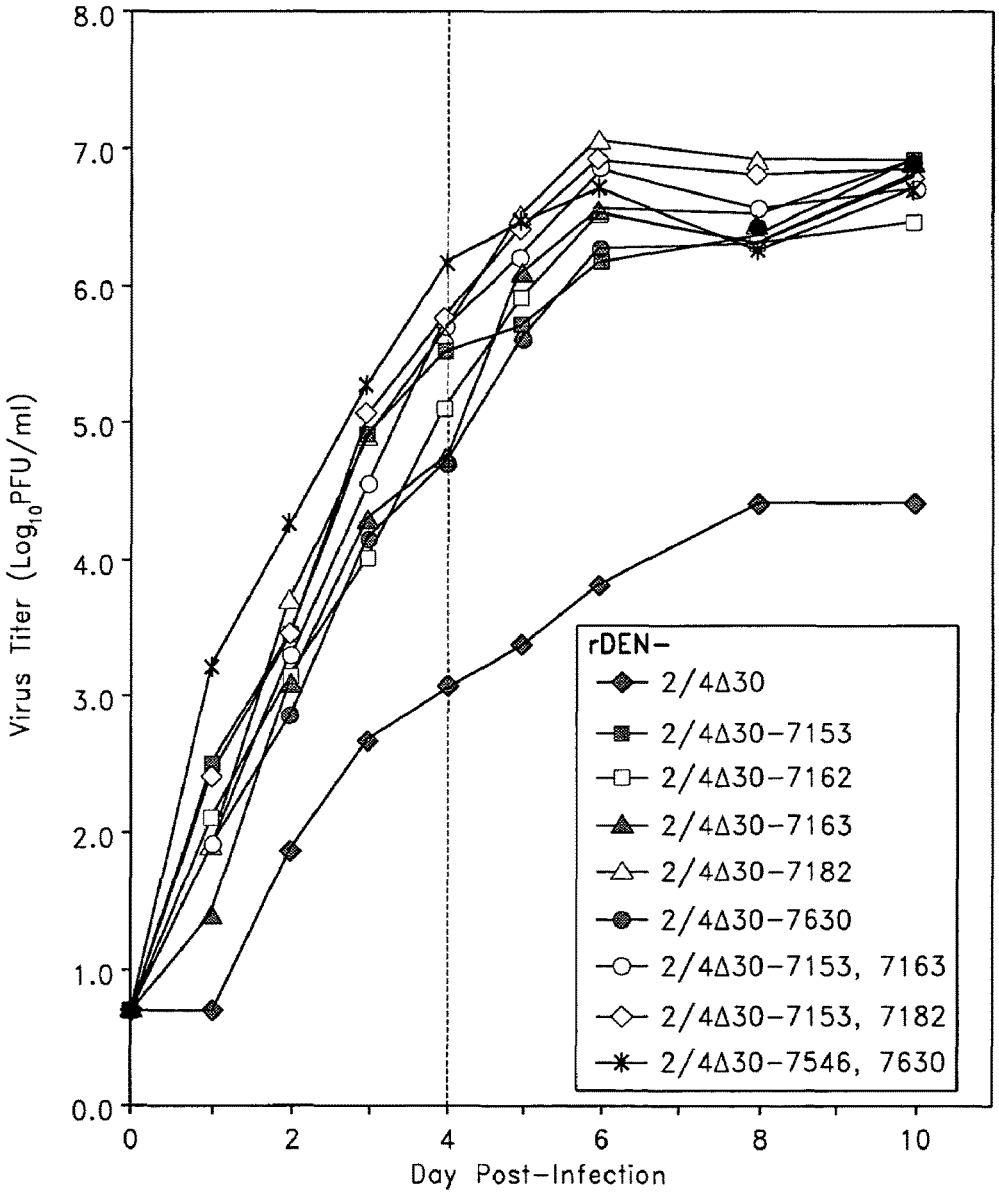
FIG. 10. Growth kinetics in Vero cells of chimeric rDEN2/4Δ30 viruses encoding single or combined Vero cell adaptation mutations. Vero cells were infected with the indicated viruses at an MOI of 0.01. At the indicated time points post-infection, 1 ml samples of tissue culture medium were removed, clarified by centrifugation, and frozen at −80° C. The level of virus replication was assayed by plaque titration in C6/36 cells. Lower limit of detection was 0.7 $\log_{10}$PFU/ml. Replication levels on day 4 post-infection are indicated by the dashed line.

The growth properties of rDEN2/4Δ30(CME) viruses bearing single Vero cell adaptation mutations at NS4B-7153, -7162, -7163, -7182, NS5-7630 or three combinations of mutations were compared in Vero cells with rDEN2/4Δ30 (CME) virus (FIG. 10). Without an introduced Vero cell adaptation mutation, rDEN2/4Δ30(CME) virus yield peaked at 4.4 $\log_{10}$PFU/ml. Each individual adaptation mutation and the combined mutations conferred a substantial increase in replication. Specifically, rDEN2/4Δ30(CME)-7182 grew to the highest titer of 7.1 $\log_{10}$PFU/ml, which was a 500-fold increase in yield. rDEN2/4Δ30(CME)-7162 had the lowest yield but still was increased 125-fold over the level of replication by rDEN2/4Δ30(CME) virus. Introduction of two adaptation mutations into rDEN2/4Δ30(CME) virus did not significantly increase virus yield over that of viruses bearing single Vero cell adaptation mutations. The observed increase of up to 500-fold in virus yield by the introduction of a Vero cell adaptation mutation into this chimeric vaccine candidate demonstrates the value of identifying and characterizing specific replication-promoting sequences in DEN viruses.

These results have particular significance for the development of a live attenuated dengue virus vaccine. First, it is clear that chimerization leads to attenuation of the resulting virus, as indicated by studies in rhesus monkeys, HuH7-SCID mice and mosquitoes. Although this conclusion was not made in the previous study with DEN2/DEN4 or DEN1/DEN4 chimeric viruses (Bray, M. et al. 1996 J Virol 70:4162-6), careful examination of the data would suggest that the chimeric viruses are more attenuated in monkeys compared to the wild-type parent viruses. Second, the Δ30 mutation can further augment this attenuation in a chimeric-dependent manner. Specifically, in this example, chimeric viruses bearing the CME region of DEN2 were over-attenuated by the addition of Δ30, whereas the attenuation phenotype of chimeric viruses bearing just the ME region of DEN2 was unaltered by the addition of the Δ30 mutation. This unexpected finding indicates that in a tetravalent vaccine comprised of individual component viruses bearing a shared attenuating mutation, such as the Δ30 mutation, only ME chimeric viruses can be utilized since CME chimeric viruses bearing the Δ30 mutation can be over-attenuated in rhesus monkeys and might provide only limited immunogenicity in humans.

EXAMPLE 6

Figure 11A:
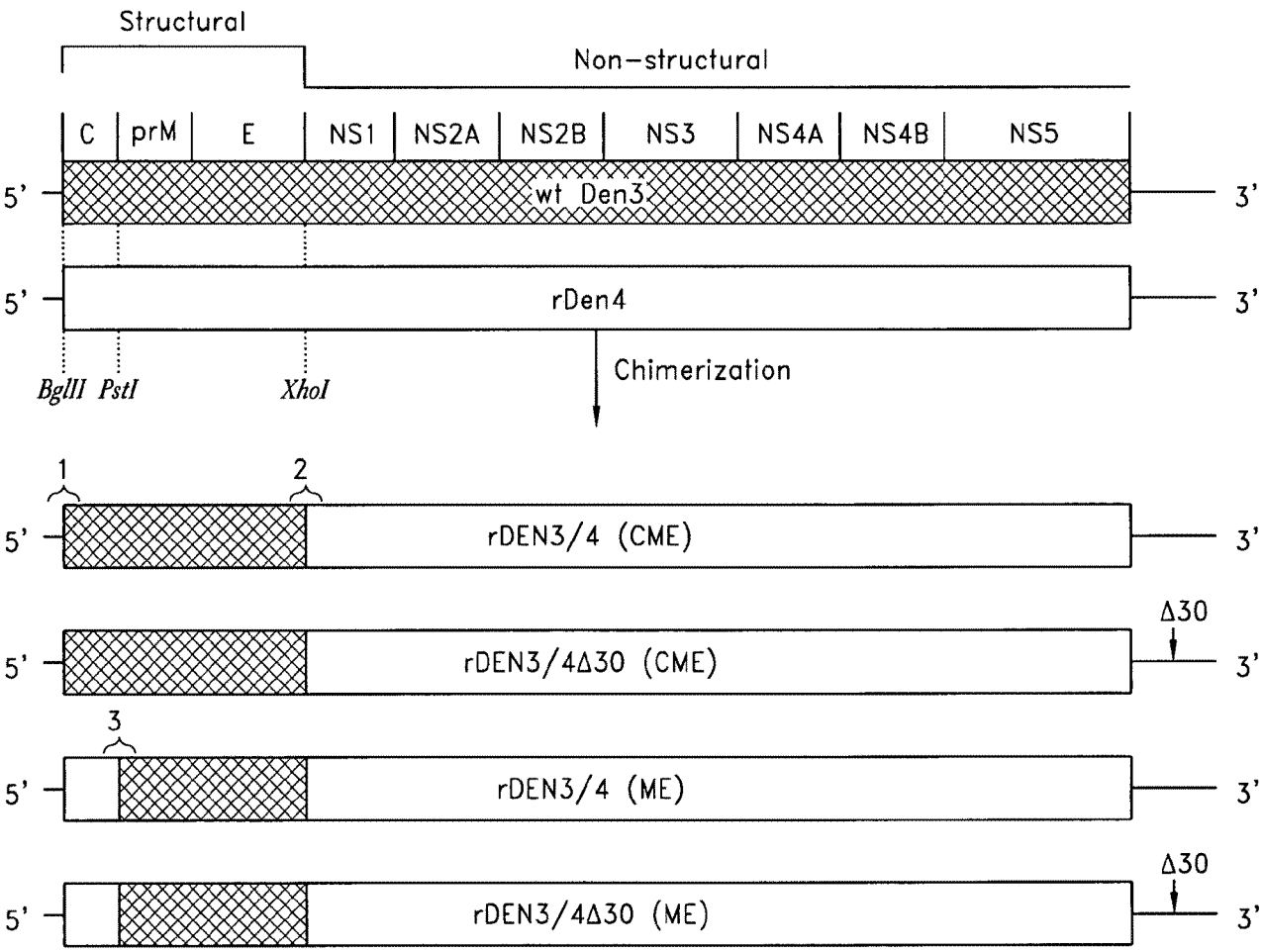
FIG. 11. A. Recombinant chimeric dengue viruses were constructed by introducing either the CME or the ME regions of DEN3 (Sleman/78) into the DEN4 genetic background. The relative location of the Δ30 mutation in the 3' UTR is indicated by an arrow and intertypic junctions 1, 2, and 3 are indicated. Restriction enzyme recognition sites used in assembly of each chimeric cDNA are indicated. B. Nucleotide and amino acid sequence of the intertypic junction regions. Restriction enzyme recognition sites used in assembly of each chimeric cDNA are indicated.

Generation and Characterization of Intertypic Chimeric DEN3 Viruses Containing the Δ30 Mutation Chimeric viruses based on the DEN4 cDNA have been generated in which the CME or ME genes have been replaced with the corresponding genes derived from DEN3 (Sleman/78), a virus isolate from the 1978 dengue outbreak in the Sleman region of Indonesia (Gubler, D. J. et al. 1981 Am J Trop Med Hyg 30:1094-1099) (Appendix 2). As described in Example 5 for the DEN2 chimeric viruses, CME chimeric viruses for DEN3 were generated by replacing the BglII/XhoI region of the cDNA for either rDEN4 or rDEN4Δ30 with a similar region derived from DEN3 (Sleman/78) (FIG. 11A). Likewise, to create the ME chimeric viruses, the PstI/XhoI region of the cDNA for either rDEN4 or rDEN4Δ30 was replaced with a similar region derived from DEN3 (Sleman/78). The nucleotide and amino acid sequences of the resulting junctions are shown in FIG. 11B. The genomes of the resulting viruses were confirmed by sequence analysis of viral RNA isolated from recovered virus as previously described (Durbin, A. P et al. 2001 Am J Trop Med Hyg 65:405-13). Incidental mutations arising from virus passage in tissue culture were identified in all viruses and are listed in Table 34. Notably, each virus contained a missense mutation in NS4B corresponding to a previously identified mutation from rDEN4 and associated with adaptation to growth in Vero cells (See Table 30 for correlation of nucleotide positions between rDEN4 and chimeric viruses). All viruses replicated in Vero cells to titers in excess of 5.7 $\log_{10}$PFU/ml, indicating that the chimeric viruses, even those containing the Δ30 mutation, replicate efficiently in cell culture, a property essential for manufacture of the vaccine.

TABLE 34

Missense mutations observed among Vero cell-grown chimeric DEN3/4 viruses

| Virus | Gene | Nucleotide position | Nucleotide change | Amino acid position | Amino acid change |
|---|---|---|---|---|---|
| rDEN3/4Δ30 (CME) | M | 825 | T > C | 242 | Phe > Leu |
| | E | 1641 | C > T | 514 | Leu > Phe |
| | E | 2113 | A > G | 671 | Lys > Arg |
| | NS4B | 7159[a] | T > C | 2353 | Leu > Ser |
| rDEN3/4(ME) | M | 460 | A > G | 120 | Asp > Gly |
| | NS4B | 7177[b] | G > U | 2359 | Gly > Val |
| | NS5 | 7702 | C > U | 2534 | Ser > Phe |
| rDEN3/4Δ30 (ME) | E | 1432 | A > U | 444 | Gln > Leu |
| | NS4B | 7156[a] | U > C | 2352 | Leu > Ser |
| | NS5 | 8692 | A > C | 2864 | Asn > His |

[a]Same nucleotide position as 7162 in rDEN4.
[b]Same nucleotide position as 7183 in rDEN4.

As described in the previous examples, SCID mice transplanted with HuH-7 cells are a sensitive model for the evaluation of dengue virus attenuation. Each chimeric DEN3/4 virus was inoculated into groups of SCID-HuH-7 mice and levels of virus in the serum were determined (Table 35). While chimeric virus rDEN3/4 (CME) was not attenuated, the remaining chimeric viruses replicated to levels between 40- and 400-fold lower than either of the parental viruses (rDEN4 and DEN3-Sleman/78). In the CME chimeric virus, the Δ30 mutation providing a remarkable 2.7 $\log_{10}$ reduction in replication. This level of attenuation conferred by the Δ30 mutation in the CME chimeric virus was much greater than that observed previously for rDEN4Δ30. The rDEN3/4 (ME) virus was 100-fold reduced in replication compared to either parent virus indicating that the ME chimerization was attenuating per se. Addition of the Δ30 mutation to rDEN3/4 (ME) did not result in additional attenuation.

TABLE 35

Chimerization between dengue virus types 3 and 4 results in recombinant viruses which are attenuated for HuH-7-SCID mice.

| Virus[a] | No. of mice | Mean peak virus titer ($\log_{10}$ pfu/ml ± SE) | Statistical group[b] |
|---|---|---|---|
| rDEN4 | 32 | 6.3 ± 0.2 | A |
| DEN3-Sleman/78 | 23 | 6.4 ± 0.2 | A |
| rDEN3/4 (CME) | 7 | 6.4 ± 0.6 | A |
| rDEN3/4Δ30 (CME) | 5 | 3.7 ± 0.4 | B |
| rDEN3/4 (ME) | 6 | 4.2 ± 0.7 | B |
| rDEN3/4Δ30 (ME) | 7 | 4.7 ± 0.4 | A, B |

[a]Groups of HuH-7-SCID mice were inoculated into the tumor with 4.0 $\log_{10}$ PFU of the indicated virus. Serum was collected on day 7 and virus titer was determined in Vero cells.
[b]Mean peak titers were assigned to statistical groups using the Tukey post-hoc test ($P < 0.05$). Groups with the same letter designation are not significantly different.

Evaluation of the replication and immunogenicity of the DEN3 chimeric recombinant viruses and wild-type DEN3 virus in monkeys was performed as described in Example 5. Results of this safety and immunogenicity study in monkeys are presented in Table 36. Monkeys inoculated with rDEN3/4(CME) and wild-type DEN (Sleman/78) were viremic for approximately 2 days with a mean peak titer of between 1.6 and 1.8 $\log_{10}$PFU/ml, respectively, indicating that chimerization of the CME structural genes of DEN3 did not lead to attenuation of virus replication, a different pattern than that observed for DEN2 chimerization (Table 31). However, chimerization of the ME structural genes resulted in attenuated viruses with undetectable viremia in monkeys, although all monkeys seroconverted with a greater than 10-fold increase in serum antibody levels. As expected for an attenuated virus, the immune response, as measured by neutralizing antibody titer, was lower following inoculation with any of the chimeric viruses compared to inoculation with wt DEN3 (Sleman/78), yet sufficiently high to protect the animals against wtDEN3 virus challenge (Table 37). It is clear that addition of the Δ30 mutation to rDEN3/4(CME) was capable of further attenuating the resulting virus rDEN3/4Δ30(CME).

TABLE 36

The Δ30 mutation further attenuates rDEN3/4(CME) for rhesus monkeys

| Virus[a] | No. of monkeys | Mean no. of viremic days per monkey[b] | Mean peak virus titer ($\log_{10}$ PFU/ml ± SE) | Geometric mean serum neutralizing antibody titer (reciprocal dilution) Day 0 | Day 28 |
|---|---|---|---|---|---|
| DEN3 (Sleman/78) | 4 | 2.3 | 1.8 | <5 | 707 |

TABLE 36-continued

The Δ30 mutation further attenuates rDEN3/4(CME) for rhesus monkeys

| Virus[a] | No. of monkeys | Mean no. of viremic days per monkey[b] | Mean peak virus titer ($\log_{10}$ PFU/ml ± SE) | Geometric mean serum neutralizing antibody titer (reciprocal dilution) Day 0 | Day 28 |
|---|---|---|---|---|---|
| rDEN3/4 (CME) | 4 | 2.0 | 1.6 | <5 | 211 |
| rDEN3/4Δ30 (CME) | 4 | 0 | <1.0 | <5 | 53 |
| rDEN3/4 (ME) | 4 | 0 | <1.0 | <5 | 70 |
| rDEN3/4Δ30 (ME) | 4 | 0 | <1.0 | <5 | 58 |

[a]Groups of rhesus monkeys were inoculated subcutaneously with $10^5$ PFU of the indicated virus in a 1 ml dose. Serum was collected on days 0 to 6, 8, 10, 12, and 28. Virus titer was determined by plaque assay in Vero cells.
[b]Viremia was not detected in any monkey after day 4.

TABLE 37 rDEN3/4 chimeric viruses protect rhesus monkeys from wt DEN3 virus challenge

| Virus[a] | No. of monkeys | Mean no. of viremic days per monkey after rDEN3 challenge | Mean peak virus titer ($\log_{10}$ PFU/ml ± SE) | Geometric mean serum neutralizing antibody titer (reciprocal dilution) Day 28 | Day 56 |
|---|---|---|---|---|---|
| Mock | 2 | 5.0 | 2.5 ± 0.4 | <5 | 372 |
| DEN3 (Sleman/78) | 4 | 0 | <1.0 | 707 | 779 |
| rDEN3/4 (CME) | 4 | 0 | <1.0 | 211 | 695 |
| rDEN3/4Δ30 (CME) | 4 | 0.8 | 1.1 ± 0.2 | 53 | 364 |
| rDEN3/4 (ME) | 4 | 0 | <1.0 | 70 | 678 |
| rDEN3/4Δ30 (ME) | 4 | 0 | <1.0 | 58 | 694 |

[a]28 days after primary inoculation with the indicated viruses, rhesus monkeys were challenged subcutaneously with 10 PFU DEN3 (Sleman/78) virus in a 1 ml dose. Serum was collected on days 28 to 34, 36, 38, and 56. Virus titer was determined by plaque assay in Vero cells.

To evaluate the replication levels of each DEN3/4 chimeric virus in mosquitoes, Aedes aegypti were infected by ingesting a virus-containing blood meal (Table 38). Parental viruses rDEN4 and DEN3 (Sleman/78) readily infect Ae. aegypti. Each of the rDEN3/4 chimeric viruses was also tested. In many cases it was not possible to infect Ae. aegypti with an undiluted virus stock of sufficient titer to achieve a detectable infection due to the very low infectivity of several of the viruses. At a dose of approximately 2.8-2.9 $\log_{10}$PFU, rDEN4, DEN3 (Sleman/78), and rDEN3/4(CME) were equally infectious and disseminated to the head with equal efficiency. For the remaining chimeric viruses, infection was not detectable even at a dose of 3.4 $\log_{10}$PFU, indicating that replication of rDEN3/4(ME) and rDEN3/4Δ30(CME) is restricted in Ae. aegypti. By comparing infectivity of rDEN3/4(CME) and rDEN3/4Δ30(CME), it is clear that the Δ30 mutation is capable of further attenuating the chimeric virus for mosquitoes.

TABLE 38

Ability of DEN3/4 chimeric viruses to infect Aedes aegypti fed an infectious bloodmeal.

| Virus Tested | Dose Ingested ($log_{10}$ pfu)[a] | No. Mosquitoes Tested | No. (%) Midgut Infections[b,c,d] | No. (%) Disseminated Infections[e] |
|---|---|---|---|---|
| rDEN4 | 3.8 | 18 | 14 (77%) | 2 (14%) |
| | 2.8 | 20 | 7 (34%) | 2 (10%) |
| | 1.8 | 18 | 0 | 0 |
| | | | $MID_{50}$ = 3.4 | $MID_{50}$ ≥ 4.4 |
| DEN3 | 2.9 | 16 | 3 (18%) | 2 (12%) |
| (Sleman) | 1.9 | 10 | 1 (10%) | 0 |
| | | | $MID_{50}$ ≥ 3.5 | $MID_{50}$+0≥ 3.5 |
| rDEN3/4 | 3.9 | 20 | 6 (30%) | 2 (10%) |
| (CME) | 2.9 | 18 | 4 (22%) | 0 |
| | 1.9 | 13 | 1 (7%) | 0 |
| | | | $MID_{50}$ ≥ 4.2 | $MID_{50}$ ≥ 4.5 |
| DEN3/4Δ30 | 3.3 | 20 | 0 | 0 |
| (CME) | | | $MID_{50}$ ≥ 4.3 | $MID_{50}$ ≥ 4.3 |
| DEN3/4 | 3.4 | 15 | 0 | 0 |
| (ME) | | | $MID_{50}$ ≥ 4.4 | $MID_{50}$ ≥ 4.4 |

aAmount of virus ingested, assuming a 2μ bloodmeal.
[b]Number (percentage) of mosquitoes with detectable dengue virus in midgut tissue; mosquitoes were assayed 21 days post feed, and dengue virus antigen was identified by IFA.
[c]When infection was detected, but did not exceed a frequency of 50% at the highest dose of virus ingested, the $MID_{50}$ was estimated by assuming that a 10-fold more concentrated virus dose would infect 100% of the mosquitoes.
[d]When no infection was detected, the $MID_{50}$ was assumed to be greater than a 10-fold higher dose of virus than the one used.
[e]Number (percentage) of mosquitoes with detectable dengue virus antigen in both midgut and head tissue.

EXAMPLE 7

Figure 12A:
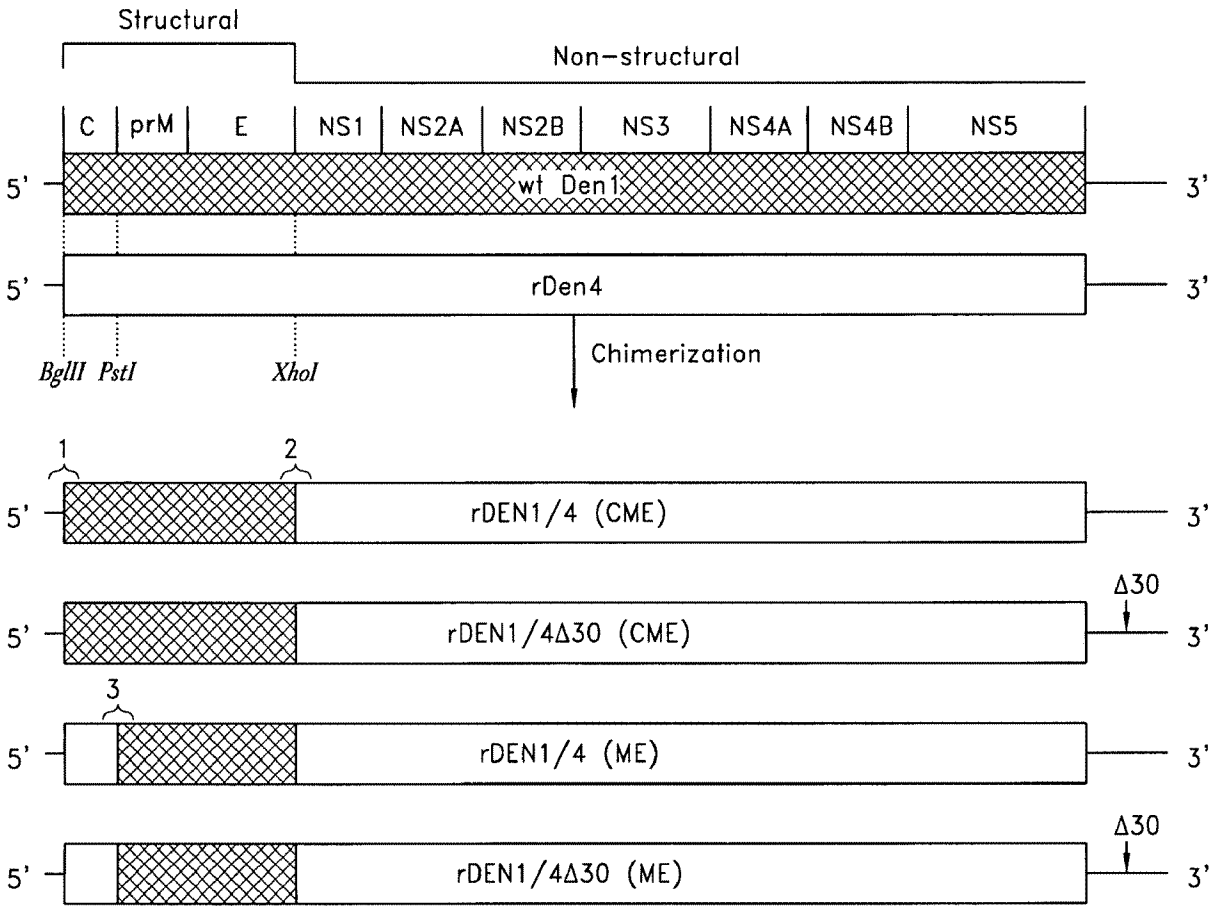
FIG. 12. A. Recombinant chimeric dengue viruses were constructed by introducing either the CME or the ME regions of DEN1 (Puerto Rico/94) into the DEN4 genetic background. The relative location of the Δ30 mutation in the 3' UTR is indicated by an arrow and intertypic junctions 1, 2, and 3 are indicated. Restriction enzyme recognition sites used in assembly of each chimeric cDNA are indicated. B. Nucleotide and amino acid sequence of the intertypic junction regions. Restriction enzyme recognition sites used in assembly of each chimeric cDNA are indicated.

Generation and Characterization of Intertypic Chimeric DEN1 Viruses Containing the Δ30 Mutation Chimeric viruses based on the DEN4 cDNA have been generated in which the CME or ME genes have been replaced with the corresponding genes derived from DEN1 (Puerto Rico/94), a virus isolate from a 1994 dengue outbreak in Puerto Rico (Appendices 3 and 4). As described in Example 4 for the DEN2 chimeric viruses, CME chimeric viruses for DEN1 were generated by replacing the BglII/XhoI region of the cDNA for either rDEN4 or rDEN4Δ30 with a similar region derived from DEN1 (Puerto Rico/94) (FIG. 12A). Likewise, to create the ME chimeric viruses, the PstI/XhoI region of the cDNA for either rDEN4 or rDEN4Δ30 was replaced with a similar region derived from DEN1 (Puerto Rico/94). The nucleotide and amino acid sequences of the resulting junctions are shown in FIG. 12B.

For transcription and generation of virus, chimeric cDNA clones were linearized and used as template in a transcription reaction using SP6 RNA polymerase as described. Transcripts were introduced into C6/36 mosquito cells using liposome-mediated transfection and recombinant dengue virus was harvested between day 7 and 14. Viruses were subsequently grown in Vero cells and biologically cloned by terminal dilution in Vero cells. All viruses replicated in Vero cells to titers in excess of 6.0 $log_{10}$PFU/ml, indicating that the chimeric viruses, even those containing the Δ30 mutation, replicate efficiently in cell culture. Genomic sequence analysis is currently underway to identify incidental mutations arising from virus passage in tissue culture.

To evaluate the replication levels of DEN1/4(CME) and rDEN1/4Δ30(CME) chimeric virus in mosquitoes, Aedes aegypti were infected by ingesting a virus-containing blood meal (Table 39). Parental virus rDEN4 infects Ae. aegypti with an MID50 of 4.0 $log_{10}$PFU. However, parental virus DEN1(Puerto Rico/94), is unable to infect Ae. aegypti at a dose of up to 3.4 $log_{10}$PFU. Thus CME chimeric viruses DEN1/4 and rDEN1/4Δ30 share this inability to infect Ae. aegypti. Therefore, it is unnecessary in Ae. aegypti to evaluate the effect of the Δ30 mutation on the infectivity of the DEN1/4 chimeric viruses, in a manner similar to that used for the DEN2/4 and DEN3/4 chimeric viruses.

TABLE 39

Inability of DEN1/4 chimeric viruses to infect Aedes aegypti fed an infectious bloodmeal.

| Virus tested | Dose ingested ($log_{10}$ pfu)[a] | No. Mosquitoes Tested | No. (%) Midgut Infections[b,c,d] | No. (%) Disseminated Infections[e] |
|---|---|---|---|---|
| rDEN4 | 4.3 | 21 | 18 (85%) | 8 (44%) |
| | 3.3 | 15 | 3 (20%) | 0 |
| | 2.3 | 20 | 0 | 0 |
| | | | $MID_{50}$ = 4.0 | $MID_{50}$ ≥ 4.3 |
| DEN1 | 3.4 | 21 | 0 | 0 |
| (Puerto Rico/94) | | | $MID_{50}$ ≥ 4.4 | $MID_{50}$ ≥ 4.4 |
| rDEN 1/4 | 3.8 | 20 | 0 | 0 |
| (CME) | | | $MID_{50}$ ≥ 4.8 | $MID_{50}$ ≥ 4.8 |
| rDEN1/4Δ30 | 2.8 | 20 | 0 | 0 |
| (CME) | | | $MID_{50}$ ≥ 3.8 | $MID_{50}$ ≥ 3.8 |

[a]Amount of virus ingested, assuming a 2μ bloodmeal.
[b]Number (percentage) of mosquitoes with detectable dengue virus in midgut tissue; mosquitoes were assayed 21 days post feed, and dengue virus antigen was identified by IFA.
[c]When infection was detected, but did not exceed a frequency of 50% at the highest dose of virus ingested, the $MID_{50}$ was estimated by assuming that a 10-fold more concentrated virus dose would infect 100% of the mosquitoes.
[d]When no infection was detected, the $MID_{50}$ was assumed to be greater than a 10-fold higher dose of virus than the one used.
[e]Number (percentage) of mosquitoes with detectable dengue virus antigen in both midgut and head tissue.

As described in the previous examples, SCID mice transplanted with the HuH-7 cells are a sensitive model for the evaluation of dengue virus attenuation. Each chimeric DEN1/4 virus was inoculated into groups of SCID-HuH-7 mice and levels of virus in the serum were determined (Table 40). Chimeric viruses replicated to levels between 15- and 250-fold lower than either of the parental viruses, rDEN4 and DEN1 (Puerto Rico/94). CME chimeric viruses were more attenuated than the comparable ME chimeric viruses, with the Δ30 mutation providing a 0.8 $log_{10}$ reduction in replication. This level of attenuation exerted by the Δ30 mutation in the CME chimeric viruses was similar to that observed previously for rDEN4Δ30. However, the attenuating effect of the Δ30 mutation in the ME chimeric viruses is indiscernible.

TABLE 40

Chimerization between dengue virus types 1 and 4 results in recombinant viruses which are attenuated for HuH-7-SCID mice.

| Virus[a] | No. of mice | Mean peak virus titer ($log_{10}$ pfu/ml ± SE) | Statistical group[b] |
|---|---|---|---|
| rDEN4 | 32 | 6.3 ± 0.2 | A |
| DEN1 | 4 | 6.4 ± 0.2 | A |
| (Puerto Rico/94) | | | |
| rDEN1/4 (CME) | 8 | 4.7 ± 0.2 | B, C |
| rDEN1/4Δ30 (CME) | 6 | 3.9 ± 0.4 | C |
| rDEN1/4 (ME) | 6 | 5.0 ± 0.2 | B |
| rDEN1/4Δ30 (ME) | 6 | 5.1 ± 0.3 | B |

[a]Groups of HuH-7-SCID mice were inoculated into the tumor with 4.0 $log_{10}$ PFU of the indicated virus. Serum was collected on day 7 and virus titer was determined in Vero cells.
[b]Mean peak titers were assigned to statistical groups using the Tukey post-hoc test ($P < 0.05$). Groups with the same letter designation are not significantly different.

APPENDIX 1

Nucleotide and amino acid sequence of DEN2 (Tonga/74) cDNA plasmid p2

```
                    10        20        30        40        50        60        70        80        90
100
AGTTGTTAGTCTACGTGGACCGACAAAGACAGATTCTTTGAGGGAGCTAAGCTCAACGTAGTTCTAACTGTTTTTTGATTAGAGAGCAGATCTCTGATGA
Met>

                   110       120       130       140       150       160       170       180       190
200
ATAACCAACGGAAAAAGGCGAGAAACACGCCTTTCAATATGCTGAAACGCGAGAGAAACCGCGTGTCAACTGTACAACAGTTGACAAAGAGATTCTCACT
AsnAsnGlnArgLysLysAlaArgAsnThrProPheAsnMetLeuLysArgGluArgAsnArgValSerThrValGlnGlnLeuThrLysArgPheSerLeu>

                   210       220       230       240       250       260       270       280       290
300
TGGAATGCTGCAGGGACGAGGACCACTAAAATTGTTCATGGCCCTGGTGGCATTCCTTCGTTTCCTAACAATCCCACCAACAGCAGGGATATTAAAAAGA
GlyMetLeuGlnGlyArgGlyProLeuLysLeuPheMetAlaLeuValAlaPheLeuArgPheLeuThrIleProProThrAlaGlyIleLeuLysArg>

                   310       320       330       340       350       360       370       380       390
400
TGGGGAACAATTAAAAAATCAAAGGCTATTAATGTTCTGAGAGGCTTCAGGAAGAGATTTGGAAGGATGCTGAATATCTTAAACAGGAGACGTAGAACTG
TrpGlyThrIleLysLysSerLysAlaIleAsnValLeuArgGlyPheArgLysGluIleGlyArgMetLeuAsnIleLeuAsnArgARgArgArgThr>

                   410       420       430       440       450       460       470       480       490
500
TAGGCATGATCATCATGCTGACTCCAACAGTGATGGCGTTTCATCTGACCACACGCAACGGAGAACCACACATGATTGTCAGTAGACAAGAAAAAGGGAA
ValGlyMetIleIleMetLeuThrProThrValMetAlaPheHisLeuThrThrArgAsnGlyGluProHisMetIleValSerArgGlnGluLysGlyLys>

                   510       520       530       540       550       560       570       580       590
600
AAGCCTTCTGTTCAAGACAAAGGATGGCACGAACATGTGTACCCTCATGGCCATGGACCTTGGTGAGTTGTGTGAAGACACAATCACGTATAAATGTCCT
SerLeuLeuPheLysThrLysAspGlyThrAsnMetCysThrLeuMetAlaMetAspLeuGlyGluLeuCysGluAspThrIleThrTyrLysCysPro>

                   610       620       630       640       650       660       670       680       690
700
TTTCTCAAGCAGAACGAACCAGAAGACATAGATTGTTGGTGCAACTCCACGTCCACATGGGTAACTTATGGGACATGTACCACCACAGGAGAGCACAGAA
PheLeuLysGlnAsnGluProGluAspIleAspCysTrpCysAsnSerThrSerThrTrpValThrTyrGlyThrCysThrThrThrGlyGluHisArg>

                   710       720       730       740       750       760       770       780       790
800
GAGAAAAAAGATCAGTGGCGCTTGTTCCACACGTGGGAATGGGATTGGAGACACGAACTGAAACATGGATCTCATCAGAAGGGGCCTGGAAACATGCCCA
ArgGluLysArgSerValAlaLeuValProHisValGlyMetGlyLeuGluThrArgThrGluThrTrpMetSerSerGluGlyAlaTrpLysHisAlaGln>

                   810       820       830       840       850       860       870       880       890
900
GAGAATTGAAACTTGGATTCTGAGACATCCAGGCTTTACCATAATGGCCGCAATCCTGGCATACACCATAGGGACGACGCATTTCCAAAGAGTCCTGATA
ArgIleGluThrTrpIleLeuArgHisProGlyPheThrIleMetAlaAlaIleLeuAlaTyrThrIleGlyThrThrHisPheGlnArgValLeuIle>

                   910       920       930       940       950       960       970       980       990
1000
TTCATCCTACTGACAGCCATCGCTCCTTCAATGACAATGCGCTGCATAGGAATATCAAATAGGGACTTTGTGGAAGGAGTGTCAGGAGGGAGTTGGGTTG
PheIleLeuLeuThrAlaIleAlaProSerMetThrMetArgCysIleGlyIleSerAsnArgAspPheValGluGlyValSerGlyGlySerTrpVal>

                  1010      1020      1030      1040      1050      1060      1070      1080      1090
1100
ACATAGTTTTAGAACATGGAAGTTGTGTGACGACGATGGCAAAAAACAAACCAACACTGGACTTTGAACTGATAAAAACAGAAGCCAAACAACCTGCCAC
AspIleValLeuGluHisGlySerCysValThrThrMetAlaLysAsnLysProThrLeuAspPheGluLeuIleLysThrGluAlaLysGlnProAlaThr>

                  1110      1120      1130      1140      1150      1160      1170      1180      1190
1200
CTTAAGGAAGTACTGTATAGAGGCCAAACTGACCAACACGACAACAGACTCGCGCTGCCCAACACAAGGGGAACCCACCCTGAATGAAGAGCAGGACAAA
LeuArgLysTyrCysIleGluAlaLysLeuThrAsnThrThrThrAspSerArgCysProThrGlnGlyGluProThrLeuAsnGluGluGlnAspLys>

                  1210      1220      1230      1240      1250      1260      1270      1280      1290
1300
AGGTTTGTCTGCAAACATTCCATGGTAGACAGAGGATGGGGAAATGGATGTGGATTGTTTGGAAAAGGAGGCATCGTGACCTGTGCTATGTTCACATGCA
ArgPheValCysLysHisSerMetValAspArgGlyTrpGlyAsnGlyCysGlyLeuPheGlyLysGlyGlyIleValThrCysAlaMetPheThrCys>

                  1310      1320      1330      1340      1350      1360      1370      1380      1390
1400
AAAAGAACATGGAAGGAAAAATTGTTCAGCCAGAAAACCTGGAATACACTGTCGTGATAACACCTCATTCAGGGGAAGAACATGCAGTGGGAAATGACAC
LysLysAsnMetGluGlyLysIleValGlnProGluAsnLeuGluTyrThrValValIleThrProHisSerGlyGluGluHisAlaValGlyAsnAspThr>

                  1410      1420      1430      1440      1450      1460      1470      1480      1490
1500
AGGAAAACATGGTAAAGAAGTCAAGATAACACCACAGAGCTCCATCACAGAGGCGGAACTGACAGGCTATGGCACTGTTACGATGGAGTGCTCTCCAAGA
GlyLysHisGlyLysGluValLysIleThrProGlnSerSerIleThrGluAlaGluLeuThrGlyTyrGlyThrValThrMetGluCysSerProArg>

                  1510      1520      1530      1540      1550      1560      1570      1580      1590
1600
ACGGGCCTCGACTTCAATGAGATGGTGTTGCTGCAAATGGAAGACAAAGCCTGGCTGGTGCACAGACAATGGTTCCTAGACCTACCGTTGCCATGGCTGC
```

APPENDIX 1-continued

Nucleotide and amino acid sequence of DEN2 (Tonga/74) cDNA plasmid p2

```
ThrGlyLeuAspPheAsnGluMetValLeuLeuGlnMetGluAspLysAlaTrpLeuValHisArgGlnTrpPheLeuAspLeuProLeuProTrpLeu>

                1610      1620      1630      1640      1650      1660      1670      1680      1690
1700
CCGGAGCAGACACACAAGGATCAAATTGGATACAGAAAGAAACACTGGTCACCTTCAAAAATCCCCATGCGAAAAAACAGGATGTTGTTGTCTTAGGATC
ProGlyAlaAspThrGlnGlySerAsnTrplleGlnLysGluThrLeuValThrPheLysAsnProHisAlaLysLysGlnAspValValValLeuGlySer>

                1710      1720      1730      1740      1750      1760      1770      1780      1790
1800
CCAAGAGGGGGCCATGCATACAGCACTCACAGGGGCTACGGAAATCCAGATGTCATCAGGAAACCTGCTGTTCACAGGACATCTCAAGTGCAGGCTGAGA
GlnGluGlyAlaMetHisThrAlaLeuThrGlyAlaThrGluIleGlnMetSerSerGlyAsnLeuLeuPheThrGlyHisLeuLysCysArgLeuArg>

                1810      1820      1830      1840      1850      1860      1870      1880      1890
1900
ATGGACAAATTACAACTTAAAGGGATGTCATACTCCATGTGCACAGGAAAGTTTAAAATTGTGAAGGAAATAGCAGAAACACAACATGGAACAATAGTCA
MetAspLysLeuGlnLeuLysGlyMetSerTyrSerMetCysThrGlyLysPheLysIleValLysGluIleAlaGluThrGlnHisGlyThrIleVal>

                1910      1920      1930      1940      1950      1960      1970      1980      1990
2000
TTAGAGTACAATATGAAGGAGACGGCTCTCCATGCAAGATCCCCTTTGAGATAATGGATCTGGAAAAAAGACATGTTTTGGGCCGCCTGATCACAGTCAA
IleArgValGlnTyrGluGlyAspGlySerProCysLysIleProPheGluIleMetAspLeuGluLysArgHisValLeuGlyArgLeuIleThrValAsn>

                2010      2020      2030      2040      2050      2060      2070      2080      2090
2100
CCCAATTGTAACAGAAAAGGACAGTCCAGTCAACATAGAAGCAGAACCTCCATTCGGAGACAGCTACATCATCATAGGAGTGGAACCAGGACAATTGAAG
ProIleValThrGluLysAspSerProValAsnIleGluAlaGluProProPheGlyAspSerTyrIleIleIleGlyValGluProGlyGlnLeuLys>

                2110      2120      2130      2140      2150      2160      2170      2180      2190
2200
CTGGACTGGTTCAAGAAAGGAAGTTCCATCGGCCAAATGTTTGAGACAACAATGAGGGGAGCGAAAAGAATGGCCATTTTGGGTGACACAGCCTGGGATT
LeuAspTrpPheLysLysGlySerSerIleGlyGlnMetPheGluThrThrMetArgGlyAlaLysArgMetAlaIleLeuGlyAspThrAlaTrpAsp>

                2210      2220      2230      2240      2250      2260      2270      2280      2290
2300
TTGGATCTCTGGGAGGAGTGTTCACATCAATAGGAAAGGCTCTCCACCAGGTTTTTGGAGCAATCTACGGGGCTGCTTTCAGTGGGGTCTCATGGACTAT
PheGlySerLeuGlyGlyValPheThrSerIleGlyLysAlaLeuHisGlnValPheGlyAlaIleTyrGlyAlaAlaPheSerGlyValSerTrpThrMet>

                2310      2320      2330      2340      2350      2360      2370      2380      2390
2400
GAAGATCCTCATAGGAGTTATCATCACATGGATAGGAATGAACTCACGTAGCACTAGTCTGAGCGTGTCACTGGTGTTAGTGGGAATCGTGACACTTTAC
LysIleLeuIleGlyValIleIleThrTrpIleGlyMetAsnSerArgSerThrSerLeuSerValSerLeuValLeuValGlyIleValThrLeuTyr>

                2410      2420      2430      2440      2450      2460      2470      2480      2490
2500
TTGGGAGTTATGGTGCAGGCCGATAGTGGTTGCGTTGTGAGCTGGAAGAACAAAGAACTAAAATGTGGCAGTGGAATATTCGTCACAGATAACGTGCATA
LeuGlyValMetValGlnAlaAspSerGlyCysValValSerTrpLysAsnLysGluLeuLysCysGlySerGlyIlePheValThrAspAsnValHis>

                2510      2520      2530      2540      2550      2560      2570      2580      2590
2600
CATGGACAGAACAATACAAGTTCCAACCAGAATCCCCTTCAAAACTGGCCTCAGCCATCCAGAAAGCGCATGAAGAGGGCATCTGTGGAATCCGCTCAGT
ThrTrpThrGluGlnTyrLysPheGlnProGluSerProSerLysLeuAlaSerAlaIleGlnLysAlaHisGluGluGlyIleCysGlyIleArgSerVal>

                2610      2620      2630      2640      2650      2660      2670      2680      2690
2700
AACAAGACTGGAAAATCTTATGTGGAAACAGATAACATCAGAATTGAATCATATTCTATCAGAAAATGAAGTGAAACTGACCATCATGACAGGAGACATC
ThrArgLeuGluAsnLeuMetTrpLysGlnIleThrSerGluLeuAsnHisIleLeuSerGluAsnGluValLysLeuThrIleMetThrGlyAspIle>

                2710      2720      2730      2740      2750      2760      2770      2780      2790
2800
AAAGGAATCATGCAGGTAGGAAAACGATCTTTGCGGCCTCAACCCACTGAGTTGAGGTATTCATGGAAAACATGGGGTAAAGCGAAAATGCTCTCCACAG
LysGlyIleMetGlnValGlyLysArgSerLeuArgProGlnProThrGluLeuArgTyrserTrpLysThrTrpGlyLysAlaLysMetLeuSerThr>

                2810      2820      2830      2840      2850      2860      2870      2880      2890
2900
AACTCCACAATCAGACCTTCCTCATTGATGGTCCCGAAACAGCAGAATGCCCCAACACAAACAGAGCTTGGAATTCACTGGAAGTTGAGGACTACGGCTT
GluLeuHisAsnGlnThrPheLeuIleAspGlyProGluThrAlaGluCysProAsnThrAsnArgAlaTrpAsnSerLeuGluValGluAspTyrGlyPhe>

                2910      2920      2930      2940      2950      2960      2970      2980      2990
3000
TGGAGTATTCACTACCAATATATGGCTAAGATTGAGAGAAAAGCAGGATGTATTTTGTGACTCAAACTCATGTGCAGCGGCCATAAAGGACAACAGAGCC
GlyValPheThrThrAsnIleTrpLeuArgLeuArgGluLysGlnAspValPheCysAspSerLysLeuMetSreAlaAlaIleLysAspAsnArgAla>

                3010      3020      3030      3040      3050      3060      3070      3080      3090
3100
GTCCATGCTGATATGGGTTATTGGATAGAAAGCGCACTCAATGATACATGGAAGATAGAGAAAGCTTCTTTCATTGAAGTCAAAAGTTGCCACTGGCCAA
ValHisAlaAspMetGlyTryTrpIleGluSerAlaLeuAsnAspThrTrpLysIleGluLysAlaSerPheIleGluValLysSerCysHisTrpPro>

                3110      3120      3130      3140      3150      3160      3170      3180      3190
```

APPENDIX 1-continued

Nucleotide and amino acid sequence of DEN2 (Tonga/74) cDNA plasmid p2

```
3200
AGTCACACACCCTATGGAGTAATGGAGTGCTAGAAAGCGAGATGGTCATTCCAAAGAATTTCGCTGGACCAGTGTCACAACATAATAACAGACCAGGCTA
LysSerHisThrLeuTrpSerAsnGlyValLeuGluSerGluMetValIleProLysAsnPheAlaGlyProValSerGlnHisAsnAsnArgProGlyTyr>

                 3210      3220      3230      3240      3250      3260      3270      3280      3290
3300
TTACACACAAACAGCAGGACCTTGGCATCTAGGCAAGCTTGAGATGGACTTTGATTTCTGCGAAGGGACTACAGTGGTGGTAACCGAGAACTGTGGAAAC
TyrThrGlnThrAlaGlyProTrpHisLeuGlyLysLeuGluMetAspPheAspPheCysGluGlyThrThrValValValThrGluAsnCysGlyAsn>

                 3310      3320      3330      3340      3350      3360      3370      3380      3390
3400
AGAGGGCCCTCTTTAAGAACAACCACTGCCTCAGGAAAACTCATAACGGAATGGTGTTGTCGATCTTGCACACTACCACCACTAAGATACAGAGGTGAGG
ArgGlyProSerLeuArgThrThrThrAlaSerGlyLysLeuIleThrGluTrpCysCysArgSerCysThrLeuProProLeuArgTyrArgGlyGlu>

                 3410      3420      3430      3440      3450      3460      3470      3480      3490
3500
ATGGATGTTGGTACGGGATGGAAATCAGACCATTGAAAGAGAAAGAAGAAAATCTGGTCAGTTCTCTGGTTACAGCCGGACATGGGCAGATTGACAATTT
AspGlyCysTrpTyrGlyMetGluIleArgProLeuLysGluLysGluGluAsnLeuValSerSerLeuValThrAlaGlyHisGlyGlnIleAspAsnPhe>

                 3510      3520      3530      3540      3550      3560      3570      3580      3590
3600
CTCATTAGGAATCTTGGGAATGGCACTGTTCCTTGAAGAAATGCTCAGGACTCGAGTAGGAACAAAACATGCAATATTACTCGTCGCAGTTTCTTTCGTG
SerLeuGlyIleLeuGlyMetAlaLeuPheLeuGluGluMetLeuArgThrArgValGlyThrLysHisAlaIleLeuLeuValAlaValSerPheVal>

                 3610      3620      3630      3640      3650      3660      3670      3680      3690
3700
ACGCTAATCACAGGGAACATGTCTTTTAGAGACCTGGGAAGAGTGATGGTTATGGTGGGTGCCACCATGACAGATGACATAGGCATGGGTGTGACTTATC
ThrLeuIleThrGlyAsnMetSerPheArgAspLeuGlyArgValMetValMetValGlyAlaThrMetThrAspAspIleGlyMetGlyValThrTyr>

                 3710      3720      3730      3740      3750      3760      3770      3780      3790
3800
TCGCTCTACTAGCAGCTTTTAGAGTCAGACCAACCTTTGCAGCTGGACTGCTCTTGAGAAAACTGACCTCCAAGGAATTAATGATGACTACCATAGGAAT
LeuAlaLeuLeuAlaAlaPheArgValArgProThrPheAlaAlaGlyLeuLeuLeuArgLysLeuThrSerLysGluLeuMetMetThrThrIleGlyIle>

                 3810      3820      3830      3840      3850      3860      3870      3880      3890
3900
CGTTCTTCTCTCCCAGAGTAGCATACCAGAGACCATTCTTGAACTGACCGACGCGTTAGCTCTAGGCATGATGGTCCTCAAGATGGTGAGAAACATGGAA
ValLeuLeuSerGlnSerSerIleProGluThrIleLeuGluLeuThrAspAlaLeuAlaLeuGlyMetMetValLeuLysMetValArgAsnMetGlu>

                 3910      3920      3930      3940      3950      3960      3970      3980      3990
4000
AAATATCAGCTGGCAGTGACCATCATGGCTATTTTGTGCGTCCCAAATGCTGTGATATTACAGAACGCATGGAAAGTGAGTTGCACAATATTGGCAGTGG
LysTyrGlnLeuAlaValThrIleMetAlaIleLeuCysValProAsnAlaValIleLeuGlnAsnAlaTrpLysValSerCysThrIleLeuAlaVal>

                 4010      4020      4030      4040      4050      4060      4070      4080      4090
4100
TGTCTGTTTCCCCCCTGCTCTTAACATCCTCACAACAGAAAGCGGACTGGATACCATTAGCGTTGACGATCAAAGGTCTTAATCCAACAGCCATTTTTCT
ValSerValSerProLeuLeuLeuThrSerSerGlnGlnLysAlaAspTrpIleProLeuAlaLeuThrIleLysGlyLeuAsnProThrAlaIlePheLeu>

                 4110      4120      4130      4140      4150      4160      4170      4180      4190
4200
AACAACCCTCTCAAGAACCAACAAGAAAAGGAGCTGGCCTTTAAATGAGGCCATCATGGCGGTTGGGATGGTGAGTATCTTGGCCAGCTCTCTCTTAAAG
ThrThrLeuSerArgThrAsnLysLysArgSerTrpProLeuAsnGluAlaIleMetAlaValGlyMetValSerIleLeuAlaSerSerLeuLeuLys>

                 4210      4220      4230      4240      4250      4260      4270      4280      4290
4300
AATGACATCCCCATGACAGGACCATTAGTGGCTGGAGGGCTCCTTACTGTGTGCTACGTGCTAACTGGGCGGTCAGCCGATCTGGAATTAGAGAGAGCTA
AsnAspIleProMetThrGlyProLeuValAlaGlyGlyLeuLeuThrValCysTyrValLeuThrGlyArgSerAlaAspLeuGluLeuGluArgAla>

                 4310      4320      4330      4340      4350      4360      4370      4380      4390
4400
CCGATGTCAAATGGGATGACCAGGCAGAGATATCAGGTAGCAGTCCAATCCTGTCAAGAACAATATCAGAAGATGGCAGCATGTCAATAAAGAATGAAGA
ThrAspValLysTrpAspAspGlnAlaGluIleSerGlySerSerProIleLeuSerIleThrIleSerGluAspGlySerMetSerIleLysAsnGluGlu>

                 4410      4420      4430      4440      4450      4460      4470      4480      4490
4500
GGAAGAGCAAACACTGACTATACTCATTAGAACAGGATTGCTTGTGATCTCAGGACTCTTTCCGGTATCAATACCAATTACAGCAGCAGCATGGTATCTG
GluGluGlnThrLeuTheIleLeuIleArgThrGlyLeuLeuValIleSerGlyLeuPheProValSerIleProIleThrAlaAlaAlaTrpTyrLeu>

                 4510      4520      4530      4540      4550      4560      4570      4580      4590
4600
TGGGAAGTAAAGAAACAACGGGCTGGAGTGCTGTGGGATGTCCCCTCACCACCACCCGTGGGAAAAGCTGAATTGGAAGATGGAGCCTACAGAATCAAGC
TrpGluValLysLysGlnArgAlaGlyValLeuTrpAspValProSerProProProValGlyLysAlaGluLeuGluAspGlyAlaTyrArgIleLys>

                 4610      4620      4630      4640      4650      4660      4670      4680      4690
```

APPENDIX 1-continued

Nucleotide and amino acid sequence of DEN2 (Tonga/74) cDNA plasmid p2

```
4700
AAAAAGGAATCCTTGGATATTCCCAGATCGGAGCTGGAGTTTACAAAGAAGGAACATTTCACACAATGTGGCACGTCACACGTGGCGCTGTCCTAATGCA
GlnLysGlyIleLeuGlyTyrSerGlnIleGlyAlaGlyValTyrLysGluGlyThrPheHisThrMetTrpHisValThrArgGlyAlaValLeuMetHis>

                 4710      4720      4730      4740      4750      4760      4770      4780      4790
4800
TAAGGGGAAGAGGATTGAACCATCATGGGCGGACGTCAAGAAAGACTTAATATCATATGGAGGAGGTTGGAAGCTAGAAGGAGAATGGAAAGAAGGAGAA
LysGlyLysArgIleGluProSerTrpAlaAspValLysLysAspLeuIleSerTyrGlyGlyGlyTrpLysLeuGluGlyGluTrpLysGluGlyGlu>

                 4810      4820      4830      4840      4850      4860      4870      4880      4890
4900
GAAGTCCAGGTCTTGGCATTGGAGCCAGGGAAAAATCCAAGAGCCGTCCAAACAAAGCCTGGCCTTTTTAGAACCAACACTGGAACCATAGGTGCCGTAT
GluValGlnValLeuAlaLeuGluProGlyLysAsnProArgAlaValGlnThrLysProGlyLeuPheArgThrAsnThrGlyThrIleGlyAlaVal>

                 4910      4920      4930      4940      4950      4960      4970      4980      4990
5000
CTCTGGACTTTTCCCCTGGGACGTCAGGATCTCCAATCGTCGACAAAAAAGGAAAAGTTGTAGGTCTCTATGGCAATGGTGTCGTTACAAGGAGTGGAGC
SerLeuAspPheSerProGlyThrSerGlySerProIleValAspLysLysGlyLysValValGlyLeuTyrGlyAsnGlyValValThrArgSerGlyAla>

                 5010      5020      5030      5040      5050      5060      5070      5080      5090
5100
ATATGTGAGTGCCATAGCTCAGACTGAAAAAAGCATTGAAGACAATCCAGAGATTGAAGATGACATCTTTCGAAAGAGAAGATTGACTATCATGGATCTC
TyrValSerAlaIleAlaGlnThrGluLysSerIleGluAspAsnProGluIleGluAspAspIlePheArgLysArgArgLeuThrIleMetAspLeu>

                 5110      5120      5130      5140      5150      5160      5170      5180      5190
5200
CACCCAGGAGCAGGAAAGACAAAGAGATACCTCCCGGCCATAGTCAGAGAGGCCATAAAAAGAGGCTTGAGAACACTAATCCTAGCCCCCACTAGAGTCG
HisProGlyAlaGlyLysThrLysArgTyrLeuProAlaIleValArgGluAlaIleLysArgGlyLeuArgThrLeuIleLeuAlaProThrArgVal>

                 5210      5220      5230      5240      5250      5260      5270      5280      5290
5300
TGGCAGCTGAAATGGAGGAAGCCCTTAGAGGACTTCCAATAAGATACCAAACTCCAGCTATCAGGGCTGAGCACACCGGGCGGGAGATTGTAGACTTAAT
ValAlaAlaGluMetGluGluAlaLeuArgGlyLeuProIleArgTyrGlnThrProAlaIleArgAlaGluHisThrGlyArgGluIleValAspLeuMet>

                 5310      5320      5330      5340      5350      5360      5370      5380      5390
5400
GTGTCATGCCACATTTACCATGAGGCTGCTATCACCAATCAGGGTGCCAAATTACAACCTGATCATCATGGACGAAGCCCATTTTACAGATCCAGCAAGC
CysHisAlaThrPheThrMetArgLeuLeuSerProIleArgValProAsnTyrAsnLeuIleIleMetAspGluAlaHisPheThrAspProAlaSer>

                 5410      5420      5430      5440      5450      5460      5470      5480      5490
5500
ATAGCAGCTAGGGGATACATCTCAACTCGAGTGGAGATGGGGGAGGCAGCTGGAATTTTTATGACAGCCACTCCTCCGGGTAGTAGAGATCCATTTCCTC
IleAlaAlaArgGlyTyrIleSerThrArgValGluMetGlyGluAlaAlaGlyIlePheMetThrAlaThrProProGlySerArgAspProPhePro>

                 5510      5520      5530      5540      5550      5560      5570      5580      5590
5600
AGAGCAATGCACCAATTATGGACGAAGAAAGAGAAATTCCGGAACGTTCATGGAACTCTGGGCACGAGTGGGTCACGGATTTTAAAGGAAAGACTGTCTG
GlnSerAsnAlaProIleMetAspGluGluArgGluIleProGluArgSerTrpAsnSerGlyHisGluTrpValThrAspPheLysGlyLysThrValTrp>

                 5610      5620      5630      5640      5650      5660      5670      5680      5690
5700
GTTTGTTCCAAGCATAAAAACCGGAAATGACATAGCAGCCTGCCTGAGAAAGAATGGAAAGAGGGTGATACAACTCAGTAGGAAGACCTTTGATTCTGAA
PheValProSerIleLysThrGlyAsnAspIleAlaAlaCysLeuArgLysAsnGlyLysArgValIleGlnLeuSerArgLysThrPheAspSerGlu>

                 5710      5720      5730      5740      5750      5760      5770      5780      5790
5800
TATGTCAAGACTAGAACCAATGACTGGGATTTCGTGGTTACAACTGACATCTCGGAAATGGGCGCCAACTTTAAAGCTGAGAGGGTCATAGACCCCAGAC
TyrValLysThrArgThrAsnAspTrpAspPheValValThrThrAspIleSerGluMetGlyAlaAsnPheLysAlaGluArgValIleAspProArg>

                 5810      5820      5830      5840      5850      5860      5870      5880      5890
5900
GCTGCATGAAACCAGTTATATTGACAGACGGCGAAGAGCGGGTGATTCTGGCAGGACCCATGCCAGTGACCCACTCTAGTGCAGCACAAAGAAGAGGGAG
ArgCysMetLysProValIleLeuThrAspGlyGluGluArgValIleLeuAlaGluProMetProValThrHisSerSerAlaAlaGlnArgArgGlyArg>

                 5910      5920      5930      5940      5950      5960      5970      5980      5990
6000
AATAGGAAGGAATCCAAGGAATGAAAATGATCAATATATATATATGGGGGAACCACTGGAAAATGATGAAGACTGTGCGCACTGGAAGGAAGCTAAGATG
IleGlyArgAsnProArgAsnGluAsnAspGlnTyrIleTyrMetGlyGluProLeuGluAsnAspGluAspCysAlaHisTrpLysGluAlaLysMet>

                 6010      6020      6030      6040      6050      6060      6070      6080      6090
6100
CTCCTAGATAATATCAACACACCTGAAGGAATCATTCCCAGCTTGTTCGAGCCAGAGCGTGAAAAGGTGGATGCCATTGACGGTGAATATCGCTTGAGAG
LeuLeuAspAsnIleAsnThrProGluGlyIleIleProSerLeuPheGluProGluArgGluLysValAspAlaIleAspGlyGluTyrArgLeuArg>

                 6110      6120      6130      6140      6150      6160      6170      6180      6190
```

APPENDIX 1-continued

Nucleotide and amino acid sequence of DEN2 (Tonga/74) cDNA plasmid p2

```
6200
GAGAAGCACGGAAAACTTTTGTGGACCTAATGAGAAGAGGAGACCTACCAGTCTGGTTGGCTTATAAAGTGGCAGCTGAAGGTATCAACTACGCAGACAG
GlyGluAlaArgLysThrPheValAspLeuMetArgArgGlyAspLeuProValTrpLeuAlaTyrLysValAlaAlaGluGlyIleAsnTyrAlaAspArg>

                6210      6220      6230      6240      6250      6260      6270      6280      6290
6300
AAGATGGTGTTTTGACGGAACCAGAAACAATCAAATCTTGGAAGAAAATGTGGAAGTGGAAATCTGGACAAAGGAAGGGGAAAGGAAAAAATTGAAACCT
ArgTrpCysPheAspGlyThrArgAsnAsnGlnIleLeuGluGluAsnValGluValGluIleTrpThrLysGluGlyGluArgLysLysLeuLysPro>

                6310      6320      6330      6340      6350      6360      6370      6380      6390
6400
AGATGGTTAGATGCTAGGATCTACTCCGACCCACTGGCGCTAAAAGAGTTCAAGGAATTTGCAGCCGGAAGAAAGTCCCTAACCCTGAACCTAATTACAG
ArgTrpLeuAspAlaArgIleTyrSerAspProLeuAlaLeuLysGluPheLysGluPheAlaAlaGlyArgLysSerLeuThrLeuAsnLeuIleThr>

                6410      6420      6430      6440      6450      6460      6470      6480      6490
6500
AGATGGGCAGACTCCCAACTTTTATGACTCAGAAGGCCAGAGATGCACTAGACAACTTGGCGGTGCTGCACACGGCTGAAGCGGGTGGAAAGGCATACAA
GluMetGlyArgLeuProThrPheMetThrGlnLysAlaArgAspAlaLeuAspAsnLeuAlaValLeuHisThrAlaGluAlaGlyGlyLysAlaTyrAsn>

                6510      6520      6530      6540      6550      6560      6570      6580      6590
6600
TCATGCTCTCAGTGAATTACCGGAGACCCTGGAGACATTGCTTTTGCTGACACTGTTGGCCACAGTCACGGGAGGAATCTTCCTATTCCTGATGAGCGGA
HisAlaLeuSerGluLeuProGluThrLeuGluThrLeuLeuLeuLeuThrLeuLeuAlaThrValThrGlyGlyIlePheLeuPheLeuMetSerGly>

                6610      6620      6630      6640      6650      6660      6670      6680      6690
6700
AGGGGTATGGGGAAGATGACCCTGGGAATGTGCTGCATAATCACGGCCAGCATCCTCTTATGGTATGCACAAATACAGCCACATTGGATAGCAGCCTCAA
ArgGlyMetGlyLysMetThrLeuGlyMetCysCysIleIleThrAlaSerIleLeuLeuTryTyrAlaGlnIleGlnProHisTrpIleAlaAlaSer>

                6710      6720      6730      6740      6750      6760      6770      6780      6790
6800
TAATATTGGAGTTCTTTCTCATAGTCTTGCTCATTCCAGAACCAGAAAAGCAGAGGACACCTCAGGATAATCAATTGACTTATGTCATCATAGCCATCCT
IleIleLeuGluPhePheLeuIleValLeuLeuIleProGluProGluLysGlnArgThrProGlnAspAsnGlnLeuThrTyrVallleIleAlaIleLeu>

                6810      6820      6830      6840      6850      6860      6870      6880      6890
6900
CACAGTGGTGGCCGCAACCATGGCAAACGAAATGGGTTTTCTGGAAAAAACAAAGAAAGACCTCGGACTGGGAAACATTGCAACTCAGCAACCTGAGAGC
ThrValValAlaAlaThrMetAlaAsnGluMetGlyPheLeuGluLysThrLysLysAspLeuGlyLeuGlyAsnIleAlaThrGlnGlnProGluSer>

                6910      6920      6930      6940      6950      6960      6970      6980      6990
7000
AACATTCTGGACATAGATCTACGTCCTGCATCAGCATGGACGTTGTATGCCGTGGCTACAACATTTATCACACCAATGTTGAGACATAGCATTGAAAATT
AsnIleLeuAspIleAspLeuArgProAlaSerAlaTrpThrLeuTyrAlaValAlaThrThrPheIleThrProMetLeuArgHisSerIleGluAsn>

                7010      7020      7030      7040      7050      7060      7070      7080      7090
7100
CCTCAGTAAATGTGTCCCTAACAGCCATAGCTAACCAAGCCACAGTGCTAATGGGTCTCGGAAAAGGATGGCCATTGTCAAAGATGGACATTGGAGTTCC
SerSerValAsnValSerLeuThrAlaIleAlaAsnGlnAlaThrValLeuMetGlyLeuGlyLysGlyTrpProLeuSerLysMetAspIleGlyValPro>

                7110      7120      7130      7140      7150      7160      7170      7180      7190
7200
CCTCCTTGCTATTGGGTGTTACTCACAAGTCAACCCTATAACCCTCACAGCGGCTCTTCTTTTATTGGTAGCACATTATGCCATCATAGGACCGGGACTT
LeuLeuAlaIleGlyCysTyrSerGlnValAsnProIleThrLeuThrAlaAlaLeuLeuLeuLeuValAlaHisTyrAlaIleIleGlyProGlyLeu>

                7210      7220      7230      7240      7250      7260      7270      7280      7290
7300
CAAGCCAAAGCAACTAGAGAAGCTCAGAAAAGAGCAGCAGCGGGCATCATGAAAAACCCAACTGTGGATGGAATAACAGTGATAGATCTAGATCCAATAC
GlnAlaLysAlaThrArgGluAlaGlnLysArgAlaAlaAlaGlyIleMetLysAsnProThrValAspGlyIleThrValIleAspLeuAspProIle>

                7310      7320      7330      7340      7350      7360      7370      7380      7390
7400
CCTATGATCCAAAGTTTGAAAAGCAGTTGGGACAAGTAATGCTCCTAGTCCTCTGCGTGACCCAAGTGCTGATGATGAGGACTACGTGGGCTTTGTGTGA
ProTyrAspProLysPheGluLysGlnLeuGlyGlnValMetLeuLeuValLeuCysValThrGlnValLeuMetMetArgThrThrTrpAlaLeuCysGlu>

                7410      7420      7430      7440      7450      7460      7470      7480      7490
7500
AGCCTTAACTCTAGCAACTGGACCCGTGTCCACATTGTGGGAAGGAAATCCAGGGAGATTCTGGAACACAACCATTGCAGTGTCAATGGCAAACATCTTT
AlaLeuThrLeuAlaThrGlyProValSerThrLeuTrpGluGlyAsnProGlyArgPheTrpAsnThrThrIleAlaValSerMetAlaAsnIlePhe>

                7510      7520      7530      7540      7550      7560      7570      7580      7590
7600
AGAGGGAGTTACCTGGCTGGAGCTGGACTTCTCTTTTCTATCATGAAGAACACAACCAGCACGAGAAGAGGAACTGGCAATATAGGAGAAACGTTAGGAG
ArgGlySerTyrLeuAlaGlyAlaGlyLeuLeuPheSerIleMetLysAsnThrThrSerThrArgArgGlyThrGlyAsnIleGlyGluThrLeuGly>

                7610      7620      7630      7640      7650      7660      7670      7680      7690
```

APPENDIX 1-continued

Nucleotide and amino acid sequence of DEN2 (Tonga/74) cDNA plasmid p2

```
7700
AGAAATGGAAAAGCAGACTGAACGCATTGGGGAAAAGTGAATTCCAGATCTACAAAAAAAGTGGAATTCAAGAAGTGGACAGAACCTTAGCAAAAGAAGG
GluLysTrpLysSerArgLeuAsnAlaLeuGlyLysSerGluPheGlnIleTyrLysLysSerGlyIleGlnGluValAspArgThrLeuAlaLysGluGly>

                 7710      7720      7730      7740      7750      7760      7770      7780      7790
7800
CATTAAAAGAGGAGAAACGGATCATCACGCTGTGTCGCGAGGCTCAGCAAAACTGAGATGGTTCGTTGAAAGGAATTTGGTCACACCAGAAGGGAAAGTA
IleLysArgGlyGluThrAspHisHisAlaValSerArgGlySerAlaLysLeuArgTrpPheValGluArgAsnLeuValThrProGluGlyLysVal>

                 7810      7820      7830      7840      7850      7860      7870      7880      7890
7900
GTGGACCTTGGTTGTGGCAGAGGGGGCTGGTCATACTATTGTGGAGGATTAAAGAATGTAAGAGAAGTTAAAGGCTTAACAAAAGGAGGACCAGGACACG
ValAspLeuGlyCysGlyArgGlyGlyTrpSerTyrTyrCysGlyGlyLeuLysAsnValArgGluValLysGlyLeuThrLysGlyGlyProGlyHis>

                 7910      7920      7930      7940      7950      7960      7970      7980      7990
8000
AAGAACCTATCCCTATGTCAACATATGGGTGGAATCTAGTACGCTTACAGAGCGGAGTTGATGTTTTTTTTGTTCCACCAGAGAAGTGTGACACATTGTT
GluGluProIleProMetSerThrTyrGlyTrpAsnLeuValArgLeuGlnSerGlyValAspValPhePheValProProGluLysCysAspThrLeuLeu>

                 8010      8020      8030      8040      8050      8060      8070      8080      8090
8100
GTGTGACATAGGGGAATCATCACCAAATCCCACGGTAGAAGCGGGACGAACACTCAGAGTCCTCAACCTAGTGGAAAATTGGCTGAACAATAACACCCAA
CysAspIleGlyGluSerSerProAsnProThrValGluAlaGlyArgThrLeuArgValLeuAsnLeuValGluAsnTrpLeuAsnAsnAsnThrGln>

                 8110      8120      8130      8140      8150      8160      8170      8180      8190
8200
TTTTGCGTAAAGGTTCTTAACCCGTACATGCCCTCAGTCATTGAAAGAATGGAAACCTTACAACGGAAATACGGAGGAGCCTTGGTGAGAAATCCACTCT
PheCysValLysValLeuAsnProTyrMetProSerValIleGluArgMetGluThrLeuGlnArgLysTyrGlyGlyAlaLeuValArgAsnProLeu>

                 8210      8220      8230      8240      8250      8260      8270      8280      8290
8300
CACGGAATTCCACACATGAGATGTACTGGGTGTCCAATGCTTCCGGGAACATAGTGTCATCAGTGAACATGATTTCAAGAATGCTGATCAACAGATTCAC
SerArgAsnSerThrHisGluMetTyrTrpValSerAsnAlaSerGlyAsnIleValSerSerValAsnMetIleSerArgMetLeuIleAsnArgPheThr>

                 8310      8320      8330      8340      8350      8360      8370      8380      8390
8400
TATGAGACACAAGAAGGCCACCTATGAGCCAGATGTCGACCTCGGAAGCGGAACCCGCAATATTGGAATTGAAAGTGAGACACCGAACCTAGACATAATT
MetArgHisLysLysAlaThrTyrGluProAspValAspLeuGlySerGlyThrArgAsnIleGlyIleGluSerGluThrProAsnLeuAspIleIle>

                 8410      8420      8430      8440      8450      8460      8470      8480      8490
8500
GGGAAAAGAATAGAAAAAATAAAACAAGAGCATGAAACGTCATGGCACTATGATCAAGACCACCCATACAAAACATGGGCTTACCATGGCAGCTATGAAA
GlyLysArgIleGluLysIleLysGlnGluHisGluThrSerTrpHisTyrAspGlnAspHisProTyrLysThrTrpAlaTyrHisGlySerTyrGlu>

                 8510      8520      8530      8540      8550      8560      8570      8580      8590
8600
CAAAACAGACTGGATCAGCATCATCCATGGTGAACGGAGTAGTCAGATTGCTGACAAAACCCTGGGACGTTGTTCCAATGGTGACACAGATGGCAATGAC
ThrLysGlnThrGlySerAlaSerSerMetValAsnGlyValValArgLeuLeuThrLysProTrpAspValValProMetValThrGlnMetAlaMetThr>

                 8610      8620      8630      8640      8650      8660      8670      8680      8690
8700
AGACACAACTCCTTTTGGACAACAGCGCGTCTTCAAAGAGAAGGTGGATACGAGAACCCAAGAACCAAAAGAAGGCACAAAAAAACTAATGAAAATCACG
AspThrThrPropheGlyGlnGlnArgValPheLysGluLysValAspThrArgThrGlnGluProLysGluGlyThrLysLysLeuMetLysIleThr>

                 8710      8720      8730      8740      8750      8760      8770      8780      8790
8800
GCAGAGTGGCTCTGGAAAGAACTAGGAAAGAAAAAGACACCTAGAATGTGTACCAGAGAAGAATTCACAAAAAAGGTGAGAAGCAATGCAGCCTTGGGGG
AlaGluTrpLeuTrpLysGluLeuGlyLysLysLysThrProArgMetCysThrArgGluGluPheThrLysLysValArgSerAsnAlaAlaLeuGly>

                 8810      8820      8830      8840      8850      8860      8870      8880      8890
8900
CCATATTCACCGATGAGAACAAGTGGAAATCGGCGCGTGAAGCCGTTGAAGATAGTAGGTTTTGGGAGCTGGTTGACAAGGAAAGGAACCTCCATCTTGA
AlaIlePheThrAspGluAsnLysTrpLysSerAlaArgGluAlaValGluAspSerArgPheTrpGluLeuValAspLysGluArgAsnLeuHisLeuGlu>

                 8910      8920      8930      8940      8950      8960      8970      8980      8990
9000
AGGGAAATGTGAAACATGTGTATACAACATGATGGGGAAAAGAGAGAAAAAACTAGGAGAGTTTGGTAAAGCAAAAGGCAGCAGAGCCATATGGTACATG
GlyLysCysGluThrCysValTyrAsnMetMetGlyLysArgGluLysLysLeuGlyGluPheGlyLysAlaLysGlySerArgAlaIleTrpTyrMet>

                 9010      9020      9030      9040      9050      9060      9070      9080      9090
9100
TGGCTCGGAGCACGCTTCTTAGAGTTTGAAGCCCTAGGATTTTTGAATGAAGACCATTGGTTCTCCAGAGAGAACTCCCTGAGTGGAGTGGAAGGAGAAG
TrpLeuGlyAlaArgPheLeuGluPheGluAlaLeuGlyPheLeuAsnGluAspHisTrpPheSerArgGluAsnSerLeuSerGlyValGluGlyGlu>

                 9110      9120      9130      9140      9150      9160      9170      9180      9190
9200
GGCTGCATAAGCTAGGTTACATCTTAAGAGAGGTGAGCAAGAAAGAAGGAGGAGCAATGTATGCCGATGACACCGCAGGCTGGGACACAAGAATCACAAT
GlyLeuHisLysLeuGlyTyrIleLeuArgGluValSerLysLysGluGlyGlyAlaMetTyrAlaAspAspThrAlaGlyTrpAspThrArgIleThrIle>
```

APPENDIX 1-continued

Nucleotide and amino acid sequence of DEN2 (Tonga/74) cDNA plasmid p2

```
                 9210      9220      9230      9240      9250      9260      9270      9280      9290
9300
AGAGGATTTGAAAAATGAAGAAATGATAACGAACCACATGGCAGGAGAACACAAGAAACTTGCCGAGGCCATTTTTAAATTGACGTACCAAAACAAGGTG
GluAspLeuLysAsnGluGluMetIleThrAsnHisMetAlaGlyGluHisLysLysLeuAlaGluAlaIlePheLysLeuThrTyrGlnAsnLysVal>

                 9310      9320      9330      9340      9350      9360      9370      9380      9390
9400
GTGCGTGTGCAAAGACCAACACCAAGAGGCACAGTAATGGACATCATATCGAGAAGAGACCAAAGGGGTAGTGGACAAGTTGGCACCTATGGCCTCAACA
ValArgValGlnArgProThrProArgGlyThrValMetAspIleIleSerArgArgAspGlnArgGlySerGlyGlnValGlyThrTyrGlyLeuAsn>

                 9410      9420      9430      9440      9450      9460      9470      9480      9490
9500
CTTTCACCAACATGGAAGCACAACTAATTAGGCAAATGGAGGGGGAAGGAATCTTCAAAAGCATCCAGCACTTGACAGCCTCAGAAGAAATCGCTGTGCA
ThrPheThrAsnMetGluAlaGlnLeuIleArgGlnMetGluGlyGluGlyIlePheLysSerIleGlnHisLeuThrAlaSerGluGluIleAlaValGln>

                 9510      9520      9530      9540      9550      9560      9570      9580      9590
9600
AGATTGGCTAGTAAGAGTAGGGCGTGAAAGGTTGTCAAGAATGGCCATCAGTGGAGATGATTGTGTTGTGAAACCTTTAGATGATAGATTTGCAAGAGCT
AspTrpLeuValArgValGlyArgGluArgLeuSerArgMetAlaIleSerGlyAspAspCysValValLysProLeuAspAspArgPheAlaArgAla>

                 9610      9620      9630      9640      9650      9660      9670      9680      9690
9700
CTAACAGCTCTAAATGACATGGGAAAGGTTAGGAAGGACATACAGCAATGGGAGCCCTCAAGAGGATGGAACGACTGGACGCAGGTGCCCTTCTGTTCAC
LeuThrAlaLeuAsnAspMetGlyLysValArgLysAspIleGlnGlnTrpGluProSerArgGlyTrpAsnAspTrpThrGlnValProPheCysSer>

                 9710      9720      9730      9740      9750      9760      9770      9780      9790
9800
ACCATTTTCACGAGTTAATTATGAAAGATGGTCGCACACTCGTAGTTCCATGCAGAAACCAAGATGAATTGATCGGCAGAGCCCGAATTTCCCAGGGAGC
HisHisPheHisGluLeuIleMetLysAspGlyArgThrLeuValValProCysArgAsnGlnAspGluLeuIleGlyArgAlaArgIleSerGlnGlyAla>

                 9810      9820      9830      9840      9850      9860      9870      9880      9890
9900
TGGGTGGTCTTTACGGGAGACGGCCTGTTTGGGGAAGTCTTACGCCCAAATGTGGAGCTTGATGTACTTCCACAGACGTGATCTCAGGCTAGCGGCAAAT
GlyTrpSerLeuArgGluThrAlaCysLeuGlyLysSerTyrAlaGlnMetTrpSerLeuMetTyrPheHisArgArgAspLeuArgLeuAlaAlaAsn>

                 9910      9920      9930      9940      9950      9960      9970      9980      9990
10000
GCCATCTGCTCGGCAGTCCCATCACACTGGATTCCAACAAGCCGGACAACCTGGTCCATACACGCCAGCCATGAATGGATGACGACGGAAGACATGTTGA
AlaIleCysSerAlaValProSerHisTrpIleProThrSerArgThrThrTrpSerIleHisAlaSerHisGluTrpMetThrThrGluAspMetLeu>

                10010     10020     10030     10040     10050     10060     10070     10080     10090
10100
CAGTTTGGAACAGAGTGTGGATCCTAGAAAATCCATGGATGGAAGACAAAACTCCAGTGGAATCATGGGAGGAAATCCCATACCTGGGAAAAAGAGAAGA
ThrValTrpAsnArgValTrpIleLeuGluAsnProTrpMetGluAspLysThrProValGluSerTrpGluGluIleProTyrLeuGlyLysArgGluAsp>

                10110     10120     10130     10140     10150     10160     10170     10180     10190
10200
CCAATGGTGCGGCTCGCTGATTGGGCTGACAAGCAGAGCCACCTGGGCGAAGAATATCCAGACAGCAATAAACCAAGTCAGATCCCTCATTGGCAATGAG
GlnTrpCysGlySerLeuIleGlyLeuThrSerArgAlaThrTrpAlaLysAsnIleGlnThrAlaIleAsnGlnValArgSerLeuIleGlyAsnGlu>

                10210     10220     10230     10240     10250     10260     10270     10280     10290
10300
GAATACACAGATTACATGCCATCCATGAAAAGATTCAGAAGAGAAGAGGAAGAGGCAGGAGTTTTGTGGTAGAAAAACATGAAACAAAACAGAAGTCAGG
            GluTyrThrAspTyrMetProSerMetLysArgPheArgArgGluGluGluGluAlaGlyValLeuTrp***>

                10310     10320     10330     10340     10350     10360     10370     10380     10390
10400
TCGGATTAAGCCATAGTACGGGAAAAACTATGCTACCTGTGAGCCCCGTCCAAGGACGTTAAAAGAAGTCAGGCCATTTTGATGCCATAGCTTGAGCAAA

                10410     10420     10430     10440     10450     10460     10470     10480     10490
10500
CTGTGCAGCCTGTAGCTCCACCTGAGAAGGTGTAAAAAATCCGGGAGGCCACAAACCATGGAAGCTGTACGCATGGCGTAGTGGACTAGCGGTTAGAGGA

                10510     10520     10530     10540     10550     10560     10570     10580     10590
10600
GACCCCTCCCTTACAGATCGCAGCAACAATGGGGGCCCAAGGTGAGATGAAGCTGTAGTCTCACTGGAAGGACTAGAGGTTAGAGGAGACCCCCCCAAAA

                10610     10620     10630     10640     10650     10660     10670     10680     10690
10700
CAAAAAACAGCATATTGACGCTGGGAAAGACCAGAGATCCTGCTGTCTCCTCAGCATCATTCCAGGCACAGGACGCCAGAAAATGGAATGGTGCTGTTGA

                10710     10720     10730     10740     10750     10760     10770     10780     10790
10800
ATCAACAGGTTCTGGTACCGGTAGGCATCGTGGTGTCACGCTCGTCGTTTGGTATGGCTTCATTCAGCTCCGGTTCCCAACGATCAAGGCGAGTTACATG

                10810     10820     10830     10840     10850     10860     10870     10880     10890
10900
```

APPENDIX 1-continued

Nucleotide and amino acid sequence of DEN2 (Tonga/74) cDNA plasmid p2

ATCCCCCATGTTGTGCAAAAAAGCGGTTAGCTCCTTCGGTCCTCCGATCGTTGTCAGAAGTAAGTTGGCCGCAGTGTTATCACTCATGGTTATGGCAGCA 10910 10920 10930 10940 10950 10960 10970 10980 10990
11000
CTGCATAATTCTCTTACTGTCATGCCATCCGTAAGATGCTTTTCTGTGACTGGTGAGTACTCAACCAAGTCATTCTGAGAATAGTGTATGCGGCGACCGA 11010 11020 11030 11040 11050 11060 11070 11080 11090
11100
GTTGCTCTTGCCCGGCGTCAACACGGGATAATACCGCGCCACATAGCAGAACTTTAAAAGTGCTCATCATTGGAAAACGTTCTTCGGGGCGAAAACTCTC 11110 11120 11130 11140 11150 11160 11170 11180 11190
11200
AAGGATCTTACCGCTGTTGAGATCCAGTTCGATGTAACCCACTCGTGCACCCAACTGATCTTCAGCATCTTTTACTTTCACCAGCGTTTCTGGGTGAGCA 11210 11220 11230 11240 11250 11260 11270 11280 11290
11300
AAAACAGGAAGGCAAAATGCCGCAAAAAAGGGAATAAGGGCGACACGGAAATGTTGAATACTCATACTCTTCCTTTTTCAATATTATTGAAGCATTTATC 11310 11320 11330 11340 11350 11360 11370 11380 11390
11400
AGGGTTATTGTCTCATGAGCGGATACATATTTGAATGTATTTAGAAAAATAAACAAATAGGGGTTCCGCGCACATTTCCCCGAAAAGTGCCACCTGACGT 11410 11420 11430 11440 11450 11460 11470 11480 11490
11500
CTAAGAAACCATTATTATCATGACATTAACCTATAAAAATAGGCGTATCACGAGGCCCTTTCGTCTTCAAGAATTCTCATGTTTGACAGCTTATCATCGA 11510 11520 11530 11540 11550 11560 11570 11580 11590
11600
TAAGCTTTAATGCGGTAGTTTATCACAGTTAAATTGCTAACGCAGTCAGGCACCGTGTATGAAATCTAACAATGCGCTCATCGTCATCCTCGGCACCGTC 11610 11620 11630 11640 11650 11660 11670 11680 11690
11700
ACCCTGGATGCTGTAGGCATAGGCTTGGTTATGCCGGTACTGCCGGGCCTCTTGCGGGATATCGTCCATTCCGACAGCATCGCCAGTCACTATGGCGTGC 11710 11720 11730 11740 11750 11760 11770 11780 11790
11800
TGCTGGCGCTATATGCGTTGATGCAATTTCTATGCGCACCCGTTCTCGGAGCACTGTCCGACCGCTTTGGCCGCCGCCCAGTCCTGCTCGCTTCGCTACT 11810 11820 11830 11840 11850 11860 11870 11880 11890
11900
TGGAGCCACTATCGACTACGCGATCATGGCGACCACACCCGTCCTGTGGATCCTCTACGCCGGACGCATCGTGGCCGGCATCACCGGCGCCACAGGTGCG 11910 11920 11930 11940 11950 11960 11970 11980 11990
12000
GTTGCTGGCGCCTATATCGCCGACATCACCGATGGGGAAGATCGGGCTCGCCACTTCGGGCTCATGAGCGCTTGTTTCGGCGTGGGTATGGTGGCAGGCC 12010 12020 12030 12040 12050 12060 12070 12080 12090
12100
CCGTGGCCGGGGGACTGTTGGGCGCCATCTCCTTGCATGCACCATTCCTTGCGGCGGCGGTGCTCAACGGCCTCAACCTACTACTGGGCTGCTTCCTAAT 12110 12120 12130 12140 12150 12160 12170 12180 12190
12200
GCAGGAGTCGCATAAGGGAGAGCGTCGACCGATGCCCTTGAGAGCCTTCAACCCAGTCAGCTCCTTCCGGTGGGCGCGGGGCATGACTATCGTCGCCGCA 12210 12220 12230 12240 12250 12260 12270 12280 12290
12300
CTTATGACTGTCTTCTTTATCATGCAACTCGTAGGACAGGTGCCGGCAGCGCTCTGGGTCATTTTCGGCGAGGACCGCTTTCGCTGGAGCGCGACGATGA 12310 12320 12330 12340 12350 12360 12370 12380 12390
12400
TCGGCCTGTCGCTTGCGGTATTCGGAATCTTGCACGCCCTCGCTCAAGCCTTCGTCACTGGTCCCGCCACCAAACGTTTCGGCGAGAAGCAGGCCATTAT 12410 12420 12430 12440 12450 12460 12470 12480 12490
12500
CGCCGGCATGGCGGCCGACGCGCTGGGCTACGTCTTGCTGGCGTTCGCGACGCGAGGCTGGATGGCCTTCCCCATTATGATTCTTCTCGCTTCCGGCGGC 12510 12520 12530 12540 12550 12560 12570 12580 12590
12600
ATCGGGATGCCCGCGTTGCAGGCCATGCTGTCCAGGCAGGTAGATGACGACCATCAGGGACAGCTTCAAGGATCGCTCGCGGCTCTTACCAGCCTAACTT 12610 12620 12630 12640 12650 12660 12670 12680 12690
12700
CGATCACTGGACCGCTGATCGTCACGGCGATTTATGCCGCCTCGGCGAGCACATGGAACGGGTTGGCATGGATTGTAGGCGCCGCCCTATACCTTGTCTG 12710 12720 12730 12740 12750 12760 12770 12780 12790
12800
CCTCCCCGCGTTGCGTCGCGGTGCATGGAGCCGGGCCACCTCGACCTGAATGGAAGCCGGCGGCACCTCGCTAACGGATTCACCACTCCAAGAATTGGAG

APPENDIX 1-continued

Nucleotide and amino acid sequence of DEN2 (Tonga/74) cDNA plasmid p2

12810 12820 12830 12840 12850 12860 12870 12880 12890
12900
CCAATCAATTCTTGCGGAGAACTGTGAATGCGCAAACCAACCCTTGGCAGAACATATCCATCGCGTCCGCCATCTCCAGCAGCCGCACGCGGCGCATCTC 12910 12920 12930 12940 12950 12960 12970 12980 12990
13000
GGGCAGCGTTGGGTCCTGGCCACGGGTGCGCATGATCGTGCTCCTGTCGTTGAGGACCCGGCTAGGCTGGCGGGGTTGCCTTACTGGTTAGCAGAATGAA 13010 13020 13030 13040 13050 13060 13070 13080 13090
13100
TCACCGATACGCGAGCGAACGTGAAGCGACTGCTGCTGCAAAACGTCTGCGACCTGAGCAACAACATGAATGGTCTTCGGTTTCCGTGTTTCGTAAAGTC 13110 13120 13130 13140 13150 13160 13170 13180 13190
13200
TGGAAACGCGGAAGTCAGCGCCCTGCACCATTATGTTCCGGATCTGCATCGCAGGATGCTGCTGGCTACCCTGTGGAACACCTACATCTGTATTAACGAA 13210 13220 13230 13240 13250 13260 13270 13280 13290
13300
GCGCTGGCATTGACCCTGAGTGATTTTTCTCTGGTCCCGCCGCATCCATACCGCCAGTTGTTTACCCTCACAACGTTCCAGTAACCGGGCATGTTCATCA 13310 13320 13330 13340 13350 13360 13370 13380 13390
13400
TCAGTAACCCGTATCGTGAGCATCCTCTCTCGTTTCATCGGTATCATTACCCCCATGAACAGAAATCCCCCTTACACGGAGGCATCAGTGACCAAACAGG 13410 13420 13430 13440 13450 13460 13470 13480 13490
13500
AAAAAACCGCCCTTAACATGGCCCGCTTTATCAGAAGCCAGACATTAACGCTTCTGGAGAAACTCAACGAGCTGGACGCGGATGAACAGGCAGACATCTG 13510 13520 13530 13540 13550 13560 13570 13580 13590
13600
TGAATCGCTTCACGACCACGCTGATGAGCTTTACCGCAGCTGCCTCGCGCGTTTCGGTGATGACGGTGAAAACCTCTGACACATGCAGCTCCCGGAGACG 13610 13620 13630 13640 13650 13660 13670 13680 13690
13700
GTCACAGCTTGTCTGTAAGCGGATGCCGGGAGCAGACAAGCCCGTCAGGGCGCGTCAGCGGGTGTTGGCGGGTGTCGGGGCGCAGCCATGACCCAGTCAC 13710 13720 13730 13740 13750 13760 13770 13780 13790
13800
GTAGCGATAGCGGAGTGTATACTGGCTTAACTATGCGGCATCAGAGCAGATTGTACTGAGAGTGCACCATATGCGGTGTGAAATACCGCACAGATGCGTA 13810 13820 13830 13840 13850 13860 13870 13880 13890
13900
AGGAGAAAATACCGCATCAGGCGCTCTTCCGCTTCCTCGCTCACTGACTCGCTGCGCTCGGTCGTTCGGCTGCGGCGAGCGGTATCAGCTCACTCAAAGG 13910 13920 13930 13940 13950 13960 13970 13980 13990
14000
CGGTAATACGGTTATCCACAGAATCAGGGGATAACGCAGGAAAGAACATGTGAGCAAAAGGCCAGCAAAAGGCCAGGAACCGTAAAAAGGCCGCGTTGCT 14010 14020 14030 14040 14050 14060 14070 14080 14090
14100
GGCGTTTTTCCATAGGCTCCGCCCCCCTGACGAGCATCACAAAAATCGACGCTCAAGTCAGAGGTGGCGAAACCCGACAGGACTATAAAGATACCAGGCG 14110 14120 14130 14140 14150 14160 14170 14180 14190
14200
TTTCCCCCTGGAAGCTCCCTCGTGCGCTCTCCTGTTCCGACCCTGCCGCTTACCGGATACCTGTCCGCCTTTCTCCCTTCGGGAAGCGTGGCGCTTTCTC 14210 14220 14230 14240 14250 14260 14270 14280 14290
14300
ATAGCTCACGCTGTAGGTATCTCAGTTCGGTGTAGGTCGTTCGCTCCAAGCTGGGCTGTGTGCACGAACCCCCCGTTCAGCCCGACCGCTGCGCCTTATC 14310 14320 14330 14340 14350 14360 14370 14380 14390
14400
CGGTAACTATCGTCTTGAGTCCAACCCGGTAAGACACGACTTATCGCCACTGGCAGCAGCCACTGGTAACAGGATTAGCAGAGCGAGGTATGTAGGCGGT 14410 14420 14430 14440 14450 14460 14470 14480 14490
14500
GCTACAGAGTTCTTGAAGTGGTGGCCTAACTACGGCTACACTAGAAGGACAGTATTTGGTATCTGCGCTCTGCTGAATCCAGTTACCTTCGGAAAAAGAG 14510 14520 14530 14540 14550 14560 14570 14580 14590
14600
TTGGTAGCTCTTGATCCGGCAAACAAACCACCGCTGGTAGCGGTGGTTTTTTTGTTTGCAAGCAGCAGATTACGCGCAGAAAAAAAGGATCTCAAGAAGA 14610 14620 14630 14640 14650 14660 14670 14680 14690
14700
TCCTTTGATCTTTTCTACGGGGTCTGACGCTCAGTGGAACGAAAACTCACGTTAAGGGATTTTGGTCATGAGATTATCAAAAAGGATCTTCACCTAGATC 14710 14720 14730 14740 14750 14760 14770 14780 14790
14800

APPENDIX 1-continued

Nucleotide and amino acid sequence of DEN2 (Tonga/74) cDNA plasmid p2

```
CTTTTAAATTAAAAATGAAGTTTTAAATCAATCTAAAGTATATATGAGTAAACTTGGTCTGACAGTTACCAATGCTTAATCAGTGAGGCACCTATCTCAG

                14810     14820     14830     14840     14850     14860     14870     14880     14890
14900
CGATCTGTCTATTTCGTTCATCCATAGTTGCCTGACTCCCCGTCGTGTAGATAACTACGATACGGGAGGGCTTACCATCTGGCCCCAGTGCTGCAATGAT

                14910     14920     14930     14940     14950     14960     14970     14980     14990
15000
ACCGCGAGACCCACGCTCACCGGCTCCAGATTTATCAGCAATAAACCAGCCAGCCGGAAGGGCCGAGCGCAGAAGTGGTCCTGCAACTTTATCCGCCTCC

                15010     15020     15030     15040     15050     15060     15070     15080     15090
15100
ATCCAGTCTATTAATTGTTGCCGGGAAGCTAGAGTAAGTAGTTCGCCAGTTAATAGTTTGCGCAACGTTGTTGCCATTGCTGCAAGATCTGGCTAGCGAT

                15110     15120     15130     15140     15150
           GACCCTGCTGATTGGTTCGCTGACCATTTCCGGGCGCGCCGATTTAGGTGACACTATAG
```

Bases 1 to 10713: DEN2 virus genome cDNA
Bases 97 to 10269: DEN2 polyprotein ORF
Bases 97 to 438: C protein ORF
Bases 439 to 936: prM protein ORF
Bases 937 to 2421: E protein ORF
Bases 2422 to 3477: NS1 protein ORF
Bases 3478 to 4131: NS2A protein ORF
Bases 4132 to 4521: NS2B protein ORF
Bases 4522 to 6375: NS3 protein ORF
Bases 6376 to 6756: NS4A protein ORF
Bases 6757 to 6825: 2K protein ORF
Bases 6826 to 7569: NS4B protein ORF
Bases 7570 to 10269: NS5 protein ORF

APPENDIX 2

Nucleotide and amino acid sequence of DEN3 (S1eman/78) cDNA plasmid p3

```
10   20   30   40   50   60   70   80   90   100
AGTTGTTAGTCTACGTGGACCGACAAGAACAGTTTCGACTCGGAAGCTTGCTTAACGTAGTACTGACAGTTTTTTATTAGAGAGCAGATCTCTGATGAACMet
Asn>

110   120   130   140   150   160   170   180   190   200
AACCAACGGAAAAAGACGGGAAAACCGTCTATCAATATGCTGAAACGCGTGAGAAACCGTGTGTCAACTGGATCACAGTTGGCGAAGAGATTCTCAAGAG
AsnGlnArgLysLysThrGlyLysProSerIleAsnMetLeuLysArgValArgAsnArgValSerThrGlySerGlnLeuAlaLysArgPheSerArg>

210   220   230   240   250   260   270   280   290   300
GACTGCTGAACGGCCAAGGACCAATGAAATTGGTTATGGCGTTCATAGCTTTCCTCAGATTTCTAGCCATTCCACCGACAGCAGGAGTCTTGGCTAGATG
GlyLeuLeuAsnGlyGlnGlyProMetLysLeuValMetAlaPheIleAlaPheLeuArgPheLeuAlaIleProProThrAlaGlyValLeuAlaArgTrp>

310   320   330   340   350   360   370   380   390   400
GGGAACCTTTAAGAAGTCGGGGGCTATTAAGGTCCTGAGAGGCTTCAAGAAGGAGATCTCAAACATGCTGAGCATTATCAACAGACGGAAAAAGACATCG
GlyThrPheLysLysSerGlyAlaIleLysValLeuArgGlyPheLysLysGluIleSerAsnMetLeuSerIleIleAsnArgArgLysLysThrSer>

410   420   430   440   450   460   470   480   490   500
CTCTGTCTCATGATGATGTTACCAGCAACACTTGCTTTCCACTTGACTTCACGAGATGGAAGCCGCGCATGATTGTGGGGAAGAATGAAAGAGGAAAAT
LeuCysLeuMetMetLeuProAlaThrLeuAlaPheHisLeuThrSerArgAspGlyGluProArgMetIleValGlyLysAsnGluArgGlyLys>

510   520   530   540   550   560   570   580   590   600
CCCTACTTTTTAAGACAGCCTCTGGAATCAACATGTGCACACTCATAGCCATGGATTTGGGAGAGATGTGTGATGACACGGTCACCTACAAATGCCCCCT
SerLeuLeuPheLysThrAlaSerGlyIleAsnMetCysThrLeuIleAlaMetAspLeuGlyGluMetCysAspAspThrValThrTyrLysCysProLeu>

610   620   630   640   650   660   670   680   690   700
CATTACTGAAGTGGAGCCTGAAGACATTGACTGCTGGTGCAACCTTACATCGACATGGGTGACCTACGGAACGTGCAATCAAGCTGGAGAGCACAGACGC
IleThrGluValGluProGluAspIleAspCysTrpCysAsnLeuThrSerThrTrpValThrTyrGlyThrCysAsnGlnAlaGlyGluHisArgArg>

710   720   730   740   750   760   770   780   790   800
GACAAAAGATCGGTGGCGTTAGCTCCCCATGTCGGCATGGGACTGGACACACGCACCCAAACCTGGATGTCGGCTGAAGGAGCTTGGAGACAGGTCGAGA
AspLysArgSerValAlaLeuAlaProHisValGlyMetGlyLeuAspThrArgThrGlnThrTrpMetSerAlaGluGlyAlaTrpArgGlnValGlu>

810   820   830   840   850   860   870   880   890   900
AGGTAGAGACATGGGCCTTTAGGCACCCAGGGTTCACAATACTAGCCCTATTTCTTGCCCATTACATAGGCACTTCCTTGACCCAGAAAGTGGTTATTTT
LysValGluThrTrpAlaPheArgHisProGlyPheThrIleLeuAlaLeuPheLeuAlaHisTyrIleGlyThrSerLeuThrGlnLysValValIlePhe>

910   920   930   940   950   960   970   980   990   1000
CATACTACTAATGCTGGTCACCCCATCCATGACAATGAGATGCGTGGGAGTAGGAAACAGAGATTTTGTGGAAGGCCTATCAGGAGCTACGTGGGTTGAC
IleLeuLeuMetLeuValThrProSerMetThrMetArgCysValGlyValGlyAsnArgAspPheValGluGlyLeuSerGlyAlaThrTrpValAsp>

1010   1020   1030   1040   1050   1060   1070   1080   1090   1100
```

APPENDIX 2-continued

Nucleotide and amino acid sequence of DEN3 (S1eman/78) cDNA plasmid p3

```
GTGGTGCTCGAGCACGGTGGGTGTGTGACTACCATGGCTAAGAACAAGCCCACGCTGGATATAGAGCTCCAGAAGACCGAGGCCACCCAACTGGCGACCC
ValValLeuGluHisGlyGlyCysValThrThrMetAlaLysAsnLysProThrLeuAspIleGluLeuGlnLysThrGluAlaThrGlnLeuAlaThr>

1110   1120   1130   1140   1150   1160   1170   1180   1190   1200
TAAGGAAACTATGTATTGAGGGAAAAATTACCAACGTAACAACCGACTCAAGGTGCCCCACCCAAGGGGAAGCGATTTTACCTGAGGAGCAGGACCAGAA
LeuArgLysLeuCysIleGluGlyLysIleThrAsnValThrThrAspSerArgCysProThrGlnGlyGluAlaIleLeuProGluGluGlnAspGlnAsn>

1210   1220   1230   1240   1250   1260   1270   1280   1290   1300
CCACGTGTGCAAGCACACATACGTGGACAGAGGCTGGGGAAACGGTTGTGGTTTGTTTGGCAAGGGAAGCCTGGTAACATGCGCGAAATTTCAATGTTTG
HisValCysLysHisThrTyrValAspArgGlyTrpGlyAsnGlyCysGlyLeuPheGlyLysGlySerLeuValThrCysAlaLysPheGlnCysLeu>

1310   1320   1330   1340   1350   1360   1370   1380   1390   1400
GAATCAATAGAGGGAAAAGTGGTGCAGCATGAGAACCTCAAATACACCGTCATCATCACAGTGCACACAGGAGATCAACACCAGGTGGGAAATGAAACGC
GluSerIleGluGlyLysValValGlnHisGluAsnLeuLysTyrThrValIleIleThrValHisThrGlyAspGlnHisGlnValGlyAsnGluThr>

1410   1420   1430   1440   1450   1460   1470   1480   1490   1500
AGGGAGTCACGGCTGAGATAACACCCCAGGCATCAACCGTTGAAGCCATCTTACCTGAATATGGAACCCTTGGGCTAGAATGCTCACCACGGACAGGTTT
GlnGlyValThrAlaGluIleThrProGlnAlaSerThrValGluAlaIleLeuProGluTyrGlyThrLeuGlyLeuGluCysSerProArgThrGlyLeu>

1510   1520   1530   1540   1550   1560   1570   1580   1590   1600
AGATTTCAATGAAATGATTTTGTTGACAATGAAGAACAAAGCATGGATGGTACATAGACAATGGTTTTTTGACCTACCTTTACCATGGACATCAGGAGCT
AspPheAsnGluMetIleLeuLeuThrMetLysAsnLysAlaTrpMetValHisArgGlnTrpPhePheAspLeuProLeuProTrpThrSerGlyAla>

1610   1620   1630   1640   1650   1660   1670   1680   1690   1700
ACAACAGAAACACCAACCTGGAATAAGAAAGAGCTTCTTGTGACATTCAAAAACGCACATGCAAAAAAGCAAGAAGTAGTAGTCCTTGGATCGCAAGAGG
ThrThrGluThrProThrTrpAsnLysLysGluLeuLeuValThrPheLysAsnAlaHisAlaLysLysGlnGluValValValLeuGlySerGlnGlu>

1710   1720   1730   1740   1750   1760   1770   1780   1790   1800
GAGCAATGCACACAGCACTGACAGGAGCTACAGAGATCCAAACCTCAGGAGGCACAAGTATTTTTGCGGGGCACTTAAAATGTAGACTCAAGATGGACAA
GlyAlaMetHisThrAlaLeuThrGlyAlaThrGluIleGlnThrSerGlyGlyThrSerIlePheAlaGlyHisLeuLysCysArgLeuLysMetAspLys>

1810   1820   1830   1840   1850   1860   1870   1880   1890   1900
ATTGGAACTCAAGGGGATGAGCTATGCAATGTGCTTGAATGCCTTTGTGTTGAAGAAAGAAGTCTCCGAAACGCAACATGGGACAATACTCATCAAGGTT
LeuGluLeuLysGlyMetSerTyrAlaMetCysLeuAsnAlaPheValLeuLysLysGluValSerGluThrGlnHisGlyThrIleLeuIleLysVal>

1910   1920   1930   1940   1950   1960   1970   1980   1990   2000
GAGTACAAAGGGGAAGATGCACCTTGCAAGATTCCTTTCTCCACGGAGGATGGACAAGGGAAAGCCCACAATGGCAGACTGATCACAGCTAACCCAGTGG
GluTyrLysGlyGluAspAlaProCysLysIleProPheSerThrGluAspGlyGlnGlyLysAlaHisAsnGlyArgLeuIleThrAlaAsnProVal>

2010   2020   2030   2040   2050   2060   2070   2080   2090   2100
TGACCAAGAAGGAGGAGCCTGTCAATATTGAGGCAGAACCTCCTTTTGGGGAAAGCAATATAGTAATTGGAATTGGAGACAAAGCCTTGAAAATCAACTG
ValThrLysLysGluGluProValAsnIleGluAlaGluProProPheGlyGluSerAsnIleValIleGlyIleGlyAspLysAlaLeuLysIleAsnTrp>

2110   2120   2130   2140   2150   2160   2170   2180   2190   2200
GTACAAGAAGGGAAGCTCGATTGGGAAGATGTTCGAGGCCACTGCCAGAGGTGCAAGGCGCATGGCCATCTTGGGAGACACAGCCTGGGACTTTGGATCA
TyrLysLysGlySerSerIleGlyLysMetPheGluAlaThrAlaArgGlyAlaArgArgMetAlaIleLeuGlyAspThrAlaTrpAspPheGlySer>

2210   2220   2230   2240   2250   2260   2270   2280   2290   2300
GTAGGTGGTGTTTTAAATTCATTAGGAAAAATGGTGCACCAAATATTTGGAAGTGCTTACACAGCCCTATTTAGTGGAGTCTCCTGGATAATGAAAATTG
ValGlyGlyValLeuAsnSerLeuGlyLysMetValHisGlnIlePheGlySerAlaTyrThrAlaLeuPheSerGlyValSerTrpIleMetLysIle>

2310   2320   2330   2340   2350   2360   2370   2380   2390   2400
GAATAGGTGTCCTTTTAACCTGGATAGGGTTGAATTCAAAAAACACTAGTATGAGCTTTAGCTGCATTGTGATAGGAATCATTACACTCTATCTGGGAGC
GlyIleGlyValLeuLeuThrTrpIleGlyLeuAsnSerLysAsnThrSerMetSerPheSerCysIleValIleGlyIleIleThrLeuTyrLeuGlyAla>

2410   2420   2430   2440   2450   2460   2470   2480   2490   2500
CGTGGTGCAAGCTGACATGGGGTGTGTCATAAACTGGAAAGGCAAAGAACTCAAATGTGGAAGTGGAATTTTCGTCACTAATGAGGTCCACACCTGGACA
ValValGlnAlaAspMetGlyCysValIleAsnTrpLysGlyLysGluLeuLysCysGlySerGlyIlePheValThrAsnGluValHisThrTrpThr>

2510   2520   2530   2540   2550   2560   2570   2580   2590   2600
GAGCAATACAAATTTCAAGCAGACTCCCCCAAAAGACTGGCGACAGCCATTGCAGGCGCTTGGGAGAATGGAGTGTGCGGAATCAGGTCGACAACCAGAA
GluGlnTyrLysPheGlnAlaAspSerProLysArgLeuAlaThrAlaIleAlaGlyAlaTrpGluAsnGlyValCysGlyIleArgSerThrThrArg>

2610   2620   2630   2640   2650   2660   2670   2680   2690   2700
TGGAGAACCTCTTGTGGAAGCAAATAGCCAATGAACTGAACTACATATTATGGGAAAACAACATCAAATTAACGGTAGTTGTGGGTGATATAATTGGGGT
MetGluAsnLeuLeuTrpLysGlnIleAlaAsnGluLeuAsnTyrIleLeuTrpGluAsnAsnIleLysLeuThrValValValGlyAspIleIleGlyVal>

2710   2720   2730   2740   2750   2760   2770   2780   2790   2800
CTTAGAGCAAGGGAAAAGAACACTAACACCACAACCCATGGAACTAAAATATTCATGGAAAACATGGGGAAAGGCGAAGATAGTGACAGCTGAAACACAA
LeuGluGlnGlyLysArgThrLeuThrProGlnProMetGluLeuLysTyrSerTrpLysThrTrpGlyLysAlaLysIleValThrAlaGluThrGln>

2810   2820   2830   2840   2850   2860   2870   2880   2890   2900
AATTCCTCTTTCATAATAGATGGGCCAAACACACCAGAGTGTCCAAGTGCCTCAAGAGCATGGAATGTGTGGGAGGTGGAAGATTACGGGTTCGGAGTCT
AsnSerSerPheIleIleAspGlyProAsnThrProGluCysProSerAlaSerArgAlaTrpAsnValTrpGluValGluAspTyrGlyPheGlyVal>

2910   2920   2930   2940   2950   2960   2970   2980   2990   3000
TCACAACTAACATATGGCTGAAACTCCGAGAGATGTACACCCAACTATGTGACCACAGGCTAATGTCGGCAGCCGTTAAGGATGAGAGGGCCGTACACGC
PheThrThrAsnIleTrpLeuLysLeuArgGluMetTyrThrGlnLeuCysAspHisArgLeuMetSerAlaAlaValLysAspGluArgAlaValHisAla>
```

APPENDIX 2-continued

Nucleotide and amino acid sequence of DEN3 (S1eman/78) cDNA plasmid p3

```
3010   3020   3030   3040   3050   3060   3070   3080   3090   3100
CGACATGGGCTATTGGATAGAAAGCCAAAAGAATGGAAGTTGGAAGCTAGAAAAGGCATCCCTCATAGAGGTAAAAACCTGCACATGGCCAAAATCACAC
AspMetGlyTyrTrpIleGluSerGlnLysAsnGlySerTrpLysLeuGluLysAlaSerLeuIleGluValLysThrCysThrTrpProLysSerHis>

3110   3120   3130   3140   3150   3160   3170   3180   3190   3200
ACTCTTTGGAGCAATGGTGTGCTAGAGAGTGACATGATCATCCCAAAGAGTCTGGCTGGTCCCATTTCGCAACACAACTACAGGCCCGGATACCACACCC
ThrLeuTrpSerAsnGlyValLeuGluSerAspMetIleIleProLysSerLeuAlaGlyProIleSerGlnHisAsnTyrArgProGlyTyrHisThr>

3210   3220   3230   3240   3250   3260   3270   3280   3290   3300
AAACGGCAGGACCCTGGCACTTAGGAAAATTGGAGCTGGACTTCAACTATTGTGAAGGAACAACAGTTGTCATCACAGAAAATTGTGGGACAAGAGGCCC
GlnThrAlaGlyProTrpHisLeuGlyLysLeuGluLeuAspPheAsnTyrCysGluGlyThrThrValValIleThrGluAsnCysGlyThrArgGlyPro>

3310   3320   3330   3340   3350   3360   3370   3380   3390   3400
ATCACTGAGAACAACAACAGTGTCAGGGAAGTTGATACACGAATGGTGTTGCCGCTCGTGTACACTTCCTCCCCTGCGATACATGGGAGAAGACGGCTGC
SerLeuArgThrThrThrValSerGlyLysLeuIleHisGluTrpCysCysArgSerCysThrLeuProProLeuArgTyrMetGlyGluAspGlyCys>

3410   3420   3430   3440   3450   3460   3470   3480   3490   3500
TrpTyrGlyMetGluIleArgProIleAsnGluLysGluGluAsnMetValLysSerLeuValSerAlaGlySerGlyLysValAspAsnPheThrMet>
TGGTATGGCATGGAAATTAGACCCATTAATGAGAAAGAAGAGAACATGGTAAAGTCTTTAGTCTCAGCAGGGAGTGGAAAGGTGGATAACTTCACAATGG

3510   3520   3530   3540   3550   3560   3570   3580   3590   3600
GTGTCTTGTGTTTGGCAATCCTTTTTGAAGAGGTGATGAGAGGAPAATTTGGGAPAAAGCACATGATTGCAGGGGTTCTCTTCACGTTTGTACTCCTCT
GlyValLeuCysLeuAlaIleLeuPheGluGluValMetArgGlyLysPheGlyLysLysHisMetIleAlaGlyValLeuPheThrPheValLeuLeuLeu>

3610   3620   3630   3640   3650   3660   3670   3680   3690   3700
CTCAGGGCAAATAACATGGAGAGACATGGCGCACACACTCATAATGATTGGGTCCAACGCCTCTGACAGAATGGGAATGGGCGTCACTTACCTAGCATTG
SerGlyGlnIleThrTrpArgAspMetAlaHisThrLeuIleMetIleGlySerAsnAlaSerAspArgMetGlyMetGlyValThrTyrLeuAlaLeu>

3710   3720   3730   3740   3750   3760   3770   3780   3790   3800
ATTGCAACATTTAAAATTCAGCCATTTTTGGCTTTGGGATTCTTCCTGAGGAAACTGACATCTAGAGAAAATTTATTGTTGGGAGTTGGGTTGGCCATGG
IleAlaThrPheLysIleGlnProPheLeuAlaLeuGlyPhePheLeuArgLysLeuThrSerArgGluAsnLeuLeuLeuGlyValGlyLeuAlaMet>

3810   3820   3830   3840   3850   3860   3870   3880   3890   3900
CAACAACGTTACAACTGCCAGAGGACATTGAACAAATGGCGAATGGAATAGCTTTAGGGCTCATGGCTCTTAAATTAATAACACAATTTGAAACATACCA
AlaThrThrLeuGlnLeuProGluAspIleGluGlnMetAlaAsnGlyIleAlaLeuGlyLeuMetAlaLeuLysLeuIleThrGlnPheGluThrTyrGln>

3910   3920   3930   3940   3950   3960   3970   3980   3990   4000
ACATGGACGGCATTAGTCTCCCTAATGTGTTCAAATACAATTTTCACGTTGACTGTTGCCTGGAGAACAGCCACCCTGATTTTGGCCGGAATTTCTCTT
LeuTrpThrAlaLeuValSerLeuMetCysSerAsnThrIlePheThrLeuThrValAlaTrpArgThrAlaThrLeuIleLeuAlaGlyIleSerLeu>

4010   4020   4030   4040   4050   4060   4070   4080   4090   4100
TTGCCAGTGTGCCAGTCTTCGAGCATGAGGAAAACAGATTGGCTCCCAATGGCTGTGGCAGCTATGGGAGTTCCACCCCTACCACTTTTTATTTTCAGTT
LeuProValCysGlnSerSerSerMetArgLysThrAspTrpLeuProMetAlaValAlaAlaMetGlyValProProLeuProLeuPheIlePheSer>

4110   4120   4130   4140   4150   4160   4170   4180   4190   4200
TGAAAGATACGCTCAAAAGGAGAAGCTGGCCACTGAATGAGGGGGTGATGGCTGTTGGACTTGTGAGTATTCTAGCTAGTTCTCTCCTTAGGAATGACGT
LeuLysAspThrLeuLysArgArgSerTrpProLeuAsnGluGlyValMetAlaValGlyLeuValSerIleLeuAlaSerSerLeuLeuArgAsnAspVal>

4210   4220   4230   4240   4250   4260   4270   4280   4290   4300
GCCCATGGCTGGACCATTAGTGGCTGGGGGCTTGCTGATAGCGTGCTACGTCATAACTGGCACGTCAGCAGACCTCACTGTAGAAAAAGCAGCAGATGTC
ProMetAlaGlyProLeuValAlaGlyGlyLeuLeuIleAlaCysTyrValIleThrGlyThrSerAlaAspLeuThrValGluLysAlaAlaAspVal>

4310   4320   4330   4340   4350   4360   4370   4380   4390   4400
ACATGGGAGGAAGAGGCTGAGCAAACAGGAGTGTCCCACAATTTAATGATCACAGTTGATGACGATGGAACAATGAGAATAAAAGATGATGAGACTGAGA
ThrTrpGluGluGluAlaGluGlnThrGlyValSerHisAsnLeuMetIleThrValAspAspAspGlyThrMetArgIleLysAspAspGluThrGlu>

4410   4420   4430   4440   4450   4460   4470   4480   4490   4500
ACATCTTAACAGTGCTTTTGAAAACAGCATTACTAATAGTGTCAGGCATTTTTCCATACTCCATACCCGCAACACTGTTGGTCTGGCACACTTGGCAAAA
AsnIleLeuThrValLeuLeuLysThrAlaLeuLeuIleValSerGlyIlePheProTyrSerIleProAlaThrLeuLeuValTrpHisThrTrpGlnLys>

4510   4520   4530   4540   4550   4560   4570   4580   4590   4600
GCAAACCCAAAGATCCGGTGTCCTATGGGACGTTCCCAGCCCCCCAGAGACACAGAAAGCAGAACTGGAAGAAGGGGTTTATAGGATCAAGCAGCAAGGA
GlnThrGlnArgSerGlyValLeuTrpAspValProSerProProGluThrGlnLysAlaGluLeuGluGluGlyValTyrArgIleLysGlnGlnGly>

4610   4620   4630   4640   4650   4660   4670   4680   4690   4700
ATTTTTGGGAAAACCCAAGTGGGGGTTGGAGTACAAAAAGAAGGAGTTTTCCACACCATGTGGCACGTCACAAGAGGAGCAGTGTTGACACACAATGGGA
IlePheGlyLysThrGlnValGlyValGlyValGlnLysGluGlyValPheHisThrMetTrpHisValThrArgGlyAlaValLeuThrHisAsnGly>

4710   4720   4730   4740   4750   4760   4770   4780   4790   4800
AAAGACTGGAACCAAACTGGGCTAGCGTGAAAAAAGATCTGATTTCATACGGAGGAGGATGGAAATTGAGTGCACAATGGCAAAAAGGAGAGGAGGTGCA
LysArgLeuGluProAsnTrpAlaSerValLysLysAspLeuIleSerTyrGlyGlyGlyTrpLysLeuSerAlaGlnTrpGlnLysGlyGluGluValGln>

4810   4820   4830   4840   4850   4860   4870   4880   4890   4900
GGTTATTGCCGTAGAGCCTGGGAAGAACCCAAAGAACTTTCAAACCATGCCAGGCATTTTCCAGACAACAACAGGGGGAGATAGGAGCGATTGCACTGGAC
ValIleAlaValGluProGlyLysAsnProLysAsnPheGlnThrMetProGlyIlePheGlnThrThrThrGlyGluIleGlyAlaIleAlaLeuAsp>

4910   4920   4930   4940   4950   4960   4970   4980   4990   5000
```

APPENDIX 2-continued

Nucleotide and amino acid sequence of DEN3 (S1eman/78) cDNA plasmid p3

```
TTCAAGCCTGGAACTTCAGGATCTCCCATCATAAACAGAGAGGGAAAGGTACTGGGATTGTATGGCAATGGAGTGGTCACAAAGAATGGTGGCTATGTCA
PheLysProGlyThrSerGlySrProIleIleAsnArgGluGlyLysValLeuGlyLeuTyrGlyAsnGlyValValThrLysAsnGlyGlyTyrVal>

5010   5020   5030   5040   5050   5060   5070   5080   5090   5100
GTGGAATAGCACAAACAAATGCAGAACCAGACGGACCGACACCAGAGTTGGAAGAAGAGATGTTCAAAAAGCGAAATCTAACCATAATGGATCTCCATCC
SerGlyIleAlaGlnThrAsnAlaGluProAspGlyProThrProGluLeuGluGluGluMetPheLysLysArgAsnLeuThrIleMetAspLeuHisPro>

5110   5120   5130   5140   5150   5160   5170   5180   5190   5200
CGGGTCAGGAAAGACGCGGAAATATCTTCCAGCTATTGTTAGAGAGGCAATCAAGAGACGCTTAAGGACTCTAATTTTGGCACCAACAAGGGTAGTTGCA
GlySerGlyLysThrArgLysTyrLeuProAlaIleValArgGluAlaIleLysArgArgLeuArgThrLeuIleLeuAlaProThrArgValValAla>

5210   5220   5230   5240   5250   5260   5270   5280   5290   5300
GCTGAGATGGAAGAAGCATTGAAAGGGCTCCCAATAAGGTATCAAACAACTGCAACAAAATCTGAACACACAGGGAGAGAGATTGTTGATCTAATGTGCC
AlaGluyMetGluGluAlaLeuLysGlyLeuProIleArgTyrGlnThrThrAlaThrLysSerGluHisThrGlyArgGluIleValAspLeuMetCys>

5310   5320   5330   5340   5350   5360   5370   5380   5390   5400
ACGCAACGTTCACAATGCGTTTGCTGTCACCAGTCAGGGTTCCAAACTACAACTTGATAATAATGGATGAGGCTCATTTCACAGACCCAGCCAGTATAGC
HisAlaThrPheThrMetArgLeuLeuSerProValArgValProAsnTyrAsnLeuIleIleMetAspGluAlaHisPheThrAspProAlaSerIleAla>

5410   5420   5430   5440   5450   5460   5470   5480   5490   5500
GGCTAGAGGGTACATATCAACTCGTGTAGGAATGGGAGAGGCAGCCGCAATTTTCATGACAGCCACACCCCCTGGAACAGCTGATGCCTTTCCTCAGAGC
AlaArgGlyTyrIleSerThrArgValGlyMetGlyGluAlaAlaAlaIlePheMetThrAlaThrProProGlyThrAlaAspAlaPheProGlnSer>

5510   5520   5530   5540   5550   5560   5570   5580   5590   5600
AACGCTCCAATTCAAGATGAAGAAAGAGACATACCAGAACGCTCATGGAATTCAGGCAATGAATGGATTACCGACTTTGCCGGGAAGACGGTGTGGTTTG
AsnAlaProIleGlnAspGluGluArgAspIleProGluArgSerTrpAsnSerGlyAsnGluTrpIleThrAspPheAlaGlyLysThrValTrpPhe>

5610   5620   5630   5640   5650   5660   5670   5680   5690   5700
TCCCTAGCATCAAAGCTGGAAATGACATAGCAAACTGCTTGCGGAAAAATGGAAAAAAGGTCATTCAACTTAGTAGGAAGACTTTTGACACAGAATATCA
ValProSerIleLysAlaGlyAsnAspIleAlaAsnCysLeuArgLysAsnGlyLysLysValIleGlnLeuSerArgLysThrPheAspThrGluTyrGln>

5710   5720   5730   5740   5750   5760   5770   5780   5790   5800
AAAGACTAAACTAAATGATTGGGACTTTGTGGTGACAACAGACATTTCAGAAATGGGAGCCAATTTCAAAGCAGACAGAGTGATCGACCCAAGAAGATGT
LysThrLysLeuAsnAspTrpAspPheValValThrThrAspIleSerGluMetGlyAlaAsnPheLysAlaAspArgValIleAspProArgArgCys>

5810   5820   5830   5840   5850   5860   5870   5880   5890   5900
CTCAAGCCAGTGATTTTGACAGACGGACCCGAGCGCGTGATCCTGGCGGGACCAATGCCAGTCACCGTAGCGAGCGCTGCGCAAAGGAGAGGGAGAGTTG
LeuLysProValIleLeuThrAspGlyProGluArgValIleLeuAlaGlyProMetProValThrValAlaSerAlaAlaGlnArgArgGlyArgVal>

5910   5920   5930   5940   5950   5960   5970   5980   5990   6000
GCAGGAACCCACAAAAAGAAAATGACCAATACATATTCATGGGCCAGCCCCTCAATAATGATGAAGACCATGCTCACTGGACAGAAGCAAAAATGCTGCT
GlyArgAsnProGlnLysGluAsnAspGlnTyrIlePheMetGlyGlnProLeuAsnAsnAspGluAspHisAlaHisTrpThrGluAlaLysMetLeuLeu>

6010   6020   6030   6040   6050   6060   6070   6080   6090   6100
AGACAACATCAACACACCAGAAGGGATCATACCAGCTCTCTTTGAACCAGAAAGGGAGAAGTCAGCCGCCATAGACGGCGAATACCGCCTGAAGGGTGAG
AspAsnIleAsnThrProGluGlyIleIleProAlaLeuPheGluProGluArgGluLysSerAlaAlaIleAspGlyGluTyrArgLeuLysGlyGlu>

6110   6120   6130   6140   6150   6160   6170   6180   6190   6200
TCCAGGAAGACCTTCGTGGAACTCATGAGGAGGGGTGACCTCCCAGTTTGGCTAGCCCATAAAGTAGCATCAGAAGGGATCAAATATACAGATAGAAAGT
SerArgLysThrPheValGluLeuMetArgArgGlyAspLeuProValTrpLeuAlaHisLysValAlaSerGluGlyIleLysTyrThrAspArgLys>

6210   6220   6230   6240   6250   6260   6270   6280   6290   6300
GGTGTTTTGATGGAGAACGCAACAATCAAATTTTAGAGGAGAATATGGATGTGGAAATCTGGACAAAGGAAGGAGAAAAGAAAAAATTGAGACCTAGGTG
TrpCysPheAspGlyGluArgAsnAsnGlnIleLeuGluGluAsnMetAspValGluIleTrpThrLysGluGlyGluLysLysLysLeuArgProArgTrp>

6310   6320   6330   6340   6350   6360   6370   6380   6390   6400
GCTTGATGCCCGCACTTATTCAGATCCCTTAGCGCTCAAGGAATTCAAGGACTTTGCGGCTGGTAGAAAGTCAATTGCCCTTGATCTTGTGACAGAAATA
LeuAspAlaArgThrTyrSerAspProLeuAlaLeuLysGluPheLysAspPheAlaAlaGlyArgLysSerIleAlaLeuAspLeuValThrGluIle>

6410   6420   6430   6440   6450   6460   6470   6480   6490   6500
GGAAGAGTGCCTTCACACTTAGCTCACAGAACGAGAAACGCCCTGGACAATCTGGTGATGTTGCACACGTCAGAACATGGCGGGAGGGCCTACAGGCATG
GlyArgValProSerHisLeuAlaHisArgThrArgAsnAAlaLeuAspAsnLeuValMetLeuHisThrSerGLuHisGlyGlyArgAlaTyrArgHis>

6510   6520   6530   6540   6550   6560   6570   6580   6590   6600
CAGTGGAGGAACTACCAGAAACAATGGAAACACTCTTACTCCTGGGACTCATGATCCTGTTAACAGGTGGAGCAATGCTTTTCTTGATATCAGGTAAAGG
AlaValGluGluLeuProGluThrMetGluThrLeuLeuLeuLeuGlyLeuMetIleLeuLeuThrGlyGlyAlaMetLeuPheLeuIleSerGlyLysGly>

6610   6620   6630   6640   6650   6660   6670   6680   6690   6700
GATTGGAAAGACTTCAATAGGACTCATTTGTGTAGCTGCTTCCAGCGGTATGTTATGGATGGCTGATGTCCCACTCCAATGGATCGCGTCTGCCATAGTC
IleGlyLysThrSerIleGLyLeuIleCysValAlaAlaSerSerGlyMetLeuTrpMetAlaAspValProLeuGlnTrpIleAlaSerAlaIleVal>

6710   6720   6730   6740   6750   6760   6770   6780   6790   6800
CTGGAGTTTTTTATGATGGTGTTACTTATACCAGAACCAGAAAAGCAGAGAACTCCCCAAGACAATCAACTCGCATATGTCGTGATAGGCATACTCACAC
LeuGluPhePheMetMetValLeuLeuIleProGluProGluLysGlnArgThrProGlnAspAsnGlnLeuAlaTyrValValIleGlyIleLeuThr>

6810   6820   6830   6840   6850   6860   6870   6880   6890   6900
TGGCTGCAATAGTAGCAGCCAATGAAATGGGACTGTTGGAAACCACAAAGAGAGATTTAGGAATGTCCAAAGAACCAGGTGTTGTTTCTCCAACCAGCTA
LeuAlaAlaIleValAlaAlaAsnGluMetGlyLeuLeuGluThrThrLysArgAspLeuGlyMetSerLysGluProGlyValValSerProThrSerTyr>
```

Nucleotide and amino acid sequence of DEN3 (S1eman/78) cDNA plasmid p3

```
6910   6920   6930   6940   6950   6960   6970   6980   6990   7000
TTTGGATGTGGACTTGCACCCAGCATCAGCCTGGACATTGTACGCTGTGGCCACAACAGTAATAACACCAATGTTGAGACATACCATAGAGAATTCCACA
LeuAspValAspLeuHisProAlaSerAlaTrpThrLeuTyrAlaValAlaThrThrValIleThrProMetLeuArgHisThrIleGluAsnSerThr>

7010   7020   7030   7040   7050   7060   7070   7080   7090   7100
GCAAATGTGTCCCTGGCAGCTATAGCCAACCAGGCAGTGGTCCTGATGGGTTTAGACAAAGGATGGCCGATATCGAAAATGGACTTAGGCGTGCCACTAT
AlaAsnValSerLeuAlaAlaIleAlaAsnGlnAlaValValLeuMetGlyLeuAspLysGlyTrpProIleSerLysMetAspLeuGLyValProLeu>

7110   7120   7130   7140   7150   7160   7170   7180   7190   7200
TGGCACTGGGTTGTTATTCACAAGTGAACCCACTAACTCTCACAGCGGCAGTTCTCCTGCTAGTCACGCATTATGCTATTATAGGTCCAGGATTGCAGGC
LeuAlaLeuGlyCysTyrSerGlnValAsnProLeuThrLeuThrAlaAlaValLeuLeuLeuValThrHisTyrAlaIleIleGlyProGlyLeuGlnAla>

7210   7220   7230   7240   7250   7260   7270   7280   7290   7300
AAAAGCCACTCGTGAAGCTCAAAAAAGGACAGCTGCTGGAATAATGAAGAATCCAACGGTGGATGGGATAATGACAATAGACCTAGATCCTGTAATATAC
LysAlaThrArgGluAlaGlnLysArgThrAlaAlaGlyIleMetLysAsnProThrValAspGlyIleMetThrIleAspLeuAspProValIleTyr>

7310   7320   7330   7340   7350   7360   7370   7380   7390   7400
GATTCAAAATTTGAAAAGCAACTAGGACAGGTTATGCTCCTGGTTCTGTGTGCAGTTCAACTTTTGTTAATGAGAACATCATGGGCTTTTTGTGAAGCTC
AspSerLysPheGluLysGlnLeuGlyGlnValMetLeuLeuValLeuCysAlaValGlnLeuLeuLeuMetArgThrSerTrpAlaPheCysGluAla>

7410   7420   7430   7440   7450   7460   7470   7480   7490   7500
TAACCCTAGCCACAGGACCAATAACAACACTCTGGGAAGGATCACCTGGGAAGTTCTGGAACACCACGATAGCTGTTTCCATGGCGAACATCTTTAGAGG
LeuThrLeuAlaThrGlyProIleThrThrLeuTrpGluGlySerProGlyLysPheTrpAsnThrThrIleAlaValSerMetAlaAsnIlePheArgGly>

7510   7520   7530   7540   7550   7560   7570   7580   7590   7600
GAGCTATTTAGCAGGAGCTGGGCTTGCTTTTTCTATCATGAAATCAGTTGGAACAGGAAAGAGAGGGACAGGGTCACAGGGTGAAACCTTGGGAGAAAAG
SerTyrLeuAlaGlyAlaGlyLeuAlaPheSerIleMetLysSerValGlyThrGlyLysArgGlyThrGlySerGlnGlyGluThrLeuGlyGluLys>

7610   7620   7630   7640   7650   7660   7670   7680   7690   7700
TGGAAAAAGAAATTGAATCAATTACCCCGGAAAGAGTTTGACCTTTACAAGAAATCCGGAATCACTGAAGTGGATAGAACAGAAGCCAAAGAAGGGTTGA
TrpLysLysLysLeuAsnGlnLeuProArgLysGluPheAspLeuTyrLysLysSerGlyIleThrGluValAspArgThrGluAlaLysGluGlyLeu>

7710   7720   7730   7740   7750   7760   7770   7780   7790   7800
AAAGAGGAGAAATAACACACCATGCCGTGTCCAGAGGCAGCGCAAAACTTCAATGGTTCGTGGAGAGAAACATGGTCATCCCCGAAGGAAGAGTCATAGA
LysArgGlyGluIleThrHisHisAlaValSerArgGlySerAlaLysLeuGlnTrpPheValGluArgAsnMetValIleProGluGlyArgValIleAsp>

7810   7820   7830   7840   7850   7860   7870   7880   7890   7900
CTTAGGCTGTGGAAGAGGAGGCTGGTCATATTATTGTGCAGGACTGAAAAAAGTTACAGAAGTGCGAGGATACACAAAAGGCGGCCCAGGACATGAAGAA
LeuGlyCysGlyArgGlyGlyTrpSerTyrTyrCysAlaGlyLeuLysLysValThrGluValArgGlyTyrThrLysGlyGlyProGlyHisGluGlu>

7910   7920   7930   7940   7950   7960   7970   7980   7990   8000
CCAGTACCTATGTCTACATACGGATGGAACATAGTCAAGTTAATGAGTGGAAAGGATGTGTTTTATCTTCCACCTGAAAAGTGTGATACTCTATTGTGTG
ProValProMetSerThrTyrGlyTrpAsnIleValLysLeuMetSerGlyLysAspValPheTyrLeuProProGluLysCysAspThrLeuLeuCys>

8010   8020   8030   8040   8050   8060   8070   8080   8090   8100
ACATTGGAGAATCTTCACCAAGCCCAACAGTGGAAGAAAGCAGAACCATAAGAGTCTTGAAGATGGTTGAACCATGGCTAAAAAATAACCAGTTTTGCAT
AspIleGlyGluSerSerProSerProThrValGluGluSerArgThrIleArgValLeuLysMetValGluProTrpLeuLysAsnAsnGlnPheCysIle>

8110   8120   8130   8140   8150   8160   8170   8180   8190   8200
TAAAGTATTGAACCCTTACATGCCAACTGTGATTGAGCACCTAGAAAGACTACAAAGGAAACATGGAGGAATGCTTGTGAGAAATCCACTCTCACGAAAC
LysValLeuAsnProTyrMetProThrValIleGluHisLeuGluArgLeuGlnArgLysHisGlyGlyMetLeuValArgAsnProLeuSerArgAsn>

8210   8220   8230   8240   8250   8260   8270   8280   8290   8300
TCCACGCACGAAATGTACTGGATATCTAATGGCACAGGCAATATCGTTTCTTCAGTCAACATGGTATCCAGATTGCTACTTAACAGATTCACAATGACAC
SerThrHisGLuMetTyrTrpIleSerAsnGlyThrGlyAsnIleValSerSerValAsnMetValSerArgLeuLeuLeuAsnArgPheThrMetThr>

8310   8320   8330   8340   8350   8360   8370   8380   8390   8400
ATAGGAGACCCACCATAGAGAAAGATGTGGATTTAGGAGCGGGGACCCGACATGTCAATGCGGAACCAGAAACACCCAACATGGATGTCATTGGGGAAAG
HisArgArgProThrIleGluLysAspValAspLeuGlyAlaGlyThrArgHisValAsnAlaGluProGluThrProAsnMetAspValIleGlyGluArg>

8410   8420   8430   8440   8450   8460   8470   8480   8490   8500
AATAAGAAGGATCAAGGAGGAGCATAGTTCAACATGGCACTATGATGATGAAAATCCTTATAAAACGTGGGCTTACCATGGATCCTATGAAGTTAAGGCC
IleArgArgIleLysGluGluHisSerSerThrTrpHisTyrAspAspGluAsnProTyrLysThrTrpAlaTyrHisGlySerTyrGluValLysAla>

8510   8520   8530   8540   8550   8560   8570   8580   8590   8600
ACAGGCTCAGCCTCCTCCATGATAAATGGAGTCGTGAAACTCCTCACGAAACCATGGGATGTGGTGCCCATGGTGACACAGATGGCAATGACGGATACAA
ThrGlySerAlaSerSerMetIleAsnGlyValValLysLeuLeuThrLysProTrpAspValValProMetValThrGlnMetAlaMetThrAspThr>

8610   8620   8630   8640   8650   8660   8670   8680   8690   8700
CCCCATTCGGCCAGCAAAGGGTTTTTAAAGAGAAAGTGGACACCAGGACACCCAGACCTATGCCAGGAACAAGAAAGGTTATGGAGATCACAGCGGAATG
ThrProPheGlyGlnGlnArgValPheLysGluLysValAspThrArgThrProArgProMetProGlyThrArgLysValMetGluIleThrAlaGluTrp>

8710   8720   8730   8740   8750   8760   8770   8780   8790   8800
GCTTTGGAGAACCCTGGGAAGGAACAAAAGACCCAGATTATGTACGAGAGAGGAGTTCACAAAAAAGGTCAGAACCAACGCAGCTATGGGCGCCGTTTTT
LeuTrpArgThrLeuGlyArgAsnLysArgProArgLeuCysThrArgGluGluPheThrLysLysValArgThrAsnAlaAlaMetGlyAlaValPhe>

8810   8820   8830   8840   8850   8860   8870   8880   8890   8900
```

APPENDIX 2-continued

Nucleotide and amino acid sequence of DEN3 (S1eman/78) cDNA plasmid p3

```
ACAGAGGAGAACCAATGGGACAGTGCTAGAGCTGCTGTTGAGGATGAAGAATTCTGGAAACTCGTGGACAGAGAACGTGAACTCCACAAATTGGGCAAGT
ThrGluGluAsnGlnTrpAspSerAlaArgAlaAlaValGluAspGluGluPheTrpLysLeuValAspArgGluArgGluLeuHisLysLeuGlyLys

8910   8920   8930   8940   8950   8960   8970   8980   8990   9000
GTGGAAGCTGCGTTTACAACATGATGGGCAAGAGAGAGAAGAAACTTGGAGAGTTTGGCAAAGCAAAAGGCAGTAGAGCCATATGGTACATGTGGTTGGG
CysGlySerCysValTyrAsnMetMetGlyLysArgGluLysLysLeuGlyGluPheGlyLysAlaLysGlySerArgAlaIleTrpTyrMetTrpLeuGly>

9010   9020   9030   9040   9050   9060   9070   9080   9090   9100
AGCCAGATACCTTGAGTTCGAAGCACTCGGATTCTTAAATGAAGACCATTGGTTCTCGCGTGAAAACTCTTACAGTGGAGTAGAAGGAGAAGGACTGCAC
AlaArgTyrLeuGluPheGluAlaLeuGlyPheLeuAsnGluAspHisTrpPheSerArgGluAsnSerTyrSerGlyValGluGlyGluGlyLeuHis>

9110   9120   9130   9140   9150   9160   9170   9180   9190   9200
AAGCTGGGATACATCTTAAGAGACATTTCCAGATACCCGGAGGAGCTATGTATGCTGATGACACAGCTGGTTGGGACACAAGAATTAACAGAAGATGACC
LysLeuGlyTyrIleLeuArgAspIleSerLysIleProGlyGlyAlaMetTyrAlaAspAspThrAlaGlyTrpAspThrArgIleThrGluAspAsp>

9210   9220   9230   9240   9250   9260   9270   9280   9290   9300
TGCACAATGAGGAAAAAATCACACAGCAAATGGACCCTGAACACAGGCAGTTAGCAAACGCTATATTCAAGCTCACATACCAAAACAAAGTGGTCAAAGT
LeuHisAsnGluGluLysIleThrGlnGlnMetAspProGluHisArgGlnLeuAlaAsnAlaIlePheLysLeuThrTyrGlnAsnLysValValLysVal>

9310   9320   9330   9340   9350   9360   9370   9380   9390   9400
TCAACGACCAACTCCAAAGGGCACGGTAATGGACATCATATCTAGGAAAGACCAAAGAGGCAGTGGACAGGTGGGAACTTATGGTCTGAATACATTCACC
GlnArgProThrProLysGlyThrValMetAspIleIleSerArgLysAspGlnArgGlySerGlyGlnValGlyThrTyrGlyLeuAsnThrPheThr>

9410   9420   9430   9440   9450   9460   9470   9480   9490   9500
AACATGGAAGCCCAGTTAATCAGACAAATGGAAGGAGAAGGTGTGTTGTCGAAGGCAGACCTCGAGAACCCTCATCTGCTAGAGAAGAAAGTTACACAAT
AsnMetGluAlaGlnLeuIleArgGlnMetGluGlyGluGlyValLeuSerLysAlaAspLeuGluAsnProHisLeuLeuGluLysLysValThrGln>

9510   9520   9530   9540   9550   9560   9570   9580   9590   9600
GGTTGGAAACAAAAGGAGTGGAGAGGTTAAAAAGAATGGCCATCAGCGGGGATGATTGCGTGGTGAAACCAATTGATGACAGGTTCGCCAATGCCCTGCT
TrpLeuGluThrLysGlyValGluArgLeuLysArgMetAlaIleSerGlyAspAspCysValValLysProIleAspAspArgPheAlaAsnAlaLeuLeu>

9610   9620   9630   9640   9650   9660   9670   9680   9690   9700
TGCCCTGAATGACATGGGAAAAGTTAGGAAGGACATACCTCAATGGCAGCCATCAAAGGGATGGCATGATTGGCAACAGGTCCCTTTCTGCTCCCACCAC
AlaLeuAsnAspMetGlyLysValArgLysAspIleProGlnTrpGlnProSerLysGlyTrpHisAspTrpGLnGlnValProPheCysSerHisHis>

9710   9720   9730   9740   9750   9760   9770   9780   9790   9800
TTTCATGAATTGATCATGAAAGATGGAAGAAAGTTGGTAGTTCCCTGCAGACCTCAGGATGAATTAATCGGGAGAGCGAGAATCTCTCAAGGAGCAGGAT
PheHisGluLeuIleMetLysAspGlyArgLysLeuValValProCysArgProGlnAspGluLeuIleGlyArgAlaArgIleSerGlnGlyAlaGly>

9810   9820   9830   9840   9850   9860   9870   9880   9890   9900
GGAGCCTTAGAGAAACTGCATGCCTAGGGAAAGCCTACGCCCAAATGTGGACTCTCATGTACTTTCACAGAAGAGATCTTAGACTAGCATCCAACGCCAT
TrpSerLeuArgGluThrAlaCysLeuGlyLysAlaTyrAlaGlnMetTrpThrLeuMetTyrPheHisArgArgAspLeuArgLeuAlaSerAsnAlaIle>

9910   9920   9930   9940   9950   9960   9970   9980   9990   10000
ATGTTCAGCAGTACCAGTCCATTGGGTCCCCACAAGCAGAACGACGTGGTCTATTCATGCTCACCATCAGTGGATGACTACAGAAGACATGCTTACTGTT
CysSerAlaValProValHisTrpValProThrSerArgThrThrTrpSerIleHisAlaHisHisGlnTrpMetThrThrGluAspMetLeuThrVal>

10010   10020   10030   10040   10050   10060   10070   10080   10090   10100
TGGAACAGGGTGTGGATAGAGGATAATCCATGGATGGAAGACAAAACTCCAGTCAAAACCTGGGAAGATGTTCCATATCTAGGGAAGAGAGAAGACCAAT
TrpAsnArgValTrpIleGluAspAsnProTrpMetGluAspLysThrProValLysThrTrpGluAspValProTyrLeuGlyLysArgGluAspGln>

10110   10120   10130   10140   10150   10160   10170   10180   10190   10200
GGTGCGGATCACTCATTGGTCTCACTTCCAGAGCAACCTGGGCCCAGAACATACTTACGGCAATCCAACAGGTGAGAAGCCTTATAGGCAATGAAGAGTT
TrpCysGlySerLeuIleGlyLeuThrSerArgAlaThrTrpAlaGlnAsnIleLeuThrAlaIleGlnGlnValArgSerLeuIleGlyAsnGluGluPhe>

10210   10220   10230   10240   10250   10260   10270   10280   10290   10300
TCTGGACTACATGCCTTCGATGAAGAGATTCAGGAAGGAGGAGGAGTCAGAGGGAGCCATTTGGTAAACGTAGGAAGTGAAAAAGAGGCAAACTGTCAGG
LeuAspTyrMetProSerMetLysArgPheArgLysGluGluGluSerGluGlyAlaIleTrp***>

10310   10320   10330   10340   10350   10360   10370   10380   10390   10400
CCACCTTAAGCCACAGTACGGAAGAAGCTGTGCAGCCTGTGAGCCCCGTCCAAGGACGTTAAAAGAAGAAGTCAGGCCCAAAAGCCACGGTTTGAGCAAA

10410   10420   10430   10440   10450   10460   10470   10480   10490   10500
CCGTGCTGCCTGTGGCTCCGTCGTGGGGACGTAAAACCTGGGAGGCTGCAAACTGTGGAAGCTGTACGCACGGTGTAGCAGACTAGCGGTTAGAGGAGAC

10510   10520   10530   10540   10550   10560   10570   10580   10590   10600
CCCTCCCATGACACAACGCAGCAGCGGGGCCCGAGCTCTGAGGGAAGCTGTACCTCCTTGCAAAGGACTAGAGGTTAGAGGAGACCCCCCCGCAAATAAAA

10610   10620   10630   10640   10650   10660   10670   10680   10690   10700
ACAGCATATTGACGCTGGGAGAGACCAGAGATCCTGCTGTCTCCTCAGCATCATTCCAGGCACAGAACGCCAGAAAATGGAATGGTGCTGTTGAATCAAC

10710   10720   10730   10740   10750   10760   10770   10780   10790   10800
AGGTTCTGGTACCGGTAGGCATCGTGGTGTCACGCTCGTCGTTTGGTATGGCTTCATTCAGCTCCGGTTCCCAACGATCAAGGCGAGTTACATGATCCCC

10810   10820   10830   10840   10850   10860   10870   10880   10890   10900
CATGTTGTGCAAAAAAGCGGTTAGCTCCTTCGGTCCTCCGATCGTTGTCAGAAGTAAGTTGGCCGCAGTGTTATCACTCATGGTTATGGCAGCACTGCAT

10910   10920   10930   10940   10950   10960   10970   10980   10990   11000
```

APPENDIX 2-continued

Nucleotide and amino acid sequence of DEN3 (S1eman/78) cDNA plasmid p3

AATTCTCTTACTGTCATGCCATCCGTAAGATGCTTTTCTGTGACTGGTGAGTACTCAACCAAGTCATTCTGAGAATAGTGTATGCGGCGACCGAGTTGCT 11010 11020 11030 11040 11050 11060 11070 11080 11090 11100
CTTGCCCGGCGTCAACACGGGATAATACCGCGCCACATAGCAGAACTTTAAAAGTGCTCATCATTGGAAAACGTTCTTCGGGGCGAAAACTCTCAAGGAT 11110 11120 11130 11140 11150 11160 11170 11180 11190 11200
CTTACCGCTGTTGAGATCCAGTTCGATGTAACCCACTCGTGCACCCAACTGATCTTCAGCATCTTTTACTTTCACCAGCGTTTCTGGGTGAGCAAAAACA 11210 11220 11230 11240 11250 11260 11270 11280 11290 11300
GGAAGGCAAAATGCCGCAAAAAAGGGAATAAGGGCGACACGGAAATGTTGAATACTCATACTCTTCCTTTTTCAATATTATTGAAGCATTTATCAGGGTT 11310 11320 11330 11340 11350 11360 11370 11380 11390 11400
ATTGTCTCATGAGCGGATACATATTTGAATGTATTTAGAAAAATAAACAAATAGGGGTTCCGCGCACATTTCCCCGAAAAGTGCCACCTGACGTCTAAGA 11410 11420 11430 11440 11450 11460 11470 11480 11490 11500
AACCATTATTATCATGACATTAACCTATAAAAATAGGCGTATCACGAGGCCCTTTCGTCTTCAAGAATTCTCATGTTTGACAGCTTATCATCGATAAGCT 11510 11520 11530 11540 11550 11560 11570 11580 11590 11600
TTAATGCGGTAGTTTATCACAGTTAAATTGCTAACGCAGTCAGGCACCGTGTATGAAATCTAACAATGCGCTCATCGTCATCCTCGGCACCGTCACCCTG 11610 11620 11630 11640 11650 11660 11670 11680 11690 11700
GATGCTGTAGGCATAGGCTTGGTTATGCCGGTACTGCCGGGCCTCTTGCGGGATATCGTCCATTCCGACAGCATCGCCAGTCACTATGGCGTGCTGCTGG 11710 11720 11730 11740 11750 11760 11770 11780 11790 11800
CGCTATATGCGTTGATGCAATTTCTATGCGCACCCGTTCTCGGAGCACTGTCCGACCGCTTTGGCCGCCGCCCAGTCCTGCTCGCTTCGCTACTTGGAGC 11810 11820 11830 11840 11850 11860 11870 11880 11890 11900
CACTATCGACTACGCGATCATGGCGACCACACCCGTCCTGTGGATCCTCTACGCCGGACGCATCGTGGCCGGCATCACCGGCGCCACAGGTGCGGTTGCT 11910 11920 11930 11940 11950 11960 11970 11980 11990 12000
GGCGCCTATATCGCGACATCACCGATGGGGAAGATCGGGCTCGCCACTTCGGGCTCATGAGCGCTTGTTTCGGCGTGGGTATGGTTGGCAGGCCCCGTGG 12010 12020 12030 12040 12050 12060 12070 12080 12090 12100
CCGGGGGACTGTTGGGCGCCATCTCCTTGCATGCACCATTCCTTGCGGCGGCGGTGCTCAACGGCCTCAACCTACTACTGGGCTGCTTCCTAATGCAGGA 12110 12120 12130 12140 12150 12160 12170 12180 12190 12200
GTCGCATAAGGGAGAGCGTCGACCGATGCCCTTGAGAGCCTTCAACCCAGTCAGCTCCTTCCGGTGGGCGCGGGGCATGACTATCGTCGCCGCACTTATG 12210 12220 12230 12240 12250 12260 12270 12280 12290 12300
ACTGTCTTCTTTATCATGCAACTCGTAGGACAGGTGCCGGCAGCGCTCTGGGTCATTTTCGGCGAGGACCGCTTTCGCTGGAGCGCGACGATGATCGGCC 12310 12320 12330 12340 12350 12360 12370 12380 12390 12400
TGTCGCTTGCGGTATTCGGAATCTTGCACGCCCTCGCTCAAGCCTTCGTCACTGGTCCCGCCACCAAACGTTCGGCGAGAAGCAGGCCATTATCGCCGG 12410 12420 12430 12440 12450 12460 12470 12480 12490 12500
CATGGCGGCCGACGCGCTGGGCTACGTCTTGCTGGCGTTCGCGACGCGAGGCTGGATGGCCTTCCCCATTATGATTCTTCTCGCTTCCGGCGGCATCGGG 12510 12520 12530 12540 12550 12560 12570 12580 12590 12600
ATGCCCGCGTTGCAGGCCATGCTGTCCAGGCAGGTAGATGACGACCATCAGGGACAGCTTCAAGGATCGCTCGCGGCTCTTACCAGCCTAACTTCGATCA 12610 12620 12630 12640 12650 12660 12670 12680 12690 12700
CTGGACCGCTGATCGTCACGGCGATTTATGCCGCCTCGGCGAGCACATGGAACGGGTTGGCATGGATTGTAGGCGCCGCCCTATACCTTGTCTGCCTCCC 12710 12720 12730 12740 12750 12760 12770 12780 12790 12800
CGCGTTGCGTCGCGGTGCATGGAGCCGGGCCACCTCGACCTGAATGGAAGCCGGCGGCACCTCGCTAACGGATTCACCACTCCAAGAATTGGAGCCAATC 12810 12820 12830 12840 12850 12860 12870 12880 12890 12900
AATTCTTGCGGAGAACTGTGAATGCGCAAACCAACCCTTGGCAGAACATATCCATCGCGTCCGCCATCTCCAGCAGCCGCACGCGGCGCATCTCGGGCAG 12910 12920 12930 12940 12950 12960 12970 12980 12990 13000
CGTTGGGTCCTGGCCACGGGTGCGCATGATCGTGCTCCTGTCGTTGAGGACCCGGCTAGGCTGGCGGGGTTGCCTTACTGGTTAGCAGAATGAATCACCG 13010 13020 13030 13040 13050 13060 13070 13080 13090 13100
ATACGCGAGCGAACGTGAAGCGACTGCTGCTGCAAAACGTCTGCGACCTGAGCAACAACATGAATGGTCTTCGGTTTCCGTGTTTCGTAAAGTCTGGAAA 13110 13120 13130 13140 13150 13160 13170 13180 13190 13200
CGCGGAAGTCAGCGCCCTGCACCATTATGTTCCGGATCTGCATCGCAGGATGCTGCTGGCTACCCTGTGGAACACCTACATCTGTATTAACGAAGCGCTG 13210 13220 13230 13240 13250 13260 13270 13280 13290 13300
GCATTGACCCTGAGTGATTTTTCTCTGGTCCCGCCGCATCCATACCGCCAGTTGTTTACCCTCACAACGTTCCAGTAACCGGGCATGTTCATCATCAGTA 13310 13320 13330 13340 13350 13360 13370 13380 13390 13400
ACCCGTATCGTGAGCATCCTCTCTCGTTTCATCGGTATCATTACCCCCATGAACAGAAATCCCCCTTACACGGAGGCATCAGTGACCAAACAGGAAAAAA 13410 13420 13430 13440 13450 13460 13470 13480 13490 13500
CCGCCCTTAACATGGCCCGCTTTATCAGAAGCCAGACATTAACGCTTCTGGAGAAACTCAACGAGCTGGACGCGGATGAACAGGCAGACATCTGTGAATC 13510 13520 13530 13540 13550 13560 13570 13580 13590 13600

APPENDIX 2-continued

Nucleotide and amino acid sequence of DEN3 (S1eman/78) cDNA plasmid p3

```
GCTTCACGACCACGCTGATGAGCTTTACCGCAGCTGCCTCGCGCGTTTCGGTGATGACGGTGAAAACCTCTGACACATGCAGCTCCCGGAGACGGTCACA

13610   13620   13630   13640   13650   13660   13670   13680   13690   13700
GCTTGTCTGTAAGCGGATGCCGGGAGCAGACAAGCCCGTCAGGGCGCGTCAGCGGGTGTTGGCGGGTGTCGGGGCGCAGCCATGACCCAGTCACGTAGCG

13710   13720   13730   13740   13750   13760   13770   13780   13790   13800
ATAGCGGAGTGTATACTGGCTTAACTATGCGGCATCAGAGCAGATTGTACTGAGAGTGCACCATATGCGGTGTGAAATACCGCACAGATGCGTAAGGAGA

13810   13820   13830   13840   13850   13860   13870   13880   13890   13900
AAATACCGCATCAGGCGCTCTTCCGCTTCCTCGCTCACTGACTCGCTGCGCTCGGTCGTTCGGCTGCGGCGAGCGGTATCAGCTCACTCAAAGGCGGTAA

13910   13920   13930   13940   13950   13960   13970   13980   13990   14000
TACGGTTATCCACAGAATCAGGGGATAACGCAGGAAAGAACATGTGAGCAAAAGGCCAGCAAAAGGCCAGGAACCGTAAAAAGGCCGCGTTGCTGGCGTT

14010   14020   14030   14040   14050   14060   14070   14080   14090   14100
TTTCCATAGGCTCCGCCCCCCTGACGAGCATCACAAAAATCGACGCTCAAGTCAGAGGTGGCGAAACCCGACAGGACTATAAAGATACCAGGCGTTTCCC

14110   14120   14130   14140   14150   14160   14170   14180   14190   14200
CCTGGAAGCTCCCTCGTGCGCTCTCCTGTTCCGACCCTGCCGCTTACCGGATACCTGTCCGCCTTTCTCCCTTCGGGAAGCGTGGCGCTTTCTCATAGCT

14210   14220   14230   14240   14250   14260   14270   14280   14290   14300
CACGCTGTAGGTATCTCAGTTCGGTGTAGGTCGTTCGCTCCAAGCTGGGCTGTGTGCACGAACCCCCCGTTCAGCCCGACCGCTGCGCCTTATCCGGTAA

14310   14320   14330   14340   14350   14360   14370   14380   14390   14400
CTATCGTCTTGAGTCCAACCCGGTAAGACACGACTTATCGCCACTGGCAGCAGCCACTGGTAACAGGATTAGCAGAGCGAGGTATGTAGGCGGTGCTACA

14410   14420   14430   14440   14450   14460   14470   14480   14490   14500
GAGTTCTTGAAGTGGTGGCCTAACTACGGCTACACTAGAAGGACAGTATTTGGTATCTGCGCTCTGCTGAAGCCAGTTACCTTCGGAAAAAGAGTTGGTA

14510   14520   14530   14540   14550   14560   14570   14580   14590   14600
GCTCTTGATCCGGCAAACAAACCACCGCTGGTAGCGGTGGTTTTTTTGTTTGCAAGCAGCAGATTACGCGCAGAAAAAAAGGATCTCAAGAAGATCCTTT

14610   14620   14630   14640   14650   14660   14670   14680   14690   14700
GATCTTTTCTACGGGGTCTGACGCTCATTGGAACGAAAACTCACGTTAAGGGATTTTGGTCATGAGATTATCAAAAAGGATCTTCACCTAGATCCTTTTA

14710   14720   14730   14740   14750   14760   14770   14780   14790   14800
AATTAAAAATGAAGTTTTAAATCAATCTAAAGTATATATGAGTAAACTTGGTCTGACAGTTACCAATGCTTAATCAGTGAGGCACCTATCTCAGCGATCT

14810   14820   14830   14840   14850   14860   14870   14880   14890   14900
GTCTATTTCGTTCATCCATAGTTGCCTGACTCCCCGTCGTGTAGATAACTACGATACGGGAGGGCTTACCATCTGGCCCCAGTGCTGCAATGATACCGCG

14910   14920   14930   14940   14950   14960   14970   14980   14990   15000
AGACCCACGCTCACCGGCTCCAGATTTATCAGCAATAAACCAGCCAGCCGGAAGGGCCGAGCGCAGAAGTGGTCCTGCAACTTTATCCGCCTCCATCCAG

15010   15020   15030   15040   15050   15060   15070   15080   15090   15100
TCTATTAATTGTTGCCGGGAAGCTAGAGTAAGTAGTTCGCCAGTTAATAGTTTGCGCAACGTTGTTGCCATTGCTGCAAGATCTGGCTAGCGATGACCCT

15110   15120   15130   15140   15150
GCTGATTGGTTCGCTGACCATTTCCGGGCGCGCCGATTTAGGTGACACTATAG
```

Bases 1 to 10707: DEN3 virus genome cDNA
Bases 95 to 10264: DEN3 polyprotein ORF
Bases 95 to 436: C protein ORF
Bases 437 to 934: prM protein ORF
Bases 935 to 2413: E protein ORF
Bases 2414 to 3469: NS1 protein ORF
Bases 3470 to 4123: NS2A protein ORF
Bases 4124 to 4513: NS2B protein ORF
Bases 4514 to 6370: NS3 protein ORF
Bases 6371 to 6751: NS4A protein ORF
Bases 6752 to 6820: 2K protein ORF
Bases 6821 to 7564: NS4B protein ORF
Bases 7575 to 10264 NS5 protein ORF

APPENDIX 3

Nucleotide and amino acid sequence of DEN1 (Puerto Rico/94) CME chimeric region

```
        10        20        30        40        50        60        70        80        90       100
AGTTGTTAGTCTGTGTGGACCGACAAGGACAGTTCCAAATCGGAAGCTTGCTTAACACAGTTCTAACAGTTTGTTTGAATAGAGAGCAGATCTCTGGAAA

       110       120       130       140       150       160       170       180       190       200
AATGAACAACCAACGGAAAAAGACGGGTCGACCGTCTTTCAATATGCTGAAACGCGCGAGAAACCGCGTGTCAACTGGTTCACAGTTGGCGAAGAGATTC
MetAsnAsnGlnArgLysLysThrGlyArgProSerPheAsnMetLeuLysArgAlaArgAsnArgValSerThrGlySerGlnLeuAlaLysArgPhe>

       210       220       230       240       250       260       270       280       290       300
```

APPENDIX 3-continued

Nucleotide and amino acid sequence of DEN1 (Puerto Rico/94) CME chimeric region

```
TCAAAAGGATTGCTTTCAGGCCAAGGACCCATGAAATTGGTGATGGCTTTCATAGCATTTCTAAGATTTCTAGCCATACCCCCAACAGCAGGAATTTTGG
SerLysGlyLeuLeuSerGlyGlnGlyProMetLysLeuValMetAlaPheIleAlaPheLeuArgPheLeuAlaIleProProThrAlaGlyIleLeu>

       310       320       330       340       350       360       370       380       390       400
CTAGATGGAGCTCATTCAAGAAGAATGGAGCGATCAAAGTGTTACGGGGTTTCAAAAAAGAGATCTCAAGCATGTTGAACATTATGAACAGGAGGAAAAA
AlaArgTrpSerSerPheLysLysAsnGlyAlaIleLysValLeuArgGlyPheLysLysGluIleSerSerMetLeuAsnIleMetAsnArgArgLysLys>

       410       420       430       440       450       460       470       480       490       500
ATCTGTGACCATGCTCCTCATGCTGCTGCCCACAGCCCTGGCGTTCCATTTGACCACACGAGGGGGAGAGCCACACATGATAGTTAGTAAGCAGGAAAGA
SerValThrMetLeuLeuMetLeuLeuProThrAlaLeuAlaPheHisLeuThrThrArgGlyGlyGluProHisMetIleValSerLysGlnGluArg>

       510       520       530       540       550       560       570       580       590       600
GGAAAGTCACTGTTGTTTAAGACCTCTGCAGGCATCAATATGTGCACTCTCATTGCGATGGATTTGGGAGAGTTATGCGAGGACACAATGACCTACAAAT
GlyLysSerLeuLeuPheLysThrSerAlaGlyIleAsnMetCysThrLeuIleAlaMetAspLeuGlyGluLeuCysGluAspThrMetThrTyrLys>

       610       620       630       640       650       660       670       680       690       700
GCCCCCGGATCACTGAGGCGGAACCAGATGACGTTGACTGCTGGTGCAATGCCACAGACACATGGGTGACCTATGGGACGTGTTCTCAAACCGGCGAACA
CysProArgIleThrGluAlaGluProAspAspValAspCysTrpCysAsnAlaThrAspThrTrpValThrTyrGlyThrCysSerGlnThrGlyGluHis>

       710       720       730       740       750       760       770       780       790       800
CCGACGAGACAAACGTTCCGTGGCACTGGCCCCACACGTGGGACTTGGTCTAGAAACAAGAACCGAAACATGGATGTCCTCTGAAGGTGCCTGGAAACAA
ArgArgAspLysArgSerValAlaLeuAlaProHisValGlyLeuGlyLeuGluThrArgThrGluThrTrpMetSerSerGluGlyAlaTrpLysGln>

       810       820       830       840       850       860       870       880       890       900
GTACAAAAAGTGGAGACTTGGGCTTTGAGACACCCAGGATTCACGGTGACAGCCCTTTTTTTAGCACATGCCATAGGAACATCCATTACTCAGAAAGGGA
ValGlnLysValGluThrTrpAlaLeuArgHisProGlyPheThrValThrAlaLeuPheLeuAlaHisAlaIleGlyThrSerIleThrGlnLysGly>

       910       920       930       940       950       960       970       980       990      1000
TCATTTTCATTCTGCTGATGCTAGTAACACCATCAATGGCCATGCGATGTGTGGGAATAGGCAACAGAGACTTCGTTGAAGGACTGTCAGGAGCAACGTG
IleIlePheIleLeuLeuMetLeuValThrProSerMetAlaMetArgCysValGlyIleGlyAsnArgAspPheValGluGlyLeuSerGlyAlaThrTrp>

      1010      1020      1030      1040      1050      1060      1070      1080      1090      1100
GGTGGACGTGGTATTGGAGCATGGAAGCTGCGTCACCACCATGGCAAAAGATAAACCAACATTGGACATTGAACTCTTGAAGACGGAGGTCACAAACCCT
ValAspValValLeuGluHisGlySerCysValThrThrMetAlaLysAspLysProThrLeuAspIleGluLeuLeuLysThrGluValThrAsnPro>

      1110      1120      1130      1140      1150      1160      1170      1180      1190      1200
GCCGTCTTGCGCAAACTGTGCATTGAAGCTAAAATATCAAACACCACCACCGATTCAAGGTGTCCAACACAAGGAGAGGCTACACTGGTGGAAGAACAGG
AlaValLeuArgLysLeuCysIleGluAlaLysIleSerAsnThrThrThrAspSerArgCysProThrGlnGlyGluAlaThrLeuValGluGluGln>

      1210      1220      1230      1240      1250      1260      1270      1280      1290      1300
ACTCGAACTTTGTGTGTCGACGAACGTTTGTGGACAGAGGCTGGGGTAATGGCTGCGGACTATTTGGAAAAGGAAGCCTACTGACGTGTGCTAAGTTCAA
AspSerAsnPheValCysArgArgThrPheValAspArgGlyTrpGlyAsnGlyCysGlyLeuPheGlyLysGlySerLeuLeuThrCysAlaLysPheLys>

      1310      1320      1330      1340      1350      1360      1370      1380      1390      1400
GTGTGTGACAAAACTAGAAGGAAAGATAGTTCAATATGAAAACTTAAAATATTCAGTGATAGTCACTGTCCACACTGGGGACCAGCACCAGGTGGGAAAC
CysValThrLysLeuGluGlyLysIleValGlnTyrGluAsnLeuLysTyrSerValIleValThrValHisThrGlyAspGlnHisGlnValGlyAsn>

      1410      1420      1430      1440      1450      1460      1470      1480      1490      1500
GAGACTACAGAACATGGAACAATTGCAACCATAACACCTCAAGCTCCTACGTCGGAAATACAGCTGACTGACTACGGAGCCCTCACATTGGACTGCTCGC
GluThrThrGluHisGlyThrIleAlaThrIleThrProGlnAlaProThrSerGluIleGlnLeuThrAspTyrGlyAlaLeuThrLeuAspCysSer>

      1510      1520      1530      1540      1550      1560      1570      1580      1590      1600
CTAGAACAGGGCTGGACTTTAATGAGATGGTTCTATTGACAATGAAAGAAAAATCATGGCTTGTCCACAAACAATGGTTTCTAGACTTACCACTGCCTTG
ProArgThrGlyLeuAspPheAsnGluMetValLeuLeuThrMetLysGluLysSerTrpLeuValHisLysGlnTrpPheLeuAspLeuProLeuProTrp>

      1610      1620      1630      1640      1650      1660      1670      1680      1690      1700
GACTTCAGGAGCTTCAACATCTCAAGAGACTTGGAACAGACAAGATTTGCTGGTCACATTCAAGACAGCTCATGCAAAGAAACAGGAAGTAGTCGTACTG
ThrSerGlyAlaSerThrSerGlnGluThrTrpAsnArgGlnAspLeuLeuValThrPheLysThrAlaHisAlaLysLysGlnGluValValValLeu>

      1710      1720      1730      1740      1750      1760      1770      1780      1790      1800
GGATCACAGGAAGGAGCAATGCACACTGCGTTGACTGGGGCGACAGAAATCCAGACGTCAGGAACGACAACAATCTTTGCAGGACACCTGAAATGCAGAC
GlySerGlnGluGlyAlaMetHisThrAlaLeuThrGlyAlaThrGluIleGlnThrSerGlyThrThrThrIlePheAlaGlyHisLeuLysCysArg>

      1810      1820      1830      1840      1850      1860      1870      1880      1890      1900
TAAAAATGGATAAACTGACTTTAAAAGGGAGTCATATGTAATGTGCACAGGCTCATTTAAGCTAGAGAAGGAAGTGGCTGAGACCCAGCATGGAACTGT
LeuLysMetAspLysLeuThrLeuLysGlyMetSerTyrValMetCysThrGlySerPheLysLeuGluLysGluValAlaGluThrGlnHisGlyThrVal>

      1910      1920      1930      1940      1950      1960      1970      1980      1990      2000
TTTAGTGCAGGTTAAATACGAAGGAACAGATGCGCCATGCAAGATCCCTTTTTCGGCCCAAGATGAGAAAGGAGTGACCCAGAATGGGAGATTGATAACA
LeuValGlnValLysTyrGluGlyThrAspAlaProCysLysIleProPheSerAlaGlnAspGluLysGlyValThrGlnAsnGlyArgLeuIleThr>

      2010      2020      2030      2040      2050      2060      2070      2080      2090      2100
GCCAACCCCATAGTCACTGACAAAGAAAAACCAGTCAACATTGAGACAGAACCACCTTTTGGTGAGAGCTACATCGTGGTAGGGGCAGGTGAAAAAGCTT
AlaAsnProIleValThrAspLysGluLysProValAsnIleGluThrGluProProPheGlyGluSerTyrIleValValGlyAlaGlyGluLysAla>

      2110      2120      2130      2140      2150      2160      2170      2180      2190      2200
TGAAACTGAGCTGGTTCAAGAAAGGGAGCAGCATAGGGAAAATGTTCGAAGCAACTGCCCGAGGAGCGCGAAGGATGGCTATCCTGGGAGACACCGCATG
LeuLysLeuSerTrpPheLysLysGlySerSerIleGlyLysMetPheGluAlaThrAlaArgGlyAlaArgArgMetAlaIleLeuGlyAspThrAlaTrp>
```

APPENDIX 3-continued

Nucleotide and amino acid sequence of DEN1 (Puerto Rico/94) CME chimeric region

```
      2210      2220      2230      2240      2250      2260      2270      2280      2290      2300
GGACTTTGGCTCTATAGGAGGAGTGTTCACATCAGTGGGAAAATTGGTACACCAGGTTTTTGGAGCCGCATATGGGGTTCTGTTCAGCGGTGTTTCTTGG
AspPheGlySerIleGlyGlyValPheThrSerValGlyLysLeuValHisGlnValPheGlyAlaAlaTyrGlyValLeuPheSerGlyValSerTyr>

      2310      2320      2330      2340      2350      2360      2370      2380      2390      2400
ACCATGAAAATAGGAATAGGGATTCTGCTGACATGGCTAGGATTAAACTCGAGGAACACTTCAATGGCTATGACGTGCATAGCTGTTGGAGGAATCACTC
ThrMetLysIleGlyIleGlyIleLeuLeuThrTrpLeuGlyLeuAsnSerArgAsnThrSerMetAlaMetThrCysIleAlaValGlyGlyIleThr>

      2410      2420
TGTTTCTGGGCTTCACAGTTCAAGCA
LeuPheLeuGlyPheThrValGlnAla>
```

Bases 1 to 88 (BglII): DEN4
Bases 89 (BglII) to 2348 (XhoI): DEN1
Bases 2349 (XhoI) to 2426: DEN4
Bases 102 to 443: C protein ORF
Bases 444 to 941: prM protein ORF
Bases 942 to 2426: E protein ORF

APPENDIX 4

Nucleotide and amino acid sequence of DEN1 (Puerto Rico/94) ME chimeric region

```
        10        20        30        40        50        60        70        80        90       100
AGTTGTTAGTCTGTGTGGACCGACAAGGACAGTTCCAAATCGGAAGCTTGCTTAACACAGTTCTAACAGTTTGTTTGAATAGAGAGCAGATCTCTGGAAA

       110       120       130       140       150       160       170       180       190       200
AATGAACCAACGAAAAAAGGTGGTTAGACCACCTTTCAATATGCTGAAACGCGAGAGAAACCGCGTATCAACCCCTCAAGGGTTGGTGAAGAGATTCTCA
MetAsnGlnArgLysLysValValArgProProPheAsnMetLeuLysArgGluArgAsnArgValSerThrProGlnGlyLeuValLysArgPheSer>

       210       220       230       240       250       260       270       280       290       300
ACCGGACTTTTTTCTGGGAAAGGACCCTTACGGATGGTGCTAGCATTCATCACGTTTTTGCGAGTCCTTTCCATCCCACCAACAGCAGGGATTCTGAAGA
ThrGlyLeuPheSerGlyLysGlyProLeuArgMetValLeuAlaPheIleThrPheLeuArgValLeuSerIleProProThrAlaGlyIleLeuLys>

       310       320       330       340       350       360       370       380       390       400
GATGGGGACAGTTGAAGAAAAATAAGGCCATCAAGATACTGATTGGATTCAGGAAGGAGATAGGCCGCATGCTGAACATCTTGAACGGGAGAAAAAGGTC
ArgTrpGlyGlnLeuLysLysAsnLysAlaIleLysIleLeuIleGlyPheArgLysGluIleGlyArgMetLeuAsnIleLeuAsnGlyArgLysArgSer>

       410       420       430       440       450       460       470       480       490       500
TGCAGCCATGCTCCTCATGCTGCTGCCCACAGCCCTGGCGTTCCATTTGACCACACGAGGGGGAGAGCCACACATGATAGTTAGTAAGCAGGAAAGAGGA
AlaAlaMetLeuLeuMetLeuLeuProThrAlaLeuAlaPheHisLeuThrThrArgGlyGlyGluProHisMetIleValSerLysGlnGluArgGly>

       510       520       530       540       550       560       570       580       590       600
AAGTCACTGTTGTTTAAGACCTCTGCAGGCATCAATATGTGCACTCTCATTGCGATGGATTTGGGAGAGTTATGCGAGGACACAATGACCTACAAATGCC
LysSerLeuLeuPheLysThrSerAlaGlyIleAsnMetCysThrLeuIleAlaMetAspLeuGlyGluLeuCysGluAspThrMetThrTyrLysCys>

       610       620       630       640       650       660       670       680       690       700
CCCGGATCACTGAGGCGGAACCAGATGACGTTGACTGCTGGTGCAATGCCACAGACACATGGGTGACCTATGGGACGTGTTCTCAAACCGGCGAACACCG
ProArgIleThrGluAlaGluProAspAspValAspCysTrpCysAsnAlaThrAspThrTrpValThrTyrGlyThrCysSerGlnThrGlyGluHisArg>

       710       720       730       740       750       760       770       780       790       800
ACGAGACAAACGTTCCGTGGCACTGGCCCCACACGTGGGACTTGGTCTAGAAACAAGAACCGAAACATGGATGTCCTCTGAAGGTGCCTGGAAACAAGTA
ArgAspLysArgSerValAlaLeuAlaProHisValGlyLeuGlyLeuGluThrArgThrGluThrTrpMetSerSerGluGlyAlaTrpLysGlnVal>

       810       820       830       840       850       860       870       880       890       900
CAAAAAGTGGAGACTTGGGCTTTGAGACACCCAGGATTCACGGTGACAGCCCTTTTTTTAGCACATGCCATAGGAACATCCATTACTCAGAAAGGGATCA
GlnLysValGluThrTrpAlaLeuArgHisProGlyPheThrValThrAlaLeuPheLeuAlaHisAlaIleGlyThrSerIleThrGlnLysGlyIle>

       910       920       930       940       950       960       970       980       990      1000
TTTTCATTCTGCTGATGCTAGTAACACCATCAATGGCCATGCGATGTGTGGGAATAGGCAACAGAGACTTCGTTGAAGGACTGTCAGGAGCAACGTGGGT
IlePheIleLeuLeuMetLeuValThrProSerMetAlaMetArgCysValGlyIleGlyAsnArgAspPheValGluGlyLeuSerGlyAlaThrTrpVal>

      1010      1020      1030      1040      1050      1060      1070      1080      1090      1100
GGACGTGGTATTGGAGCATGGAAGCTGCGTCACCACCATGGCAAAAGATAAACCAACATTGGACATTGAACTCTTGAAGACGGAGGTCACAAACCCTGCC
AspValValLeuGluHisGlySerCysValThrThrMetAlaLysAspLysProThrLeuAspIleGluLeuLeuLysThrGluValThrAsnProAla>

      1110      1120      1130      1140      1150      1160      1170      1180      1190      1200
GTCTTGCGCAAACTGTGCATTGAAGCTAAAATATCAAACACCACCACCGATTCAAGGTGTCCAACACAAGGAGAGGCTACACTGGTGGAAGAACAGGACT
ValLeuArgLysLeuCysIleGluAlaLysIleSerAsnThrThrThrAspSerArgCysProThrGlnGlyGluAlaThrLeuValGluGluGlnAsp>

      1210      1220      1230      1240      1250      1260      1270      1280      1290      1300
CGAACTTTGTGTGTCGACGAACGTTTGTGGACAGAGGCTGGGGTAATGGCTGCGGACTATTTGGAAAAGGAAGCCTACTGACGTGTGCTAAGTTCAAGTG
SerAsnPheValCysArgArgThrPheValAspArgGlyTrpGlyAsnGlyCysGlyLeuPheGlyLysGlySerLeuLeuThrCysAlaLysPheLysCys>

      1310      1320      1330      1340      1350      1360      1370      1380      1390      1400
```

APPENDIX 4-continued

Nucleotide and amino acid sequence of DEN1 (Puerto Rico/94) ME chimeric region

```
TGTGACAAAACTAGAAGGAAAGATAGTTCAATATGAAAACTTAAAATATTCAGTGATAGTCACTGTCCACACTGGGGACCAGCACCAGGTGGGAAACGAG
ValThrLysLeuGluGlyLysIleValGlnTyrGluAsnLeuLysTyrSerValIleValThrValHisThrGlyAspGlnHisGlnValGlyAsnGlu>

      1410      1420      1430      1440      1450      1460      1470      1480      1490      1500
ACTACAGAACATGGAACAATTGCAACCATAACACCTCAAGCTCCTACGTCGGAAATACAGCTGACTGACTACGGAGCCCTCACATTGGACTGCTCGCCTA
ThrThrGluHisGlyThrIleAlaThrIleThrProGlnAlaProThrSerGluIleGlnLeuThrAspTyrGlyAlaLeuThrLeuAspCysSerPro>

      1510      1520      1530      1540      1550      1560      1570      1580      1590      1600
GAACAGGGCTGGACTTTAATGAGATGGTTCTATTGACAATGAAAGAAAAATCATGGCTTGTCCACAAACAATGGTTTCTAGACTTACCACTGCCTTGGAC
ArgThrGlyLeuAspPheAsnGluMetValLeuLeuThrMetLysGluLysSerTrpLeuValHisLysGlnTrpPheLeuAspLeuProLeuProTrpThr>

      1610      1620      1630      1640      1650      1660      1670      1680      1690      1700
TTCAGGAGCTTCAACATCTCAAGAGACTTGGAACAGACAAGATTTGCTGGTCACATTCAAGACAGCTCATGCAAAGAAACAGGAAGTAGTCGTACTGGGA
SerGlyAlaSerThrSerGlnGluThrTrpAsnArgGlnAspLeuLeuValThrPheLysThrAlaHisAlaLysLysGlnGluValValValLeuGly>

      1710      1720      1730      1740      1750      1760      1770      1780      1790      1800
TCACAGGAAGGAGCAATGCACACTGCGTTGACTGGGGCGACAGAAATCCAGACGTCAGGAACGACAACAATCTTTGCAGGACACCTGAAATGCAGACTAA
SerGlnGluGlyAlaMetHisThrAlaLeuThrGlyAlaThrGluIleGlnThrSerGlyThrThrThrIlePheAlaGlyHisLeuLysCysArgLeu>

      1810      1820      1830      1840      1850      1860      1870      1880      1890      1900
AAATGGATAAACTGACTTTAAAAGGGATGTCATATGTAATGTGCACAGGCTCATTTAAGCTAGAGAAGGAAGTGGCTGAGACCCAGCATGGAACTGTTTT
LysMetAspLysLeuThrLeuLysGlyMetSerTyrValMetCysThrGlySerPheLysLeuGluLysGluValAlaGluThrGlnHisGlyThrValLeu>

      1910      1920      1930      1940      1950      1960      1970      1980      1990      2000
AGTGCAGGTTAAATACGAAGGAACAGATGCGCCATGCAAGATCCCTTTTTCGGCCCAAGATGAGAAAGGAGTGACCCAGAATGGGAGATTGATAACAGCC
ValGlnValLysTyrGluGlyThrAspAlaProCysLysIleProPheSerAlaGlnAspGluLysGlyValThrGlnAsnGlyArgLeuIleThrAla>

      2010      2020      2030      2040      2050      2060      2070      2080      2090      2100
AACCCCATAGTCACTGACAAAGAAAAACCAGTCAACATTGAGACAGAACCACCTTTTGGTGAGAGCTACATCGTGGTAGGGGCAGGTGAAAAAGCTTTGA
AsnProIleValThrAspLysGluLysProValAsnIleGluThrGluProProPheGlyGluSerTyrIleValValGlyAlaGlyGluLysAlaLeu>

      2110      2120      2130      2140      2150      2160      2170      2180      2190      2200
AACTGAGCTGGTTCAAGAAAGGGAGCAGCATAGGGAAAATGTTCGAAGCAACTGCCCGAGGAGCGCGAAGGATGGCTATCCTGGGAGACACCGCATGGGA
LysLeuSerTrpPheLysLysGlySerSerIleGlyLysMetPheGluAlaThrAlaArgGlyAlaArgArgMetAlaIleLeuGlyAspThrAlaTrpAsp>

      2210      2220      2230      2240      2250      2260      2270      2280      2290      2300
CTTTGGCTCTATAGGAGGAGTGTTCACATCAGTGGGAAAATTGGTACACCAGGTTTTTGGAGCCGCATATGGGGTTCTGTTCAGCGGTGTTTCTTGGACC
PheGlySerIleGlyGlyValPheThrSerValGlyLysLeuValHisGlnValPheGlyAlaAlaTyrGlyValLeuPheSerGlyValSerTrpThr>

      2310      2320      2330      2340      2350      2360      2370      2380      2390      2400
ATGAAAATAGGAATAGGGATTCTGCTGACATGGCTAGGATTAAACTCGAGGAACACTTCAATGGCTATGACGTGCATAGCTGTTGGAGGAATCACTCTGT
MetLysIleGlyIleGlyIleLeuLeuThrTrpLeuGlyLeuAsnSerArgAsnThrSerMetAlaMetThrCysIleAlaValGlyGlyIleThrLeu>

      2410      2420
TTCTGGGCTTCACAGTTCAAGCA
PheLeuGlyPheThrValGlnAla
```

Bases 1 to 404 (PstI): DEN4
Bases 405 (PstI) to 2345 (XhoI): DEN1
Bases 2346 (XhoI) to 2423: DEN4
Bases 102 to 440: C protein ORF
Bases 441 to 938: prM protein ORF
Bases 939 to 2423: E protein ORF While the present invention has been described in some detail for purposes of clarity and understanding, one skilled in the art will appreciate that various changes in form and detail can be made without departing from the true scope of the invention. All figures, tables, appendices, patents, patent applications and publications, referred to above, are hereby incorporated by reference.

SEQUENCE LISTING

<160> NUMBER OF SEQ ID NOS: 53

<210> SEQ ID NO 1
<211> LENGTH: 82
<212> TYPE: RNA
<213> ORGANISM: Dengue 1 virus

<400> SEQUENCE: 1 gcagcagcgg ggcccaacac caggggaagc uguacccugg ugguaaggac uagagguuag 60 aggagacccc ccgcaacaac aa 82

<210> SEQ ID NO 2
<211> LENGTH: 84
<212> TYPE: RNA
<213> ORGANISM: Dengue 2 virus

<400> SEQUENCE: 2 agcaacaaug ggggcccaag gugagaugaa gcuguagucu cacuggaagg acuagagguu 60 agaggagacc cccccaaaac aaaa 84

<210> SEQ ID NO 3
<211> LENGTH: 83
<212> TYPE: RNA
<213> ORGANISM: Dengue 3 virus

<400> SEQUENCE: 3 gcagcagcgg ggcccgagcu cugagggaag cuguaccucc uugcaaagga cuagagguua 60 gaggagaccc cccgcaaaua aaa 83

<210> SEQ ID NO 4
<211> LENGTH: 83
<212> TYPE: RNA
<213> ORGANISM: Dengue 4 virus

<400> SEQUENCE: 4 agcaaaaggg ggcccgaagc caggaggaag cuguacuccu gguggaagga cuagagguua 60 gaggagaccc ccccaacaca aaa 83

<210> SEQ ID NO 5
<211> LENGTH: 16
<212> TYPE: RNA
<213> ORGANISM: Artificial Sequence
<220> FEATURE:
<223> OTHER INFORMATION: Dengue 1 delta 30

<400> SEQUENCE: 5 ggggcccaag acuaga 16

<210> SEQ ID NO 6
<211> LENGTH: 16
<212> TYPE: RNA
<213> ORGANISM: Artificial Sequence
<220> FEATURE:
<223> OTHER INFORMATION: Dengue 2 delta 30

<400> SEQUENCE: 6 ggggcccaag acuaga 16

<210> SEQ ID NO 7
<211> LENGTH: 16
<212> TYPE: RNA
<213> ORGANISM: Artificial Sequence
<220> FEATURE:
<223> OTHER INFORMATION: Dengue 3 delta 30

<400> SEQUENCE: 7 ggggcccaag acuaga 16

<210> SEQ ID NO 8
<211> LENGTH: 16

<212> TYPE: RNA
<213> ORGANISM: Artificial Sequence
<220> FEATURE:
<223> OTHER INFORMATION: Dengue 4 delta 30

<400> SEQUENCE: 8 ggggcccaag acuaga 16

<210> SEQ ID NO 9
<211> LENGTH: 51
<212> TYPE: DNA
<213> ORGANISM: Artificial Sequence
<220> FEATURE:
<223> OTHER INFORMATION: TL2 region of p2 plasmid

<400> SEQUENCE: 9 tgggggcccca aggtgagatg aagctgtagt ctcactggaa ggactagagg t 51

<210> SEQ ID NO 10
<211> LENGTH: 21
<212> TYPE: DNA
<213> ORGANISM: Artificial Sequence
<220> FEATURE:
<223> OTHER INFORMATION: TL2 region of p2 delta 30

<400> SEQUENCE: 10 tgggggcccca agactagagg t 21

<210> SEQ ID NO 11
<211> LENGTH: 51
<212> TYPE: DNA
<213> ORGANISM: Artificial Sequence
<220> FEATURE:
<223> OTHER INFORMATION: TL2 region of p3 plasmid

<400> SEQUENCE: 11 cggggcccga gctctgaggg aagctgtacc tccttgcaaa ggactagagg t 51

<210> SEQ ID NO 12
<211> LENGTH: 20
<212> TYPE: DNA
<213> ORGANISM: Artificial Sequence
<220> FEATURE:
<223> OTHER INFORMATION: TL2 region of p3 delta 30

<400> SEQUENCE: 12 gggggcccaa gactagaggt 20

<210> SEQ ID NO 13
<211> LENGTH: 29
<212> TYPE: DNA
<213> ORGANISM: Artificial Sequence
<220> FEATURE:
<223> OTHER INFORMATION: Spe1 linker in p3

<400> SEQUENCE: 13 actagttaga ctaacttaag tcaactagt 29

<210> SEQ ID NO 14
<211> LENGTH: 51
<212> TYPE: DNA
<213> ORGANISM: Artificial Sequence
<220> FEATURE:
<223> OTHER INFORMATION: rDEN2/4 junction 1

<400> SEQUENCE: 14 cagtttgttt gaatagagag cagatctctg atgaataacc aacgaaaaaa g 51

<210> SEQ ID NO 15
<211> LENGTH: 7
<212> TYPE: PRT
<213> ORGANISM: Artificial Sequence
<220> FEATURE:
<223> OTHER INFORMATION: rDEN2/4 junction 1

<400> SEQUENCE: 15

Met Asn Asn Gln Arg Lys Lys
1 5

<210> SEQ ID NO 16
<211> LENGTH: 51
<212> TYPE: DNA
<213> ORGANISM: Artificial Sequence
<220> FEATURE:
<223> OTHER INFORMATION: rDEN2/4 junction 2

<400> SEQUENCE: 16 attatcacat ggataggaat gaactcgagg aacacttcaa tggctatgac g 51

<210> SEQ ID NO 17
<211> LENGTH: 17
<212> TYPE: PRT
<213> ORGANISM: Artificial Sequence
<220> FEATURE:
<223> OTHER INFORMATION: rDEN2/4 junction 2

<400> SEQUENCE: 17

Ile Ile Thr Trp Ile Gly Met Asn Ser Arg Asn Thr Ser Met Ala Met
1 5 10 15

Thr

<210> SEQ ID NO 18
<211> LENGTH: 51
<212> TYPE: DNA
<213> ORGANISM: Artificial Sequence
<220> FEATURE:
<223> OTHER INFORMATION: rDEN2/4 junction 3

<400> SEQUENCE: 18 atcttgaacg ggagaaaaag gtctgcaggc atgatcatta tgctgattcc a 51

<210> SEQ ID NO 19
<211> LENGTH: 17
<212> TYPE: PRT
<213> ORGANISM: Artificial Sequence
<220> FEATURE:
<223> OTHER INFORMATION: rDEN2/4 junction 3

<400> SEQUENCE: 19

Ile Leu Asn Gly Arg Lys Arg Ser Ala Gly Met Ile Ile Met Leu Ile
1 5 10 15

Pro

<210> SEQ ID NO 20
<211> LENGTH: 50
<212> TYPE: DNA
<213> ORGANISM: Artificial Sequence
<220> FEATURE:
<223> OTHER INFORMATION: rDEN3/4 junction 1

<400> SEQUENCE: 20 cagtttgttt gaatagagag cagatctctg gaaaaatgaa caaccaacgg 50

<210> SEQ ID NO 21
<211> LENGTH: 5
<212> TYPE: PRT
<213> ORGANISM: Artificial Sequence
<220> FEATURE:
<223> OTHER INFORMATION: rDEN3/4 junction 1

<400> SEQUENCE: 21

Met Asn Asn Gln Arg
1 5

<210> SEQ ID NO 22
<211> LENGTH: 51
<212> TYPE: DNA
<213> ORGANISM: Artificial Sequence
<220> FEATURE:
<223> OTHER INFORMATION: rDEN3/4 junction 2

<400> SEQUENCE: 22 cttttaacct ggatagggtt gaactcgagg aacacttcaa tggctatgac g 51

<210> SEQ ID NO 23
<211> LENGTH: 17
<212> TYPE: PRT
<213> ORGANISM: Artificial Sequence
<220> FEATURE:
<223> OTHER INFORMATION: rDEN3/4 junction 2

<400> SEQUENCE: 23

Leu Leu Thr Trp Ile Gly Leu Asn Ser Arg Asn Thr Ser Met Ala Met
1 5 10 15

Thr

<210> SEQ ID NO 24
<211> LENGTH: 51
<212> TYPE: DNA
<213> ORGANISM: Artificial Sequence
<220> FEATURE:
<223> OTHER INFORMATION: rDEN3/4 junction 3

<400> SEQUENCE: 24 atcttgaacg ggagaaaaag gtctgcagtc tgtctcatga tgatgttacc a 51

<210> SEQ ID NO 25
<211> LENGTH: 17
<212> TYPE: PRT
<213> ORGANISM: Artificial Sequence
<220> FEATURE:
<223> OTHER INFORMATION: rDEN3/4 junction 3

<400> SEQUENCE: 25

Ile Leu Asn Gly Arg Lys Arg Ser Ala Val Cys Leu Met Met Met Leu
1 5 10 15

Pro

<210> SEQ ID NO 26
<211> LENGTH: 50
<212> TYPE: DNA
<213> ORGANISM: Artificial Sequence
<220> FEATURE:
<223> OTHER INFORMATION: rDEN1/4 junction 1

<400> SEQUENCE: 26 cagtttgttt gaatagagag cagatctctg gaaaaatgaa caaccaacgg 50

<210> SEQ ID NO 27
<211> LENGTH: 5
<212> TYPE: PRT
<213> ORGANISM: Artificial Sequence
<220> FEATURE:
<223> OTHER INFORMATION: rDEN1/4 junction 1

<400> SEQUENCE: 27

Met Asn Asn Gln Arg
1 5

<210> SEQ ID NO 28
<211> LENGTH: 51
<212> TYPE: DNA
<213> ORGANISM: Artificial Sequence
<220> FEATURE:
<223> OTHER INFORMATION: rDEN1/4 junction 2

<400> SEQUENCE: 28 ctgctgacat ggctaggatt aaactcgagg aacacttcaa tggctatgac g 51

<210> SEQ ID NO 29
<211> LENGTH: 17
<212> TYPE: PRT
<213> ORGANISM: Artificial Sequence
<220> FEATURE:
<223> OTHER INFORMATION: rDEN1/4 junction 2

<400> SEQUENCE: 29

Leu Leu Thr Trp Leu Gly Leu Asn Ser Arg Asn Thr Ser Met Ala Met
1 5 10 15

Thr

<210> SEQ ID NO 30
<211> LENGTH: 51
<212> TYPE: DNA
<213> ORGANISM: Artificial Sequence
<220> FEATURE:
<223> OTHER INFORMATION: rDEN1/4 junction 3

<400> SEQUENCE: 30 atcttgaacg ggagaaaaag gtctgcagcc atgctcctca tgctgctgcc c 51

<210> SEQ ID NO 31
<211> LENGTH: 17
<212> TYPE: PRT
<213> ORGANISM: Artificial Sequence
<220> FEATURE:
<223> OTHER INFORMATION: rDEN1/4 junction 3

<400> SEQUENCE: 31

Ile Leu Asn Gly Arg Lys Arg Ser Ala Ala Met Leu Leu Met Leu Leu
1 5 10 15

Pro

<210> SEQ ID NO 32
<211> LENGTH: 60
<212> TYPE: RNA
<213> ORGANISM: Dengue 4 virus

<400> SEQUENCE: 32 ccaacaaccu ugacagcauc cuuagucaug cuuuuagucc auuaugcaau aauaggccca 60

<210> SEQ ID NO 33
<211> LENGTH: 20
<212> TYPE: PRT
<213> ORGANISM: Dengue 4 virus

<400> SEQUENCE: 33

Pro Thr Thr Leu Thr Ala Ser Leu Val Met Leu Leu Val His Thr Ala
1 5 10 15

Ile Ile Gly Pro
20

<210> SEQ ID NO 34
<211> LENGTH: 60
<212> TYPE: RNA
<213> ORGANISM: Dengue 1 virus

<400> SEQUENCE: 34 ccgcugacgc ugacagcggc gguauuuaug cuaguggcuc auuaugccau aauuggaccc 60

<210> SEQ ID NO 35
<211> LENGTH: 20
<212> TYPE: PRT
<213> ORGANISM: Dengue 1 virus

<400> SEQUENCE: 35

Pro Leu Thr Leu Thr Ala Ala Val Pro Met Leu Val Ala His Thr Ala
1 5 10 15

Ile Ile Gly Pro
20

<210> SEQ ID NO 36
<211> LENGTH: 60
<212> TYPE: RNA
<213> ORGANISM: Dengue 2 virus

<400> SEQUENCE: 36 ccuauaaccc ucacagcggc ucuucuuuua uugguagcac auuaugccau cauaggaccg 60

<210> SEQ ID NO 37
<211> LENGTH: 20
<212> TYPE: PRT
<213> ORGANISM: Dengue 2 virus

<400> SEQUENCE: 37

Pro Ile Thr Leu Thr Ala Ala Leu Leu Leu Leu Val Ala His Thr Ala
1 5 10 15

Ile Ile Gly Pro
20

<210> SEQ ID NO 38
<211> LENGTH: 60
<212> TYPE: RNA
<213> ORGANISM: Dengue 3 virus

<400> SEQUENCE: 38 ccacuaacuc ucacagcggc aguucuccug cuagucacgc auuaugcuau uauaggucca 60

<210> SEQ ID NO 39
<211> LENGTH: 20
<212> TYPE: PRT
<213> ORGANISM: Dengue 3 virus

<400> SEQUENCE: 39

Pro Leu Thr Leu Thr Ala Ala Val Leu Leu Leu Val Thr His Thr Ala
1 5 10 15

Ile Ile Gly Pro
20

<210> SEQ ID NO 40
<211> LENGTH: 13
<212> TYPE: DNA
<213> ORGANISM: Artificial Sequence
<220> FEATURE:
<223> OTHER INFORMATION: primer

<400> SEQUENCE: 40 ccacgggcgc cgt 13

<210> SEQ ID NO 41
<211> LENGTH: 10
<212> TYPE: DNA
<213> ORGANISM: Artificial Sequence
<220> FEATURE:
<223> OTHER INFORMATION: primer

<400> SEQUENCE: 41 aaggcctgga 10

<210> SEQ ID NO 42
<211> LENGTH: 12
<212> TYPE: DNA
<213> ORGANISM: Artificial Sequence
<220> FEATURE:
<223> OTHER INFORMATION: primer

<400> SEQUENCE: 42 tatccccggg ac 12

<210> SEQ ID NO 43
<211> LENGTH: 11
<212> TYPE: DNA
<213> ORGANISM: Artificial Sequence
<220> FEATURE:
<223> OTHER INFORMATION: primer

<400> SEQUENCE: 43 agagctctct c 11

<210> SEQ ID NO 44
<211> LENGTH: 15
<212> TYPE: DNA
<213> ORGANISM: Artificial Sequence
<220> FEATURE:
<223> OTHER INFORMATION: primer

<400> SEQUENCE: 44 gaatctccac ccgga 15

<210> SEQ ID NO 45
<211> LENGTH: 10
<212> TYPE: DNA
<213> ORGANISM: Artificial Sequence
<220> FEATURE:
<223> OTHER INFORMATION: primer

<400> SEQUENCE: 45 ctgtcgaatc 10

<210> SEQ ID NO 46
<211> LENGTH: 15159
<212> TYPE: DNA
<213> ORGANISM: Artificial Sequence
<220> FEATURE:
<223> OTHER INFORMATION: Dengue 2 plasmid p2

<400> SEQUENCE: 46 agttgttagt ctacgtggac cgacaaagac agattctttg agggagctaa gctcaacgta 60 gttctaactg ttttttgatt agagagcaga tctctgatga ataaccaacg gaaaaaggcg 120 agaaacacgc ctttcaatat gctgaaacgc gagagaaacc gcgtgtcaac tgtacaacag 180 ttgacaaaga gattctcact tggaatgctg cagggacgag gaccactaaa attgttcatg 240 gccctggtgg cattccttcg tttcctaaca atcccaccaa cagcagggat attaaaaaga 300 tggggaacaa ttaaaaaatc aaaggctatt aatgttctga gaggcttcag gaaagagatt 360 ggaaggatgc tgaatatctt aaacaggaga cgtagaactg taggcatgat catcatgctg 420 actccaacag tgatggcgtt tcatctgacc acacgcaacg gagaaccaca catgattgtc 480 agtagacaag aaaaagggaa aagccttctg ttcaagacaa aggatggcac gaacatgtgt 540 accctcatgg ccatggacct tggtgagttg tgtgaagaca caatcacgta taaatgtcct 600 tttctcaagc agaacgaacc agaagacata gattgttggt gcaactccac gtccacatgg 660 gtaacttatg ggacatgtac caccacagga gagcacagaa gagaaaaaag atcagtggcg 720 cttgttccac acgtgggaat gggattggag acacgaactg aaacatggat gtcatcagaa 780 ggggcctgga aacatgccca gagaattgaa acttggattc tgagacatcc aggctttacc 840 ataatggccg caatcctggc atacaccata gggacgacgc atttccaaag agtcctgata 900 ttcatcctac tgacagccat cgctccttca atgacaatgc gctgcatagg aatatcaaat 960 agggactttg tggaaggagt gtcaggaggg agttgggttg acatagtttt agaacatgga 1020 agttgtgtga cgacgatggc aaaaaacaaa ccaacactgg actttgaact gataaaaaca 1080 gaagccaaac aacctgccac cttaaggaag tactgtatag aggccaaact gaccaacacg 1140 acaacagact cgcgctgccc aacacaaggg gaacccaccc tgaatgaaga gcaggacaaa 1200 aggtttgtct gcaaacattc catggtagac agaggatggg gaaatggatg tggattgttt 1260 ggaaaaggag gcatcgtgac ctgtgctatg ttcacatgca aaaagaacat ggaaggaaaa 1320 attgtgcagc cagaaaacct ggaatacact gtcgtgataa cacctcattc aggggaagaa 1380 catgcagtgg gaaatgacac aggaaaacat ggtaaagaag tcaagataac accacagagc 1440 tccatcacag aggcggaact gacaggctat ggcactgtta cgatggagtg ctctccaaga 1500 acgggcctcg acttcaatga gatggtgttg ctgcaaatgg aagacaaagc ctggctggtg 1560 cacagacaat ggttcctaga cctaccgttg ccatggctgc ccggagcaga cacacaagga 1620 tcaaattgga tacagaaaga aacactggtc accttcaaaa atccccatgc gaaaaaacag 1680 gatgttgttg tcttaggatc ccaagagggg gccatgcata cagcactcac aggggctacg 1740 gaaatccaga tgtcatcagg aaacctgctg ttcacaggac atctcaagtg caggctgaga 1800 atggacaaat tacaacttaa agggatgtca tactccatgt gcacaggaaa gtttaaaatt 1860 gtgaaggaaa tagcagaaac acaacatgga acaatagtca ttagagtaca atatgaagga 1920 gacggctctc catgcaagat ccccttttgag ataatggatc tggaaaaaag acatgttttg 1980 ggccgcctga tcacagtcaa cccaattgta acagaaaagg acagtccagt caacatagaa 2040 gcagaacctc cattcggaga cagctacatc atcataggag tggaaccagg acaattgaag 2100

```
ctggactggt tcaagaaagg aagttccatc ggccaaatgt ttgagacaac aatgagggga   2160
gcgaaaagaa tggccatttt gggtgacaca gcctgggatt ttggatctct gggaggagtg   2220
ttcacatcaa taggaaaggc tctccaccag gtttttggag caatctacgg ggctgctttc   2280
agtggggtct catggactat gaagatcctc ataggagtta tcatcacatg gataggaatg   2340
aactcacgta gcactagtct gagcgtgtca ctggtgttag tgggaatcgt gacactttac   2400
ttgggagtta tggtgcaggc cgatagtggt tgcgttgtga gctggaagaa caaagaacta   2460
aaatgtggca gtggaatatt cgtcacagat aacgtgcata catggacaga acaatacaag   2520
ttccaaccag aatccccttc aaaactggcc tcagccatcc agaaagcgca tgaagagggc   2580
atctgtggaa tccgctcagt aacaagactg gaaaatctta tgtggaaaca gataacatca   2640
gaattgaatc atattctatc agaaaatgaa gtgaaactga ccatcatgac aggagacatc   2700
aaaggaatca tgcaggtagg aaaacgatct ttgcggcctc aacccactga gttgaggtat   2760
tcatggaaaa catggggtaa agcgaaaatg ctctccacag aactccacaa tcagaccttc   2820
ctcattgatg gtcccgaaac agcagaatgc cccaacacaa acagagcttg gaattcactg   2880
gaagttgagg actacggctt tggagtattc actaccaata tatggctaag attgagagaa   2940
aagcaggatg tattttgtga ctcaaaactc atgtcagcgg ccataaagga caacagagcc   3000
gtccatgctg atatgggtta ttggatagaa agcgcactca atgatacatg gaagatagag   3060
aaagcttctt tcattgaagt caaaagttgc cactggccaa agtcacacac cctatggagt   3120
aatggagtgc tagaaagcga gatggtcatt ccaaagaatt tcgctggacc agtgtcacaa   3180
cataataaca gaccaggcta ttacacacaa acagcaggac cttggcatct aggcaagctt   3240
gagatggact ttgatttctg cgaagggact acagtggtgg taaccgagaa ctgtggaaac   3300
agagggccct ctttaagaac aaccactgcc tcaggaaaac tcataacgga atggtgttgt   3360
cgatcttgca cactaccacc actaagatac agaggtgagg atggatgttg gtacgggatg   3420
gaaatcagac cattgaaaga gaaagaagaa aatctggtca gttctctggt tacagccgga   3480
catgggcaga ttgacaattt ctcattagga atcttgggaa tggcactgtt ccttgaagaa   3540
atgctcagga ctcgagtagg aacaaaacat gcaatattac tcgtcgcagt ttctttcgtg   3600
acgctaatca cagggaacat gtcttttaga gacctgggaa gagtgatggt tatggtgggt   3660
gccaccatga cagatgacat aggcatgggt gtgacttatc tcgctctact agcagctttt   3720
agagtcagac caacctttgc agctggactg ctcttgagaa aactgacctc caaggaatta   3780
atgatgacta ccataggaat cgttcttctc tcccagagta gcataccaga gaccattctt   3840
gaactgaccg acgcgttagc tctaggcatg atggtcctca agatggtgag aaacatggaa   3900
aaatatcagc tggcagtgac catcatggct attttgtgcg tcccaaatgc tgtgatatta   3960
cagaacgcat ggaaagtgag ttgcacaata ttggcagtgg tgtctgtttc ccccctgctc   4020
ttaacatcct cacaacagaa agcggactgg ataccattag cgttgacgat caaaggtctt   4080
aatccaacag ccatttttct aacaaccctc tcaagaacca acaagaaaag gagctggcct   4140
ttaaatgagg ccatcatggc ggttgggatg gtgagtatct tggccagctc tctcttaaag   4200
aatgacatcc ccatgacagg accattagtg gctggagggc tccttactgt gtgctacgtg   4260
ctaactgggc ggtcagccga tctggaatta gagagagcta ccgatgtcaa atgggatgac   4320
caggcagaga tatcaggtag cagtccaatc ctgtcaataa caatatcaga agatggcagc   4380
atgtcaataa agaatgaaga ggaagagcaa acactgacta tactcattag aacaggattg   4440
```

```
cttgtgatct caggactctt tccggtatca ataccaatta cagcagcagc atggtatctg   4500
tgggaagtaa agaaacaacg ggctggagtg ctgtgggatg tcccctcacc accacccgtg   4560
ggaaaagctg aattggaaga tggagcctac agaatcaagc aaaaaggaat ccttggatat   4620
tcccagatcg gagctggagt ttacaaagaa ggaacatttc acacaatgtg gcacgtcaca   4680
cgtggcgctg tcctaatgca taaggggaag aggattgaac catcatgggc ggacgtcaag   4740
aaagacttaa tatcatatgg aggaggttgg aagctagaag gagaatggaa agaaggagaa   4800
gaagtccagg tcttggcatt ggagccaggg aaaaatccaa gagccgtcca aacaaagcct   4860
ggccttttta gaaccaacac tggaaccata ggtgccgtat ctctggactt ttcccctggg   4920
acgtcaggat ctccaatcgt cgacaaaaaa ggaaaagttg taggtctcta tggcaatggt   4980
gtcgttacaa ggagtggagc atatgtgagt gccatagctc agactgaaaa aagcattgaa   5040
gacaatccag agattgaaga tgacatcttt cgaaagagaa gattgactat catggatctc   5100
cacccaggag caggaaagac aaagagatac ctcccggcca tagtcagaga ggccataaaa   5160
agaggcttga gaacactaat cctagccccc actagagtcg tggcagctga aatggaggaa   5220
gcccttagag gacttccaat aagataccaa actccagcta tcagggctga gcacaccggg   5280
cgggagattg tagacttaat gtgtcatgcc acatttacca tgaggctgct atcaccaatc   5340
agggtgccaa attacaacct gatcatcatg gacgaagccc attttacaga tccagcaagc   5400
atagcagcta ggggatacat ctcaactcga gtggagatgg gggaggcagc tggaattttt   5460
atgacagcca ctcctccggg tagtagagat ccatttcctc agagcaatgc accaattatg   5520
gacgaagaaa gagaaattcc ggaacgttca tggaactctg ggcacgagtg ggtcacggat   5580
tttaaaggaa agactgtctg gtttgttcca agcataaaaa ccggaaatga catagcagcc   5640
tgcctgagaa agaatggaaa gagggtgata caactcagta ggaagacctt tgattctgaa   5700
tatgtcaaga ctagaaccaa tgactgggat ttcgtggtta caactgacat ctcggaaatg   5760
ggcgccaact ttaaagctga gagggtcata gaccccagac gctgcatgaa accagttata   5820
ttgacagacg gcgaagagcg ggtgattctg gcaggaccca tgccagtgac ccactctagt   5880
gcagcacaaa gaagagggag aataggaagg aatccaagga atgaaaatga tcaatatata   5940
tatatggggg aaccactgga aaatgatgaa gactgtgcgc actggaagga agctaagatg   6000
ctcctagata atatcaacac acctgaagga atcattccca gcttgttcga gccagagcgt   6060
gaaaaggtgg atgccattga cggtgaatat cgcttgagag gagaagcacg gaaaactttt   6120
gtggacctaa tgagaagagg agacctacca gtctggttgg cttataaagt ggcagctgaa   6180
ggtatcaact acgcagacag aagatggtgt tttgacggaa ccagaaacaa tcaaatcttg   6240
gaagaaaatg tggaagtgga aatctggaca aaggaagggg aaaggaaaaa attgaaacct   6300
agatggttag atgctaggat ctactccgac ccactggcgc taaaagagtt caaggaattt   6360
gcagccggaa gaaagtccct aaccctgaac ctaattacag agatgggcag actcccaact   6420
tttatgactc agaaggccag agatgcacta gacaacttgg cggtgctgca cacggctgaa   6480
gcgggtggaa aggcatacaa tcatgctctc agtgaattac cggagaccct ggagacattg   6540
cttttgctga cactgttggc cacagtcacg ggaggaatct tcctattcct gatgagcgga   6600
aggggtatgg ggaagatgac cctgggaatg tgctgcataa tcacggccag catcctctta   6660
tggtatgcac aaatacagcc acattggata gcagcctcaa taatattgga gttctttctc   6720
atagtcttgc tcattccaga accagaaaag cagaggacac ctcaggataa tcaattgact   6780
tatgtcatca tagccatcct cacagtggtg gccgcaacca tggcaaacga aatgggtttt   6840
```

```
ctggaaaaaa caaagaaaga cctcggactg ggaaacattg caactcagca acctgagagc   6900
aacattctgg acatagatct acgtcctgca tcagcatgga cgttgtatgc cgtggctaca   6960
acatttatca caccaatgtt gagacatagc attgaaaatt cctcagtaaa tgtgtcccta   7020
acagccatag ctaaccaagc cacagtgcta atgggtctcg gaaaaggatg gccattgtca   7080
aagatggaca ttggagttcc cctccttgct attgggtgtt actcacaagt caaccctata   7140
accctcacag cggctcttct tttattggta gcacattatg ccatcatagg accgggactt   7200
caagccaaag caactagaga agctcagaaa agagcagcag cgggcatcat gaaaaaccca   7260
actgtggatg gaataacagt gatagatcta gatccaatac cctatgatcc aaagtttgaa   7320
aagcagttgg gacaagtaat gctcctagtc ctctgcgtga cccaagtgct gatgatgagg   7380
actacgtggg ctttgtgtga agccttaact ctagcaactg gacccgtgtc cacattgtgg   7440
gaaggaaatc cagggagatt ctggaacaca accattgcag tgtcaatggc aaacatcttt   7500
agagggagtt acctggctgg agctggactt ctcttttcta tcatgaagaa cacaaccagc   7560
acgagaagag gaactggcaa tataggagaa acgttaggag agaaatggaa aagcagactg   7620
aacgcattgg ggaaaagtga attccagatc tacaaaaaaa gtggaattca agaagtggac   7680
agaaccttag caaaagaagg cattaaaaga ggagaaacgg atcatcacgc tgtgtcgcga   7740
ggctcagcaa aactgagatg gttcgttgaa aggaatttgg tcacaccaga agggaaagta   7800
gtggaccttg gttgtggcag agggggctgg tcatactatt gtggaggatt aaagaatgta   7860
agagaagtta aaggcttaac aaaaggagga ccaggacacg aagaacctat ccctatgtca   7920
acatatgggt ggaatctagt acgcttacag agcggagttg atgtttttt tgttccacca   7980
gagaagtgtg acacattgtt gtgtgacata ggggaatcat caccaaatcc cacggtagaa   8040
gcgggacgaa cactcagagt cctcaaccta gtggaaaatt ggctgaacaa taacacccaa   8100
ttttgcgtaa aggttcttaa cccgtacatg ccctcagtca ttgaaagaat ggaaacctta   8160
caacggaaat acggaggagc cttggtgaga aatccactct cacggaattc cacacatgag   8220
atgtactggg tgtccaatgc ttccgggaac atagtgtcat cagtgaacat gatttcaaga   8280
atgctgatca acagattcac tatgagacac aagaaggcca cctatgagcc agatgtcgac   8340
ctcggaagcg gaacccgcaa tattggaatt gaaagtgaga caccgaacct agacataatt   8400
gggaaaagaa tagaaaaaat aaaacaagag catgaaacgt catggcacta tgatcaagac   8460
cacccataca aaacatgggc ttaccatggc agctatgaaa caaaacagac tggatcagca   8520
tcatccatgg tgaacggagt agtcagattg ctgacaaaac cctgggacgt tgttccaatg   8580
gtgacacaga tggcaatgac agacacaact ccttttggac aacagcgcgt cttcaaagag   8640
aaggtggata cgagaaccca agaaccaaaa gaaggcacaa aaaaactaat gaaaatcacg   8700
gcagagtggc tctggaaaga actaggaaag aaaaagacac ctagaatgtg taccagagaa   8760
gaattcacaa aaaaggtgag aagcaatgca gccttggggg ccatattcac cgatgagaac   8820
aagtggaaat cggcgcgtga agccgttgaa gatagtaggt tttgggagct ggttgacaag   8880
gaaaggaacc tccatcttga agggaaatgt gaaacatgtg tatacaacat gatggggaaa   8940
agagagaaaa aactaggaga gtttggtaaa gcaaaaggca gcagagccat atggtacatg   9000
tggctcggag cacgcttctt agagtttgaa gccctaggat ttttgaatga agaccattgg   9060
ttctccagag agaactccct gagtggagtg gaaggagaag ggctgcataa gctaggttac   9120
atcttaagag aggtgagcaa gaaagaagga ggagcaatgt atgccgatga caccgcaggc   9180
```

```
tgggacacaa gaatcacaat agaggatttg aaaaatgaag aaatgataac gaaccacatg   9240
gcaggagaac acaagaaact tgccgaggcc atttttaaat tgacgtacca aaacaaggtg   9300
gtgcgtgtgc aaagaccaac accaagaggc acagtaatgg acatcatatc gagaagagac   9360
caaaggggta gtggacaagt tggcacctat ggcctcaaca ctttcaccaa catggaagca   9420
caactaatta ggcaaatgga gggggaagga atcttcaaaa gcatccagca cttgacagcc   9480
tcagaagaaa tcgctgtgca agattggcta gtaagagtag ggcgtgaaag gttgtcaaga   9540
atggccatca gtggagatga ttgtgttgtg aaacctttag atgatagatt tgcaagagct   9600
ctaacagctc taaatgacat gggaaaggtt aggaaggaca tacagcaatg ggagccctca   9660
agaggatgga acgactggac gcaggtgccc ttctgttcac accattttca cgagttaatt   9720
atgaaagatg gtcgcacact cgtagttcca tgcagaaacc aagatgaatt gatcggcaga   9780
gcccgaattt cccagggagc tgggtggtct ttacgggaga cggcctgttt ggggaagtct   9840
tacgcccaaa tgtggagctt gatgtacttc cacagacgtg atctcaggct agcggcaaat   9900
gccatctgct cggcagtccc atcacactgg attccaacaa gccggacaac ctggtccata   9960
cacgccagcc atgaatggat gacgacggaa gacatgttga cagtttggaa cagagtgtgg  10020
atcctagaaa atccatggat ggaagacaaa actccagtgg aatcatggga ggaaatccca  10080
tacctgggaa aaagagaaga ccaatggtgc ggctcgctga ttgggctgac aagcagagcc  10140
acctgggcga agaatatcca gacagcaata aaccaagtca gatccctcat tggcaatgag  10200
gaatacacag attacatgcc atccatgaaa agattcagaa gagaagagga agaggcagga  10260
gttttgtggt agaaaaacat gaaacaaaac agaagtcagg tcggattaag ccatagtacg  10320
ggaaaaacta tgctacctgt gagccccgtc caaggacgtt aaaagaagtc aggccatttt  10380
gatgccatag cttgagcaaa ctgtgcagcc tgtagctcca cctgagaagg tgtaaaaaat  10440
ccgggaggcc acaaaccatg gaagctgtac gcatggcgta gtggactagc ggttagagga  10500
gacccctccc ttacagatcg cagcaacaat gggggcccaa ggtgagatga agctgtagtc  10560
tcactggaag gactagaggt tagaggagac ccccccaaaa caaaaaacag catattgacg  10620
ctgggaaaga ccagagatcc tgctgtctcc tcagcatcat tccaggcaca ggacgccaga  10680
aaatggaatg gtgctgttga atcaacaggt tctggtaccg gtaggcatcg tggtgtcacg  10740
ctcgtcgttt ggtatggctt cattcagctc cggttcccaa cgatcaaggc gagttacatg  10800
atcccccatg ttgtgcaaaa aagcggttag ctccttcggt cctccgatcg ttgtcagaag  10860
taagttggcc gcagtgttat cactcatggt tatggcagca ctgcataatt ctcttactgt  10920
catgccatcc gtaagatgct tttctgtgac tggtgagtac tcaaccaagt cattctgaga  10980
atagtgtatg cggcgaccga gttgctcttg cccggcgtca acacgggata ataccgcgcc  11040
acatagcaga actttaaaag tgctcatcat tggaaaacgt tcttcggggc gaaaactctc  11100
aaggatctta ccgctgttga gatccagttc gatgtaaccc actcgtgcac ccaactgatc  11160
ttcagcatct tttactttca ccagcgtttc tgggtgagca aaaacaggaa ggcaaaatgc  11220
cgcaaaaaag ggaataaggg cgacacggaa atgttgaata ctcatactct tccttttca  11280
atattattga agcatttatc agggttattg tctcatgagc ggatacatat ttgaatgtat  11340
ttagaaaaat aaacaaatag gggttccgcg cacatttccc cgaaaagtgc cacctgacgt  11400
ctaagaaacc attattatca tgacattaac ctataaaaat aggcgtatca cgaggccctt  11460
tcgtcttcaa gaattctcat gtttgacagc ttatcatcga taagctttaa tgcggtagtt  11520
tatcacagtt aaattgctaa cgcagtcagg caccgtgtat gaaatctaac aatgcgctca  11580
```

```
tcgtcatcct cggcaccgtc accctggatg ctgtaggcat aggcttggtt atgccggtac  11640
tgccgggcct cttgcgggat atcgtccatt ccgacagcat cgccagtcac tatggcgtgc  11700
tgctggcgct atatgcgttg atgcaatttc tatgcgcacc cgttctcgga gcactgtccg  11760
accgctttgg ccgccgccca gtcctgctcg cttcgctact tggagccact atcgactacg  11820
cgatcatggc gaccacaccc gtcctgtgga tcctctacgc cggacgcatc gtggccggca  11880
tcaccggcgc cacaggtgcg gttgctggcg cctatatcgc cgacatcacc gatggggaag  11940
atcgggctcg ccacttcggg ctcatgagcg cttgtttcgg cgtgggtatg gtggcaggcc  12000
ccgtggccgg gggactgttg ggcgccatct ccttgcatgc accattcctt gcggcggcgg  12060
tgctcaacgg cctcaaccta ctactgggct gcttcctaat gcaggagtcg cataagggag  12120
agcgtcgacc gatgcccttg agagccttca acccagtcag ctccttccgg tgggcgcggg  12180
gcatgactat cgtcgccgca cttatgactg tcttctttat catgcaactc gtaggacagg  12240
tgccggcagc gctctgggtc attttcggcg aggaccgctt tcgctggagc gcgacgatga  12300
tcggcctgtc gcttgcggta ttcggaatct tgcacgccct cgctcaagcc ttcgtcactg  12360
gtcccgccac caaacgtttc ggcgagaagc aggccattat cgccggcatg gcggccgacg  12420
cgctgggcta cgtcttgctg gcgttcgcga cgcgaggctg gatggccttc cccattatga  12480
ttcttctcgc ttccggcggc atcgggatgc ccgcgttgca ggccatgctg tccaggcagg  12540
tagatgacga ccatcaggga cagcttcaag gatcgctcgc ggctcttacc agcctaactt  12600
cgatcactgg accgctgatc gtcacggcga tttatgccgc ctcggcgagc acatggaacg  12660
ggttggcatg gattgtaggc gccgccctat accttgtctg cctccccgcg ttgcgtcgcg  12720
gtgcatggag ccgggccacc tcgacctgaa tggaagccgg cggcacctcg ctaacggatt  12780
caccactcca agaattggag ccaatcaatt cttgcggaga actgtgaatg cgcaaaccaa  12840
cccttggcag aacatatcca tcgcgtccgc catctccagc agccgcacgc ggcgcatctc  12900
gggcagcgtt gggtcctggc cacgggtgcg catgatcgtg ctcctgtcgt tgaggacccg  12960
gctaggctgg cggggttgcc ttactggtta gcagaatgaa tcaccgatac gcgagcgaac  13020
gtgaagcgac tgctgctgca aaacgtctgc gacctgagca acaacatgaa tggtcttcgg  13080
tttccgtgtt tcgtaaagtc tggaaacgcg gaagtcagcg ccctgcacca ttatgttccg  13140
gatctgcatc gcaggatgct gctggctacc ctgtggaaca cctacatctg tattaacgaa  13200
gcgctggcat tgaccctgag tgatttttct ctggtcccgc cgcatccata ccgccagttg  13260
tttaccctca caacgttcca gtaaccgggc atgttcatca tcagtaaccc gtatcgtgag  13320
catcctctct cgtttcatcg gtatcattac ccccatgaac agaaatcccc cttacacgga  13380
ggcatcagtg accaaacagg aaaaaaccgc ccttaacatg gcccgcttta tcagaagcca  13440
gacattaacg cttctggaga aactcaacga gctggacgcg gatgaacagg cagacatctg  13500
tgaatcgctt cacgaccacg ctgatgagct ttaccgcagc tgcctcgcgc gtttcggtga  13560
tgacggtgaa aacctctgac acatgcagct cccggagacg gtcacagctt gtctgtaagc  13620
ggatgccggg agcagacaag cccgtcaggg cgcgtcagcg ggtgttggcg ggtgtcgggg  13680
cgcagccatg acccagtcac gtagcgatag cggagtgtat actggcttaa ctatgcggca  13740
tcagagcaga ttgtactgag agtgcaccat atgcggtgtg aaataccgca cagatgcgta  13800
aggagaaaat accgcatcag gcgctcttcc gcttcctcgc tcactgactc gctgcgctcg  13860
gtcgttcggc tgcggcgagc ggtatcagct cactcaaagg cggtaatacg gttatccaca  13920
```

```
gaatcagggg ataacgcagg aaagaacatg tgagcaaaag gccagcaaaa ggccaggaac  13980

cgtaaaaagg ccgcgttgct ggcgtttttc cataggctcc gcccccctga cgagcatcac  14040

aaaaatcgac gctcaagtca gaggtggcga aacccgacag gactataaag ataccaggcg  14100

tttccccctg gaagctccct cgtgcgctct cctgttccga ccctgccgct taccggatac  14160

ctgtccgcct ttctcccttc gggaagcgtg gcgctttctc atagctcacg ctgtaggtat  14220

ctcagttcgg tgtaggtcgt tcgctccaag ctgggctgtg tgcacgaacc ccccgttcag  14280

cccgaccgct gcgccttatc cggtaactat cgtcttgagt ccaacccggt aagacacgac  14340

ttatcgccac tggcagcagc cactggtaac aggattagca gagcgaggta tgtaggcggt  14400

gctacagagt tcttgaagtg gtggcctaac tacggctaca ctagaaggac agtatttggt  14460

atctgcgctc tgctgaagcc agttaccttc ggaaaaagag ttggtagctc ttgatccggc  14520

aaacaaacca ccgctggtag cggtggtttt tttgtttgca agcagcagat tacgcgcaga  14580

aaaaaaggat ctcaagaaga tcctttgatc ttttctacgg ggtctgacgc tcagtggaac  14640

gaaaactcac gttaagggat tttggtcatg agattatcaa aaaggatctt cacctagatc  14700

cttttaaatt aaaaatgaag ttttaaatca atctaaagta tatatgagta aacttggtct  14760

gacagttacc aatgcttaat cagtgaggca cctatctcag cgatctgtct atttcgttca  14820

tccatagttg cctgactccc cgtcgtgtag ataactacga tacgggaggg cttaccatct  14880

ggccccagtg ctgcaatgat accgcgagac ccacgctcac cggctccaga tttatcagca  14940

ataaaccagc cagccggaag ggccgagcgc agaagtggtc ctgcaacttt atccgcctcc  15000

atccagtcta ttaattgttg ccgggaagct agagtaagta gttcgccagt taatagtttg  15060

cgcaacgttg ttgccattgc tgcaagatct ggctagcgat gaccctgctg attggttcgc  15120

tgaccatttc cgggcgcgcc gatttaggtg acactatag                         15159
```

<210> SEQ ID NO 47
<211> LENGTH: 3391
<212> TYPE: PRT
<213> ORGANISM: Dengue 2 virus (Tonga/74)

<400> SEQUENCE: 47

```
Met Asn Asn Gln Arg Lys Lys Ala Arg Asn Thr Pro Phe Asn Met Leu
 1               5                  10                  15

Lys Arg Glu Arg Asn Arg Val Ser Thr Val Gln Gln Leu Thr Lys Arg
            20                  25                  30

Phe Ser Leu Gly Met Leu Gln Gly Arg Gly Pro Leu Lys Leu Phe Met
        35                  40                  45

Ala Leu Val Ala Phe Leu Arg Phe Leu Thr Ile Pro Pro Thr Ala Gly
    50                  55                  60

Ile Leu Lys Arg Trp Gly Thr Ile Lys Lys Ser Lys Ala Ile Asn Val
65                  70                  75                  80

Leu Arg Gly Phe Arg Lys Glu Ile Gly Arg Met Leu Asn Ile Leu Asn
                85                  90                  95

Arg Arg Arg Arg Thr Val Gly Met Ile Ile Met Leu Thr Pro Thr Val
            100                 105                 110

Met Ala Phe His Leu Thr Thr Arg Asn Gly Glu Pro His Met Ile Val
        115                 120                 125

Ser Arg Gln Glu Lys Gly Lys Ser Leu Leu Phe Lys Thr Lys Asp Gly
    130                 135                 140

Thr Asn Met Cys Thr Leu Met Ala Met Asp Leu Gly Glu Leu Cys Glu
145                 150                 155                 160
```

```
Asp Thr Ile Thr Tyr Lys Cys Pro Phe Leu Lys Gln Asn Glu Pro Glu
                165                 170                 175

Asp Ile Asp Cys Trp Cys Asn Ser Thr Ser Thr Trp Val Thr Tyr Gly
            180                 185                 190

Thr Cys Thr Thr Thr Gly Glu His Arg Arg Glu Lys Arg Ser Val Ala
        195                 200                 205

Leu Val Pro His Val Gly Met Gly Leu Glu Thr Arg Thr Glu Thr Trp
    210                 215                 220

Met Ser Ser Glu Gly Ala Trp Lys His Ala Gln Arg Ile Glu Thr Trp
225                 230                 235                 240

Ile Leu Arg His Pro Gly Phe Thr Ile Met Ala Ala Ile Leu Ala Tyr
                245                 250                 255

Thr Ile Gly Thr Thr His Phe Gln Arg Val Leu Ile Phe Ile Leu Leu
            260                 265                 270

Thr Ala Ile Ala Pro Ser Met Thr Met Arg Cys Ile Gly Ile Ser Asn
        275                 280                 285

Arg Asp Phe Val Glu Gly Val Ser Gly Gly Ser Trp Val Asp Ile Val
    290                 295                 300

Leu Glu His Gly Ser Cys Val Thr Thr Met Ala Lys Asn Lys Pro Thr
305                 310                 315                 320

Leu Asp Phe Glu Leu Ile Lys Thr Glu Ala Lys Gln Pro Ala Thr Leu
                325                 330                 335

Arg Lys Tyr Cys Ile Glu Ala Lys Leu Thr Asn Thr Thr Thr Asp Ser
            340                 345                 350

Arg Cys Pro Thr Gln Gly Glu Pro Thr Leu Asn Glu Glu Gln Asp Lys
        355                 360                 365

Arg Phe Val Cys Lys His Ser Met Val Asp Arg Gly Trp Gly Asn Gly
    370                 375                 380

Cys Gly Leu Phe Gly Lys Gly Gly Ile Val Thr Cys Ala Met Phe Thr
385                 390                 395                 400

Cys Lys Lys Asn Met Glu Gly Lys Ile Val Gln Pro Glu Asn Leu Glu
                405                 410                 415

Tyr Thr Val Val Ile Thr Pro His Ser Gly Glu Glu His Ala Val Gly
            420                 425                 430

Asn Asp Thr Gly Lys His Gly Lys Glu Val Lys Ile Thr Pro Gln Ser
        435                 440                 445

Ser Ile Thr Glu Ala Glu Leu Thr Gly Tyr Gly Thr Val Thr Met Glu
    450                 455                 460

Cys Ser Pro Arg Thr Gly Leu Asp Phe Asn Glu Met Val Leu Leu Gln
465                 470                 475                 480

Met Glu Asp Lys Ala Trp Leu Val His Arg Gln Trp Phe Leu Asp Leu
                485                 490                 495

Pro Leu Pro Trp Leu Pro Gly Ala Asp Thr Gln Gly Ser Asn Trp Ile
            500                 505                 510

Gln Lys Glu Thr Leu Val Thr Phe Lys Asn Pro His Ala Lys Lys Gln
        515                 520                 525

Asp Val Val Val Leu Gly Ser Gln Glu Gly Ala Met His Thr Ala Leu
    530                 535                 540

Thr Gly Ala Thr Glu Ile Gln Met Ser Ser Gly Asn Leu Leu Phe Thr
545                 550                 555                 560

Gly His Leu Lys Cys Arg Leu Arg Met Asp Lys Leu Gln Leu Lys Gly
                565                 570                 575
```

```
Met Ser Tyr Ser Met Cys Thr Gly Lys Phe Lys Ile Val Lys Glu Ile
            580                 585                 590

Ala Glu Thr Gln His Gly Thr Ile Val Ile Arg Val Gln Tyr Glu Gly
        595                 600                 605

Asp Gly Ser Pro Cys Lys Ile Pro Phe Glu Ile Met Asp Leu Glu Lys
    610                 615                 620

Arg His Val Leu Gly Arg Leu Ile Thr Val Asn Pro Ile Val Thr Glu
625                 630                 635                 640

Lys Asp Ser Pro Val Asn Ile Glu Ala Glu Pro Pro Phe Gly Asp Ser
                645                 650                 655

Tyr Ile Ile Ile Gly Val Glu Pro Gly Gln Leu Lys Leu Asp Trp Phe
            660                 665                 670

Lys Lys Gly Ser Ser Ile Gly Gln Met Phe Glu Thr Thr Met Arg Gly
        675                 680                 685

Ala Lys Arg Met Ala Ile Leu Gly Asp Thr Ala Trp Asp Phe Gly Ser
    690                 695                 700

Leu Gly Gly Val Phe Thr Ser Ile Gly Lys Ala Leu His Gln Val Phe
705                 710                 715                 720

Gly Ala Ile Tyr Gly Ala Ala Phe Ser Gly Val Ser Trp Thr Met Lys
                725                 730                 735

Ile Leu Ile Gly Val Ile Ile Thr Trp Ile Gly Met Asn Ser Arg Ser
            740                 745                 750

Thr Ser Leu Ser Val Ser Leu Val Leu Val Gly Ile Val Thr Leu Tyr
        755                 760                 765

Leu Gly Val Met Val Gln Ala Asp Ser Gly Cys Val Val Ser Trp Lys
    770                 775                 780

Asn Lys Glu Leu Lys Cys Gly Ser Gly Ile Phe Val Thr Asp Asn Val
785                 790                 795                 800

His Thr Trp Thr Glu Gln Tyr Lys Phe Gln Pro Glu Ser Pro Ser Lys
                805                 810                 815

Leu Ala Ser Ala Ile Gln Lys Ala His Glu Glu Gly Ile Cys Gly Ile
            820                 825                 830

Arg Ser Val Thr Arg Leu Glu Asn Leu Met Trp Lys Gln Ile Thr Ser
        835                 840                 845

Glu Leu Asn His Ile Leu Ser Glu Asn Glu Val Lys Leu Thr Ile Met
    850                 855                 860

Thr Gly Asp Ile Lys Gly Ile Met Gln Val Gly Lys Arg Ser Leu Arg
865                 870                 875                 880

Pro Gln Pro Thr Glu Leu Arg Tyr Ser Trp Lys Thr Trp Gly Lys Ala
                885                 890                 895

Lys Met Leu Ser Thr Glu Leu His Asn Gln Thr Phe Leu Ile Asp Gly
            900                 905                 910

Pro Glu Thr Ala Glu Cys Pro Asn Thr Asn Arg Ala Trp Asn Ser Leu
        915                 920                 925

Glu Val Glu Asp Tyr Gly Phe Gly Val Phe Thr Thr Asn Ile Trp Leu
    930                 935                 940

Arg Leu Arg Glu Lys Gln Asp Val Phe Cys Asp Ser Lys Leu Met Ser
945                 950                 955                 960

Ala Ala Ile Lys Asp Asn Arg Ala Val His Ala Asp Met Gly Tyr Trp
                965                 970                 975

Ile Glu Ser Ala Leu Asn Asp Thr Trp Lys Ile Glu Lys Ala Ser Phe
            980                 985                 990

Ile Glu Val Lys Ser Cys His Trp Pro Lys Ser His Thr Leu Trp Ser
```

```
        995                 1000                1005

Asn Gly Val Leu Glu Ser Glu Met Val Ile Pro Lys Asn Phe Ala Gly
    1010                1015                1020

Pro Val Ser Gln His Asn Asn Arg Pro Gly Tyr Tyr Thr Gln Thr Ala
1025                1030                1035                1040

Gly Pro Trp His Leu Gly Lys Leu Glu Met Asp Phe Asp Phe Cys Glu
                1045                1050                1055

Gly Thr Thr Val Val Val Thr Glu Asn Cys Gly Asn Arg Gly Pro Ser
            1060                1065                1070

Leu Arg Thr Thr Thr Ala Ser Gly Lys Leu Ile Thr Glu Trp Cys Cys
        1075                1080                1085

Arg Ser Cys Thr Leu Pro Pro Leu Arg Tyr Arg Gly Glu Asp Gly Cys
    1090                1095                1100

Trp Tyr Gly Met Glu Ile Arg Pro Leu Lys Glu Lys Glu Glu Asn Leu
1105                1110                1115                1120

Val Ser Ser Leu Val Thr Ala Gly His Gly Gln Ile Asp Asn Phe Ser
                1125                1130                1135

Leu Gly Ile Leu Gly Met Ala Leu Phe Leu Glu Glu Met Leu Arg Thr
            1140                1145                1150

Arg Val Gly Thr Lys His Ala Ile Leu Leu Val Ala Val Ser Phe Val
        1155                1160                1165

Thr Leu Ile Thr Gly Asn Met Ser Phe Arg Asp Leu Gly Arg Val Met
    1170                1175                1180

Val Met Val Gly Ala Thr Met Thr Asp Asp Ile Gly Met Gly Val Thr
1185                1190                1195                1200

Tyr Leu Ala Leu Leu Ala Ala Phe Arg Val Arg Pro Thr Phe Ala Ala
                1205                1210                1215

Gly Leu Leu Leu Arg Lys Leu Thr Ser Lys Glu Leu Met Met Thr Thr
            1220                1225                1230

Ile Gly Ile Val Leu Leu Ser Gln Ser Ser Ile Pro Glu Thr Ile Leu
        1235                1240                1245

Glu Leu Thr Asp Ala Leu Ala Leu Gly Met Met Val Leu Lys Met Val
    1250                1255                1260

Arg Asn Met Glu Lys Tyr Gln Leu Ala Val Thr Ile Met Ala Ile Leu
1265                1270                1275                1280

Cys Val Pro Asn Ala Val Ile Leu Gln Asn Ala Trp Lys Val Ser Cys
                1285                1290                1295

Thr Ile Leu Ala Val Val Ser Val Ser Pro Leu Leu Leu Thr Ser Ser
            1300                1305                1310

Gln Gln Lys Ala Asp Trp Ile Pro Leu Ala Leu Thr Ile Lys Gly Leu
        1315                1320                1325

Asn Pro Thr Ala Ile Phe Leu Thr Thr Leu Ser Arg Thr Asn Lys Lys
    1330                1335                1340

Arg Ser Trp Pro Leu Asn Glu Ala Ile Met Ala Val Gly Met Val Ser
1345                1350                1355                1360

Ile Leu Ala Ser Ser Leu Leu Lys Asn Asp Ile Pro Met Thr Gly Pro
                1365                1370                1375

Leu Val Ala Gly Gly Leu Leu Thr Val Cys Tyr Val Leu Thr Gly Arg
            1380                1385                1390

Ser Ala Asp Leu Glu Leu Glu Arg Ala Thr Asp Val Lys Trp Asp Asp
        1395                1400                1405

Gln Ala Glu Ile Ser Gly Ser Ser Pro Ile Leu Ser Ile Thr Ile Ser
    1410                1415                1420
```

```
Glu Asp Gly Ser Met Ser Ile Lys Asn Glu Glu Glu Glu Gln Thr Leu
1425                1430                1435                1440

Thr Ile Leu Ile Arg Thr Gly Leu Leu Val Ile Ser Gly Leu Phe Pro
                1445                1450                1455

Val Ser Ile Pro Ile Thr Ala Ala Ala Trp Tyr Leu Trp Glu Val Lys
            1460                1465                1470

Lys Gln Arg Ala Gly Val Leu Trp Asp Val Pro Ser Pro Pro Pro Val
        1475                1480                1485

Gly Lys Ala Glu Leu Glu Asp Gly Ala Tyr Arg Ile Lys Gln Lys Gly
    1490                1495                1500

Ile Leu Gly Tyr Ser Gln Ile Gly Ala Gly Val Tyr Lys Glu Gly Thr
1505                1510                1515                1520

Phe His Thr Met Trp His Val Thr Arg Gly Ala Val Leu Met His Lys
                1525                1530                1535

Gly Lys Arg Ile Glu Pro Ser Trp Ala Asp Val Lys Lys Asp Leu Ile
            1540                1545                1550

Ser Tyr Gly Gly Gly Trp Lys Leu Glu Gly Glu Trp Lys Glu Gly Glu
        1555                1560                1565

Glu Val Gln Val Leu Ala Leu Glu Pro Gly Lys Asn Pro Arg Ala Val
    1570                1575                1580

Gln Thr Lys Pro Gly Leu Phe Arg Thr Asn Thr Gly Thr Ile Gly Ala
1585                1590                1595                1600

Val Ser Leu Asp Phe Ser Pro Gly Thr Ser Gly Ser Pro Ile Val Asp
                1605                1610                1615

Lys Lys Gly Lys Val Val Gly Leu Tyr Gly Asn Gly Val Val Thr Arg
            1620                1625                1630

Ser Gly Ala Tyr Val Ser Ala Ile Ala Gln Thr Glu Lys Ser Ile Glu
        1635                1640                1645

Asp Asn Pro Glu Ile Glu Asp Asp Ile Phe Arg Lys Arg Arg Leu Thr
    1650                1655                1660

Ile Met Asp Leu His Pro Gly Ala Gly Lys Thr Lys Arg Tyr Leu Pro
1665                1670                1675                1680

Ala Ile Val Arg Glu Ala Ile Lys Arg Gly Leu Arg Thr Leu Ile Leu
                1685                1690                1695

Ala Pro Thr Arg Val Val Ala Ala Glu Met Glu Glu Ala Leu Arg Gly
            1700                1705                1710

Leu Pro Ile Arg Tyr Gln Thr Pro Ala Ile Arg Ala Glu His Thr Gly
        1715                1720                1725

Arg Glu Ile Val Asp Leu Met Cys His Ala Thr Phe Thr Met Arg Leu
    1730                1735                1740

Leu Ser Pro Ile Arg Val Pro Asn Tyr Asn Leu Ile Ile Met Asp Glu
1745                1750                1755                1760

Ala His Phe Thr Asp Pro Ala Ser Ile Ala Ala Arg Gly Tyr Ile Ser
                1765                1770                1775

Thr Arg Val Glu Met Gly Glu Ala Ala Gly Ile Phe Met Thr Ala Thr
            1780                1785                1790

Pro Pro Gly Ser Arg Asp Pro Phe Pro Gln Ser Asn Ala Pro Ile Met
        1795                1800                1805

Asp Glu Glu Arg Glu Ile Pro Glu Arg Ser Trp Asn Ser Gly His Glu
    1810                1815                1820

Trp Val Thr Asp Phe Lys Gly Lys Thr Val Trp Phe Val Pro Ser Ile
1825                1830                1835                1840
```

```
Lys Thr Gly Asn Asp Ile Ala Ala Cys Leu Arg Lys Asn Gly Lys Arg
                1845                1850                1855

Val Ile Gln Leu Ser Arg Lys Thr Phe Asp Ser Glu Tyr Val Lys Thr
            1860                1865                1870

Arg Thr Asn Asp Trp Asp Phe Val Val Thr Thr Asp Ile Ser Glu Met
        1875                1880                1885

Gly Ala Asn Phe Lys Ala Glu Arg Val Ile Asp Pro Arg Arg Cys Met
    1890                1895                1900

Lys Pro Val Ile Leu Thr Asp Gly Glu Glu Arg Val Ile Leu Ala Gly
1905                1910                1915                1920

Pro Met Pro Val Thr His Ser Ser Ala Ala Gln Arg Arg Gly Arg Ile
                1925                1930                1935

Gly Arg Asn Pro Arg Asn Glu Asn Asp Gln Tyr Ile Tyr Met Gly Glu
            1940                1945                1950

Pro Leu Glu Asn Asp Glu Asp Cys Ala His Trp Lys Glu Ala Lys Met
        1955                1960                1965

Leu Leu Asp Asn Ile Asn Thr Pro Glu Gly Ile Ile Pro Ser Leu Phe
    1970                1975                1980

Glu Pro Glu Arg Glu Lys Val Asp Ala Ile Asp Gly Glu Tyr Arg Leu
1985                1990                1995                2000

Arg Gly Glu Ala Arg Lys Thr Phe Val Asp Leu Met Arg Arg Gly Asp
                2005                2010                2015

Leu Pro Val Trp Leu Ala Tyr Lys Val Ala Ala Glu Gly Ile Asn Tyr
            2020                2025                2030

Ala Asp Arg Arg Trp Cys Phe Asp Gly Thr Arg Asn Asn Gln Ile Leu
        2035                2040                2045

Glu Glu Asn Val Glu Val Glu Ile Trp Thr Lys Glu Gly Glu Arg Lys
    2050                2055                2060

Lys Leu Lys Pro Arg Trp Leu Asp Ala Arg Ile Tyr Ser Asp Pro Leu
2065                2070                2075                2080

Ala Leu Lys Glu Phe Lys Glu Phe Ala Ala Gly Arg Lys Ser Leu Thr
                2085                2090                2095

Leu Asn Leu Ile Thr Glu Met Gly Arg Leu Pro Thr Phe Met Thr Gln
            2100                2105                2110

Lys Ala Arg Asp Ala Leu Asp Asn Leu Ala Val Leu His Thr Ala Glu
        2115                2120                2125

Ala Gly Gly Lys Ala Tyr Asn His Ala Leu Ser Glu Leu Pro Glu Thr
    2130                2135                2140

Leu Glu Thr Leu Leu Leu Leu Thr Leu Leu Ala Thr Val Thr Gly Gly
2145                2150                2155                2160

Ile Phe Leu Phe Leu Met Ser Gly Arg Gly Met Gly Lys Met Thr Leu
                2165                2170                2175

Gly Met Cys Cys Ile Ile Thr Ala Ser Ile Leu Leu Trp Tyr Ala Gln
            2180                2185                2190

Ile Gln Pro His Trp Ile Ala Ala Ser Ile Ile Leu Glu Phe Phe Leu
        2195                2200                2205

Ile Val Leu Leu Ile Pro Glu Pro Glu Lys Gln Arg Thr Pro Gln Asp
    2210                2215                2220

Asn Gln Leu Thr Tyr Val Ile Ile Ala Ile Leu Thr Val Val Ala Ala
2225                2230                2235                2240

Thr Met Ala Asn Glu Met Gly Phe Leu Glu Lys Thr Lys Lys Asp Leu
                2245                2250                2255

Gly Leu Gly Asn Ile Ala Thr Gln Gln Pro Glu Ser Asn Ile Leu Asp
```

```
            2260                2265                2270

Ile Asp Leu Arg Pro Ala Ser Ala Trp Thr Leu Tyr Ala Val Ala Thr
        2275                2280                2285

Thr Phe Ile Thr Pro Met Leu Arg His Ser Ile Glu Asn Ser Ser Val
    2290                2295                2300

Asn Val Ser Leu Thr Ala Ile Ala Asn Gln Ala Thr Val Leu Met Gly
2305                2310                2315                2320

Leu Gly Lys Gly Trp Pro Leu Ser Lys Met Asp Ile Gly Val Pro Leu
                2325                2330                2335

Leu Ala Ile Gly Cys Tyr Ser Gln Val Asn Pro Ile Thr Leu Thr Ala
            2340                2345                2350

Ala Leu Leu Leu Leu Val Ala His Tyr Ala Ile Ile Gly Pro Gly Leu
        2355                2360                2365

Gln Ala Lys Ala Thr Arg Glu Ala Gln Lys Arg Ala Ala Ala Gly Ile
    2370                2375                2380

Met Lys Asn Pro Thr Val Asp Gly Ile Thr Val Ile Asp Leu Asp Pro
2385                2390                2395                2400

Ile Pro Tyr Asp Pro Lys Phe Glu Lys Gln Leu Gly Gln Val Met Leu
                2405                2410                2415

Leu Val Leu Cys Val Thr Gln Val Leu Met Met Arg Thr Thr Trp Ala
            2420                2425                2430

Leu Cys Glu Ala Leu Thr Leu Ala Thr Gly Pro Val Ser Thr Leu Trp
        2435                2440                2445

Glu Gly Asn Pro Gly Arg Phe Trp Asn Thr Thr Ile Ala Val Ser Met
    2450                2455                2460

Ala Asn Ile Phe Arg Gly Ser Tyr Leu Ala Gly Ala Gly Leu Leu Phe
2465                2470                2475                2480

Ser Ile Met Lys Asn Thr Thr Ser Thr Arg Arg Gly Thr Gly Asn Ile
                2485                2490                2495

Gly Glu Thr Leu Gly Glu Lys Trp Lys Ser Arg Leu Asn Ala Leu Gly
            2500                2505                2510

Lys Ser Glu Phe Gln Ile Tyr Lys Lys Ser Gly Ile Gln Glu Val Asp
        2515                2520                2525

Arg Thr Leu Ala Lys Glu Gly Ile Lys Arg Gly Glu Thr Asp His His
    2530                2535                2540

Ala Val Ser Arg Gly Ser Ala Lys Leu Arg Trp Phe Val Glu Arg Asn
2545                2550                2555                2560

Leu Val Thr Pro Glu Gly Lys Val Val Asp Leu Gly Cys Gly Arg Gly
                2565                2570                2575

Gly Trp Ser Tyr Tyr Cys Gly Gly Leu Lys Asn Val Arg Glu Val Lys
            2580                2585                2590

Gly Leu Thr Lys Gly Gly Pro Gly His Glu Glu Pro Ile Pro Met Ser
        2595                2600                2605

Thr Tyr Gly Trp Asn Leu Val Arg Leu Gln Ser Gly Val Asp Val Phe
    2610                2615                2620

Phe Val Pro Pro Glu Lys Cys Asp Thr Leu Leu Cys Asp Ile Gly Glu
2625                2630                2635                2640

Ser Ser Pro Asn Pro Thr Val Glu Ala Gly Arg Thr Leu Arg Val Leu
                2645                2650                2655

Asn Leu Val Glu Asn Trp Leu Asn Asn Asn Thr Gln Phe Cys Val Lys
            2660                2665                2670

Val Leu Asn Pro Tyr Met Pro Ser Val Ile Glu Arg Met Glu Thr Leu
        2675                2680                2685
```

```
Gln Arg Lys Tyr Gly Gly Ala Leu Val Arg Asn Pro Leu Ser Arg Asn
    2690                2695                2700

Ser Thr His Glu Met Tyr Trp Val Ser Asn Ala Ser Gly Asn Ile Val
2705                2710                2715                2720

Ser Ser Val Asn Met Ile Ser Arg Met Leu Ile Asn Arg Phe Thr Met
                2725                2730                2735

Arg His Lys Lys Ala Thr Tyr Glu Pro Asp Val Asp Leu Gly Ser Gly
            2740                2745                2750

Thr Arg Asn Ile Gly Ile Glu Ser Glu Thr Pro Asn Leu Asp Ile Ile
        2755                2760                2765

Gly Lys Arg Ile Glu Lys Ile Lys Gln Glu His Glu Thr Ser Trp His
    2770                2775                2780

Tyr Asp Gln Asp His Pro Tyr Lys Thr Trp Ala Tyr His Gly Ser Tyr
2785                2790                2795                2800

Glu Thr Lys Gln Thr Gly Ser Ala Ser Ser Met Val Asn Gly Val Val
                2805                2810                2815

Arg Leu Leu Thr Lys Pro Trp Asp Val Val Pro Met Val Thr Gln Met
            2820                2825                2830

Ala Met Thr Asp Thr Thr Pro Phe Gly Gln Gln Arg Val Phe Lys Glu
        2835                2840                2845

Lys Val Asp Thr Arg Thr Gln Glu Pro Lys Glu Gly Thr Lys Lys Leu
    2850                2855                2860

Met Lys Ile Thr Ala Glu Trp Leu Trp Lys Glu Leu Gly Lys Lys Lys
2865                2870                2875                2880

Thr Pro Arg Met Cys Thr Arg Glu Glu Phe Thr Lys Lys Val Arg Ser
                2885                2890                2895

Asn Ala Ala Leu Gly Ala Ile Phe Thr Asp Glu Asn Lys Trp Lys Ser
            2900                2905                2910

Ala Arg Glu Ala Val Glu Asp Ser Arg Phe Trp Glu Leu Val Asp Lys
        2915                2920                2925

Glu Arg Asn Leu His Leu Glu Gly Lys Cys Glu Thr Cys Val Tyr Asn
    2930                2935                2940

Met Met Gly Lys Arg Glu Lys Lys Leu Gly Glu Phe Gly Lys Ala Lys
2945                2950                2955                2960

Gly Ser Arg Ala Ile Trp Tyr Met Trp Leu Gly Ala Arg Phe Leu Glu
                2965                2970                2975

Phe Glu Ala Leu Gly Phe Leu Asn Glu Asp His Trp Phe Ser Arg Glu
            2980                2985                2990

Asn Ser Leu Ser Gly Val Glu Gly Glu Gly Leu His Lys Leu Gly Tyr
        2995                3000                3005

Ile Leu Arg Glu Val Ser Lys Lys Glu Gly Gly Ala Met Tyr Ala Asp
    3010                3015                3020

Asp Thr Ala Gly Trp Asp Thr Arg Ile Thr Ile Glu Asp Leu Lys Asn
3025                3030                3035                3040

Glu Glu Met Ile Thr Asn His Met Ala Gly Glu His Lys Lys Leu Ala
                3045                3050                3055

Glu Ala Ile Phe Lys Leu Thr Tyr Gln Asn Lys Val Val Arg Val Gln
            3060                3065                3070

Arg Pro Thr Pro Arg Gly Thr Val Met Asp Ile Ile Ser Arg Arg Asp
        3075                3080                3085

Gln Arg Gly Ser Gly Gln Val Gly Thr Tyr Gly Leu Asn Thr Phe Thr
    3090                3095                3100
```

```
Asn Met Glu Ala Gln Leu Ile Arg Gln Met Glu Gly Glu Gly Ile Phe
3105                3110                3115                3120

Lys Ser Ile Gln His Leu Thr Ala Ser Glu Glu Ile Ala Val Gln Asp
                3125                3130                3135

Trp Leu Val Arg Val Gly Arg Glu Arg Leu Ser Arg Met Ala Ile Ser
            3140                3145                3150

Gly Asp Asp Cys Val Val Lys Pro Leu Asp Asp Arg Phe Ala Arg Ala
        3155                3160                3165

Leu Thr Ala Leu Asn Asp Met Gly Lys Val Arg Lys Asp Ile Gln Gln
    3170                3175                3180

Trp Glu Pro Ser Arg Gly Trp Asn Asp Trp Thr Gln Val Pro Phe Cys
3185                3190                3195                3200

Ser His His Phe His Glu Leu Ile Met Lys Asp Gly Arg Thr Leu Val
                3205                3210                3215

Val Pro Cys Arg Asn Gln Asp Glu Leu Ile Gly Arg Ala Arg Ile Ser
            3220                3225                3230

Gln Gly Ala Gly Trp Ser Leu Arg Glu Thr Ala Cys Leu Gly Lys Ser
        3235                3240                3245

Tyr Ala Gln Met Trp Ser Leu Met Tyr Phe His Arg Arg Asp Leu Arg
    3250                3255                3260

Leu Ala Ala Asn Ala Ile Cys Ser Ala Val Pro Ser His Trp Ile Pro
3265                3270                3275                3280

Thr Ser Arg Thr Thr Trp Ser Ile His Ala Ser His Glu Trp Met Thr
                3285                3290                3295

Thr Glu Asp Met Leu Thr Val Trp Asn Arg Val Trp Ile Leu Glu Asn
            3300                3305                3310

Pro Trp Met Glu Asp Lys Thr Pro Val Glu Ser Trp Glu Glu Ile Pro
        3315                3320                3325

Tyr Leu Gly Lys Arg Glu Asp Gln Trp Cys Gly Ser Leu Ile Gly Leu
    3330                3335                3340

Thr Ser Arg Ala Thr Trp Ala Lys Asn Ile Gln Thr Ala Ile Asn Gln
3345                3350                3355                3360

Val Arg Ser Leu Ile Gly Asn Glu Glu Tyr Thr Asp Tyr Met Pro Ser
                3365                3370                3375

Met Lys Arg Phe Arg Arg Glu Glu Glu Glu Ala Gly Val Leu Trp
            3380                3385                3390


<210> SEQ ID NO 48
<211> LENGTH: 15153
<212> TYPE: DNA
<213> ORGANISM: Artificial Sequence
<220> FEATURE:
<223> OTHER INFORMATION: Dengue 3 plasmid p3

<400> SEQUENCE: 48

agttgttagt ctacgtggac cgacaagaac agtttcgact cggaagcttg cttaacgtag      60

tactgacagt tttttattag agagcagatc tctgatgaac aaccaacgga aaaagacggg     120

aaaaccgtct atcaatatgc tgaaacgcgt gagaaaccgt gtgtcaactg gatcacagtt     180

ggcgaagaga ttctcaagag gactgctgaa cggccaagga ccaatgaaat tggttatggc     240

gttcatagct ttcctcagat ttctagccat tccaccgaca gcaggagtct tggctagatg     300

gggaaccttt aagaagtcgg gggctattaa ggtcctgaga ggcttcaaga aggagatctc     360

aaacatgctg agcattatca acagacggaa aaagacatcg ctctgtctca tgatgatgtt     420

accagcaaca cttgctttcc acttgacttc acgagatgga gagccgcgca tgattgtggg     480
```

```
gaagaatgaa agaggaaaat ccctactttt taagacagcc tctggaatca acatgtgcac    540
actcatagcc atggatttgg gagagatgtg tgatgacacg gtcacctaca aatgccccct    600
cattactgaa gtggagcctg aagacattga ctgctggtgc aaccttacat cgacatgggt    660
gacctacgga acgtgcaatc aagctggaga gcacagacgc gacaaaagat cggtggcgtt    720
agctccccat gtcggcatgg gactggacac acgcacccaa acctggatgt cggctgaagg    780
agcttggaga caggtcgaga aggtagagac atgggccttt aggcacccag ggttcacaat    840
actagcccta tttcttgccc attacatagg cacttccttg acccagaaag tggttatttt    900
catactacta atgctggtca ccccatccat gacaatgaga tgcgtgggag taggaaacag    960
agattttgtg gaaggcctat caggagctac gtgggttgac gtggtgctcg agcacggtgg   1020
gtgtgtgact accatggcta agaacaagcc cacgctggat atagagctcc agaagaccga   1080
ggccacccaa ctggcgaccc taaggaaact atgtattgag ggaaaaatta ccaacgtaac   1140
aaccgactca aggtgcccca cccaagggga agcgatttta cctgaggagc aggaccagaa   1200
ccacgtgtgc aagcacacat acgtggacag aggctgggga aacggttgtg gtttgtttgg   1260
caagggaagc ctggtaacat gcgcgaaatt tcaatgtttg gaatcaatag agggaaaagt   1320
ggtgcagcat gagaacctca aatacaccgt catcatcaca gtgcacacag gagatcaaca   1380
ccaggtggga aatgaaacgc agggagtcac ggctgagata acaccccagg catcaaccgt   1440
tgaagccatc ttacctgaat atggaaccct tgggctagaa tgctcaccac ggacaggttt   1500
agatttcaat gaaatgattt tgttgacaat gaagaacaaa gcatggatgg tacatagaca   1560
atggtttttt gacctacctt taccatggac atcaggagct acaacagaaa caccaacctg   1620
gaataagaaa gagcttcttg tgacattcaa aaacgcacat gcaaaaaagc aagaagtagt   1680
agtccttgga tcgcaagagg gagcaatgca cacagcactg acaggagcta cagagatcca   1740
aacctcagga ggcacaagta tttttgcggg gcacttaaaa tgtagactca agatggacaa   1800
attggaactc aaggggatga gctatgcaat gtgcttgaat gcctttgtgt tgaagaaaga   1860
agtctccgaa acgcaacatg ggacaatact catcaaggtt gagtacaaag gggaagatgc   1920
accttgcaag attcctttct ccacggagga tggacaaggg aaagcccaca atggcagact   1980
gatcacagct aacccagtgg tgaccaagaa ggaggagcct gtcaatattg aggcagaacc   2040
tccttttggg gaaagcaata tagtaattgg aattggagac aaagccttga aaatcaactg   2100
gtacaagaag ggaagctcga ttgggaagat gttcgaggcc actgccagag gtgcaaggcg   2160
catggccatc ttgggagaca cagcctggga ctttggatca gtaggtggtg ttttaaattc   2220
attaggaaaa atggtgcacc aaatatttgg aagtgcttac acagccctat ttagtggagt   2280
ctcctggata atgaaaattg gaataggtgt ccttttaacc tggatagggt tgaattcaaa   2340
aaacactagt atgagcttta gctgcattgt gataggaatc attacactct atctgggagc   2400
cgtggtgcaa gctgacatgg ggtgtgtcat aaactggaaa ggcaaagaac tcaaatgtgg   2460
aagtggaatt ttcgtcacta atgaggtcca cacctggaca gagcaataca aatttcaagc   2520
agactccccc aaaagactgg cgacagccat tgcaggcgct tgggagaatg gagtgtgcgg   2580
aatcaggtcg acaaccagaa tggagaacct cttgtggaag caaatagcca atgaactgaa   2640
ctacatatta tgggaaaaca acatcaaatt aacggtagtt gtgggtgata taattggggt   2700
cttagagcaa gggaaaagaa cactaacacc acaacccatg gaactaaaat attcatggaa   2760
aacatgggga aaggcgaaga tagtgacagc tgaaacacaa aattcctctt tcataataga   2820
```

```
tgggccaaac acaccagagt gtccaagtgc ctcaagagca tggaatgtgt gggaggtgga   2880
agattacggg ttcggagtct tcacaactaa catatggctg aaactccgag agatgtacac   2940
ccaactatgt gaccacaggc taatgtcggc agccgttaag gatgagaggg ccgtacacgc   3000
cgacatgggc tattggatag aaagccaaaa gaatggaagt tggaagctag aaaaggcatc   3060
cctcatagag gtaaaaacct gcacatggcc aaaatcacac actctttgga gcaatggtgt   3120
gctagagagt gacatgatca tcccaaagag tctggctggt cccatttcgc aacacaacta   3180
caggcccgga taccacaccc aaacggcagg accctggcac ttaggaaaat tggagctgga   3240
cttcaactat tgtgaaggaa caacagttgt catcacagaa aattgtggga caagaggccc   3300
atcactgaga acaacaacag tgtcagggaa gttgatacac gaatggtgtt gccgctcgtg   3360
tacacttcct cccctgcgat acatgggaga agacggctgc tggtatggca tggaaattag   3420
acccattaat gagaaagaag agaacatggt aaagtcttta gtctcagcag ggagtggaaa   3480
ggtggataac ttcacaatgg gtgtcttgtg tttggcaatc ctttttgaag aggtgatgag   3540
aggaaaattt gggaaaaagc acatgattgc aggggttctc ttcacgtttg tactccttct   3600
ctcagggcaa ataacatgga gagacatggc gcacacactc ataatgattg ggtccaacgc   3660
ctctgacaga atgggaatgg gcgtcactta cctagcattg attgcaacat ttaaaattca   3720
gccatttttg gctttgggat tcttcctgag gaaactgaca tctagagaaa atttattgtt   3780
gggagttggg ttggccatgg caacaacgtt acaactgcca gaggacattg aacaaatggc   3840
gaatggaata gctttagggc tcatggctct taaattaata acacaatttg aaacatacca   3900
actatggacg gcattagtct ccctaatgtg ttcaaataca attttcacgt tgactgttgc   3960
ctggagaaca gccaccctga ttttggccgg aatttctctt ttgccagtgt gccagtcttc   4020
gagcatgagg aaaacagatt ggctcccaat ggctgtggca gctatgggag ttccacccct   4080
accacttttt attttcagtt tgaaagatac gctcaaaagg agaagctggc cactgaatga   4140
gggggtgatg gctgttggac ttgtgagtat tctagctagt tctctcctta ggaatgacgt   4200
gcccatggct ggaccattag tggctggggg cttgctgata gcgtgctacg tcataactgg   4260
cacgtcagca gacctcactg tagaaaaagc agcagatgtg acatgggagg aagaggctga   4320
gcaaacagga gtgtcccaca atttaatgat cacagttgat gacgatggaa caatgagaat   4380
aaaagatgat gagactgaga acatcttaac agtgcttttg aaaacagcat tactaatagt   4440
gtcaggcatt tttccatact ccatacccgc aacactgttg gtctggcaca cttggcaaaa   4500
gcaaacccaa agatccggtg tcctatggga cgttcccagc cccccagaga cacagaaagc   4560
agaactggaa gaaggggttt ataggatcaa gcagcaagga atttttggga aaacccaagt   4620
gggggttgga gtacaaaaag aaggagtttt ccacaccatg tggcacgtca caagaggagc   4680
agtgttgaca cacaatggga aaagactgga accaaactgg gctagcgtga aaaaagatct   4740
gatttcatac ggaggaggat ggaaattgag tgcacaatgg caaaaaggag aggaggtgca   4800
ggttattgcc gtagagcctg ggaagaaccc aaagaacttt caaaccatgc caggcatttt   4860
ccagacaaca acaggggaga taggagcgat tgcactggac ttcaagcctg gaacttcagg   4920
atctcccatc ataaacagag agggaaaggt actgggattg tatggcaatg gagtggtcac   4980
aaagaatggt ggctatgtca gtggaatagc acaaacaaat gcagaaccag acggaccgac   5040
accagagttg gaagaagaga tgttcaaaaa gcgaaatcta accataatgg atctccatcc   5100
cgggtcagga aagacgcgga aatatcttcc agctattgtt agagaggcaa tcaagagacg   5160
cttaaggact ctaattttgg caccaacaag ggtagttgca gctgagatgg aagaagcatt   5220
```

```
gaaagggctc ccaataaggt atcaaacaac tgcaacaaaa tctgaacaca cagggagaga   5280
gattgttgat ctaatgtgcc acgcaacgtt cacaatgcgt ttgctgtcac cagtcagggt   5340
tccaaactac aacttgataa taatggatga ggctcatttc acagacccag ccagtatagc   5400
ggctagaggg tacatatcaa ctcgtgtagg aatgggagag gcagccgcaa ttttcatgac   5460
agccacaccc cctggaacag ctgatgcctt tcctcagagc aacgctccaa ttcaagatga   5520
agaaagagac ataccagaac gctcatggaa ttcaggcaat gaatggatta ccgactttgc   5580
cgggaagacg gtgtggtttg tccctagcat caaagctgga aatgacatag caaactgctt   5640
gcggaaaaat ggaaaaaagg tcattcaact tagtaggaag acttttgaca cagaatatca   5700
aaagactaaa ctaaatgatt gggactttgt ggtgacaaca gacatttcag aaatgggagc   5760
caatttcaaa gcagacagag tgatcgaccc aagaagatgt ctcaagccag tgattttgac   5820
agacggaccc gagcgcgtga tcctggcggg accaatgcca gtcaccgtag cgagcgctgc   5880
gcaaaggaga gggagagttg gcaggaaccc acaaaaagaa aatgaccaat acatattcat   5940
gggccagccc ctcaataatg atgaagacca tgctcactgg acagaagcaa aaatgctgct   6000
agacaacatc aacacaccag aagggatcat accagctctc tttgaaccag aaagggagaa   6060
gtcagccgcc atagacggcg aataccgcct gaagggtgag tccaggaaga ccttcgtgga   6120
actcatgagg aggggtgacc tcccagtttg gctagcccat aaagtagcat cagaagggat   6180
caaatataca gatagaaagt ggtgttttga tggagaacgc aacaatcaaa ttttagagga   6240
gaatatggat gtggaaatct ggacaaagga aggagaaaag aaaaaattga gacctaggtg   6300
gcttgatgcc cgcacttatt cagatccctt agcgctcaag gaattcaagg actttgcggc   6360
tggtagaaag tcaattgccc ttgatcttgt gacagaaata ggaagagtgc cttcacactt   6420
agctcacaga acgagaaacg ccctggacaa tctggtgatg ttgcacacgt cagaacatgg   6480
cgggagggcc tacaggcatg cagtggagga actaccagaa acaatggaaa cactcttact   6540
cctgggactc atgatcctgt taacaggtgg agcaatgctt ttcttgatat caggtaaagg   6600
gattggaaag acttcaatag gactcatttg tgtagctgct tccagcggta tgttatggat   6660
ggctgatgtc ccactccaat ggatcgcgtc tgccatagtc ctggagtttt ttatgatggt   6720
gttacttata ccagaaccag aaaagcagag aactccccaa gacaatcaac tcgcatatgt   6780
cgtgataggc atactcacac tggctgcaat agtagcagcc aatgaaatgg gactgttgga   6840
aaccacaaag agagatttag gaatgtccaa agaaccaggt gttgtttctc caaccagcta   6900
tttggatgtg gacttgcacc cagcatcagc ctggacattg tacgctgtgg ccacaacagt   6960
aataacacca atgttgagac ataccataga gaattccaca gcaaatgtgt ccctggcagc   7020
tatagccaac caggcagtgg tcctgatggg tttagacaaa ggatggccga tatcgaaaat   7080
ggacttaggc gtgccactat tggcactggg ttgttattca caagtgaacc cactaactct   7140
cacagcggca gttctcctgc tagtcacgca ttatgctatt ataggtccag gattgcaggc   7200
aaaagccact cgtgaagctc aaaaaaggac agctgctgga ataatgaaga atccaacggt   7260
ggatgggata atgacaatag acctagatcc tgtaatatac gattcaaaat ttgaaaagca   7320
actaggacag gttatgctcc tggttctgtg tgcagttcaa cttttgttaa tgagaacatc   7380
atgggctttt tgtgaagctc taaccctagc cacaggacca ataacaacac tctgggaagg   7440
atcacctggg aagttctgga acaccacgat agctgtttcc atggcgaaca tctttagagg   7500
gagctattta gcaggagctg ggcttgcttt ttctatcatg aaatcagttg gaacaggaaa   7560
```

```
gagagggaca gggtcacagg gtgaaacctt gggagaaaag tggaaaaaga aattgaatca   7620
attaccccgg aaagagtttg acctttacaa gaaatccgga atcactgaag tggatagaac   7680
agaagccaaa gaagggttga aaagaggaga aataacacac catgccgtgt ccagaggcag   7740
cgcaaaactt caatggttcg tggagagaaa catggtcatc cccgaaggaa gagtcataga   7800
cttaggctgt ggaagaggag gctggtcata ttattgtgca ggactgaaaa aagttacaga   7860
agtgcgagga tacacaaaag gcggcccagg acatgaagaa ccagtaccta tgtctacata   7920
cggatggaac atagtcaagt taatgagtgg aaaggatgtg ttttatcttc cacctgaaaa   7980
gtgtgatact ctattgtgtg acattggaga atcttcacca agcccaacag tggaagaaag   8040
cagaaccata agagtcttga agatggttga accatggcta aaaaataacc agttttgcat   8100
taaagtattg aacccttaca tgccaactgt gattgagcac ctagaaagac tacaaaggaa   8160
acatggagga atgcttgtga gaaatccact ctcacgaaac tccacgcacg aaatgtactg   8220
gatatctaat ggcacaggca atatcgtttc ttcagtcaac atggtatcca gattgctact   8280
taacagattc acaatgacac ataggagacc caccatagag aaagatgtgg atttaggagc   8340
ggggacccga catgtcaatg cggaaccaga aacacccaac atggatgtca ttggggaaag   8400
aataagaagg atcaaggagg agcatagttc aacatggcac tatgatgatg aaaatcctta   8460
taaaacgtgg gcttaccatg gatcctatga agttaaggcc acaggctcag cctcctccat   8520
gataaatgga gtcgtgaaac tcctcacgaa accatgggat gtggtgccca tggtgacaca   8580
gatggcaatg acggatacaa ccccattcgg ccagcaaagg gtttttaaag agaaagtgga   8640
caccaggaca cccagaccta tgccaggaac aagaaaggtt atggagatca cagcggaatg   8700
gctttggaga accctgggaa ggaacaaaag acccagatta tgtacgagag aggagttcac   8760
aaaaaaggtc agaaccaacg cagctatggg cgccgttttt acagaggaga accaatggga   8820
cagtgctaga gctgctgttg aggatgaaga attctggaaa ctcgtggaca gagaacgtga   8880
actccacaaa ttgggcaagt gtggaagctg cgtttacaac atgatgggca agagagagaa   8940
gaaacttgga gagtttggca aagcaaaagg cagtagagcc atatggtaca tgtggttggg   9000
agccagatac cttgagttcg aagcactcgg attcttaaat gaagaccatt ggttctcgcg   9060
tgaaaactct tacagtggag tagaaggaga aggactgcac aagctgggat acatcttaag   9120
agacatttcc aagatacccg gaggagctat gtatgctgat gacacagctg gttgggacac   9180
aagaataaca gaagatgacc tgcacaatga ggaaaaaatc acacagcaaa tggaccctga   9240
acacaggcag ttagcaaacg ctatattcaa gctcacatac caaaacaaag tggtcaaagt   9300
tcaacgacca actccaaagg gcacggtaat ggacatcata tctaggaaag accaaagagg   9360
cagtggacag gtgggaactt atggtctgaa tacattcacc aacatggaag cccagttaat   9420
cagacaaatg gaaggagaag gtgtgttgtc gaaggcagac ctcgagaacc ctcatctgct   9480
agagaagaaa gttacacaat ggttggaaac aaaaggagtg gagaggttaa aaagaatggc   9540
catcagcggg gatgattgcg tggtgaaacc aattgatgac aggttcgcca atgccctgct   9600
tgccctgaat gacatgggaa aagttaggaa ggacatacct caatggcagc catcaaaggg   9660
atggcatgat tggcaacagg tccctttctg ctcccaccac tttcatgaat tgatcatgaa   9720
agatggaaga aagttggtag ttccctgcag acctcaggat gaattaatcg ggagagcgag   9780
aatctctcaa ggagcaggat ggagccttag agaaactgca tgcctaggga aagcctacgc   9840
ccaaatgtgg actctcatgt actttcacag aagagatctt agactagcat ccaacgccat   9900
atgttcagca gtaccagtcc attgggtccc cacaagcaga acgacgtggt ctattcatgc   9960
```

```
tcaccatcag tggatgacta cagaagacat gcttactgtt tggaacaggg tgtggataga  10020
ggataatcca tggatggaag acaaaactcc agtcaaaacc tgggaagatg ttccatatct  10080
agggaagaga gaagaccaat ggtgcggatc actcattggt ctcacttcca gagcaacctg  10140
ggcccagaac atacttacgg caatccaaca ggtgagaagc cttataggca atgaagagtt  10200
tctggactac atgccttcga tgaagagatt caggaaggag gaggagtcag agggagccat  10260
ttggtaaacg taggaagtga aaaagaggca aactgtcagg ccaccttaag ccacagtacg  10320
gaagaagctg tgcagcctgt gagccccgtc caaggacgtt aaaagaagaa gtcaggccca  10380
aaagccacgg tttgagcaaa ccgtgctgcc tgtggctccg tcgtggggac gtaaaacctg  10440
ggaggctgca aactgtggaa gctgtacgca cggtgtagca gactagcggt tagaggagac  10500
ccctcccatg acacaacgca gcagcggggc ccgagctctg agggaagctg tacctccttg  10560
caaaggacta gaggttagag gagacccccc gcaaataaaa acagcatatt gacgctggga  10620
gagaccagag atcctgctgt ctcctcagca tcattccagg cacagaacgc cagaaaatgg  10680
aatggtgctg ttgaatcaac aggttctggt accggtaggc atcgtggtgt cacgctcgtc  10740
gtttggtatg gcttcattca gctccggttc ccaacgatca aggcgagtta catgatcccc  10800
catgttgtgc aaaaaagcgg ttagctcctt cggtcctccg atcgttgtca gaagtaagtt  10860
ggccgcagtg ttatcactca tggttatggc agcactgcat aattctctta ctgtcatgcc  10920
atccgtaaga tgcttttctg tgactggtga gtactcaacc aagtcattct gagaatagtg  10980
tatgcggcga ccgagttgct cttgcccggc gtcaacacgg gataataccg cgccacatag  11040
cagaacttta aaagtgctca tcattggaaa acgttcttcg gggcgaaaac tctcaaggat  11100
cttaccgctg ttgagatcca gttcgatgta acccactcgt gcacccaact gatcttcagc  11160
atcttttact ttcaccagcg tttctgggtg agcaaaaaca ggaaggcaaa atgccgcaaa  11220
aaagggaata agggcgacac ggaaatgttg aatactcata ctcttccttt ttcaatatta  11280
ttgaagcatt tatcagggtt attgtctcat gagcggatac atatttgaat gtatttagaa  11340
aaataaacaa ataggggttc cgcgcacatt tccccgaaaa gtgccacctg acgtctaaga  11400
aaccattatt atcatgacat taacctataa aaataggcgt atcacgaggc cctttcgtct  11460
tcaagaattc tcatgtttga cagcttatca tcgataagct ttaatgcggt agtttatcac  11520
agttaaattg ctaacgcagt caggcaccgt gtatgaaatc taacaatgcg ctcatcgtca  11580
tcctcggcac cgtcaccctg gatgctgtag gcataggctt ggttatgccg gtactgccgg  11640
gcctcttgcg ggatatcgtc cattccgaca gcatcgccag tcactatggc gtgctgctgg  11700
cgctatatgc gttgatgcaa tttctatgcg cacccgttct cggagcactg tccgaccgct  11760
ttggccgccg cccagtcctg ctcgcttcgc tacttggagc cactatcgac tacgcgatca  11820
tggcgaccac acccgtcctg tggatcctct acgccggacg catcgtggcc ggcatcaccg  11880
gcgccacagg tgcggttgct ggcgcctata tcgccgacat caccgatggg gaagatcggg  11940
ctcgccactt cgggctcatg agcgcttgtt tcggcgtggg tatggtggca ggccccgtgg  12000
ccgggggact gttgggcgcc atctccttgc atgcaccatt ccttgcggcg gcggtgctca  12060
acggcctcaa cctactactg ggctgcttcc taatgcagga gtcgcataag ggagagcgtc  12120
gaccgatgcc cttgagagcc ttcaacccag tcagctcctt ccggtgggcg cggggcatga  12180
ctatcgtcgc cgcacttatg actgtcttct ttatcatgca actcgtagga caggtgccgg  12240
cagcgctctg ggtcattttc ggcgaggacc gctttcgctg gagcgcgacg atgatcggcc  12300
```

```
tgtcgcttgc ggtattcgga atcttgcacg ccctcgctca agccttcgtc actggtcccg  12360
ccaccaaacg tttcggcgag aagcaggcca ttatcgccgg catggcggcc gacgcgctgg  12420
gctacgtctt gctggcgttc gcgacgcgag gctggatggc cttccccatt atgattcttc  12480
tcgcttccgg cggcatcggg atgcccgcgt tgcaggccat gctgtccagg caggtagatg  12540
acgaccatca gggacagctt caaggatcgc tcgcggctct taccagccta acttcgatca  12600
ctggaccgct gatcgtcacg gcgatttatg ccgcctcggc gagcacatgg aacgggttgg  12660
catggattgt aggcgccgcc ctataccttg tctgcctccc cgcgttgcgt cgcggtgcat  12720
ggagccgggc cacctcgacc tgaatggaag ccggcggcac ctcgctaacg gattcaccac  12780
tccaagaatt ggagccaatc aattcttgcg gagaactgtg aatgcgcaaa ccaacccttg  12840
gcagaacata tccatcgcgt ccgccatctc cagcagccgc acgcggcgca tctcgggcag  12900
cgttgggtcc tggccacggg tgcgcatgat cgtgctcctg tcgttgagga cccggctagg  12960
ctggcggggt tgccttactg gttagcagaa tgaatcaccg atacgcgagc gaacgtgaag  13020
cgactgctgc tgcaaaacgt ctgcgacctg agcaacaaca tgaatggtct tcggtttccg  13080
tgtttcgtaa agtctggaaa cgcggaagtc agcgccctgc accattatgt tccggatctg  13140
catcgcagga tgctgctggc taccctgtgg aacacctaca tctgtattaa cgaagcgctg  13200
gcattgaccc tgagtgattt ttctctggtc ccgccgcatc cataccgcca gttgtttacc  13260
ctcacaacgt tccagtaacc gggcatgttc atcatcagta acccgtatcg tgagcatcct  13320
ctctcgtttc atcggtatca ttacccccat gaacagaaat cccccttaca cggaggcatc  13380
agtgaccaaa caggaaaaaa ccgcccttaa catggcccgc tttatcagaa gccagacatt  13440
aacgcttctg gagaaactca acgagctgga cgcggatgaa caggcagaca tctgtgaatc  13500
gcttcacgac cacgctgatg agctttaccg cagctgcctc gcgcgtttcg gtgatgacgg  13560
tgaaaacctc tgacacatgc agctcccgga gacggtcaca gcttgtctgt aagcggatgc  13620
cgggagcaga caagcccgtc agggcgcgtc agcgggtgtt ggcgggtgtc ggggcgcagc  13680
catgacccag tcacgtagcg atagcggagt gtatactggc ttaactatgc ggcatcagag  13740
cagattgtac tgagagtgca ccatatgcgg tgtgaaatac cgcacagatg cgtaaggaga  13800
aaataccgca tcaggcgctc ttccgcttcc tcgctcactg actcgctgcg ctcggtcgtt  13860
cggctgcggc gagcggtatc agctcactca aaggcggtaa tacggttatc cacagaatca  13920
ggggataacg caggaaagaa catgtgagca aaaggccagc aaaaggccag gaaccgtaaa  13980
aaggccgcgt tgctggcgtt tttccatagg ctccgccccc ctgacgagca tcacaaaaat  14040
cgacgctcaa gtcagaggtg gcgaaacccg acaggactat aaagatacca ggcgtttccc  14100
cctggaagct ccctcgtgcg ctctcctgtt ccgaccctgc cgcttaccgg atacctgtcc  14160
gcctttctcc cttcgggaag cgtggcgctt tctcatagct cacgctgtag gtatctcagt  14220
tcggtgtagg tcgttcgctc caagctgggc tgtgtgcacg aaccccccgt tcagcccgac  14280
cgctgcgcct tatccggtaa ctatcgtctt gagtccaacc cggtaagaca cgacttatcg  14340
ccactggcag cagccactgg taacaggatt agcagagcga ggtatgtagg cggtgctaca  14400
gagttcttga agtggtggcc taactacggc tacactagaa ggacagtatt tggtatctgc  14460
gctctgctga agccagttac cttcggaaaa agagttggta gctcttgatc cggcaaacaa  14520
accaccgctg gtagcggtgg tttttttgtt tgcaagcagc agattacgcg cagaaaaaaa  14580
ggatctcaag aagatccttt gatcttttct acggggtctg acgctcagtg gaacgaaaac  14640
tcacgttaag ggattttggt catgagatta tcaaaaagga tcttcaccta gatcctttta  14700
```

```
aattaaaaat gaagttttaa atcaatctaa agtatatatg agtaaacttg gtctgacagt  14760

taccaatgct taatcagtga ggcacctatc tcagcgatct gtctatttcg ttcatccata  14820

gttgcctgac tccccgtcgt gtagataact acgatacggg agggcttacc atctggcccc  14880

agtgctgcaa tgataccgcg agacccacgc tcaccggctc cagatttatc agcaataaac  14940

cagccagccg gaagggccga gcgcagaagt ggtcctgcaa ctttatccgc ctccatccag  15000

tctattaatt gttgccggga agctagagta agtagttcgc cagttaatag tttgcgcaac  15060

gttgttgcca ttgctgcaag atctggctag cgatgaccct gctgattggt tcgctgacca  15120

tttccgggcg cgccgattta ggtgacacta tag                               15153
```

<210> SEQ ID NO 49
<211> LENGTH: 3390
<212> TYPE: PRT
<213> ORGANISM: Dengue 3 (Sleman/78) virus

<400> SEQUENCE: 49

```
Met Asn Asn Gln Arg Lys Lys Thr Gly Lys Pro Ser Ile Asn Met Leu
 1               5                  10                  15

Lys Arg Val Arg Asn Arg Val Ser Thr Gly Ser Gln Leu Ala Lys Arg
            20                  25                  30

Phe Ser Arg Gly Leu Leu Asn Gly Gln Gly Pro Met Lys Leu Val Met
        35                  40                  45

Ala Phe Ile Ala Phe Leu Arg Phe Leu Ala Ile Pro Pro Thr Ala Gly
    50                  55                  60

Val Leu Ala Arg Trp Gly Thr Phe Lys Lys Ser Gly Ala Ile Lys Val
65                  70                  75                  80

Leu Arg Gly Phe Lys Lys Glu Ile Ser Asn Met Leu Ser Ile Ile Asn
                85                  90                  95

Arg Arg Lys Lys Thr Ser Leu Cys Leu Met Met Met Leu Pro Ala Thr
            100                 105                 110

Leu Ala Phe His Leu Thr Ser Arg Asp Gly Glu Pro Arg Met Ile Val
        115                 120                 125

Gly Lys Asn Glu Arg Gly Lys Ser Leu Leu Phe Lys Thr Ala Ser Gly
    130                 135                 140

Ile Asn Met Cys Thr Leu Ile Ala Met Asp Leu Gly Glu Met Cys Asp
145                 150                 155                 160

Asp Thr Val Thr Tyr Lys Cys Pro Leu Ile Thr Glu Val Glu Pro Glu
                165                 170                 175

Asp Ile Asp Cys Trp Cys Asn Leu Thr Ser Thr Trp Val Thr Tyr Gly
            180                 185                 190

Thr Cys Asn Gln Ala Gly Glu His Arg Arg Asp Lys Arg Ser Val Ala
        195                 200                 205

Leu Ala Pro His Val Gly Met Gly Leu Asp Thr Arg Thr Gln Thr Trp
    210                 215                 220

Met Ser Ala Glu Gly Ala Trp Arg Gln Val Glu Lys Val Glu Thr Trp
225                 230                 235                 240

Ala Phe Arg His Pro Gly Phe Thr Ile Leu Ala Leu Phe Leu Ala His
                245                 250                 255

Tyr Ile Gly Thr Ser Leu Thr Gln Lys Val Val Ile Phe Ile Leu Leu
            260                 265                 270

Met Leu Val Thr Pro Ser Met Thr Met Arg Cys Val Gly Val Gly Asn
        275                 280                 285
```

```
Arg Asp Phe Val Glu Gly Leu Ser Gly Ala Thr Trp Val Asp Val Val
    290                 295                 300

Leu Glu His Gly Gly Cys Val Thr Thr Met Ala Lys Asn Lys Pro Thr
305                 310                 315                 320

Leu Asp Ile Glu Leu Gln Lys Thr Glu Ala Thr Gln Leu Ala Thr Leu
                325                 330                 335

Arg Lys Leu Cys Ile Glu Gly Lys Ile Thr Asn Val Thr Thr Asp Ser
            340                 345                 350

Arg Cys Pro Thr Gln Gly Glu Ala Ile Leu Pro Glu Glu Gln Asp Gln
        355                 360                 365

Asn His Val Cys Lys His Thr Tyr Val Asp Arg Gly Trp Gly Asn Gly
    370                 375                 380

Cys Gly Leu Phe Gly Lys Gly Ser Leu Val Thr Cys Ala Lys Phe Gln
385                 390                 395                 400

Cys Leu Glu Ser Ile Glu Gly Lys Val Val Gln His Glu Asn Leu Lys
                405                 410                 415

Tyr Thr Val Ile Ile Thr Val His Thr Gly Asp Gln His Gln Val Gly
            420                 425                 430

Asn Glu Thr Gln Gly Val Thr Ala Glu Ile Thr Pro Gln Ala Ser Thr
        435                 440                 445

Val Glu Ala Ile Leu Pro Glu Tyr Gly Thr Leu Gly Leu Glu Cys Ser
    450                 455                 460

Pro Arg Thr Gly Leu Asp Phe Asn Glu Met Ile Leu Leu Thr Met Lys
465                 470                 475                 480

Asn Lys Ala Trp Met Val His Arg Gln Trp Phe Phe Asp Leu Pro Leu
                485                 490                 495

Pro Trp Thr Ser Gly Ala Thr Thr Glu Thr Pro Thr Trp Asn Lys Lys
            500                 505                 510

Glu Leu Leu Val Thr Phe Lys Asn Ala His Ala Lys Lys Gln Glu Val
        515                 520                 525

Val Val Leu Gly Ser Gln Glu Gly Ala Met His Thr Ala Leu Thr Gly
    530                 535                 540

Ala Thr Glu Ile Gln Thr Ser Gly Gly Thr Ser Ile Phe Ala Gly His
545                 550                 555                 560

Leu Lys Cys Arg Leu Lys Met Asp Lys Leu Glu Leu Lys Gly Met Ser
                565                 570                 575

Tyr Ala Met Cys Leu Asn Ala Phe Val Leu Lys Lys Glu Val Ser Glu
            580                 585                 590

Thr Gln His Gly Thr Ile Leu Ile Lys Val Glu Tyr Lys Gly Glu Asp
        595                 600                 605

Ala Pro Cys Lys Ile Pro Phe Ser Thr Glu Asp Gly Gln Gly Lys Ala
    610                 615                 620

His Asn Gly Arg Leu Ile Thr Ala Asn Pro Val Val Thr Lys Lys Glu
625                 630                 635                 640

Glu Pro Val Asn Ile Glu Ala Glu Pro Pro Phe Gly Glu Ser Asn Ile
                645                 650                 655

Val Ile Gly Ile Gly Asp Lys Ala Leu Lys Ile Asn Trp Tyr Lys Lys
            660                 665                 670

Gly Ser Ser Ile Gly Lys Met Phe Glu Ala Thr Ala Arg Gly Ala Arg
        675                 680                 685

Arg Met Ala Ile Leu Gly Asp Thr Ala Trp Asp Phe Gly Ser Val Gly
    690                 695                 700

Gly Val Leu Asn Ser Leu Gly Lys Met Val His Gln Ile Phe Gly Ser
```

```
705                 710                 715                 720

Ala Tyr Thr Ala Leu Phe Ser Gly Val Ser Trp Ile Met Lys Ile Gly
                725                 730                 735

Ile Gly Val Leu Leu Thr Trp Ile Gly Leu Asn Ser Lys Asn Thr Ser
            740                 745                 750

Met Ser Phe Ser Cys Ile Val Ile Gly Ile Ile Thr Leu Tyr Leu Gly
        755                 760                 765

Ala Val Val Gln Ala Asp Met Gly Cys Val Ile Asn Trp Lys Gly Lys
    770                 775                 780

Glu Leu Lys Cys Gly Ser Gly Ile Phe Val Thr Asn Glu Val His Thr
785                 790                 795                 800

Trp Thr Glu Gln Tyr Lys Phe Gln Ala Asp Ser Pro Lys Arg Leu Ala
                805                 810                 815

Thr Ala Ile Ala Gly Ala Trp Glu Asn Gly Val Cys Gly Ile Arg Ser
            820                 825                 830

Thr Thr Arg Met Glu Asn Leu Leu Trp Lys Gln Ile Ala Asn Glu Leu
        835                 840                 845

Asn Tyr Ile Leu Trp Glu Asn Asn Ile Lys Leu Thr Val Val Val Gly
    850                 855                 860

Asp Ile Ile Gly Val Leu Glu Gln Gly Lys Arg Thr Leu Thr Pro Gln
865                 870                 875                 880

Pro Met Glu Leu Lys Tyr Ser Trp Lys Thr Trp Gly Lys Ala Lys Ile
                885                 890                 895

Val Thr Ala Glu Thr Gln Asn Ser Ser Phe Ile Ile Asp Gly Pro Asn
            900                 905                 910

Thr Pro Glu Cys Pro Ser Ala Ser Arg Ala Trp Asn Val Trp Glu Val
        915                 920                 925

Glu Asp Tyr Gly Phe Gly Val Phe Thr Thr Asn Ile Trp Leu Lys Leu
    930                 935                 940

Arg Glu Met Tyr Thr Gln Leu Cys Asp His Arg Leu Met Ser Ala Ala
945                 950                 955                 960

Val Lys Asp Glu Arg Ala Val His Ala Asp Met Gly Tyr Trp Ile Glu
                965                 970                 975

Ser Gln Lys Asn Gly Ser Trp Lys Leu Glu Lys Ala Ser Leu Ile Glu
            980                 985                 990

Val Lys Thr Cys Thr Trp Pro Lys Ser His Thr Leu Trp Ser Asn Gly
        995                 1000                1005

Val Leu Glu Ser Asp Met Ile Ile Pro Lys Ser Leu Ala Gly Pro Ile
    1010                1015                1020

Ser Gln His Asn Tyr Arg Pro Gly Tyr His Thr Gln Thr Ala Gly Pro
1025                1030                1035                1040

Trp His Leu Gly Lys Leu Glu Leu Asp Phe Asn Tyr Cys Glu Gly Thr
                1045                1050                1055

Thr Val Val Ile Thr Glu Asn Cys Gly Thr Arg Gly Pro Ser Leu Arg
            1060                1065                1070

Thr Thr Thr Val Ser Gly Lys Leu Ile His Glu Trp Cys Cys Arg Ser
        1075                1080                1085

Cys Thr Leu Pro Pro Leu Arg Tyr Met Gly Glu Asp Gly Cys Trp Tyr
    1090                1095                1100

Gly Met Glu Ile Arg Pro Ile Asn Glu Lys Glu Glu Asn Met Val Lys
1105                1110                1115                1120

Ser Leu Val Ser Ala Gly Ser Gly Lys Val Asp Asn Phe Thr Met Gly
                1125                1130                1135
```

```
Val Leu Cys Leu Ala Ile Leu Phe Glu Glu Val Met Arg Gly Lys Phe
            1140                1145                1150

Gly Lys Lys His Met Ile Ala Gly Val Leu Phe Thr Phe Val Leu Leu
        1155                1160                1165

Leu Ser Gly Gln Ile Thr Trp Arg Asp Met Ala His Thr Leu Ile Met
    1170                1175                1180

Ile Gly Ser Asn Ala Ser Asp Arg Met Gly Met Gly Val Thr Tyr Leu
1185                1190                1195                1200

Ala Leu Ile Ala Thr Phe Lys Ile Gln Pro Phe Leu Ala Leu Gly Phe
                1205                1210                1215

Phe Leu Arg Lys Leu Thr Ser Arg Glu Asn Leu Leu Leu Gly Val Gly
            1220                1225                1230

Leu Ala Met Ala Thr Thr Leu Gln Leu Pro Glu Asp Ile Glu Gln Met
        1235                1240                1245

Ala Asn Gly Ile Ala Leu Gly Leu Met Ala Leu Lys Leu Ile Thr Gln
    1250                1255                1260

Phe Glu Thr Tyr Gln Leu Trp Thr Ala Leu Val Ser Leu Met Cys Ser
1265                1270                1275                1280

Asn Thr Ile Phe Thr Leu Thr Val Ala Trp Arg Thr Ala Thr Leu Ile
                1285                1290                1295

Leu Ala Gly Ile Ser Leu Leu Pro Val Cys Gln Ser Ser Ser Met Arg
            1300                1305                1310

Lys Thr Asp Trp Leu Pro Met Ala Val Ala Ala Met Gly Val Pro Pro
        1315                1320                1325

Leu Pro Leu Phe Ile Phe Ser Leu Lys Asp Thr Leu Lys Arg Arg Ser
    1330                1335                1340

Trp Pro Leu Asn Glu Gly Val Met Ala Val Gly Leu Val Ser Ile Leu
1345                1350                1355                1360

Ala Ser Ser Leu Leu Arg Asn Asp Val Pro Met Ala Gly Pro Leu Val
                1365                1370                1375

Ala Gly Gly Leu Leu Ile Ala Cys Tyr Val Ile Thr Gly Thr Ser Ala
            1380                1385                1390

Asp Leu Thr Val Glu Lys Ala Ala Asp Val Thr Trp Glu Glu Glu Ala
        1395                1400                1405

Glu Gln Thr Gly Val Ser His Asn Leu Met Ile Thr Val Asp Asp Asp
    1410                1415                1420

Gly Thr Met Arg Ile Lys Asp Asp Glu Thr Glu Asn Ile Leu Thr Val
1425                1430                1435                1440

Leu Leu Lys Thr Ala Leu Leu Ile Val Ser Gly Ile Phe Pro Tyr Ser
                1445                1450                1455

Ile Pro Ala Thr Leu Leu Val Trp His Thr Trp Gln Lys Gln Thr Gln
            1460                1465                1470

Arg Ser Gly Val Leu Trp Asp Val Pro Ser Pro Pro Glu Thr Gln Lys
        1475                1480                1485

Ala Glu Leu Glu Glu Gly Val Tyr Arg Ile Lys Gln Gln Gly Ile Phe
    1490                1495                1500

Gly Lys Thr Gln Val Gly Val Gly Val Gln Lys Glu Gly Val Phe His
1505                1510                1515                1520

Thr Met Trp His Val Thr Arg Gly Ala Val Leu Thr His Asn Gly Lys
                1525                1530                1535

Arg Leu Glu Pro Asn Trp Ala Ser Val Lys Lys Asp Leu Ile Ser Tyr
            1540                1545                1550
```

```
Gly Gly Gly Trp Lys Leu Ser Ala Gln Trp Gln Lys Gly Glu Glu Val
        1555                1560                1565

Gln Val Ile Ala Val Glu Pro Gly Lys Asn Pro Lys Asn Phe Gln Thr
    1570                1575                1580

Met Pro Gly Ile Phe Gln Thr Thr Thr Gly Glu Ile Gly Ala Ile Ala
1585                1590                1595                1600

Leu Asp Phe Lys Pro Gly Thr Ser Gly Ser Pro Ile Ile Asn Arg Glu
                1605                1610                1615

Gly Lys Val Leu Gly Leu Tyr Gly Asn Gly Val Val Thr Lys Asn Gly
            1620                1625                1630

Gly Tyr Val Ser Gly Ile Ala Gln Thr Asn Ala Glu Pro Asp Gly Pro
        1635                1640                1645

Thr Pro Glu Leu Glu Glu Glu Met Phe Lys Lys Arg Asn Leu Thr Ile
    1650                1655                1660

Met Asp Leu His Pro Gly Ser Gly Lys Thr Arg Lys Tyr Leu Pro Ala
1665                1670                1675                1680

Ile Val Arg Glu Ala Ile Lys Arg Arg Leu Arg Thr Leu Ile Leu Ala
                1685                1690                1695

Pro Thr Arg Val Val Ala Ala Glu Met Glu Glu Ala Leu Lys Gly Leu
            1700                1705                1710

Pro Ile Arg Tyr Gln Thr Thr Ala Thr Lys Ser Glu His Thr Gly Arg
        1715                1720                1725

Glu Ile Val Asp Leu Met Cys His Ala Thr Phe Thr Met Arg Leu Leu
    1730                1735                1740

Ser Pro Val Arg Val Pro Asn Tyr Asn Leu Ile Ile Met Asp Glu Ala
1745                1750                1755                1760

His Phe Thr Asp Pro Ala Ser Ile Ala Ala Arg Gly Tyr Ile Ser Thr
                1765                1770                1775

Arg Val Gly Met Gly Glu Ala Ala Ala Ile Phe Met Thr Ala Thr Pro
            1780                1785                1790

Pro Gly Thr Ala Asp Ala Phe Pro Gln Ser Asn Ala Pro Ile Gln Asp
        1795                1800                1805

Glu Glu Arg Asp Ile Pro Glu Arg Ser Trp Asn Ser Gly Asn Glu Trp
    1810                1815                1820

Ile Thr Asp Phe Ala Gly Lys Thr Val Trp Phe Val Pro Ser Ile Lys
1825                1830                1835                1840

Ala Gly Asn Asp Ile Ala Asn Cys Leu Arg Lys Asn Gly Lys Lys Val
                1845                1850                1855

Ile Gln Leu Ser Arg Lys Thr Phe Asp Thr Glu Tyr Gln Lys Thr Lys
            1860                1865                1870

Leu Asn Asp Trp Asp Phe Val Val Thr Thr Asp Ile Ser Glu Met Gly
        1875                1880                1885

Ala Asn Phe Lys Ala Asp Arg Val Ile Asp Pro Arg Arg Cys Leu Lys
    1890                1895                1900

Pro Val Ile Leu Thr Asp Gly Pro Glu Arg Val Ile Leu Ala Gly Pro
1905                1910                1915                1920

Met Pro Val Thr Val Ala Ser Ala Ala Gln Arg Arg Gly Arg Val Gly
                1925                1930                1935

Arg Asn Pro Gln Lys Glu Asn Asp Gln Tyr Ile Phe Met Gly Gln Pro
            1940                1945                1950

Leu Asn Asn Asp Glu Asp His Ala His Trp Thr Glu Ala Lys Met Leu
        1955                1960                1965

Leu Asp Asn Ile Asn Thr Pro Glu Gly Ile Ile Pro Ala Leu Phe Glu
```

```
    1970                1975                1980

Pro Glu Arg Glu Lys Ser Ala Ala Ile Asp Gly Glu Tyr Arg Leu Lys
1985                1990                1995                2000

Gly Glu Ser Arg Lys Thr Phe Val Glu Leu Met Arg Arg Gly Asp Leu
                2005                2010                2015

Pro Val Trp Leu Ala His Lys Val Ala Ser Glu Gly Ile Lys Tyr Thr
            2020                2025                2030

Asp Arg Lys Trp Cys Phe Asp Gly Glu Arg Asn Asn Gln Ile Leu Glu
        2035                2040                2045

Glu Asn Met Asp Val Glu Ile Trp Thr Lys Glu Gly Glu Lys Lys Lys
    2050                2055                2060

Leu Arg Pro Arg Trp Leu Asp Ala Arg Thr Tyr Ser Asp Pro Leu Ala
2065                2070                2075                2080

Leu Lys Glu Phe Lys Asp Phe Ala Ala Gly Arg Lys Ser Ile Ala Leu
                2085                2090                2095

Asp Leu Val Thr Glu Ile Gly Arg Val Pro Ser His Leu Ala His Arg
            2100                2105                2110

Thr Arg Asn Ala Leu Asp Asn Leu Val Met Leu His Thr Ser Glu His
        2115                2120                2125

Gly Gly Arg Ala Tyr Arg His Ala Val Glu Glu Leu Pro Glu Thr Met
    2130                2135                2140

Glu Thr Leu Leu Leu Leu Gly Leu Met Ile Leu Leu Thr Gly Gly Ala
2145                2150                2155                2160

Met Leu Phe Leu Ile Ser Gly Lys Gly Ile Gly Lys Thr Ser Ile Gly
                2165                2170                2175

Leu Ile Cys Val Ala Ala Ser Ser Gly Met Leu Trp Met Ala Asp Val
            2180                2185                2190

Pro Leu Gln Trp Ile Ala Ser Ala Ile Val Leu Glu Phe Phe Met Met
        2195                2200                2205

Val Leu Leu Ile Pro Glu Pro Glu Lys Gln Arg Thr Pro Gln Asp Asn
    2210                2215                2220

Gln Leu Ala Tyr Val Val Ile Gly Ile Leu Thr Leu Ala Ala Ile Val
2225                2230                2235                2240

Ala Ala Asn Glu Met Gly Leu Leu Glu Thr Thr Lys Arg Asp Leu Gly
                2245                2250                2255

Met Ser Lys Glu Pro Gly Val Val Ser Pro Thr Ser Tyr Leu Asp Val
            2260                2265                2270

Asp Leu His Pro Ala Ser Ala Trp Thr Leu Tyr Ala Val Ala Thr Thr
        2275                2280                2285

Val Ile Thr Pro Met Leu Arg His Thr Ile Glu Asn Ser Thr Ala Asn
    2290                2295                2300

Val Ser Leu Ala Ala Ile Ala Asn Gln Ala Val Val Leu Met Gly Leu
2305                2310                2315                2320

Asp Lys Gly Trp Pro Ile Ser Lys Met Asp Leu Gly Val Pro Leu Leu
                2325                2330                2335

Ala Leu Gly Cys Tyr Ser Gln Val Asn Pro Leu Thr Leu Thr Ala Ala
            2340                2345                2350

Val Leu Leu Leu Val Thr His Tyr Ala Ile Ile Gly Pro Gly Leu Gln
        2355                2360                2365

Ala Lys Ala Thr Arg Glu Ala Gln Lys Arg Thr Ala Ala Gly Ile Met
    2370                2375                2380

Lys Asn Pro Thr Val Asp Gly Ile Met Thr Ile Asp Leu Asp Pro Val
2385                2390                2395                2400
```

```
Ile Tyr Asp Ser Lys Phe Glu Lys Gln Leu Gly Gln Val Met Leu Leu
                2405                2410                2415

Val Leu Cys Ala Val Gln Leu Leu Leu Met Arg Thr Ser Trp Ala Phe
            2420                2425                2430

Cys Glu Ala Leu Thr Leu Ala Thr Gly Pro Ile Thr Thr Leu Trp Glu
        2435                2440                2445

Gly Ser Pro Gly Lys Phe Trp Asn Thr Thr Ile Ala Val Ser Met Ala
    2450                2455                2460

Asn Ile Phe Arg Gly Ser Tyr Leu Ala Gly Ala Gly Leu Ala Phe Ser
2465                2470                2475                2480

Ile Met Lys Ser Val Gly Thr Gly Lys Arg Gly Thr Gly Ser Gln Gly
                2485                2490                2495

Glu Thr Leu Gly Glu Lys Trp Lys Lys Lys Leu Asn Gln Leu Pro Arg
            2500                2505                2510

Lys Glu Phe Asp Leu Tyr Lys Lys Ser Gly Ile Thr Glu Val Asp Arg
        2515                2520                2525

Thr Glu Ala Lys Glu Gly Leu Lys Arg Gly Glu Ile Thr His His Ala
    2530                2535                2540

Val Ser Arg Gly Ser Ala Lys Leu Gln Trp Phe Val Glu Arg Asn Met
2545                2550                2555                2560

Val Ile Pro Glu Gly Arg Val Ile Asp Leu Gly Cys Gly Arg Gly Gly
                2565                2570                2575

Trp Ser Tyr Tyr Cys Ala Gly Leu Lys Lys Val Thr Glu Val Arg Gly
            2580                2585                2590

Tyr Thr Lys Gly Gly Pro Gly His Glu Glu Pro Val Pro Met Ser Thr
        2595                2600                2605

Tyr Gly Trp Asn Ile Val Lys Leu Met Ser Gly Lys Asp Val Phe Tyr
    2610                2615                2620

Leu Pro Pro Glu Lys Cys Asp Thr Leu Leu Cys Asp Ile Gly Glu Ser
2625                2630                2635                2640

Ser Pro Ser Pro Thr Val Glu Glu Ser Arg Thr Ile Arg Val Leu Lys
                2645                2650                2655

Met Val Glu Pro Trp Leu Lys Asn Asn Gln Phe Cys Ile Lys Val Leu
            2660                2665                2670

Asn Pro Tyr Met Pro Thr Val Ile Glu His Leu Glu Arg Leu Gln Arg
        2675                2680                2685

Lys His Gly Gly Met Leu Val Arg Asn Pro Leu Ser Arg Asn Ser Thr
    2690                2695                2700

His Glu Met Tyr Trp Ile Ser Asn Gly Thr Gly Asn Ile Val Ser Ser
2705                2710                2715                2720

Val Asn Met Val Ser Arg Leu Leu Leu Asn Arg Phe Thr Met Thr His
                2725                2730                2735

Arg Arg Pro Thr Ile Glu Lys Asp Val Asp Leu Gly Ala Gly Thr Arg
            2740                2745                2750

His Val Asn Ala Glu Pro Glu Thr Pro Asn Met Asp Val Ile Gly Glu
        2755                2760                2765

Arg Ile Arg Arg Ile Lys Glu Glu His Ser Ser Thr Trp His Tyr Asp
    2770                2775                2780

Asp Glu Asn Pro Tyr Lys Thr Trp Ala Tyr His Gly Ser Tyr Glu Val
2785                2790                2795                2800

Lys Ala Thr Gly Ser Ala Ser Ser Met Ile Asn Gly Val Val Lys Leu
                2805                2810                2815
```

```
Leu Thr Lys Pro Trp Asp Val Val Pro Met Val Thr Gln Met Ala Met
            2820                2825                2830

Thr Asp Thr Thr Pro Phe Gly Gln Gln Arg Val Phe Lys Glu Lys Val
        2835                2840                2845

Asp Thr Arg Thr Pro Arg Pro Met Pro Gly Thr Arg Lys Val Met Glu
    2850                2855                2860

Ile Thr Ala Glu Trp Leu Trp Arg Thr Leu Gly Arg Asn Lys Arg Pro
2865                2870                2875                2880

Arg Leu Cys Thr Arg Glu Glu Phe Thr Lys Lys Val Arg Thr Asn Ala
                2885                2890                2895

Ala Met Gly Ala Val Phe Thr Glu Glu Asn Gln Trp Asp Ser Ala Arg
            2900                2905                2910

Ala Ala Val Glu Asp Glu Glu Phe Trp Lys Leu Val Asp Arg Glu Arg
        2915                2920                2925

Glu Leu His Lys Leu Gly Lys Cys Gly Ser Cys Val Tyr Asn Met Met
    2930                2935                2940

Gly Lys Arg Glu Lys Lys Leu Gly Glu Phe Gly Lys Ala Lys Gly Ser
2945                2950                2955                2960

Arg Ala Ile Trp Tyr Met Trp Leu Gly Ala Arg Tyr Leu Glu Phe Glu
                2965                2970                2975

Ala Leu Gly Phe Leu Asn Glu Asp His Trp Phe Ser Arg Glu Asn Ser
            2980                2985                2990

Tyr Ser Gly Val Glu Gly Glu Gly Leu His Lys Leu Gly Tyr Ile Leu
        2995                3000                3005

Arg Asp Ile Ser Lys Ile Pro Gly Gly Ala Met Tyr Ala Asp Asp Thr
    3010                3015                3020

Ala Gly Trp Asp Thr Arg Ile Thr Glu Asp Asp Leu His Asn Glu Glu
3025                3030                3035                3040

Lys Ile Thr Gln Gln Met Asp Pro Glu His Arg Gln Leu Ala Asn Ala
                3045                3050                3055

Ile Phe Lys Leu Thr Tyr Gln Asn Lys Val Val Lys Val Gln Arg Pro
            3060                3065                3070

Thr Pro Lys Gly Thr Val Met Asp Ile Ile Ser Arg Lys Asp Gln Arg
        3075                3080                3085

Gly Ser Gly Gln Val Gly Thr Tyr Gly Leu Asn Thr Phe Thr Asn Met
    3090                3095                3100

Glu Ala Gln Leu Ile Arg Gln Met Glu Gly Glu Gly Val Leu Ser Lys
3105                3110                3115                3120

Ala Asp Leu Glu Asn Pro His Leu Leu Glu Lys Lys Val Thr Gln Trp
                3125                3130                3135

Leu Glu Thr Lys Gly Val Glu Arg Leu Lys Arg Met Ala Ile Ser Gly
            3140                3145                3150

Asp Asp Cys Val Val Lys Pro Ile Asp Asp Arg Phe Ala Asn Ala Leu
        3155                3160                3165

Leu Ala Leu Asn Asp Met Gly Lys Val Arg Lys Asp Ile Pro Gln Trp
    3170                3175                3180

Gln Pro Ser Lys Gly Trp His Asp Trp Gln Gln Val Pro Phe Cys Ser
3185                3190                3195                3200

His His Phe His Glu Leu Ile Met Lys Asp Gly Arg Lys Leu Val Val
                3205                3210                3215

Pro Cys Arg Pro Gln Asp Glu Leu Ile Gly Arg Ala Arg Ile Ser Gln
            3220                3225                3230

Gly Ala Gly Trp Ser Leu Arg Glu Thr Ala Cys Leu Gly Lys Ala Tyr
```

```
        3235                3240                3245

Ala Gln Met Trp Thr Leu Met Tyr Phe His Arg Arg Asp Leu Arg Leu
    3250                3255                3260

Ala Ser Asn Ala Ile Cys Ser Ala Val Pro Val His Trp Val Pro Thr
3265                3270                3275                3280

Ser Arg Thr Thr Trp Ser Ile His Ala His His Gln Trp Met Thr Thr
                3285                3290                3295

Glu Asp Met Leu Thr Val Trp Asn Arg Val Trp Ile Glu Asp Asn Pro
            3300                3305                3310

Trp Met Glu Asp Lys Thr Pro Val Lys Thr Trp Glu Asp Val Pro Tyr
        3315                3320                3325

Leu Gly Lys Arg Glu Asp Gln Trp Cys Gly Ser Leu Ile Gly Leu Thr
    3330                3335                3340

Ser Arg Ala Thr Trp Ala Gln Asn Ile Leu Thr Ala Ile Gln Gln Val
3345                3350                3355                3360

Arg Ser Leu Ile Gly Asn Glu Glu Phe Leu Asp Tyr Met Pro Ser Met
                3365                3370                3375

Lys Arg Phe Arg Lys Glu Glu Glu Ser Glu Gly Ala Ile Trp
            3380                3385                3390


<210> SEQ ID NO 50
<211> LENGTH: 2426
<212> TYPE: DNA
<213> ORGANISM: Artificial Sequence
<220> FEATURE:
<223> OTHER INFORMATION: Dengue 1 CME chimeric region

<400> SEQUENCE: 50

agttgttagt ctgtgtggac cgacaaggac agttccaaat cggaagcttg cttaacacag     60

ttctaacagt ttgtttgaat agagagcaga tctctggaaa aatgaacaac caacggaaaa    120

agacgggtcg accgtctttc aatatgctga aacgcgcgag aaaccgcgtg tcaactggtt    180

cacagttggc gaagagattc tcaaaaggat tgctttcagg ccaaggaccc atgaaattgg    240

tgatggcttt catagcattt ctaagatttc tagccatacc cccaacagca ggaattttgg    300

ctagatggag ctcattcaag aagaatggag cgatcaaagt gttacggggt ttcaaaaaag    360

agatctcaag catgttgaac attatgaaca ggaggaaaaa atctgtgacc atgctcctca    420

tgctgctgcc cacagccctg gcgttccatt tgaccacacg agggggagag ccacacatga    480

tagttagtaa gcaggaaaga ggaaagtcac tgttgtttaa gacctctgca ggcatcaata    540

tgtgcactct cattgcgatg gatttgggag agttatgcga ggacacaatg acctacaaat    600

gcccccggat cactgaggcg gaaccagatg acgttgactg ctggtgcaat gccacagaca    660

catgggtgac ctatgggacg tgttctcaaa ccggcgaaca ccgacgagac aaacgttccg    720

tggcactggc cccacacgtg ggacttggtc tagaaacaag aaccgaaaca tggatgtcct    780

ctgaaggtgc ctggaaacaa gtacaaaaag tggagacttg ggctttgaga cacccaggat    840

tcacggtgac agccctttt ttagcacatg ccataggaac atccattact cagaaaggga    900

tcattttcat tctgctgatg ctagtaacac catcaatggc catgcgatgt gtgggaatag    960

gcaacagaga cttcgttgaa ggactgtcag gagcaacgtg ggtggacgtg gtattggagc   1020

atggaagctg cgtcaccacc atggcaaaag ataaaccaac attggacatt gaactcttga   1080

agacggaggt cacaaaccct gccgtcttgc gcaaactgtg cattgaagct aaaatatcaa   1140

acaccaccac cgattcaagg tgtccaacac aaggagaggc tacactggtg gaagaacagg   1200
```

```
actcgaactt tgtgtgtcga cgaacgtttg tggacagagg ctggggtaat ggctgcggac   1260

tatttggaaa aggaagccta ctgacgtgtg ctaagttcaa gtgtgtgaca aaactagaag   1320

gaaagatagt tcaatatgaa aacttaaaat attcagtgat agtcactgtc cacactgggg   1380

accagcacca ggtgggaaac gagactacag aacatggaac aattgcaacc ataacacctc   1440

aagctcctac gtcggaaata cagctgactg actacggagc cctcacattg gactgctcgc   1500

ctagaacagg gctggacttt aatgagatgg ttctattgac aatgaaagaa aaatcatggc   1560

ttgtccacaa acaatggttt ctagacttac cactgccttg gacttcagga gcttcaacat   1620

ctcaagagac ttggaacaga caagatttgc tggtcacatt caagacagct catgcaaaga   1680

aacaggaagt agtcgtactg ggatcacagg aaggagcaat gcacactgcg ttgactgggg   1740

cgacagaaat ccagacgtca ggaacgacaa caatctttgc aggacacctg aaatgcagac   1800

taaaaatgga taaactgact ttaaaaggga tgtcatatgt aatgtgcaca ggctcattta   1860

agctagagaa ggaagtggct gagacccagc atggaactgt tttagtgcag gttaaatacg   1920

aaggaacaga tgcgccatgc aagatccctt tttcggccca agatgagaaa ggagtgaccc   1980

agaatgggag attgataaca gccaacccca tagtcactga caaagaaaaa ccagtcaaca   2040

ttgagacaga accacctttt ggtgagagct acatcgtggt aggggcaggt gaaaaagctt   2100

tgaaactgag ctggttcaag aaagggagca gcatagggaa aatgttcgaa gcaactgccc   2160

gaggagcgcg aaggatggct atcctgggag acaccgcatg ggactttggc tctataggag   2220

gagtgttcac atcagtggga aaattggtac accaggtttt tggagccgca tatggggttc   2280

tgttcagcgg tgtttcttgg accatgaaaa taggaatagg gattctgctg acatggctag   2340

gattaaactc gaggaacact tcaatggcta tgacgtgcat agctgttgga ggaatcactc   2400

tgtttctggg cttcacagtt caagca                                        2426
```

```
<210> SEQ ID NO 51
<211> LENGTH: 775
<212> TYPE: PRT
<213> ORGANISM: Artificial Sequence
<220> FEATURE:
<223> OTHER INFORMATION: Dengue 1 CME chimeric region

<400> SEQUENCE: 51

Met Asn Asn Gln Arg Lys Lys Thr Gly Arg Pro Ser Phe Asn Met Leu
 1               5                  10                  15

Lys Arg Ala Arg Asn Arg Val Ser Thr Gly Ser Gln Leu Ala Lys Arg
            20                  25                  30

Phe Ser Lys Gly Leu Leu Ser Gly Gln Gly Pro Met Lys Leu Val Met
        35                  40                  45

Ala Phe Ile Ala Phe Leu Arg Phe Leu Ala Ile Pro Pro Thr Ala Gly
    50                  55                  60

Ile Leu Ala Arg Trp Ser Ser Phe Lys Lys Asn Gly Ala Ile Lys Val
65                  70                  75                  80

Leu Arg Gly Phe Lys Lys Glu Ile Ser Ser Met Leu Asn Ile Met Asn
                85                  90                  95

Arg Arg Lys Lys Ser Val Thr Met Leu Leu Met Leu Leu Pro Thr Ala
            100                 105                 110

Leu Ala Phe His Leu Thr Thr Arg Gly Gly Glu Pro His Met Ile Val
        115                 120                 125

Ser Lys Gln Glu Arg Gly Lys Ser Leu Leu Phe Lys Thr Ser Ala Gly
    130                 135                 140
```

```
Ile Asn Met Cys Thr Leu Ile Ala Met Asp Leu Gly Glu Leu Cys Glu
145                 150                 155                 160

Asp Thr Met Thr Tyr Lys Cys Pro Arg Ile Thr Glu Ala Glu Pro Asp
                165                 170                 175

Asp Val Asp Cys Trp Cys Asn Ala Thr Asp Thr Trp Val Thr Tyr Gly
            180                 185                 190

Thr Cys Ser Gln Thr Gly Glu His Arg Arg Asp Lys Arg Ser Val Ala
        195                 200                 205

Leu Ala Pro His Val Gly Leu Gly Leu Glu Thr Arg Thr Glu Thr Trp
    210                 215                 220

Met Ser Ser Glu Gly Ala Trp Lys Gln Val Gln Lys Val Glu Thr Trp
225                 230                 235                 240

Ala Leu Arg His Pro Gly Phe Thr Val Thr Ala Leu Phe Leu Ala His
                245                 250                 255

Ala Ile Gly Thr Ser Ile Thr Gln Lys Gly Ile Ile Phe Ile Leu Leu
            260                 265                 270

Met Leu Val Thr Pro Ser Met Ala Met Arg Cys Val Gly Ile Gly Asn
        275                 280                 285

Arg Asp Phe Val Glu Gly Leu Ser Gly Ala Thr Trp Val Asp Val Val
    290                 295                 300

Leu Glu His Gly Ser Cys Val Thr Thr Met Ala Lys Asp Lys Pro Thr
305                 310                 315                 320

Leu Asp Ile Glu Leu Leu Lys Thr Glu Val Thr Asn Pro Ala Val Leu
                325                 330                 335

Arg Lys Leu Cys Ile Glu Ala Lys Ile Ser Asn Thr Thr Thr Asp Ser
            340                 345                 350

Arg Cys Pro Thr Gln Gly Glu Ala Thr Leu Val Glu Glu Gln Asp Ser
        355                 360                 365

Asn Phe Val Cys Arg Arg Thr Phe Val Asp Arg Gly Trp Gly Asn Gly
    370                 375                 380

Cys Gly Leu Phe Gly Lys Gly Ser Leu Leu Thr Cys Ala Lys Phe Lys
385                 390                 395                 400

Cys Val Thr Lys Leu Glu Gly Lys Ile Val Gln Tyr Glu Asn Leu Lys
                405                 410                 415

Tyr Ser Val Ile Val Thr Val His Thr Gly Asp Gln His Gln Val Gly
            420                 425                 430

Asn Glu Thr Thr Glu His Gly Thr Ile Ala Thr Ile Thr Pro Gln Ala
        435                 440                 445

Pro Thr Ser Glu Ile Gln Leu Thr Asp Tyr Gly Ala Leu Thr Leu Asp
    450                 455                 460

Cys Ser Pro Arg Thr Gly Leu Asp Phe Asn Glu Met Val Leu Leu Thr
465                 470                 475                 480

Met Lys Glu Lys Ser Trp Leu Val His Lys Gln Trp Phe Leu Asp Leu
                485                 490                 495

Pro Leu Pro Trp Thr Ser Gly Ala Ser Thr Ser Gln Glu Thr Trp Asn
            500                 505                 510

Arg Gln Asp Leu Leu Val Thr Phe Lys Thr Ala His Ala Lys Lys Gln
        515                 520                 525

Glu Val Val Val Leu Gly Ser Gln Glu Gly Ala Met His Thr Ala Leu
    530                 535                 540

Thr Gly Ala Thr Glu Ile Gln Thr Ser Gly Thr Thr Thr Ile Phe Ala
545                 550                 555                 560

Gly His Leu Lys Cys Arg Leu Lys Met Asp Lys Leu Thr Leu Lys Gly
```

```
                565                 570                 575

Met Ser Tyr Val Met Cys Thr Gly Ser Phe Lys Leu Glu Lys Glu Val
            580                 585                 590

Ala Glu Thr Gln His Gly Thr Val Leu Val Gln Val Lys Tyr Glu Gly
        595                 600                 605

Thr Asp Ala Pro Cys Lys Ile Pro Phe Ser Ala Gln Asp Glu Lys Gly
    610                 615                 620

Val Thr Gln Asn Gly Arg Leu Ile Thr Ala Asn Pro Ile Val Thr Asp
625                 630                 635                 640

Lys Glu Lys Pro Val Asn Ile Glu Thr Glu Pro Pro Phe Gly Glu Ser
                645                 650                 655

Tyr Ile Val Val Gly Ala Gly Glu Lys Ala Leu Lys Leu Ser Trp Phe
            660                 665                 670

Lys Lys Gly Ser Ser Ile Gly Lys Met Phe Glu Ala Thr Ala Arg Gly
        675                 680                 685

Ala Arg Arg Met Ala Ile Leu Gly Asp Thr Ala Trp Asp Phe Gly Ser
    690                 695                 700

Ile Gly Gly Val Phe Thr Ser Val Gly Lys Leu Val His Gln Val Phe
705                 710                 715                 720

Gly Ala Ala Tyr Gly Val Leu Phe Ser Gly Val Ser Trp Thr Met Lys
                725                 730                 735

Ile Gly Ile Gly Ile Leu Leu Thr Trp Leu Gly Leu Asn Ser Arg Asn
            740                 745                 750

Thr Ser Met Ala Met Thr Cys Ile Ala Val Gly Gly Ile Thr Leu Phe
        755                 760                 765

Leu Gly Phe Thr Val Gln Ala
    770                 775


<210> SEQ ID NO 52
<211> LENGTH: 2423
<212> TYPE: DNA
<213> ORGANISM: Artificial Sequence
<220> FEATURE:
<223> OTHER INFORMATION: Dengue 1 ME chimeric region

<400> SEQUENCE: 52

agttgttagt ctgtgtggac cgacaaggac agttccaaat cggaagcttg cttaacacag     60

ttctaacagt ttgtttgaat agagagcaga tctctggaaa aatgaaccaa cgaaaaaagg    120

tggttagacc acctttcaat atgctgaaac gcgagagaaa ccgcgtatca acccctcaag    180

ggttggtgaa gagattctca accggacttt tttctgggaa aggaccctta cggatggtgc    240

tagcattcat cacgtttttg cgagtccttt ccatcccacc aacagcaggg attctgaaga    300

gatggggaca gttgaagaaa aataaggcca tcaagatact gattggattc aggaaggaga    360

taggccgcat gctgaacatc ttgaacggga gaaaaaggtc tgcagccatg ctcctcatgc    420

tgctgcccac agccctggcg ttccatttga ccacacgagg gggagagcca cacatgatag    480

ttagtaagca ggaaagagga aagtcactgt tgtttaagac ctctgcaggc atcaatatgt    540

gcactctcat tgcgatggat ttgggagagt tatgcgagga cacaatgacc tacaaatgcc    600

cccggatcac tgaggcggaa ccagatgacg ttgactgctg gtgcaatgcc acagacacat    660

gggtgaccta tgggacgtgt tctcaaaccg gcgaacaccg acgagacaaa cgttccgtgg    720

cactggcccc acacgtggga cttggtctag aaacaagaac cgaaacatgg atgtcctctg    780

aaggtgcctg gaaacaagta caaaaagtgg agacttgggc tttgagacac ccaggattca    840
```

```
cggtgacagc cctttttta gcacatgcca taggaacatc cattactcag aaagggatca    900

ttttcattct gctgatgcta gtaacaccat caatggccat gcgatgtgtg ggaataggca    960

acagagactt cgttgaagga ctgtcaggag caacgtgggt ggacgtggta ttggagcatg   1020

gaagctgcgt caccaccatg gcaaaagata aaccaacatt ggacattgaa ctcttgaaga   1080

cggaggtcac aaaccctgcc gtcttgcgca aactgtgcat tgaagctaaa atatcaaaca   1140

ccaccaccga ttcaaggtgt ccaacacaag gagaggctac actggtggaa gaacaggact   1200

cgaactttgt gtgtcgacga acgtttgtgg acagaggctg gggtaatggc tgcggactat   1260

ttggaaaagg aagcctactg acgtgtgcta agttcaagtg tgtgacaaaa ctagaaggaa   1320

agatagttca atatgaaaac ttaaaatatt cagtgatagt cactgtccac actggggacc   1380

agcaccaggt gggaaacgag actacagaac atggaacaat tgcaaccata acacctcaag   1440

ctcctacgtc ggaaatacag ctgactgact acggagccct cacattggac tgctcgccta   1500

gaacagggct ggactttaat gagatggttc tattgacaat gaaagaaaaa tcatggcttg   1560

tccacaaaca atggtttcta gacttaccac tgccttggac ttcaggagct tcaacatctc   1620

aagagacttg gaacagacaa gatttgctgg tcacattcaa gacagctcat gcaaagaaac   1680

aggaagtagt cgtactggga tcacaggaag gagcaatgca cactgcgttg actggggcga   1740

cagaaatcca gacgtcagga acgacaacaa tctttgcagg acacctgaaa tgcagactaa   1800

aaatggataa actgacttta aaagggatgt catatgtaat gtgcacaggc tcatttaagc   1860

tagagaagga agtggctgag acccagcatg gaactgtttt agtgcaggtt aaatacgaag   1920

gaacagatgc gccatgcaag atccctttt cggcccaaga tgagaaagga gtgacccaga   1980

atgggagatt gataacagcc aaccccatag tcactgacaa agaaaaacca gtcaacattg   2040

agacagaacc acctttggt gagagctaca tcgtggtagg ggcaggtgaa aaagctttga   2100

aactgagctg gttcaagaaa gggagcagca tagggaaaat gttcgaagca actgcccgag   2160

gagcgcgaag gatggctatc ctgggagaca ccgcatggga ctttggctct ataggaggag   2220

tgttcacatc agtgggaaaa ttggtacacc aggtttttgg agccgcatat ggggttctgt   2280

tcagcggtgt ttcttggacc atgaaaatag gaatagggat tctgctgaca tggctaggat   2340

taaactcgag gaacacttca atggctatga cgtgcatagc tgttggagga atcactctgt   2400

ttctgggctt cacagttcaa gca                                           2423
```

<210> SEQ ID NO 53
<211> LENGTH: 774
<212> TYPE: PRT
<213> ORGANISM: Artificial Sequence
<220> FEATURE:
<223> OTHER INFORMATION: Dengue 1 ME chimeric region

<400> SEQUENCE: 53

```
Met Asn Gln Arg Lys Lys Val Val Arg Pro Pro Phe Asn Met Leu Lys
 1               5                  10                  15

Arg Glu Arg Asn Arg Val Ser Thr Pro Gln Gly Leu Val Lys Arg Phe
            20                  25                  30

Ser Thr Gly Leu Phe Ser Gly Lys Gly Pro Leu Arg Met Val Leu Ala
        35                  40                  45

Phe Ile Thr Phe Leu Arg Val Leu Ser Ile Pro Pro Thr Ala Gly Ile
    50                  55                  60

Leu Lys Arg Trp Gly Gln Leu Lys Lys Asn Lys Ala Ile Lys Ile Leu
65                  70                  75                  80
```

```
Ile Gly Phe Arg Lys Glu Ile Gly Arg Met Leu Asn Ile Leu Asn Gly
                85                  90                  95

Arg Lys Arg Ser Ala Ala Met Leu Leu Met Leu Leu Pro Thr Ala Leu
            100                 105                 110

Ala Phe His Leu Thr Thr Arg Gly Gly Glu Pro His Met Ile Val Ser
        115                 120                 125

Lys Gln Glu Arg Gly Lys Ser Leu Leu Phe Lys Thr Ser Ala Gly Ile
    130                 135                 140

Asn Met Cys Thr Leu Ile Ala Met Asp Leu Gly Glu Leu Cys Glu Asp
145                 150                 155                 160

Thr Met Thr Tyr Lys Cys Pro Arg Ile Thr Glu Ala Glu Pro Asp Asp
                165                 170                 175

Val Asp Cys Trp Cys Asn Ala Thr Asp Thr Trp Val Thr Tyr Gly Thr
            180                 185                 190

Cys Ser Gln Thr Gly Glu His Arg Arg Asp Lys Arg Ser Val Ala Leu
        195                 200                 205

Ala Pro His Val Gly Leu Gly Leu Glu Thr Arg Thr Glu Thr Trp Met
    210                 215                 220

Ser Ser Glu Gly Ala Trp Lys Gln Val Gln Lys Val Glu Thr Trp Ala
225                 230                 235                 240

Leu Arg His Pro Gly Phe Thr Val Thr Ala Leu Phe Leu Ala His Ala
                245                 250                 255

Ile Gly Thr Ser Ile Thr Gln Lys Gly Ile Ile Phe Ile Leu Leu Met
            260                 265                 270

Leu Val Thr Pro Ser Met Ala Met Arg Cys Val Gly Ile Gly Asn Arg
        275                 280                 285

Asp Phe Val Glu Gly Leu Ser Gly Ala Thr Trp Val Asp Val Val Leu
    290                 295                 300

Glu His Gly Ser Cys Val Thr Thr Met Ala Lys Asp Lys Pro Thr Leu
305                 310                 315                 320

Asp Ile Glu Leu Leu Lys Thr Glu Val Thr Asn Pro Ala Val Leu Arg
                325                 330                 335

Lys Leu Cys Ile Glu Ala Lys Ile Ser Asn Thr Thr Thr Asp Ser Arg
            340                 345                 350

Cys Pro Thr Gln Gly Glu Ala Thr Leu Val Glu Glu Gln Asp Ser Asn
        355                 360                 365

Phe Val Cys Arg Arg Thr Phe Val Asp Arg Gly Trp Gly Asn Gly Cys
    370                 375                 380

Gly Leu Phe Gly Lys Gly Ser Leu Leu Thr Cys Ala Lys Phe Lys Cys
385                 390                 395                 400

Val Thr Lys Leu Glu Gly Lys Ile Val Gln Tyr Glu Asn Leu Lys Tyr
                405                 410                 415

Ser Val Ile Val Thr Val His Thr Gly Asp Gln His Gln Val Gly Asn
            420                 425                 430

Glu Thr Thr Glu His Gly Thr Ile Ala Thr Ile Thr Pro Gln Ala Pro
        435                 440                 445

Thr Ser Glu Ile Gln Leu Thr Asp Tyr Gly Ala Leu Thr Leu Asp Cys
    450                 455                 460

Ser Pro Arg Thr Gly Leu Asp Phe Asn Glu Met Val Leu Leu Thr Met
465                 470                 475                 480

Lys Glu Lys Ser Trp Leu Val His Lys Gln Trp Phe Leu Asp Leu Pro
                485                 490                 495

Leu Pro Trp Thr Ser Gly Ala Ser Thr Ser Gln Glu Thr Trp Asn Arg
```

-continued

```
            500                 505                 510

Gln Asp Leu Leu Val Thr Phe Lys Thr Ala His Ala Lys Lys Gln Glu
        515                 520                 525

Val Val Val Leu Gly Ser Gln Glu Gly Ala Met His Thr Ala Leu Thr
    530                 535                 540

Gly Ala Thr Glu Ile Gln Thr Ser Gly Thr Thr Thr Ile Phe Ala Gly
545                 550                 555                 560

His Leu Lys Cys Arg Leu Lys Met Asp Lys Leu Thr Leu Lys Gly Met
                565                 570                 575

Ser Tyr Val Met Cys Thr Gly Ser Phe Lys Leu Glu Lys Glu Val Ala
            580                 585                 590

Glu Thr Gln His Gly Thr Val Leu Val Gln Val Lys Tyr Glu Gly Thr
        595                 600                 605

Asp Ala Pro Cys Lys Ile Pro Phe Ser Ala Gln Asp Glu Lys Gly Val
    610                 615                 620

Thr Gln Asn Gly Arg Leu Ile Thr Ala Asn Pro Ile Val Thr Asp Lys
625                 630                 635                 640

Glu Lys Pro Val Asn Ile Glu Thr Glu Pro Pro Phe Gly Glu Ser Tyr
                645                 650                 655

Ile Val Val Gly Ala Gly Glu Lys Ala Leu Lys Leu Ser Trp Phe Lys
            660                 665                 670

Lys Gly Ser Ser Ile Gly Lys Met Phe Glu Ala Thr Ala Arg Gly Ala
        675                 680                 685

Arg Arg Met Ala Ile Leu Gly Asp Thr Ala Trp Asp Phe Gly Ser Ile
    690                 695                 700

Gly Gly Val Phe Thr Ser Val Gly Lys Leu Val His Gln Val Phe Gly
705                 710                 715                 720

Ala Ala Tyr Gly Val Leu Phe Ser Gly Val Ser Trp Thr Met Lys Ile
                725                 730                 735

Gly Ile Gly Ile Leu Leu Thr Trp Leu Gly Leu Asn Ser Arg Asn Thr
            740                 745                 750

Ser Met Ala Met Thr Cys Ile Ala Val Gly Gly Ile Thr Leu Phe Leu
        755                 760                 765

Gly Phe Thr Val Gln Ala
    770
```

What is claimed is:

1. A tetravalent immunogenic composition comprising a) a first attenuated virus that is immunogenic against dengue serotype 1, b) a second attenuated virus that is immunogenic against dengue serotype 2, c) a third attenuated virus that is immunogenic against dengue serotype 3, and d) a fourth attenuated virus that is immunogenic against dengue serotype 4, wherein each of a), b), c) and d) comprises a nucleic acid comprising i) a first nucleotide sequence encoding at least one structural protein from a first dengue virus, ii) a second nucleotide sequence encoding nonstructural proteins from the first dengue virus or a second dengue virus, and iii) a 3' untranslated region, wherein the 3' untranslated region contains a deletion of about 30 nucleotides corresponding to the TL2 stem-loop structure, and wherein both the 3' untranslated region and the second nucleotide sequence encoding nonstructural proteins are from either the first dengue virus or the second dengue virus;

wherein the tetravalent immunogenic composition is not rDEN1/4Δ30, rDEN2/4Δ30, rDEN3/4Δ30, rDEN4Δ30.

2. The tetravalent immunogenic composition of claim 1, wherein the nucleic acid of at least one of a), b), c) or d) further comprises a mutation that confers a phenotype wherein the phenotype is temperature sensitivity in Vero cells or the human liver cell line HuH-7, host-cell restriction in mosquito cells or the human liver cell line HuH-7, host-cell adaptation for improved replication in Vero cells, or attenuation in mice or monkeys.

3. The composition of claim 1, wherein the first nucleotide sequence encoding at least one structural protein and the second nucleotide sequence encoding nonstructural proteins of at least one of a), b), c) and d) are from the first dengue virus.

4. The composition of claim 3, wherein the deletion of a) is a deletion of about 30 nucleotides from the 3' untranslated region of the dengue type 1 genome corresponding to the TL2 stem-loop structure between about nucleotides 10562-10591.

5. The composition of claim 3, wherein the deletion of b) is a deletion of about 30 nucleotides from the 3' untranslated region of the dengue type 2 genome corresponding to the TL2 stem-loop structure between about nucleotides 10541-10570.

6. The composition of claim 3, wherein the deletion of c) is by a deletion of about 30 nucleotides from the 3' untranslated region of the dengue type 3 genome corresponding to the TL2 stem-loop structure between about nucleotides 10535-10565.

7. The composition of claim 3, herein the deletion of d) is a deletion of about 30 nucleotides from the 3' untranslated region of the dengue type 4 genome corresponding to the TL2 stem-loop structure between about nucleotides 10478-10507.

8. The composition of claim 1, wherein the first nucleotide sequence encoding at least one structural protein of at least one of a), b), c), and d) is from the first dengue virus and the second nucleotide sequence encoding nonstructural proteins of at least one of a), b), c), and d) is from the second dengue virus, wherein the serotype of the first dengue virus and the second dengue virus are different.

9. The composition of claim 8, wherein the serotype of the second dengue virus having the deletion is type 1.

10. The composition of claim 9, wherein the serotype of the first dengue virus of b) is type 2.

11. The composition of claim 9, wherein the serotype of the first dengue virus of c) is type 3.

12. The composition of claim 9, wherein the serotype of the first dengue virus of d) is type 4.

13. The composition of claim 9, wherein the first nucleotide sequence encodes at least two structural proteins of the first dengue virus.

14. The composition of claim 13, wherein the structural proteins are prM and E proteins.

15. The composition of claim 9, wherein the deletion of a) is a deletion of about 30 nucleotides from the 3' untranslated region of the dengue type 1 genome corresponding to the TL2 stem-loop structure between about nucleotides 10562 and 10591.

16. The composition of claim 8, wherein the serotype of the second dengue virus having the deletion is type 2.

17. The composition of claim 16, wherein the serotype of the first dengue virus of a) is type 1.

18. The composition of claim 16, wherein the serotype of the first dengue virus of c) is type 3.

19. The composition of claim 16, wherein the serotype of the first dengue of d) virus is type 4.

20. The composition of claim 16, wherein the first nucleotide sequence encodes at least two structural proteins of the first dengue virus.

21. The composition of claim 20, wherein the structural proteins are prM and E proteins.

22. The composition of claim 16, wherein the deletion is a deletion of about 30 nucleotides from the 3' untranslated region of the dengue type 2 genome corresponding to the TL2 stem-loop structure between about nucleotides 10541 and 10570.

23. The composition of claim 8, wherein the serotype of the second dengue virus having the deletion is type 3.

24. The composition of claim 23, wherein the serotype of the first dengue virus of a) is type 1.

25. The composition of claim 23, wherein the serotype of the first dengue virus of b) is type 2.

26. The composition of claim 23, wherein the serotype of the first dengue virus of d) is type 4.

27. The composition of claim 23, wherein the first nucleotide sequence encodes at least two structural proteins of the first dengue virus.

28. The composition of claim 27, wherein the structural proteins are prM and E proteins.

29. The composition of claim 23, wherein the deletion is a deletion of about 30 nucleotides from the 3' untranslated region of the dengue type 3 genome corresponding to the TL2 stem-loop structure between about nucleotides 10535 and 10565.

30. The composition of claim 8, wherein the serotype of the second dengue virus having the deletion is type 4.

31. The composition of claim 30, wherein the serotype of the first dengue virus of a) is type 1.

32. The composition of claim 30, wherein the serotype of the first dengue virus of b) is type 2.

33. The composition of claim 30, wherein the serotype of the first dengue virus of c) is type 3.

34. The composition of claim 30, wherein the first nucleotide sequence encodes at least two structural proteins of the first dengue virus.

35. The composition of claim 34, wherein the structural proteins are prM and E proteins.

36. The composition of claim 30, wherein the deletion is a deletion of about 30 nucleotides from the 3' untranslated region of the dengue type 4 genome corresponding to the TL2 stem-loop structure between about nucleotides 10478 and 10507.

37. A method of inducing an immune response in a subject comprising administering an effective amount of the composition of claim 1 to the subject.

38. The method of claim 37 wherein the subject is a human.

39. A tetravalent vaccine comprising the composition of claim 1.

40. A method of preventing disease caused by dengue virus in a subject comprising administering an effective amount of the vaccine of claim 39 to the subject.

41. The method of claim 40 wherein the subject is a human.

42. The tetravalent immunogenic composition defined in claim 1, selected from the group consisting of:

(1) rDEN1Δ30, rDEN2Δ30, rDEN3Δ30, rDEN4Δ30,
(2) rDEN1Δ30, rDEN2Δ30, rDEN3Δ30, rDEN4/1Δ30,
(3) rDEN1Δ30, rDEN2Δ30, rDEN3Δ30, rDEN4/2Δ30,
(4) rDEN1Δ30, rDEN2Δ30, rDEN3Δ30, rDEN4/3Δ30,
(5) rDEN1Δ30, rDEN2Δ30, rDEN3/1Δ30, rDEN4Δ30,
(6) rDEN1Δ30, rDEN2Δ30, rDEN3/1Δ30, rDEN4/1Δ30,
(7) rDEN1Δ30, rDEN2Δ30, rDEN3/1Δ30, rDEN4/2Δ30,
(8) rDEN1Δ30, rDEN2Δ30, rDEN3/1Δ30, rDEN4/3Δ30,
(9) rDEN1Δ30, rDEN2Δ30, rDEN3/2Δ30, rDEN4Δ30,
(10) rDEN1Δ30, rDEN2Δ30, rDEN3/2Δ30, rDEN4/1Δ30,
(11) rDEN1Δ30, rDEN2Δ30, rDEN3/2Δ30, rDEN4/2Δ30,
(12) rDEN1Δ30, rDEN2Δ30, rDEN3/2Δ30, rDEN4/3Δ30,
(13) rDEN1Δ30, rDEN2Δ30, rDEN3/4Δ30, rDEN4Δ30,
(14) rDEN1Δ30, rDEN2Δ30, rDEN3/4Δ30, rDEN4/1Δ30,
(15) rDEN1Δ30, rDEN2Δ30, rDEN3/4Δ30, rDEN4/2Δ30,
(16) rDEN1Δ30, rDEN2Δ30, rDEN3/4Δ30, rDEN4/3Δ30,
(17) rDEN1Δ30, rDEN2/1Δ30, rDEN3Δ30, rDEN4Δ30,

(18) rDEN1Δ30, rDEN2/1Δ30, rDEN3Δ30, rDEN4/1Δ30,
(19) rDEN1Δ30, rDEN2/1Δ30, rDEN3Δ30, rDEN4/2Δ30,
(20) rDEN1Δ30, rDEN2/1Δ30, rDEN3Δ30, rDEN4/3Δ30,
(21) rDEN1Δ30, rDEN2/1Δ30, rDEN3/1Δ30, rDEN4Δ30,
(22) rDEN1Δ30, rDEN2/1Δ30, rDEN3/1Δ30, rDEN4/1Δ30,
(23) rDEN1Δ30, rDEN2/1Δ30, rDEN3/1Δ30, rDEN4/2Δ30,
(24) rDEN1Δ30, rDEN2/1Δ30, rDEN3/1Δ30, rDEN4/3Δ30,
(25) rDEN1Δ30, rDEN2/1Δ30, rDEN3/2Δ30, rDEN4Δ30,
(26) rDEN1Δ30, rDEN2/1Δ30, rDEN3/2Δ30, rDEN4/1Δ30,
(27) rDEN1Δ30, rDEN2/1Δ30, rDEN3/2Δ30, rDEN4/2Δ30,
(28) rDEN1Δ30, rDEN2/1Δ30, rDEN3/2Δ30, rDEN4/3Δ30,
(29) rDEN1Δ30, rDEN2/1Δ30, rDEN3/4Δ30, rDEN4Δ30,
(30) rDEN1Δ30, rDEN2/1Δ30, rDEN3/4Δ30, rDEN4/1Δ30,
(31) rDEN1Δ30, rDEN2/1Δ30, rDEN3/4Δ30, rDEN4/2Δ30,
(32) rDEN1Δ30, rDEN2/1Δ30, rDEN3/4Δ30, rDEN4/3Δ30,
(33) rDEN1Δ30, rDEN2/3Δ30, rDEN3Δ30, rDEN4Δ30,
(34) rDEN1Δ30, rDEN2/3Δ30, rDEN3Δ30, rDEN4/1Δ30,
(35) rDEN1Δ30, rDEN2/3Δ30, rDEN3Δ30, rDEN4/2Δ30,
(36) rDEN1Δ30, rDEN2/3Δ30, rDEN3Δ30, rDEN4/3Δ30,
(37) rDEN1Δ30, rDEN2/3Δ30, rDEN3/1Δ30, rDEN4Δ30,
(38) rDEN1Δ30, rDEN2/3Δ30, rDEN3/1Δ30, rDEN4/1Δ30,
(39) rDEN1Δ30, rDEN2/3Δ30, rDEN3/1Δ30, rDEN4/2Δ30,
(40) rDEN1Δ30, rDEN2/3Δ30, rDEN3/1Δ30, rDEN4/3Δ30,
(41) rDEN1Δ30, rDEN2/3Δ30, rDEN3/2Δ30, rDEN4Δ30,
(42) rDEN1Δ30, rDEN2/3Δ30, rDEN3/2Δ30, rDEN4/1Δ30,
(43) rDEN1Δ30, rDEN2/3Δ30, rDEN3/2Δ30, rDEN4/2Δ30,
(44) rDEN1Δ30, rDEN2/3Δ30, rDEN3/2Δ30, rDEN4/3Δ30,
(45) rDEN1Δ30, rDEN2/3Δ30, rDEN3/4Δ30, rDEN4Δ30,
(46) rDEN1Δ30, rDEN2/3Δ30, rDEN3/4Δ30, rDEN4/1Δ30,
(47) rDEN1Δ30, rDEN2/3Δ30, rDEN3/4Δ30, rDEN4/2Δ30,
(48) rDEN1Δ30, rDEN2/3Δ30, rDEN3/4Δ30, rDEN4/3Δ30,
(49) rDEN1Δ30, rDEN2/4Δ30, rDEN3Δ30, rDEN4Δ30,
(50) rDEN1Δ30, rDEN2/4Δ30, rDEN3Δ30, rDEN4/1Δ30,
(51) rDEN1Δ30, rDEN2/4Δ30, rDEN3Δ30, rDEN4/2Δ30,
(52) rDEN1Δ30, rDEN2/4Δ30, rDEN3Δ30, rDEN4/3Δ30,
(53) rDEN1Δ30, rDEN2/4Δ30, rDEN3/1Δ30, rDEN4Δ30,
(54) rDEN1Δ30, rDEN2/4Δ30, rDEN3/1Δ30, rDEN4/1Δ30,
(55) rDEN1Δ30, rDEN2/4Δ30, rDEN3/1Δ30, rDEN4/2Δ30,
(56) rDEN1Δ30, rDEN2/4Δ30, rDEN3/1Δ30, rDEN4/3Δ30,
(57) rDEN1Δ30, rDEN2/4Δ30, rDEN3/2Δ30, rDEN4Δ30,
(58) rDEN1Δ30, rDEN2/4Δ30, rDEN3/2Δ30, rDEN4/1Δ30,
(59) rDEN1Δ30, rDEN2/4Δ30, rDEN3/2Δ30, rDEN4/2Δ30,
(60) rDEN1Δ30, rDEN2/4Δ30, rDEN3/2Δ30, rDEN4/3Δ30,
(61) rDEN1Δ30, rDEN2/4Δ30, rDEN3/4Δ30, rDEN4Δ30,
(62) rDEN1Δ30, rDEN2/4Δ30, rDEN3/4Δ30, rDEN4/1Δ30,
(63) rDEN1Δ30, rDEN2/4Δ30, rDEN3/4Δ30, rDEN4/2Δ30,
(64) rDEN1Δ30, rDEN2/4Δ30, rDEN3/4Δ30, rDEN4/3Δ30,
(65) rDEN1/2Δ30, rDEN2Δ30, rDEN3Δ30, rDEN4Δ30,
(66) rDEN1/2Δ30, rDEN2Δ30, rDEN3Δ30, rDEN4/1Δ30,
(67) rDEN1/2Δ30, rDEN2Δ30, rDEN3Δ30, rDEN4/2Δ30,
(68) rDEN1/2Δ30, rDEN2Δ30, rDEN3Δ30, rDEN4/3Δ30,
(69) rDEN1/2Δ30, rDEN2Δ30, rDEN3/1Δ30, rDEN4Δ30,
(70) rDEN1/2Δ30, rDEN2Δ30, rDEN3/1Δ30, rDEN4/1Δ30,
(71) rDEN1/2Δ30, rDEN2Δ30, rDEN3/1Δ30, rDEN4/2Δ30,
(72) rDEN1/2Δ30, rDEN2Δ30, rDEN3/1Δ30, rDEN4/3Δ30,
(73) rDEN1/2Δ30, rDEN2Δ30, rDEN3/2Δ30, rDEN4Δ30,
(74) rDEN1/2Δ30, rDEN2Δ30, rDEN3/2Δ30, rDEN4/1Δ30,
(75) rDEN1/2Δ30, rDEN2Δ30, rDEN3/2Δ30, rDEN4/2Δ30,
(76) rDEN1/2Δ30, rDEN2Δ30, rDEN3/2Δ30, rDEN4/3Δ30,
(77) rDEN1/2Δ30, rDEN2Δ30, rDEN3/4Δ30, rDEN4Δ30,
(78) rDEN1/2Δ30, rDEN2Δ30, rDEN3/4Δ30, rDEN4/1Δ30,
(79) rDEN1/2Δ30, rDEN2Δ30, rDEN3/4Δ30, rDEN4/2Δ30,
(80) rDEN1/2Δ30, rDEN2Δ30, rDEN3/4Δ30, rDEN4/3Δ30,
(81) rDEN1/2Δ30, rDEN2/1Δ30, rDEN3Δ30, rDEN4Δ30,
(82) rDEN1/2Δ30, rDEN2/1Δ30, rDEN3Δ30, rDEN4/1Δ30,
(83) rDEN1/2Δ30, rDEN2/1Δ30, rDEN3Δ30, rDEN4/2Δ30,
(84) rDEN1/2Δ30, rDEN2/1Δ30, rDEN3Δ30, rDEN4/3Δ30,
(85) rDEN1/2Δ30, rDEN2/1Δ30, rDEN3/1Δ30, rDEN4Δ30,

(86) rDEN1/2Δ30, rDEN2/1Δ30, rDEN3/1Δ30, rDEN4/1Δ30,
(87) rDEN1/2Δ30, rDEN2/1Δ30, rDEN3/1Δ30, rDEN4/2Δ30,
(88) rDEN1/2Δ30, rDEN2/1Δ30, rDEN3/1Δ30, rDEN4/3Δ30,
(89) rDEN1/2Δ30, rDEN2/1Δ30, rDEN3/2Δ30, rDEN4Δ30,
(90) rDEN1/2Δ30, rDEN2/1Δ30, rDEN3/2Δ30, rDEN4/1Δ30,
(91) rDEN1/2Δ30, rDEN2/1Δ30, rDEN3/2Δ30, rDEN4/2Δ30,
(92) rDEN1/2Δ30, rDEN2/1Δ30, rDEN3/2Δ30, rDEN4/3Δ30,
(93) rDEN1/2Δ30, rDEN2/1Δ30, rDEN3/4Δ30, rDEN4Δ30,
(94) rDEN1/2Δ30, rDEN2/1Δ30, rDEN3/4Δ30, rDEN4/1Δ30,
(95) rDEN1/2Δ30, rDEN2/1Δ30, rDEN3/4Δ30, rDEN4/2Δ30,
(96) rDEN1/2Δ30, rDEN2/1Δ30, rDEN3/4Δ30, rDEN4/3Δ30,
(97) rDEN1/2Δ30, rDEN2/3Δ30, rDEN3Δ30, rDEN4Δ30,
(98) rDEN1/2Δ30, rDEN2/3Δ30, rDEN3Δ30, rDEN4/1Δ30,
(99) rDEN1/2Δ30, rDEN2/3Δ30, rDEN3Δ30, rDEN4/2Δ30,
(100) rDEN1/2Δ30, rDEN2/3Δ30, rDEN3Δ30, rDEN4/3Δ30,
(101) rDEN1/2Δ30, rDEN2/3Δ30, rDEN3/1Δ30, rDEN4Δ30,
(102) rDEN1/2Δ30, rDEN2/3Δ30, rDEN3/1Δ30, rDEN4/1Δ30,
(103) rDEN1/2Δ30, rDEN2/3Δ30, rDEN3/1Δ30, rDEN4/2Δ30,
(104) rDEN1/2Δ30, rDEN2/3Δ30, rDEN3/1Δ30, rDEN4/3Δ30,
(105) rDEN1/2Δ30, rDEN2/3Δ30, rDEN3/2Δ30, rDEN4Δ30,
(106) rDEN1/2Δ30, rDEN2/3Δ30, rDEN3/2Δ30, rDEN4/1Δ30,
(107) rDEN1/2Δ30, rDEN2/3Δ30, rDEN3/2Δ30, rDEN4/2Δ30,
(108) rDEN1/2Δ30, rDEN2/3Δ30, rDEN3/2Δ30, rDEN4/3Δ30,
(109) rDEN1/2Δ30, rDEN2/3Δ30, rDEN3/4Δ30, rDEN4Δ30,
(110) rDEN1/2Δ30, rDEN2/3Δ30, rDEN3/4Δ30, rDEN4/1Δ30,
(111) rDEN1/2Δ30, rDEN2/3Δ30, rDEN3/4Δ30, rDEN4/2Δ30,
(112) rDEN1/2Δ30, rDEN2/3Δ30, rDEN3/4Δ30, rDEN4/3Δ30,
(113) rDEN1/2Δ30, rDEN2/4Δ30, rDEN3Δ30, rDEN4Δ30,
(114) rDEN1/2Δ30, rDEN2/4Δ30, rDEN3Δ30, rDEN4/1Δ30,
(115) rDEN1/2Δ30, rDEN2/4Δ30, rDEN3Δ30, rDEN4/2Δ30,
(116) rDEN1/2Δ30, rDEN2/4Δ30, rDEN3Δ30, rDEN4/3Δ30,
(117) rDEN1/2Δ30, rDEN2/4Δ30, rDEN3/1Δ30, rDEN4Δ30,
(118) rDEN1/2Δ30, rDEN2/4Δ30, rDEN3/1Δ30, rDEN4/1Δ30,
(119) rDEN1/2Δ30, rDEN2/4Δ30, rDEN3/1Δ30, rDEN4/2Δ30,
(120) rDEN1/2Δ30, rDEN2/4Δ30, rDEN3/1Δ30, rDEN4/3Δ30,
(121) rDEN1/2Δ30, rDEN2/4Δ30, rDEN3/2Δ30, rDEN4Δ30,
(122) rDEN1/2Δ30, rDEN2/4Δ30, rDEN3/2Δ30, rDEN4/1Δ30,
(123) rDEN1/2Δ30, rDEN2/4Δ30, rDEN3/2Δ30, rDEN4/2Δ30,
(124) rDEN1/2Δ30, rDEN2/4Δ30, rDEN3/2Δ30, rDEN4/3Δ30,
(125) rDEN1/2Δ30, rDEN2/4Δ30, rDEN3/4Δ30, rDEN4Δ30,
(126) rDEN1/2Δ30, rDEN2/4Δ30, rDEN3/4Δ30, rDEN4/1Δ30,
(127) rDEN1/2Δ30, rDEN2/4Δ30, rDEN3/4Δ30, rDEN4/2Δ30,
(128) rDEN1/2Δ30, rDEN2/4Δ30, rDEN3/4Δ30, rDEN4/3Δ30,
(129) rDEN1/3Δ30, rDEN2Δ30, rDEN3Δ30, rDEN4Δ30,
(130) rDEN1/3Δ30, rDEN2Δ30, rDEN3Δ30, rDEN4/1Δ30,
(131) rDEN1/3Δ30, rDEN2Δ30, rDEN3Δ30, rDEN4/2Δ30,
(132) rDEN1/3Δ30, rDEN2Δ30, rDEN3Δ30, rDEN4/3Δ30,
(133) rDEN1/3Δ30, rDEN2Δ30, rDEN3/1Δ30, rDEN4Δ30,
(134) rDEN1/3Δ30, rDEN2Δ30, rDEN3/1Δ30, rDEN4/1Δ30,
(135) rDEN1/3Δ30, rDEN2Δ30, rDEN3/1Δ30, rDEN4/2Δ30,
(136) rDEN1/3Δ30, rDEN2Δ30, rDEN3/1Δ30, rDEN4/3Δ30,
(137) rDEN1/3Δ30, rDEN2Δ30, rDEN3/2Δ30, rDEN4Δ30,
(138) rDEN1/3Δ30, rDEN2Δ30, rDEN3/2Δ30, rDEN4/1Δ30,
(139) rDEN1/3Δ30, rDEN2Δ30, rDEN3/2Δ30, rDEN4/2Δ30,
(140) rDEN1/3Δ30, rDEN2Δ30, rDEN3/2Δ30, rDEN4/3Δ30,
(141) rDEN1/3Δ30, rDEN2Δ30, rDEN3/4Δ30, rDEN4Δ30,
(142) rDEN1/3Δ30, rDEN2Δ30, rDEN3/4Δ30, rDEN4/1Δ30,
(143) rDEN1/3Δ30, rDEN2Δ30, rDEN3/4Δ30, rDEN4/2Δ30,
(144) rDEN1/3Δ30, rDEN2Δ30, rDEN3/4Δ30, rDEN4/3Δ30,
(145) rDEN1/3Δ30, rDEN2/1Δ30, rDEN3Δ30, rDEN4Δ30,
(146) rDEN1/3Δ30, rDEN2/1Δ30, rDEN3Δ30, rDEN4/1Δ30,
(147) rDEN1/3Δ30, rDEN2/1Δ30, rDEN3Δ30, rDEN4/2Δ30,
(148) rDEN1/3Δ30, rDEN2/1Δ30, rDEN3Δ30, rDEN4/3Δ30,
(149) rDEN1/3Δ30, rDEN2/1Δ30, rDEN3/1Δ30, rDEN4Δ30,
(150) rDEN1/3Δ30, rDEN2/1Δ30, rDEN3/1Δ30, rDEN4/1Δ30,
(151) rDEN1/3Δ30, rDEN2/1Δ30, rDEN3/1Δ30, rDEN4/2Δ30,
(152) rDEN1/3Δ30, rDEN2/1Δ30, rDEN3/1Δ30, rDEN4/3Δ30, (153) rDEN1/3Δ30, rDEN2/1Δ30, rDEN3/2Δ30, rDEN4Δ30,
(154) rDEN1/3Δ30, rDEN2/1Δ30, rDEN3/2Δ30, rDEN4/1Δ30,
(155) rDEN1/3Δ30, rDEN2/1Δ30, rDEN3/2Δ30, rDEN4/2Δ30,
(156) rDEN1/3Δ30, rDEN2/1Δ30, rDEN3/2Δ30, rDEN4/3Δ30,
(157) rDEN1/3Δ30, rDEN2/1Δ30, rDEN3/4Δ30, rDEN4Δ30,
(158) rDEN1/3Δ30, rDEN2/1Δ30, rDEN3/4Δ30, rDEN4/1Δ30,
(159) rDEN1/3Δ30, rDEN2/1Δ30, rDEN3/4Δ30, rDEN4/2Δ30,
(160) rDEN1/3Δ30, rDEN2/1Δ30, rDEN3/4Δ30, rDEN4/3Δ30,
(161) rDEN1/3Δ30, rDEN2/3Δ30, rDEN3Δ30, rDEN4Δ30,
(162) rDEN1/3Δ30, rDEN2/3Δ30, rDEN3Δ30, rDEN4/1Δ30,
(163) rDEN1/3Δ30, rDEN2/3Δ30, rDEN3Δ30, rDEN4/2Δ30,
(164) rDEN1/3Δ30, rDEN2/3Δ30, rDEN3Δ30, rDEN4/3Δ30,
(165) rDEN1/3Δ30, rDEN2/3Δ30, rDEN3/1Δ30, rDEN4Δ30,
(166) rDEN1/3Δ30, rDEN2/3Δ30, rDEN3/1Δ30, rDEN4/1Δ30,
(167) rDEN1/3Δ30, rDEN2/3Δ30, rDEN3/1Δ30, rDEN4/2Δ30,
(168) rDEN1/3Δ30, rDEN2/3Δ30, rDEN3/1Δ30, rDEN4/3Δ30,
(169) rDEN1/3Δ30, rDEN2/3Δ30, rDEN3/2Δ30, rDEN4Δ30,
(170) rDEN1/3Δ30, rDEN2/3Δ30, rDEN3/2Δ30, rDEN4/1Δ30,
(171) rDEN1/3Δ30, rDEN2/3Δ30, rDEN3/2Δ30, rDEN4/2Δ30,
(172) rDEN1/3Δ30, rDEN2/3Δ30, rDEN3/2Δ30, rDEN4/3Δ30,
(173) rDEN1/3Δ30, rDEN2/3Δ30, rDEN3/4Δ30, rDEN4Δ30,
(174) rDEN1/3Δ30, rDEN2/3Δ30, rDEN3/4Δ30, rDEN4/1Δ30,
(175) rDEN1/3Δ30, rDEN2/3Δ30, rDEN3/4Δ30, rDEN4/2Δ30,
(176) rDEN1/3Δ30, rDEN2/3Δ30, rDEN3/4Δ30, rDEN4/3Δ30,
(177) rDEN1/3Δ30, rDEN2/4Δ30, rDEN3Δ30, rDEN4Δ30,
(178) rDEN1/3Δ30, rDEN2/4Δ30, rDEN3Δ30, rDEN4/1Δ30,
(179) rDEN1/3Δ30, rDEN2/4Δ30, rDEN3Δ30, rDEN4/2Δ30,
(180) rDEN1/3Δ30, rDEN2/4Δ30, rDEN3Δ30, rDEN4/3Δ30,
(181) rDEN1/3Δ30, rDEN2/4Δ30, rDEN3/1Δ30, rDEN4Δ30,
(182) rDEN1/3Δ30, rDEN2/4Δ30, rDEN3/1Δ30, rDEN4/1Δ30,
(183) rDEN1/3Δ30, rDEN2/4Δ30, rDEN3/1Δ30, rDEN4/2Δ30,
(184) rDEN1/3Δ30, rDEN2/4Δ30, rDEN3/1Δ30, rDEN4/3Δ30,
(185) rDEN1/3Δ30, rDEN2/4Δ30, rDEN3/2Δ30, rDEN4Δ30,
(186) rDEN1/3Δ30, rDEN2/4Δ30, rDEN3/2Δ30, rDEN4/1Δ30,
(187) rDEN1/3Δ30, rDEN2/4Δ30, rDEN3/2Δ30, rDEN4/2Δ30,
(188) rDEN1/3Δ30, rDEN2/4Δ30, rDEN3/2Δ30, rDEN4/3Δ30,
(189) rDEN1/3Δ30, rDEN2/4Δ30, rDEN3/4Δ30, rDEN4Δ30,
(190) rDEN1/3Δ30, rDEN2/4Δ30, rDEN3/4Δ30, rDEN4/1Δ30,
(191) rDEN1/3Δ30, rDEN2/4Δ30, rDEN3/4Δ30, rDEN4/2Δ30,
(192) rDEN1/3Δ30, rDEN2/4Δ30, rDEN3/4Δ30, rDEN4/3Δ30,
(193) rDEN1/4Δ30, rDEN2Δ30, rDEN3Δ30, rDEN4Δ30,
(194) rDEN1/4Δ30, rDEN2Δ30, rDEN3Δ30, rDEN4/1Δ30,
(195) rDEN1/4Δ30, rDEN2Δ30, rDEN3Δ30, rDEN4/2Δ30,
(196) rDEN1/4Δ30, rDEN2Δ30, rDEN3Δ30, rDEN4/3Δ30,
(197) rDEN1/4Δ30, rDEN2Δ30, rDEN3/1Δ30, rDEN4Δ30,
(198) rDEN1/4Δ30, rDEN2Δ30, rDEN3/1Δ30, rDEN4/1Δ30,
(199) rDEN1/4Δ30, rDEN2Δ30, rDEN3/1Δ30, rDEN4/2Δ30,
(200) rDEN1/4Δ30, rDEN2Δ30, rDEN3/1Δ30, rDEN4/3Δ30,
(201) rDEN1/4Δ30, rDEN2Δ30, rDEN3/2Δ30, rDEN4Δ30,
(202) rDEN1/4Δ30, rDEN2Δ30, rDEN3/2Δ30, rDEN4/1Δ30,
(203) rDEN1/4Δ30, rDEN2Δ30, rDEN3/2Δ30, rDEN4/2Δ30,
(204) rDEN1/4Δ30, rDEN2Δ30, rDEN3/2Δ30, rDEN4/3Δ30,
(205) rDEN1/4Δ30, rDEN2Δ30, rDEN3/4Δ30, rDEN4Δ30,
(206) rDEN1/4Δ30, rDEN2Δ30, rDEN3/4Δ30, rDEN4/1Δ30,
(207) rDEN1/4Δ30, rDEN2Δ30, rDEN3/4Δ30, rDEN4/2Δ30,
(208) rDEN1/4Δ30, rDEN2Δ30, rDEN3/4Δ30, rDEN4/3Δ30,
(209) rDEN1/4Δ30, rDEN2/1Δ30, rDEN3Δ30, rDEN4Δ30,
(210) rDEN1/4Δ30, rDEN2/1Δ30, rDEN3Δ30, rDEN4/1Δ30,
(211) rDEN1/4Δ30, rDEN2/1Δ30, rDEN3Δ30, rDEN4/2Δ30,
(212) rDEN1/4Δ30, rDEN2/1Δ30, rDEN3Δ30, rDEN4/3Δ30,
(213) rDEN1/4Δ30, rDEN2/1Δ30, rDEN3/1Δ30, rDEN4Δ30,
(214) rDEN1/4Δ30, rDEN2/1Δ30, rDEN3/1Δ30, rDEN4/1Δ30,
(215) rDEN1/4Δ30, rDEN2/1Δ30, rDEN3/1Δ30, rDEN4/2Δ30,
(216) rDEN1/4Δ30, rDEN2/1Δ30, rDEN3/1Δ30, rDEN4/3Δ30,
(217) rDEN1/4Δ30, rDEN2/1Δ30, rDEN3/2Δ30, rDEN4Δ30,
(218) rDEN1/4Δ30, rDEN2/1Δ30, rDEN3/2Δ30, rDEN4/1Δ30,
(219) rDEN1/4Δ30, rDEN2/1Δ30, rDEN3/2Δ30, rDEN4/2Δ30, (220) rDEN1/4Δ30, rDEN2/1Δ30, rDEN3/2Δ30, rDEN4/3Δ30,
(221) rDEN1/4Δ30, rDEN2/1Δ30, rDEN3/4Δ30, rDEN4Δ30,
(222) rDEN1/4Δ30, rDEN2/1Δ30, rDEN3/4Δ30, rDEN4/1Δ30,
(223) rDEN1/4Δ30, rDEN2/1Δ30, rDEN3/4Δ30, rDEN4/2Δ30,
(224) rDEN1/4Δ30, rDEN2/1Δ30, rDEN3/4Δ30, rDEN4/3Δ30,
(225) rDEN1/4Δ30, rDEN2/3Δ30, rDEN3Δ30, rDEN4Δ30,
(226) rDEN1/4Δ30, rDEN2/3Δ30, rDEN3Δ30, rDEN4/1Δ30,
(227) rDEN1/4Δ30, rDEN2/3Δ30, rDEN3Δ30, rDEN4/2Δ30,
(228) rDEN1/4Δ30, rDEN2/3Δ30, rDEN3Δ30, rDEN4/3Δ30,
(229) rDEN1/4Δ30, rDEN2/3Δ30, rDEN3/1Δ30, rDEN4Δ30,
(230) rDEN1/4Δ30, rDEN2/3Δ30, rDEN3/1Δ30, rDEN4/1Δ30,
(231) rDEN1/4Δ30, rDEN2/3Δ30, rDEN3/1Δ30, rDEN4/2Δ30,
(232) rDEN1/4Δ30, rDEN2/3Δ30, rDEN3/1Δ30, rDEN4/3Δ30,
(233) rDEN1/4Δ30, rDEN2/3Δ30, rDEN3/2Δ30, rDEN4Δ30,
(234) rDEN1/4Δ30, rDEN2/3Δ30, rDEN3/2Δ30, rDEN4/1Δ30,
(235) rDEN1/4Δ30, rDEN2/3Δ30, rDEN3/2Δ30, rDEN4/2Δ30,
(236) rDEN1/4Δ30, rDEN2/3Δ30, rDEN3/2Δ30, rDEN4/3Δ30,
(237) rDEN1/4Δ30, rDEN2/3Δ30, rDEN3/4Δ30, rDEN4Δ30,
(238) rDEN1/4Δ30, rDEN2/3Δ30, rDEN3/4Δ30, rDEN4/1Δ30,
(239) rDEN1/4Δ30, rDEN2/3Δ30, rDEN3/4Δ30, rDEN4/2Δ30,
(240) rDEN1/4Δ30, rDEN2/3Δ30, rDEN3/4Δ30, rDEN4/3Δ30,
(241) rDEN1/4Δ30, rDEN2/4Δ30, rDEN3Δ30, rDEN4Δ30,
(242) rDEN1/4Δ30, rDEN2/4Δ30, rDEN3Δ30, rDEN4/1Δ30,
(243) rDEN1/4Δ30, rDEN2/4Δ30, rDEN3Δ30, rDEN4/2Δ30,
(244) rDEN1/4Δ30, rDEN2/4Δ30, rDEN3Δ30, rDEN4/3Δ30,
(245) rDEN1/4Δ30, rDEN2/4Δ30, rDEN3/1Δ30, rDEN4Δ30,
(246) rDEN1/4Δ30, rDEN2/4Δ30, rDEN3/1Δ30, rDEN4/1Δ30,
(247) rDEN1/4Δ30, rDEN2/4Δ30, rDEN3/1Δ30, rDEN4/2Δ30,
(248) rDEN1/4Δ30, rDEN2/4Δ30, rDEN3/1Δ30, rDEN4/3Δ30,
(249) rDEN1/4Δ30, rDEN2/4Δ30, rDEN3/2Δ30, rDEN4Δ30,
(250) rDEN1/4Δ30, rDEN2/4Δ30, rDEN3/2Δ30, rDEN4/1Δ30,
(251) rDEN1/4Δ30, rDEN2/4Δ30, rDEN3/2Δ30, rDEN4/2Δ30,
(252) rDEN1/4Δ30, rDEN2/4Δ30, rDEN3/2Δ30, rDEN4/3Δ30,
(254) rDEN1/4Δ30, rDEN2/4Δ30, rDEN3/4Δ30, rDEN4/1Δ30,
(255) rDEN1/4Δ30, rDEN2/4Δ30, rDEN3/4Δ30, rDEN4/2Δ30, and
(256) rDEN1/4Δ30, rDEN2/4Δ30, rDEN3/4Δ30, rDEN4/3Δ30.

* * * * *